US011512410B2

(12) United States Patent
Yapara et al.

(10) Patent No.: US 11,512,410 B2
(45) Date of Patent: Nov. 29, 2022

(54) ANTIBODY PHAGE DISPLAY LIBRARY

(71) Applicant: GENNOVA BIOPHARMACEUTICALS LIMITED, Pune (IN)

(72) Inventors: Suneelshekar Yapara, Pune (IN); Ashwin Shete, Pune (IN); Vrushali Sagare, Pune (IN); Praveen Kumar Agarwal, Pune (IN); Jaideep Moitra, Pune (IN)

(73) Assignee: GENNOVA BIOPHARMACEUTICALS LIMITED, Pune (IN)

( * ) Notice: Subject to any disclaimer, the term of this patent is extended or adjusted under 35 U.S.C. 154(b) by 902 days.

(21) Appl. No.: 16/312,274

(22) PCT Filed: Jun. 23, 2017

(86) PCT No.: PCT/IN2017/050257
§ 371 (c)(1),
(2) Date: Dec. 20, 2018

(87) PCT Pub. No.: WO2018/002952
PCT Pub. Date: Jan. 4, 2018

(65) Prior Publication Data
US 2020/0308256 A1 Oct. 1, 2020

(30) Foreign Application Priority Data

Jun. 26, 2016 (IN) .............................. 201621006661
Jul. 3, 2016 (IN) .............................. 201621019380

(51) Int. Cl.
*C40B 50/06* (2006.01)
*C07K 16/00* (2006.01)
(Continued)

(52) U.S. Cl.
CPC ............ *C40B 50/06* (2013.01); *C07K 16/005* (2013.01); *C12N 15/1037* (2013.01);
(Continued)

(58) Field of Classification Search
None
See application file for complete search history.

(56) References Cited

U.S. PATENT DOCUMENTS 6,696,248 B1  2/2004  Knappik et al.
6,794,128 B2  9/2004  Marks et al.
(Continued)

FOREIGN PATENT DOCUMENTS

KR  100961392 B1  6/2010
WO  WO-92/01047 A1  1/1992

OTHER PUBLICATIONS

Scaviner et al. (1999) Experimental and Clinical Immunogenetics vol. 16 pp. 234 to 240.*
(Continued)

*Primary Examiner* — Christian C Boesen
(74) *Attorney, Agent, or Firm* — Foley & Lardner LLP

(57) ABSTRACT

The present invention discloses a naïve antibody phage display library (APDL), a process for producing the same and a method of obtaining manufacturable antibodies as soluble Fabs from the antibody phage display library.

19 Claims, 61 Drawing Sheets

Specification includes a Sequence Listing.

(51) Int. Cl.
    C12N 15/10    (2006.01)
    C12Q 1/686    (2018.01)
(52) U.S. Cl.
    CPC .......... *C12Q 1/686* (2013.01); *C07K 2317/21* (2013.01); *C07K 2317/55* (2013.01); *C12Q 2527/101* (2013.01); *C12Q 2527/107* (2013.01)

(56) References Cited

U.S. PATENT DOCUMENTS

| | | |
|---|---|---|
| 2003/0166871 A1 | 9/2003 | Barbas, III et al. |
| 2005/0119455 A1 | 6/2005 | Fuh et al. |
| 2005/0164180 A1 | 7/2005 | Tanha et al. |
| 2009/0054254 A1 | 2/2009 | Throsby et al. |
| 2011/0236372 A1 | 9/2011 | Villa |
| 2013/0288908 A1 | 10/2013 | Fujino et al. |

OTHER PUBLICATIONS

Zurdo et al., "Early Implementation of QbD in Biopharmaceutical Development: A Practical Example," Biomedical Research International, vol. 2015, No. 605427, 2015, pp. 1-19.
Levy et al., "Enhancement of antibody fragment secretion into the *Escherichia coli* periplasm by coexpression with the peptidyl prolyl isomerase, FkpA, in the cytoplasm," Journal of Immunological Methods, vol. 394, 2013, pp. 10-21.
Schwimmer et al., "Discovery of diverse and functional antibodies from large human repertoire antibody libraries," Journal of Immunological Methods, vol. 391, 2013, pp. 60-71.
Jiang et al., "Advances in the assessment and control of the effector functions of therapeutic antibodies," Nature Reviews, Drug Discovery, vol. 10, Feb. 2011, pp. 101-110.
Lukasz et al., "Role of Angiopoietin/Tie2 in Critical Illness: Promising Biomarker, Disease Mediator, and Therapeutic Target?" Hindawi Publishing Corporation, Scientifica, vol. 2012, Article ID 160174, 2012, pp. 1-8.
Abdiche et al., "Expanding the ProteOn XPR36 biosensor into a 36-ligand array expedites protein interaction analysis," Analytical Biochemistry, 2011, pp. 1-13.
Alt et al., Determination of critical quality attributes for monoclonal antibodies using quality by design principles, Biologicals, vol. 44, 2016, pp. 291-305.
Andris-Widhopf et al., "Generation of antibody libraries: PCR amplification and assembly of light-and heavy-chain coding sequences," Phage Display: A Laboratory Manual, Chapter 9, 2001, pp. 9.1-9.113.
"Cleavage close to the end of DNA fragments (linearized vectors)," New England Biolabs Product Catalog and Technical Reference, Appendix 10, 2007-2008, p. 358.
"Protocol: Use of Glycerol Stocks and Preparation of Transfection-Quality Plasmid DNA," Broad Institute, 2015, pp. 1-5.
Azzazy et al., "Phage display technology: clinical applications and recent innovations," Clinical Biochemistry, vol. 35, 2002, 425-445.
Barbas et al., "Assembly of combinatorial antibody libraries on phage surfaces: The gene III site," Proc. Natl. Acad. Sci. USA, vol. 88, Sep. 1991, pp. 7978-7982.
Barnes, Wayne M., "PCR amplification of up to 35-kb DNA with high fidelity and high yield from λ bacteriophage templates," Proc. Natl. Acad. Sci. USA, vol. 91, Mar. 1994, pp. 2216-2220.
Better et al., "*Escherichia coli* Secretion of an Active Chimeric Antibody Fragment," Science, vol. 240, May 20, 1988, pp. 1041-1043.
Boder et al., "Yeast surface display for screening combinatorial polypeptide libraries," Nature Biotechnology, vol. 15, Jun. 1997, pp. 553-557.
Bonnycastle et al., "General Phage Methods," Phage Display: A Laboratory Manual, Chapter 15, 2001, pp. 15.1-15.30.
Bradbury, Andrew, "Coning Hybridoma cDNA by RACE," Antibody Engineering, vol. 1, Chapter 2, 2010, pp. 15-20.
Bruggemann et al., "Production of human antibody repertoires in transgenic mice," Current Opinion in Biotechnology, vol. 8, 1997, pp. 455-458.
Buckler et al., "Screening isolates from antibody phage-display libraries," Drug Discovery Today, vol. 13, Nos. 7/8, Apr. 2008, pp. 318-324.
Burton, Dennis, "Phage display," Immunotechnology, vol. 1, 1995, pp. 87-94.
Burton, Dennis R., "Overview: Amplication of Antibody Genes,": Phage Display: A Laboratory Manual, Chapter 7, 2001, pp. 7.1-7.4.
Canziani GA, Klakamp S, Myszka DG. (2004) Kinetic screening of antipodies from crude hybridoma samples using Biacore. *Anal Biochem* 325:301-307.
Carter P, Presta L, Gorman CM, Ridgway JB, Henner D, Wong WL, Rowland AM, Kotts C, Carver ME, Shepard HM. (1992) Humanization of an anti-p185$^{HER2}$ antibody for human cancer therapy. *P Natl Acad Sci USA* 89:4285-4289.
Casadevall A, Janda A. (2012) Immunoglobulin isotype influences affinity and specificity. *P Natl Acad Sci USA* 109:12272-12273. doi: 10.1073/pnas.1209750109.
Chames P, Van Regenmortel M, Weiss E, Baty D. (2009) Therapeutic antibodies: successes, limitations and hopes for the future. *Br J Pharmacol* 157:220-33. doi: 10.1111/j.1476-5381.2009.00190.x.
Chames, P and Baty, D. (2010) Phage display and selections on biotinylated antigens; *Chapter 11 in: Antibody Engineering*, vol. 1 (eds. Roland E Kontermann and Stefan Dubel); Springer-Verlag, Berlin Heidelberg; pp. 151-164.
Chen C, Snedecor B, Nishihara JC, Joly JC, McFarland N, Andersen DC, Battersby JE, Champion KM. (2004) High-level accumulation of a recombinant antibody fragment in the periplasm of *Escherichia coli* requires a triple-mutant (degP pre spr) host strain. *Biotechnol Bioeng* 85:463-474.
Chester KA, Hawkins RE. (1995) Clinical issues in antibody design. *Trends Biotechnol* 13:294-300. DOI: 10.1016/S0167-7799(00)88968-4.
Cho N, Hwang B, Yoon JK, Park S, Lee J, Seo HN, Lee J, Huh S, Chung J, Bang D. (2015) De novo assembly and next-generation sequencing to analyse full-length gene variants from codon-barcoded libraries. *Nat Commun* 6:8351. doi: 10.1038/ncomms9351.
Chowdhury PS. (2002) Targeting random mutations to hotspots in antibody variable domains for affinity improvement. Chapter 24 in: *Methods in Molecular Biology, vol. 178: Antibody Phage Display: Methods and Protocols* (eds. Philippa M. O'Brien and Robert Aitken); Humana Press Inc., Totowa, NJ; pp. 269-285.
De Boer M, Chang SY, Eichinger G, Wong HC. (1994) Design and analysis of PCR primers for the amplification and cloning of human immunoglobulin Fab fragments. *Hum Antibodies Hybridomas* 5:57-64.
De Bruin R, Spelt K, Mol J, Koes R, Quattrocchio F. (1999) Selection of high-affinity phage antibodies from phage display libraries. *Nat Biotechnol* 17:397-399.
De Haard HJ, van Neer N, Reurs A, Hufton SE, Roovers RC, Henderikx P, de Bruïne AP, Arends JW, Hoogenboom HR. (1999) A large non-immunized human Fab fragment phage library that permits rapid isolation and kinetic analysis of high affinity antibodies. *J Biol Chem* 274:18218-18230.
De Haard, HJW (2002) Construction of large naïve Fab libraries; *Chapter 5 in Methods in Molecular Biology, vol. 178: Antibody Phage Display: Methods and Protocols* (eds. Philippa M. O'Brien and Robert Aitken); Humana Press, Totowa, NJ; pp. 87-100.
Dechiara TM, Poueymirou WT, Auerbach W, Frendewey D, Yancopoulos GD, Valenzuela DM. (2009) VelociMouse: fully ES cell-derived F0-generation mice obtained from the injection of ES cells into eight-cell-stage embryos. *Methods Mol Biol* 530:311-324. doi: 10.1007/978-1-59745-471-1_16.
Diamante L, Gatti-Lafranconi P, Schaerli Y, Hollfelder F. (2013) In vitro affinity screening of protein and peptide binders by megavalent bead surface display. *Protein Eng Des Sei* 26:713-724.
Dobson CL, Minter RR, Hart-Shorrock CP. (2012) Naïve antibody libraries from natural repertoires. Chapter 17 in: *Phage Display in*

(56) References Cited

OTHER PUBLICATIONS

*Biotechnology and Drug Discovery* (eds. Sachdev S Sidhu and Clarence Ronald Geyer), 2$^{nd}$ Ed. CRC Press, Boca Raton, FL; pp. 455-493.

Drake AW, Papalia GA. (2012) Biophysical considerations for development of antibody-based therapeutics. Chapter 5 in: *Development of antibody-based therapeutics* (eds. Mohmmad A. Tabrizi, Gadi G. Bornstein and Scott L. Klakamp); Springer Science + Business Media, New York, NY; pp 95-139.

Eisenhardt SU, Peter K (2010) Phage display and subtractive selection on cells. Chapter 12 in: *Antibody Engineering*; vol. 1; (eds. Roland E Kontermann and Stefan Dübel); Springer-Verlag, Berlin-Heidelberg; pp. 165-181.

Ewert S, Honegger A, Plückthun A. (2004) Stability improvement of antibodies for extracellular and intracellular applications: CDR grafting to stable frameworks and structure-based framework engineering. *Methods* 34:184-100. DOI: 10.1016/j.ymeth.2004.04.007.

Foote J, Eisen HN. (1005) Kinetic and affinity limits on antibodies produced during immune responses. *P Natl Acad Sci USA* 92:1254-1256.

Frenzel A, Schirrmann T, Hust M. (2016) Phage display-derived human antibodies in clinical development and therapy. *mAbs* 8:1177-1194. DOI: 10.1080/19420862.2016.1212149.

Gelfand DH, White TJ. (1990) Thermostable DNA polymerases. Chapter 16 in: *PCR protocols: A guide to methods and applications*, (eds. Michael J. Innis, David H. Gelfand, John J. Sninsky, and Thomas J. White); Academic Press, Inc.; San Diego, CA; pp. 129-141.

Geyer CR, McCafferty J, Dubel S, Bradbury ARM, Sidhu SS. (2012) Recombinant antibodies and in vitro selection technologies. Chapter 2 in: *Antibody Methods and Protocols* (eds. Gabriele Proetzel and Hilmer Ebersbach); *Method Mol Biol* 901:11-32. DOI 10.1007/978-1-61779-931-0_2.

Glanville J, D'Angelo S, Khan TA, Reddy ST, Naranjo L, Ferrara F, Bradbury AR. (2015) Deep sequencing in library selection projects: what insight does it bring? *Curr Opin Struct Biol* 33:146-160. doi: 10.1016/j.sbi.2015.09.001.

Glennie MJ, Johnson PWM. (2000) Clinical trials of antibody therapy. *Immunol Today* 21:403-410.

Green LL. (1999) Antibody engineering via genetic engineering of the mouse: XenoMouse strains are a vehicle for the facile generation of therapeutic human monoclonal antibodies. *J Immunol Methods* 231:11-23.

Green MR, Sambrook J. (2012a) Concentrating and desalting nucleic acids with microconcentrators. Protocol 6 of Chapter 1 in: *Molecular Cloning: A Laboratory Manual*; vol. 1 (eds. Michael R Green and Joseph Sambrook); 4$^{th}$ Ed. Cold Spring Harbor Laboratory Press; Cold Spring Harbor, NY; pp. 28-29.

Green MR, Sambrook J. (2012b) PCR amplification of GC-Rich Templates. Protocol 4 of Chapter 7 in: *Molecular Cloning: A Laboratory Manual*; vol. 1 (eds. Michael R Green and Joseph Sambrook); 4$^{th}$ Ed. Cold Spring Harbor Laboratory Press; Cold Spring Harbor, NY; pp. 484-489.

Green MR, Sambrook J (2012c) Cloning in plasmid vectors: Blunt end cloning; *Protocol 6 of Chapters in Molecular Cloning: A Laboratory Manual*; 4$^{th}$ Ed.; vol. 1 (eds. Michael R Green and Joseph Sambrook); Cold Spring Harbor Laboratory Press; Cold Spring Harbor, NY; pp. 186-188.

Griffiths AD, Williams SC, Hartley O, Tomlinson IM, Waterhouse P, Crosby WL, Kontermann RE, Jones PT, Low NM, Allison TJ, Prospero TD, Hoogenboom HR, Nissim A, Cox JPL, Harrison JL, Zaccolo M, Gherardi E, Winter G. (1994) Isolation of high affinity human antibodies directly from large synthetic repertoires. *EMBO J* 13:3245-3260.

Hai S-H, McMurry JA, Knopf PM, Martin W, de Groot AS (2009) Immunogenicity screening using in silico methods: Correlation between T-Cell epitope Content and clinical immunogenicity of monoclonal antibodies. Chapter 22 in: *Therapeutic Monoclonal Antibodies: From Bench to Clinic* (ed. Zhiqiang An); John Wiley & Sons, Inc., Hoboken, NJ; pp. 417-437.

Hanes J, Pluckthun A. (1997) In vitro selection and evolution of functional proteins by using ribosome display. *P Natl Acad Sci USA* 94:4937-4942.

Harlow E, Lane D. (1988) Immunoassays. Chapter 14 in *Antibodies: A Laboratory Manual* (eds. Ed Harlow and David Lane); Cold Spring Harbor Laboratory Press; Cold Spring Harbor, NY; pp. 553-612.

Hawkins RE, Russell SJ, Winter G. (1992) Selection of phage antibodies by binding affinity: Mimicking affinity maturation. *J Mol Biol* 226:889-896.

Hay FC, Westwood OMR. (2002) Preparation of human B-cell hybridoma. Section 2.8.2. of Chapter 1 : Isolation and structure of immunoglobulins in: Practical Immunology; 4$^{th}$ Ed. (eds. Frank C. Hay and Olwyn M.R. Westwood); Blackwell Science Ltd; Oxford, UK; pp. 58-59.

Heckman KL, Pease LR. (2007) Gene splicing and mutagenesis by PCR-driven overlap extension. *Nat Protocols* 2:924-932.

Higuchi R, Krummell B, Saiki RK. (1988). A general method of in vitro preparation and specific mutagenesis of DNA fragments: study of protein and DNA interactions. *Nucl Acids Res* 16:7351-7367.

Hoet RM, Cohen EH, Kent RB, Rookey K, Schoonbroodt S, Hogan S, Rem L, Frans N, Daukandt M, Pieters H, van Hegelsom R, Neer NC, Nastri HG, Rondon IJ, Leeds JA, Hufton SE, Huang L, Kashin I, Devlin M, Kuang G, Steukers M, Viswanathan M, Nixon AE, Sexton DJ, Hoogenboom HR, Ladner RC. (2005) Generation of high-affinity human antibodies by combining donor-derived and synthetic complementarity-determining-region diversity.*Nat Biotechnol* 23:344-448. DOI: 10.1038/nbt1067.

Holliger P, Prospero T, Winter G. (1993) "Diabodies": Small bivalent and bispecific antibody fragments. *P Natl Acad Sci* 90:6444-6448.

Honegger A. (2008) Engineering antibodies for stability and efficient folding. *Handb Exp Pharmacol* vol. 181; pp. 47-68. DOI: 10.1007/978-3-540-73259-4_3.

Hoogenboom HR, Griffiths AD, Johnson KS, Chiswell DJ, Hudson P, Winter G. (1991) Multi-subunit proteins on the surface of filamentous phage: methodologies for displaying antibody (Fab) heavy and light chains. *Nucl Acids Res* 19:4133-4137.

Horlick RA, Macomber JL, Bowers PM, Neben TY, Tomlinson GL, Krapf IP, Dalton JL, Verdino P, King DJ. (2013) Simultaneous surface display and secretion of proteins from mammalian cells facilitate efficient in vitro selection and maturation of antibodies. *J Biol Chem* 288:19861-19869.

Horton RM, Hunt HD, Ho SN, Pullen JK, Pease LR. (1989) Engineering hybrid genes without the use of restriction enzymes: gene splicing by overlap extension. *Gene* 77:61-68.

Humphreys DP. (2003) Production of antibodies and antibody fragments in *Escherichia coli* and a comparison of their functions, uses and modification. *Curr Opin Drug Disc* 6:188-196.

Humphreys DP, Bowering L. (2009) Production of antibody Fab' fragments in *E. coli*. Chapter 27 in: *Therapeutic Monoclonal Antibodies: From Bench to Clinic* (ed. Zhiqiang An); John Wiley & Sons, Inc., Hoboken, NJ; pp. 589-622.

Hust M, Thie H, Schirrmann, Dübel S. (2009) Antibody phage display; Chapter 8 in: *Therapeutic Monoclonal Antibodies: From Bench to Clinic* (ed. Zhiqiang An); John Wiley & Sons, Inc., Hoboken, NJ; pp. 191-211.

Hust M, Mersmann M. (2010) Phage display and selection in microtitre plates. Chapter 10 in : *Antibody Engineering*; vol. 1, (eds. Roland E Kontermann and Stefan Dubel); Springer-Verlag, Berlin-Heidelberg; pp. 139-149.

Jones RH, Mollitoris BA (1984) A statistical method for determining the breakpoint of two lines; *Anal Biochem* 141:287-290.

Jones PT, Dear PH, Foote J, Neuberger M, Winter G. (1986) Replacing the complementarity-determining regions in a human antibody with those from a mouse. *Nature* 321:522-525.

Kepert JF, Cromwell M, Engler N, Finkler C, Gellermann G, Gennaro L, Harris R, Iverson R, Kelley B, Krummen L, McKnight N, Motchnik P, Schnaible V, Taticek R. (2016) Establishing a control system using QbD principles. *Biologicals* 44: 319-331.

Kirsch M, Zaman M, Meier D, Dubel S, Hust M. (2005) Parameters affecting the display of antibodies on phage. *J Immunol Methods* 301:173-185.

(56) References Cited

OTHER PUBLICATIONS

Knappik A, Ge L, Honegger A, Pack P, Fischer M, Wellnhofer G, Hoess A, Wölle J, Plückthun A, Virnekäs B. (2000) Fully synthetic human combinatorial antibody libraries (HuCAL) based on modular consensus frameworks and CDRs randomized with trinucleotides. *J Mol Biol* 296:57-86. DOI: 10.1006/jmbi. 1999.3444.

Köhler G, Milstein C. (1975) Continuous cultures of fused cells secreting antibody of predefined specificity. *Nature* 256:495-497.

Kontermann RE. (2010) Immunotube selections. Chapter 9 in : *Antibody Engineering*; vol. 1; (eds. Roland E Kontermann and Stefan Dübel); Springer-Verlag, Berlin-Heidelberg; pp. 127-137.

Kortt AA, Lah M, Oddie GW, Gruen CL, Burns JE, Pearce LA, Atwell JL, McCoy AJ, Howlett GJ, Metzger DW, Webster RG, Hudson PJ. (1997) Single-chain Fv fragments of anti-neuraminidase antibody NC10 containing five- and ten-residue linkers form dimers and with zero-residue linker a trimer. *Protein Eng* 10:423-433.

Küchenhoff H (1996) An exact algorithm for estimating breakpoints in segmented generalized linear models; *Sonderforschungsbereich* 386: Paper 27; 1-12.

Labrijn AF, Aalberse RC, Schuurman J. (2008) When binding is enough: nonactivating antibody formats. *Curr Opin Immunol* 20:479-485. doi: 10.1016/j.coi.2008.05.010.

Lawson ADG, Chaplin LC, Lang V, Sehdev M, Spitali M, Popplewell A, Weir N, King DJ. (1997) Two-site assays for measuring recombinant antibody quality. *BIA J* 1:23.

Lefranc M-P. (2001) IMGT, the international ImMunoGeneTics database. *Nucl Acids Res* 29:207-209.

Leonard P, Safsten P, Hearty S, McDonell B, Finlay W, O'Kennedy R. (2007) High throughput ranking of recombinant avian scFv antibody fragments from crude lysates using Biacore A100. *J Immunol Methods* 323:172-179.

Liu AY, Robinson RR, Murray ED Jr, Ledbetter JA, Hellström I, Hellström KE. (1987) Production of a mouse-human chimeric monoclonal antibody to CD20 with potent Fc-dependent biologic activity. *J Immunol* 139:3521-3526.

Lonberg N. (2008) Fully human antibodies from transgenic mouse and phage display platforms. *Curr Opin Immunol* 20:450-459. doi: 10.1016/j.coi.2008.06.004.

Løset GÅ, Løbersli I, Kavlie A, Stacy JE, Borgen T, Kausmally L, Hvattum E, Simonsen B, Hovda MB, Brekke OH. (2005) Construction, evaluation and refinement of a large human antibody phage library based on the IgD and IgM variable gene repertoire. *J Immunol Methods* 299:47-62. DOI: 10.1016/j.jim.2005.01.014.

Lou J, Marzan R, Verzillo V, Ferrero F, Pak D, Sheng M, Yang C, Sblattero D, Bradbury A. (2001) Antibodies in haystacks: how selection strategy influences the outcome of selection from molecular diversity libraries. *J Immunol Methods* 253:233-242.

Lowe D, Vaughan TJ (2009) Human antibody repertoire libraries; Chapter 7 in: *Therapeutic Monoclonal Antibodies: From Bench to Clinic* (ed. Zhiqiang An); John Wiley & Sons, Inc., Hoboken, NJ; pp. 169-188.

Marks JD, Tristem M, Karpas A, Winter G. (1991) Oligonucleotide primers for polymerase chain reaction amplification of human immunoglobulin variable genes and design of family-specific oligonucleotide probes. *Eur J Immunol* 21:985-991.

Martineau P. (2010) Synthetic antibody libraries. Chapter 6 in : *Antibody Engineering*; vol. 1, (eds. Roland E Kontermann and Stefan Dübel); Springer-Verlag, Berlin-Heidelberg; pp. 85-97.

McCafferty J. (1996) Phage display: Factors affecting panning efficiency. Chapter 15 in: *Phage Display of Peptides and Proteins: A Laboratory Manual*; (eds. Brian K. Kay, Jill Winter, John McCafferty); Academic Press Inc., San Diego, CA; pp. 261-276.

Meijer PJ, Andersen PS, Haahr Hansen M, Steinaa L, Jensen A, Lantto J, Oleksiewicz MB, Tengbjerg K, Poulsen TR, Coljee VW, Bregenholt S, Haurum JS, Nielsen LS. (2006) Isolation of human antibody repertoires with preservation of the natural heavy and light chain pairing. *J Mol Biol* 358:764-772. DOI: 10.1016/j.jmb. 2006. 02.040.

Ostermeier M, Benkovic SJ. (2000) A two-phagemid system for the creation of non-phage displayed antibody libraries approaching one trillion members. *J Immunol Methods* 237:175-186.

Pavoni E, Monteriù G, Cianfriglia M, Minenkova O. (2007) New display vector reduces biological bias forexpression of antibodies in *E. coli. Gene* 391:120-129. DOI: 10.1016/j.gene.2006.12.009.

Persic L, Roberts A, Wilton J, Cattaneo A, Bradbury A, Hoogenboom HR. (1997) An integrated vector system for the eukaryotic expression of antibodies or their fragments after selection from phage display libraries. *Gene* 187:9-18.

Petropoulos K. (2012) Phage display. Chapter 3 in: *Antibody Methods and Protocols* (eds. Gabriele Proetzel and Hilmer Ebersbach); *Methods Mol Biol* 901:33-51. doi: 10.1007/978-1-61779-931-0_3.

Plassmeyer ML, Reiter K, Shimp RL Jr, Kotova S, Smith PD, Hurt DE, House B, Zou X, Zhang Y, Hickman M, Uchime O, Herrera R, Nguyen V, Glen J, Lebowitz J, Jin AJ, Miller LH, MacDonald NJ, Wu Y, Narum DL. (2009) Structure of the *Plasmodium falciparum* circumsporozoite protein, a leading malaria vaccine candidate. *J Biol Chem* 284:26951-26963. doi: 10.1074/jbc.M109.013706.

Prassler J, Thiel S, Pracht C, Polzer A, Peters S, Bauer M, Nörenberg S, Stark Y, Kölln J, Popp A, Urlinger S, Enzelberger M. (2011) HuCAL PLATINUM, a synthetic Fab library optimized for sequence diversity and superior performance in mammalian expression systems. *J Mol Biol* 413:261-278. doi: 10.1016/j.jmb.2011.08. 012.

Quintero-Hernández V, Juárez-González VR, Ortíz-León M, Sánchez R, Possani LD, Becerril B. (2007) The change of the scFv into the Fab format improves the stability and in vivo toxin neutralization capacity of recombinant antibodies. *Mol Immunol* 44:1307-1315.

Rader C. (2012a) Selection of human Fab libraries by phage display. Chapter 5 in: *Antibody Methods and Protocols* (eds. Gabriele Proetzel and Hilmer Ebersbach); *Methods Mol Biol.* 901:81-99. doi: 10.1007/978-1-61779-931-0_5.

Rader C. (2012b) Generation of human Fab libraries for phage display. Chapter 4 in: *Antibody Methods and Protocols* (eds. Gabriele Proetzel and Hilmer Ebersbach); *Methods Mol Biol.* 901:53-79. doi: 10.1007/978-1-61779-931-0_5.

Ravn U, Didelot G, Venet S, Ng KT, Gueneau F, Rousseau F, Calloud S, Kosco-Vilbois M, Fischer N. (2013) Deep sequencing of phage display libraries to support antibody discovery. *Methods* 60:99-110. doi: 10.1016/j.ymeth.2013.03.001.

Roberts RW, Szostak JW. (1997) RNA-peptide fusions for the in vitro selection of peptides and proteins. *P Natl Acad Sci USA* 94:12297-12302.

Rothe C, Urlinger S, Löhning C, Prassler J, Stark Y, Jäger U, Hubner B, Bardroff M, Pradel I, Boss M, Bittlingmaier R, Bataa T, Frisch C, Brocks B, Honegger A, Urban M. (2008) The human combinatorial antibody library HuCAL GOLD combines diversification of all six CDRs according to the natural immune system with a novel display method for efficient selection of high-affinity antibodies. *J Mol Biol* 376:1182-1200. doi: 10.1016/j.jmb.2007.12.018.

Röthlisberger D, Honegger A, Plückthun A. (2005) Domain interactions in the Fab fragment: a comparative evaluation of the single-chain Fv and Fab format engineered with variable domains of different stability. *J Mol Biol* 347:773-789. DOI: 10.1016/j.jmb. 2005.01.053.

Sambrook J, Russell DW. (2001a) Preparation of cDNA libraries and gene identification. Chapter 11 in: *Molecular Cloning: A Laboratory Manual*; vol. 2 (eds. Joseph Sambrook and David W. Russell); $3^{rd}$ Ed. Cold Spring Harbor Laboratory Press; Cold Spring Harbor, NY; pp. 11.1-11.133.

Sambrook J, Russell DW. (2001b) The Hanahan method for preparation and transformation of competent *E. coli.* High efficiency transformation. Protocol 23 of Chapter 1 in: *Molecular Cloning: A Laboratory Manual*; vol. 1 (eds. Joseph Sambrook and David W. Russell); $3^{rd}$ Ed. Cold Spring Harbor Laboratory Press; Cold Spring Harbor, NY; pp. 1.105-1.111.

Sambrook J and Russell DW (2001c) Recovery of DNA from agarose gels: electroelution in dialysis bags; *Protocol 4 of Chapter 5 in Molecular Cloning: A Laboratory Manual*; vol. 1 (eds. Joseph Sambrook and David W. Russell); $3^{rd}$ Ed; Cold Spring Harbor Laboratory Press, Cold Spring Harbor, NY; pp. 5.23-5.25.

(56) References Cited

OTHER PUBLICATIONS

Sblattero D, Bradbury A. (1998) A definitive set of oligonucleotide primers for amplifying human V regions. *Immunotechnology* 3:271-278.

Schräml M, Biehl M. (2012) Kinetic screening in the antibody development process. Chapter 11 in: *Antibody Methods and Protocols* (eds. Gabriele Proetzel and Hilmer Ebersbach); *Method Mol Biol* 901:171-181. DOI 10.1007/978-1-61779-931-0_11.

Schräml M, von Proff L. (2012) Temperature-dependent antibody kinetics as a tool in antibody lead selection. Chapter 12 in: *Antibody Methods and Protocols* (eds. Gabriele Proetzel and Hilmer Ebersbach); *Method Mol Biol* 901:183-194. DOI 10.1007/978-1-61779-931-0_12.

Schwimmer LJ, Huang B, Giang H, Cotter RL, Chemla-Vogel DS, Dy FV, Tam EM, Zhang F, Toy P, Bohmann DJ, Watson SR, Beaber JW, Reddy N, Kuan HF, Bedinger DH, Rondon IJ. (2013) Discovery of diverse and functional antibodies from large human repertoire antibody libraries. *J Immunol Methods* 391:60-71. doi: 10.1016/j.jim.2013.02.010.

Scott JK, CF Barbas III. (2001). Phage-display vectors. Chapter 2 in: *Phage Display: A Laboratory Manual*; (eds. Carlos F. Barbas III, Dennis R. Burton, Jamie K. Scott and Gregg J. Silverman); Cold Spring Harbor Laboratory Press, Cold Spring Harbor, NY; pp. 2.1 to 2.19.

Skerra A, Plückthun A. (1991) Secretion and in vivo folding of the Fab fragment of the antibody McPC603 in *Escherichia coli*: influence of disulphides and cis-prolines. *Protein Eng* 4:971-979.

Smith GP. (1985) Filamentous fusion phage: Novel expression vectors that display cloned antigens on the virion surface. *Science* 228:1315-1317.

Steukers M, Schaus J-M, van Gool R, Hoyoux A, Richalet P, Sexton DJ, Nixon AE, Vanhove M. (2006) Rapid kinetic-based screening of Fab fragments. *J Immunol Methods* 310:126-135.

Sumida T, Doi N, Yanagawa H. (2009) Bicistronic DNA display for in vitro selection of Fab fragments. *Nucl Acids Res* 37(22):e147. doi:10.1093/nar/gkp776.

Tabrizi MA. (2012) Considerations in establishing affinity design goals for development of antibody-based therapeutics. Chapter 6 in: *Development of antibody-based therapeutics* (eds. Mohmmad A. Tabrizi, Gadi G. Bornstein and Scott L. Klakamp); Springer, New York, NY; pp. 141-151.

Thiagarajan G, Semple A, James JK, Cheung JK, Shameem M. (2016) A comparison of biophysical characterization techniques in predicting monoclonal antibody stability. *mAbs* 8:1088-1097. doi: 10.1080/19420862.2016.1189048.

Thie H, Schirrmann T, Paschke M, Dübel S, Hust M. (2008) SRP and Sec pathway leader peptides for antibody phage display and antibody fragment production in *E. coli*. *N Biotechnol*. 25:49-54. doi: 10.1016/j.nbt.2008.01.001.

Tiller T, Meffre E, Yurasov S, Tsuiji M, Nussenzweig MC, Wardemann H. (2008) Efficient generation of monoclonal antibodies from single human B cells by single cell RT-PCR and expression vector cloning. *J Immunol Methods* 329:112-124. DOI: 10.1016/j.jim.2007.09.017.

Tiller T, Schuster I, Deppe D, Siegers K, Strohner R, Herrmann T, Berenguer M, Poujol D, Stehle J, Stark Y, Heßling M, Daubert D, Felderer K, Kaden S, Kölln J, Enzelberger M, Urlinger S. (2013) A fully synthetic human Fab antibody library based on fixed VH/VL framework pairings with favorable biophysical properties. *mAbs* 5:445-470. doi: 10.4161/mabs.24218.

Tindall KR, Kunkel TA. (1988) Fidelity of DNA synthesis by the *Thermus aquaticus* DNA polymerase. *Biochemistry* 27:6008-6013.

Tomimatsu K, Matsumoto SE, Tanaka H, Yamashita M, Nakanishi H, Teruya K, Kazuno S, Kinjo T, Hamasaki T, Kusumoto K, Kabayama S, Katakura Y, Shirahata S. (2013) A rapid screening and production method using a novel mammalian cell display to isolate human monoclonal antibodies. *Biochem Biophys Res Commun* 441:59-64. doi: 10.1016/j.bbrc.2013.10.007.

Van Blarcom TJ, Harvey BR. (2009) Bacterial display of antibodies. Chapter 11 in: *Therapeutic Monoclonal Antibodies: From Bench to Clinic* (ed. Zhiqiang An); John Wiley & Sons, Inc., Hoboken, NJ; pp. 255-281.

Vaughan TJ, Williams AJ, Pritchard K, Osbourn JK, Pope AR, Earnshaw JC, McCafferty J, Hodits RA, Wilton J, Johnson KS. (1996) Human antibodies with sub-nanomolar affinities isolated from a large non-immunized phage display library. *Nat Biotechnol* 14:309-314.

Von Behring EA, Kitasato S. (1890) Ueberdas Zustandekommen der Diphtherie-Immunität und der Tetanus-Immunität bei Thieren. *Deutsch Med. Wochenschr* 49:1113-1114.

Warrens AN, Jones MD, Lechler RI. (1997) Splicing by overlap extension by PCR using asymmetric amplification: an improved technique for the generation of hybrid proteins of immunological interest. *Gene* 186:29-35.

Waterhouse P, Griffiths AD, Johnson KS, Winter G. (1993) Combinatorial infection and in vivo recombination: a strategy for making large phage antibody repertoires. *Nucl Acids Res* 21:2265-2266.

Weaver-Feldhaus JM, Lou J, Coleman JR, Siegel RW, Marks JD, Feldhaus MJ. (2004) Yeast mating for combinatorial Fab library generation and surface display. *FEBS Lett* 564:24-34.

Webster R. (2001). Filamentous phage biology. Chapter 1 in: *Phage Display: A Laboratory Manual*; (eds. Carlos F. Barbas III, Dennis R. Burton, Jamie K. Scott and Gregg J. Silverman); Cold Spring Harbor Laboratory Press, Cold Spring Harbor, NY; pp. 1.1-1.37.

Weidner KM, Denzin LK, Voss EW, Jr. (1992) Molecular stabilization effects of interactions between anti-metatype antibodies and liganded antibody. *J Biol Chem* 267:10281-10288.

Winter G, Griffiths AD, Hawkins RE, Hoogenboom HR. (1994) Making antibodies by phage display technology. *Annu Rev Immunol* 12:433-455.

International Searching Authority, "International Search Report," issued in connection with International Patent Application No. PCT/IN2017/050257, dated Jan. 19, 2018.

International Searching Authority, "Written Opinion," issued in connection with International Patent Application No. PCT/IN2017/050257, dated Jan. 19, 2018.

\* cited by examiner

Final Fab amplification primers:

| Name | Orientation | Sequence (5'->3') | Length |
|---|---|---|---|
| SEQ ID 32 | Forward | GAGGAGGAGGAGGAGGAGGCGG*GGCCCAGGCGGCCGAGCTC* | 41 |
| SEQ ID 34 | Reverse | GAGGAGGAGGAGGAGGAGAGAAGCGTAGTCCGGAACGTC | 39 |

```
SEQ ID 32    GAGGAGGAGGAGGAGGAG-----GCGGGCCCAGGCGGCCGAGCTC      41nt
SEQ ID 34    GAGGAGGAGGAGGAGGAGAGAAGCGTAGTCCGGAACGTC-----       39nt
             ******************   ***  * ** *    *  *
```

| Sensogram Langmuir 1:1 | Langmuir 1:1 | Clone sub-type | ka 1/Ms | kd 1/s | KD M | Rmax RU | Chi2 RU |
|---|---|---|---|---|---|---|---|
| bC3 | bC3 | λ | 1.79E+02 | 2.26E-15 | 1.26E-17 | 806.75 | 1.64 |
| bC52 | bC52 | λ | 2.90E+03 | 1.15E-05 | 3.97E-09 | 16.26 | 2.19 |
| bC61 | bC61 | λ | 1.47E+03 | 3.67E-19 | 2.49E-22 | 54.63 | 2.63 |
| bC71 | bC71 | λ | 1.41E+03 | 8.42E-14 | 5.96E-17 | 16.11 | 1.93 |
| bC72 | bC72 | λ | 5.81E+03 | 1.45E-18 | 2.49E-22 | 10.68 | 1.71 |

Figure 60

SEQUENCE LISTING

```
<160> NUMBER OF SEQ ID NOS: 330

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctgcccaac cagccatggc ccaggtgcag ctggtgcagt ctgg                           44

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctgcccaac cagccatggc ccagatcacc ttgaaggagt ctgg                           44

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctgcccaac cagccatggc cgaggtgcag ctggtgsagt ctgg                           44

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctgcccaac cagccatggc cgaggtgcag ctgktggagt ctg                            43

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 5
gctgcccaac cagccatggc ccaggtgcag ctgcaggagt cggg					44

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctgcccaac cagccatggc ccaggtgcag ctacagcagt gggg					44

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgatgggccc ttggtggagg ctgaggagac ggtgaccagg gttcc					45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgatgggccc ttggtggagg cwgrggagac ggtgaccagg gtbcc					45

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggcccaggc ggccgagctc cagatgaccc agtctcc					37

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggcccaggc ggccgagctc gtgatgacyc agtctcc					37

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggcccaggc ggccgagctc gtgwtgacrc agtctcc                                37

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggcccaggc ggccgagctc acactcacgc agtctcc                                37

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaagacagat ggtgcagcca cagt                                              24

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggcccaggc ggccgagctc gtgbtgacgc agccgccct                              39

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggcccaggc ggccgagctc gtgctgactc agccaccctc                             40

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gggcccaggc ggccgagctc gccctgactc agcctccctc cgt                         43

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gggcccaggc ggccgagctc gagctgactc agccaccctc agtgtc       46

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggcccaggc ggccgagctc gtgctgactc aatcgccctc             40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggcccaggc ggccgagctc atgctgactc agccccactc             40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gggcccaggc ggccgagctc gtggtgacyc aggagccmtc             40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gggcccaggc ggccgagctc gtgctgactc agccaccttc             40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gggcccaggc ggccgagctc gggcagactc agcagctctc             40

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
cgaggggca gccttgggct gacc                                         24
```

<210> SEQ ID NO 24
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
cgaattggcg gaaggccgtc aaggccacgt gtcttgtcca gagctcgcct ccaccaaggg   60
cccatcggtc tttccgctgg caccgagcag caaaagcacc agcggtggca cagcagcact  120
gggttgtctg gttaaagatt attttccgga accggttacc gttagctgga atagcggtgc  180
actgaccagc ggtgttcata cctttccggc agttctgcag agcagcggtc tgtatagcct  240
gagcagcgtt gttaccgttc cgagcagcag cctgggcacc cagacctata tttgtaatgt  300
taatcataaa ccgagcaata ccaaagtgga taaaaaagtt tagggcccag gcggccgacg  360
ttccggacta cgcttctggt acctggagca caagactggc ctcatgggcc ttccgctcac  420
tgc                                                                423
```

<210> SEQ ID NO 25
<211> LENGTH: 502
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
ggcgaattgg cggaaggccg tcaaggccta ggcgcgccat gagctccgaa ctgtggctgc   60
accatctgtc tttatctttc cgcctagtga tgaacagctg aaaagcggca ccgcaagcgt  120
tgtttgtctg ctgaataact tttatccgcg tgaagcaaaa gtgcagtgga agttgataa   180
tgcactgcag agcggtaata gccaagaaag cgttaccgaa caggatagca agatagcac   240
ctatagcctg agcagcaccc tgaccctgag caaagcagat tatgaaaagc ataaagtgta  300
tgcctgcgaa gtgacccatc agggtctgag cagtccggtt accaaaagct taatcgtgg   360
tgaatgctaa ttaattagga ggaatttaaa atgaaatacc tattgcctac ggcagccgct  420
ggattgttat tactcgctgc ccaaccagcc atggccggta cctcttaatt aactggcctc  480
atgggccttc cgctcactgc cc                                           502
```

<210> SEQ ID NO 26
<211> LENGTH: 499
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
cgaattggcg gaaggccgtc aaggccacgt gtcttgtcca gagctcggtc agcccaaggc   60
tgcccccagc gttaccctgt ttccgcctag cagcgaagaa ctgcaggcaa ataaagcaac  120
cctggtttgt ctgattagcg attttttatcc gggtgcagtt accgttgcat ggaaagcaga  180
tagcagtccg gttaaagccg gtgttgaaac caccaccccg agcaaacaga gcaataacaa  240
atatgcagca agcagctatc tgagcctgac accggaacag tggaaaagcc atcgtagcta  300
```
tagctgtcag gttacccatg aaggtagcac cgttgaaaaa accgttgcac cgaccgaatg        360
tagctaatta attaggagga atttaaaatg aaatacctat tgcctacggc agccgctgga        420
ttgttattac tcgctgccca accagccatg gccggtacct ggagcacaag actggcctca        480
tgggccttcc gctcactgc                                                     499

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcctccacca agggcccatc ggtc                                                24

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agaagcgtag tccggaacgt c                                                   21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggtcagccca aggctgcccc c                                                   21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggccatggct ggttgggcag c                                                   21

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgaactgtgg ctgcaccatc tgtc                                                24

<210> SEQ ID NO 32
<211> LENGTH: 41
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 32
gaggaggagg aggaggaggc ggggcccagg cggccgagct c                        41

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gctgcccaac cagccatggc c                                              21

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaggaggagg aggaggagag aagcgtagtc cggaacgtc                           39

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gggcccaggc ggccgagctc                                                20

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aatgggccca ggcggccgag ctc                                            23

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgatgaatgg gcccaggcgg ccgagctc                                       28

<210> SEQ ID NO 38
<211> LENGTH: 5000
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 38

| | | | | | | |
|---|---|---|---|---|---|---|
| agagcgccca | atacgcaaac | cgcctctccc | cgcgcgttgg | ccgattcatt | aatgcagctg | 60 |
| gcacgcacagg | tttcccgact | ggaaagcggg | cagtgagcgc | aacgcaatta | atgtgagtta | 120 |
| gctcactcat | taggcacccc | aggctttaca | ctttatgctt | ccggctcgta | tgttgtgtgg | 180 |
| aattgtgagc | ggataacaat | tgaattcagg | aggaatttaa | atgaaaaag | acagctatcg | 240 |
| cgattgcagt | ggcactggct | ggtttcgcta | ccgtggccca | agcggccgag | ctccattctc | 300 |
| gaagtaaggg | atctaattct | aagctaaata | attagaataa | gacaactata | cataataatg | 360 |
| gaaataataa | gcgaaataca | tataaataag | gaacaaataa | tagtaatcat | ggtcatagct | 420 |
| gttaacgtcc | tttacctaat | agtaattatc | aaattattta | tatattatat | atatatatta | 480 |
| tattatatta | tatacatata | tttatatata | tatatatata | tatatttact | taatcaatta | 540 |
| atcaatcatc | aatcaatcaa | tcattaatca | atcaactaat | gatggtgatg | gtgatcaatc | 600 |
| aatcattcgt | acgcctaggc | catctgtctt | cggttaccaa | tcatcatcat | acatatattt | 660 |
| atatatatta | tttatatatc | aatttatatc | aatttatatc | atattaacta | attaactaat | 720 |
| aattatttt | tttattttta | tataaatata | ttttttaata | tatatttata | tttatattta | 780 |
| tatttattat | taatatatta | ttatattata | tattatatcc | cccaatatca | aattaaccat | 840 |
| cttgctaacg | aaacgttcgt | tatataaacc | caagctaagg | actattgagg | tgattcctat | 900 |
| atccatattc | caagacatcg | aattaaccaa | attcatagta | aaacagtgtt | actcccaacg | 960 |
| gacaagctca | gtccagtctt | agctcttcct | ttaaattagt | aaccattcta | cacaataaac | 1020 |
| gatatattaa | cttctctaag | acacacccaa | gctaaggatg | ttaaaggcta | ttcctaatct | 1080 |
| agattaatta | ggaggaattt | aaaatgaaat | acctattgcc | tacggcagcc | gctggattgt | 1140 |
| tattactcgc | tgcccaacca | gccatggccc | tcgagatcca | taggaattaa | attaccattt | 1200 |
| tataatttga | tgcctaaatt | tatataacca | agttgaggct | atcctatatt | ttcttctctc | 1260 |
| tttctctttc | cccctttctt | ttcaatcaaa | tcaaatcaaa | tactatatat | attttcttct | 1320 |
| atatactatt | tatctctttc | tttttcctta | caatttaaat | tacacttatt | taaaacatcc | 1380 |
| taatagtccc | tattatccta | attgtttctt | atcttataat | agttatttc | ctttattttt | 1440 |
| atactattca | ttttcatata | attataatac | atatcgttca | aatatatatc | attatttact | 1500 |
| taatttatcg | ctagcgggcc | catatttata | tttactaata | cctataaatt | ctcatcattt | 1560 |
| acataaattta | tatctaaaac | ctatactacc | ttatcctaat | tataagaatt | ataattgtta | 1620 |
| tataaatcct | cattattcat | ataataatta | caataatcat | tataattacc | ctaatttaaa | 1680 |
| acatacaaat | ctaaattatt | caaagataca | taataaactt | tcatgtaatt | atggtaatat | 1740 |
| aaattaatat | ccttatatac | ctcctagttt | tttttttattt | cgtcgaataa | tacataatta | 1800 |
| tatatgtaat | acatcaagta | ataaatacaa | taatagttat | cataattata | tacatcatat | 1860 |
| gttattacat | ctaatacatt | gttatttatc | attttattat | agttatctta | atgtttcaca | 1920 |
| taataattat | cctaattact | atcctaatcc | tcattgtggt | aatcatggtc | actagtggcc | 1980 |
| cgagtggccc | gtaccctgtat | gacgttccgg | actacgctgg | cgcacaccat | caccatcacc | 2040 |
| attaggaggg | tggtggctct | gagggtggcg | gttctgaggg | tggcggctct | gagggaggcg | 2100 |
| gttccggtgg | tggctctggt | tccggtgatt | ttgattatga | aaagatggca | aacgctaata | 2160 |
| aggggggctat | gaccgaaaat | gccgatgaaa | acgcgctaca | gtctgacgct | aaaggcaaac | 2220 |
| ttgattctgt | cgctactgat | tacggtgctg | ctatcgatgg | tttcattggt | gacgtttccg | 2280 |

```
gccttgctaa tggtaatggt gctactggtg attttgctgg ctctaattcc caaatggctc    2340
aagtcggtga cggtgataat tcacctttaa tgaataattt ccgtcaatat ttaccttccc    2400
tccctcaatc ggttgaatgt cgccttttg tctttagcgc tggtaaacca tatgaatttt    2460
ctattgattg tgacaaaata aacttattcc gtggtgtctt tgcgtttctt ttatatgttg    2520
ccacctttat gtatgtattt tctacgtttg ctaacatact gcgtaataag gagtcttaag    2580
cgagctaatt aatttaagcg gccgcagatc tgggaaattg taagcgttaa tattttgtta    2640
aaattcgcgt taaattttg ttaaatcagc tcattttta accaataggc cgaaatcggc      2700
aaaatccctt ataaatcaaa agaatagacc gagatagggt tgagtgttgt tccagtttgg    2760
aacaagagtc cactattaaa gaacgtggac tccaacgtca aagggcgaaa aaccgtctat    2820
cagggcgatg gcccactacg tgaaccatca ccctaatcaa gttttttggg gtcgaggtgc    2880
cgtaaagcac taaatcggaa ccctaaaggg agccccgat ttagagcttg acggggaaag    2940
ccggcgaacg tggcgagaaa ggaagggaag aaagcgaaag gagcgggcgc tagggcgctg    3000
gcaagtgtag cggtcacgct gcgcgtaacc accacaccg ccgcgcttaa tgcgccgcta    3060
cagggcgcgt caggtggcac ttttcgggga aatgtgcgcg gaaccctat ttgtttattt      3120 ttctaaatac attcaaatat gtatccgctc atgagacaat aaccctgata aatgcttcaa    3180
taatattgaa aaaggaagag tatgagtatt caacatttcc gtgtcgccct tattcccttt     3240
tttgcggcat tttgccttcc tgtttttgct cacccagaaa cgctggtgaa agtaaaagat    3300
gctgaagatc agttgggtgc acgagtgggt tacatcgaac tggatctcaa cagcggtaag    3360
atccttgaga gttttcgccc cgaagaacgt tttccaatga tgagcacttt taaagttctg    3420
ctatgtggcg cggtattatc ccgtattgac gccgggcaag agcaactcgg tcgccgcata    3480
cactattctc agaatgactt ggttgagtac tcaccagtca cagaaaagca tcttacggat    3540
ggcatgacag taagagaatt atgcagtgct gccataacca tgagtgataa cactgcggcc    3600
aacttacttc tgacaacgat cggaggaccg aaggagctaa ccgcttttt gcacaacatg    3660 ggggatcatg taactcgcct tgatcgttgg gaaccggagc tgaatgaagc cataccaaac    3720
gacgagcgtg acaccacgat gcctgtagca atggcaacaa cgttgcgcaa actattaact    3780
ggcgaactac ttactctagc ttcccggcaa caattaatag actggatgga ggcggataaa    3840
gttgcaggac cacttctgcg ctcggccctt ccggctggct ggtttattgc tgataaatct    3900
ggagccggtg agcgtgggtc tcgcggtatc attgcagcac tggggccaga tggtaagccc    3960
tcccgtatcg tagttatcta cacgacgggg agtcaggcaa ctatggatga acgaaataga    4020
cagatcgctg agataggtgc ctcactgatt aagcattggt aactgtcaga ccaagtttac    4080
tcatatatac tttagattga tttaaaactt cattttaat ttaaaaggat ctaggtgaag    4140 atccttttg ataatctcat gaccaaaatc ccttaacgtg agttttcgtt ccactgagcg    4200 tcagacccg tagaaaagat caaaggatct tcttgagatc cttttttct gcgcgtaatc     4260 tgctgcttgc aaacaaaaaa accaccgcta ccagcggtgg tttgtttgcc ggatcaagag    4320
ctaccaactc tttttccgaa ggtaactggc ttcagcagag cgcagatacc aaatactgtc    4380
cttctagtgt agccgtagtt aggccaccac ttcaagaact ctgtagcacc gcctacatac    4440
ctcgctctgc taatcctgtt accagtggct gctgccagtg gcgataagtc gtgtcttacc    4500
gggttggact caagacgata gttaccggat aaggcgcagc ggtcgggctg aacggggggt    4560
tcgtgcacac agcccagctt ggagcgaacg acctacaccg aactgagata cctacagcgt    4620
```

```
gagctatgag aaagcgccac gcttcccgaa gggagaaagg cggacaggta tccggtaagc    4680
ggcagggtcg gaacaggaga gcgcacgagg gagcttccag ggggaaacgc ctggtatctt    4740
tatagtcctg tcgggtttcg ccacctctga cttgagcgtc gattttgtgt atgctcgtca    4800 gggggggcgga gcctatggaa aaacgccagc aacgcggcct ttttacggtt cctggccttt    4860
tgctggcctt ttgctcacat gttctttcct gcgttatccc ctgattctgt ggataaccgt    4920
attaccgcct ttgagtgagc tgataccgct cgccgcagcc gaacgaccga gcgcagcgag    4980
tcagtgagcg aggaagcgga                                                 5000

<210> SEQ ID NO 39
<211> LENGTH: 361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gcctccacca agggcccatc ggtctttccg ctggcaccga gcagcaaaag caccagcggt      60
ggcacagcag cactgggttg tctggttaaa gattattttc cggaaccggt tacggttagc     120
tggaatagcg gtgcactgac cagcggtgtt catacctttc cggcagttct gcagagcagc     180
ggtctgtata gcctgagcag cgttgttacc gttccgagca gcctgggc acccagacc       240 tatatttgta atgttaatca taaaccgagc aataccaaag tggataaaaa agttgaaccg     300
aaatcgtgtg ataaaaccca tactagtggc ccgagtggcc gacgttccgg actacgcttc     360
t                                                                    361

<210> SEQ ID NO 40
<211> LENGTH: 416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
cgaactgtgg ctgcaccatc tgtcttcatc tttccgccta gtgatgaaca gctgaaaagc      60
ggcaccgcaa gcgttgtttg tctgctgaat aacttttatc cgcgtgaagc aaaagtgcag     120
tggaaagttg ataatgcact gcagagcggt aatagccaag aaagcgttac cgaacaggat     180
agcaaagata gcacctatag cctgagcagc acctgaccc tgagcaaagc agattatgaa     240
aagcataaag tgtatgcctg cgaagtgacc catcagggtc tgagcagtcc ggttaccaaa     300
agctttaatc gtggtgaatg ctaatctaga ttaattagga ggaatttaaa atgaaatacc     360
tattgcctac ggcagccgct ggattgttat tactcgctgc caaccagcc atggcc          416

<210> SEQ ID NO 41
<211> LENGTH: 413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ggtcagccca aggctgcccc ctcggttacc ctgtttccgc ctagcagcga agaactgcag      60
gcaaataaag caaccctggt tgtctgatt agcgattttt atccgggtgc agttaccgtt     120
```

```
gcatggaaag cagatagcag tccggttaaa gccggtgttg aaaccaccac cccgagcaaa    180
cagagcaata acaaatatgc agcaagcagc tatctgagcc tgacaccgga acagtggaaa    240
agccatcgta gctatagctg tcaggttacg catgaaggta gcaccgttga aaaaaccgtt    300
gcaccgaccg aatgtagcta atctagatta attaggagga atttaaaatg aaataccta t    360 tgcctacggc agccgctgga ttgttattac tcgctgccca accagccatg gcc          413
```

```
<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gggcccaagc ggccgagctc cagatgaccc agtctcc                              37
```

```
<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gggcccaagc ggccgagctc gtgatgacyc agtctcc                              37
```

```
<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gggcccaagc ggccgagctc gtgwtgacrc agtctcc                              37
```

```
<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gggcccaagc ggccgagctc acactcacgc agtctcc                              37
```

```
<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gggcccaagc ggccgagctc gtgbtgacgc agccgccct                            39
```

```
<210> SEQ ID NO 47
<211> LENGTH: 40
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 47
gggcccaagc ggccgagctc gtgctgactc agccaccctc                          40

<210> SEQ ID NO 48
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gggcccaagc ggccgagctc gccctgactc agcctccctc cgt                      43

<210> SEQ ID NO 49
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gggcccaagc ggccgagctc gagctgactc agccaccctc agtgtc                   46

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gggcccaagc ggccgagctc gtgctgactc aatcgccctc                          40

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gggcccaagc ggccgagctc atgctgactc agccccactc                          40

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gggcccaagc ggccgagctc gtggtgacyc aggagccmtc                          40

<210> SEQ ID NO 53
<211> LENGTH: 40
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 53
gggcccaagc ggccgagctc gtgctgactc agccaccttc                                40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gggcccaagc ggccgagctc gggcagactc agcagctctc                                40

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aatgggccca agcggccgag ctc                                                  23

<210> SEQ ID NO 56
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggcccaggcg gcc                                                             13

<210> SEQ ID NO 57
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggccaggccg gcc                                                             13

<210> SEQ ID NO 58
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggcccaggcg acc                                                             13

<210> SEQ ID NO 59
<211> LENGTH: 110
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 59

Glu Leu Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Glu Arg Asp
            20                  25                  30

Thr Val Ile Trp Tyr Gln Lys Val Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Arg Ser Gly Ala Ser Ala Ser Leu Ala Ile Ser Gly Leu Gln
65                  70                  75                  80

Ser Asp Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 60

Glu Leu Val Leu Thr Gln Pro Pro Ser Val Ser Gly Thr Pro Gly Gln
1               5                   10                  15

Lys Val Thr Ile Ser Cys Ser Gly Ser Ser Ser Asn Ile Glu Ser Asn
            20                  25                  30

Asn Val Asn Trp Tyr His Gln Leu Pro Gly Arg Ala Pro Lys Leu Leu
        35                  40                  45

Leu Tyr Ile Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110

<210> SEQ ID NO 61
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 61

Glu Leu Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Glu Asn Asn Lys Arg Pro Ser Gly Ile Pro Asp Arg Phe Ser

```
                50                  55                  60
Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Phe Gly Phe Gly Gly Thr Lys Leu Thr Val Leu
                100                 105                 110

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Leu Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Ala Tyr
                20                  25                  30

Asn Tyr Val Ser Trp Tyr Gln Gln His Pro Gly Lys Ala Pro Lys Leu
             35                  40                  45

Met Ile Tyr Asp Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Glu Val Phe Gly Gly Gly Thr Lys Leu Thr Val Leu
                100                 105                 110

<210> SEQ ID NO 63
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Leu Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
             35                  40                  45

Met Ile Tyr Glu Val Ser Lys Arg Pro Ser Gly Val Pro Asp Arg Phe
         50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Leu Lys Val Phe Gly Gly Gly Thr Lys Leu Thr Val Leu
                100                 105                 110

<210> SEQ ID NO 64
<211> LENGTH: 109
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 64

Glu Leu Val Leu Thr Gln Pro Pro Ser Ala Ser Gly Thr Pro Gly Gln
1               5                   10                  15

Arg Val Thr Ile Ser Ser Ser Gly Ser Ser Asn Ile Gly Asn Asn
            20                  25                  30

Tyr Val Phe Trp Tyr Gln Gln Pro Pro Gly Thr Ala Pro Lys Leu Ile
        35                  40                  45

Ile Tyr Glu Val Thr Asn Arg Pro Ser Gly Val Pro Asp Arg Phe Ser
50                  55                  60

Gly Ser Lys Ser Gly Asn Thr Ala Ser Leu Thr Ile Thr Gly Leu Gln
65                  70                  75                  80

Ala Glu Asp Glu Ala Asn Tyr Tyr Cys Val Ser Gln Ser Thr Thr Thr
                85                  90                  95

Thr Trp Val Phe Gly Gly Gly Thr Lys Val Thr Val Leu
            100                 105

<210> SEQ ID NO 65
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Leu Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Ala Tyr Val Val Phe Gly Gly Gly Thr
            100                 105                 110

Lys Leu Thr Val Leu
        115

<210> SEQ ID NO 66
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
            35                  40                  45

Leu Ile Tyr Asp Thr Ser Asn Lys His Ser Trp Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Gly Asp Glu Ala Glu Tyr Tyr Cys Leu Leu Ser Tyr Ser Gly
                 85                  90                  95

Ala Gly Val Phe Gly Gly Gly Thr Lys Leu Thr Val Leu
            100                 105

<210> SEQ ID NO 67
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Leu Met Leu Thr Gln Pro His Ser Val Ser Glu Ser Pro Gly Lys
 1               5                  10                  15

Thr Val Thr Ile Ser Cys Thr Arg Ser Ser Gly Asn Ile Ala Gly Asp
                20                  25                  30

Tyr Val Gln Trp Phe Gln Arg Pro Gly Ser Val Pro Thr Thr Val
            35                  40                  45

Ile Tyr Glu Asp Asp Arg Arg Pro Ser Gly Val Pro Asp Arg Phe Ser
 50                  55                  60

Gly Ser Ile Asp Ser Ser Asn Ser Ala Thr Leu Thr Ile Ser Gly
 65                  70                  75                  80

Leu Thr Thr Glu Asp Glu Ala Asp Tyr Tyr Cys Gln Ser Tyr Gln Thr
                 85                  90                  95

Asn Ser Phe Trp Val Phe Gly Gly Gly Thr Lys Leu Thr Val Leu
            100                 105                 110

<210> SEQ ID NO 68
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Leu Val Val Thr Gln Glu Pro Ser Phe Ser Val Ser Pro Gly Gly
 1               5                  10                  15

Thr Val Thr Leu Thr Cys Gly Leu Arg Tyr Gly Ser Val Ser Thr Ala
                20                  25                  30

Asp Tyr Pro Ser Trp Tyr Gln Arg Thr Pro Gly Gln Ala Pro Arg Met
            35                  40                  45

Leu Ile Tyr Thr Thr Asn Thr Arg Ser Ser Gly Val Pro Asp Arg Phe
 50                  55                  60

Ser Gly Ser Ile Ile Gly Asn Lys Ala Ala Leu Thr Ile Thr Gly Ala
 65                  70                  75                  80

Gln Pro Asp Asp Glu Ser Asp Tyr Tyr Cys Leu Leu Tyr Met Gly Ser
                 85                  90                  95

Gly Ile Ser Val Phe Gly Gly Gly Thr Lys Leu Thr Val Leu
            100                 105                 110

<210> SEQ ID NO 69
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Leu Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Gly Trp Val Phe Gly Gly Gly Thr Lys Leu Thr Val Leu
            100                 105                 110

<210> SEQ ID NO 70
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Leu Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Asp
            20                  25                  30

Tyr His Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ile Ser
                85                  90                  95

Leu Asn Gly Trp Val Phe Gly Gly Gly Thr Lys Leu Thr Val Leu
            100                 105                 110

<210> SEQ ID NO 71
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Leu Thr Leu Thr Gln Ser Pro Ser Ala Ser Gly Ser Pro Gly Gln
1               5                   10                  15

```
Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Thr Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Asn Ser Tyr Ala Gly Ser
                85                  90                  95

Asn Asn Cys Val Phe Gly Gly Gly Thr Lys Leu Thr Val Leu
            100                 105                 110
```

<210> SEQ ID NO 72
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Glu Leu Val Leu Thr Gln Pro Pro Ser Val Ser Ala Ala Pro Gly Gln
1               5                   10                  15

Arg Val Thr Ile Ser Cys Ser Gly Ser Ser Ser Asn Ile Gly Glu Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Val Thr Gly Leu Gln
65                  70                  75                  80

Thr Gly Asp Glu Ala Asp Tyr Tyr Cys Gly Thr Trp Asp Ser Ser Leu
                85                  90                  95

Thr Ala Val Val Phe Gly Gly Gly Thr Lys Leu Thr Val Leu
            100                 105                 110
```

<210> SEQ ID NO 73
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Glu Leu Val Leu Thr Gln Pro Pro Ser Ala Ser Gly Ser Pro Gly Gln
1               5                   10                  15

Ser Val Thr Ile Ser Cys Thr Gly Thr Ser Arg Asp Ile Gly Arg Tyr
            20                  25                  30

Asn Tyr Val Ser Trp Tyr Gln Gln His Pro Gly Lys Ala Pro Lys Val
        35                  40                  45

Met Ile Tyr Glu Val Ser Lys Arg Pro Ser Gly Val Pro Asp Arg Phe
50                  55                  60

Thr Gly Ser Lys Ser Gly Asn Thr Ala Ser Leu Thr Val Ser Gly Leu
65                  70                  75                  80

Gln Val Glu Asp Glu Ala Asp Tyr Tyr Cys Gly Ser Tyr Gly Gly Asn
                85                  90                  95
```

-continued

Asp Asn Pro Val Val Leu Gly Gly Thr Lys Val Thr Val Leu
            100                 105                 110

<210> SEQ ID NO 74
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Leu Thr Leu Thr Gln Ser Ser Ala Ser Gly Ser Pro Gly Gln
1               5                   10                  15

Ser Val Ala Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Asn
                85                  90                  95

Leu Ser Gly Trp Val Phe Gly Gly Gly Thr Lys Leu Thr Val Leu
            100                 105                 110

<210> SEQ ID NO 75
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Leu Ala Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Ser Tyr
            20                  25                  30

Lys Tyr Val Ser Trp Tyr Gln Gln His Pro Gly Lys Val Pro Lys Ile
        35                  40                  45

Met Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

<210> SEQ ID NO 76
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Leu Val Val Thr Gln Glu Pro Ser Leu Thr Val Ser Pro Gly Gly
1               5                   10                  15

Thr Val Thr Leu Thr Cys Gly Ser Ser Ser Gly Ala Val Thr Ser Gly
            20                  25                  30

His Tyr Pro Tyr Trp Val Gln Gln Lys Pro Gly Gln Ala Pro Arg Ala

```
                35                  40                  45
Leu Ile Tyr Asp Val Thr Lys Lys Tyr Ser Trp Thr Pro Ala Arg Phe
         50                  55                  60
Ser Gly Ser Leu Leu Gly Gly Lys Ala Ala Leu Thr Leu Ser Gly Ala
 65                  70                  75                  80
Gln Pro Glu Asp Glu Ala Glu Tyr Phe Cys Phe Leu Ser Tyr Ser Asp
                 85                  90                  95
Gly Arg Val Phe Gly Gly Gly Thr Lys Leu Thr Val Leu
             100                 105
```

<210> SEQ ID NO 77
<211> LENGTH: 105
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 77

```
Ser Ser His Phe Thr Gln Ser Pro Ser Val Ser Val Ser Pro Gly Gln
 1               5                  10                  15
Thr Ala Ser Ile Thr Cys Ser Gly Asp Lys Leu Gly Asp Lys Tyr Ala
             20                  25                  30
Cys Trp Tyr Gln Gln Lys Pro Gly Gln Ser Pro Val Leu Val Ile Tyr
         35                  40                  45
Gln Asp Ser Lys Arg Pro Ser Gly Ile Pro Glu Arg Phe Ser Gly Ser
     50                  55                  60
Asn Ser Gly Asn Thr Ala Thr Leu Thr Ile Ser Gly Thr Gln Ala Met
 65                  70                  75                  80
Asp Glu Ala Asp Tyr Tyr Cys Gln Ala Trp Asp Ser Ser Val Val Phe
                 85                  90                  95
Gly Gly Gly Thr Lys Leu Thr Val Leu
             100                 105
```

<210> SEQ ID NO 78
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 78

```
Glu Leu Val Val Thr Gln Glu Pro Ser Val Ser Ala Ala Pro Gly Gln
 1               5                  10                  15
Lys Val Thr Ile Ser Cys Ser Gly Ser Ser Ser Asn Ile Gly Ala Gly
             20                  25                  30
Tyr Asp Val His Trp Tyr Gln Gln Leu Pro Gly Thr Ala Pro Lys Leu
         35                  40                  45
Leu Ile Tyr Gly Asn Ser Asn Arg Pro Ser Gly Val Pro Asp Arg Phe
     50                  55                  60
Ser Gly Ser Lys Ser Gly Thr Ser Ala Ser Leu Ala Ile Thr Gly Leu
 65                  70                  75                  80
Gln Ala Glu Asp Glu Ala Asp Tyr Tyr Cys Gln Ser Tyr Asp Ser Ser
                 85                  90                  95
Leu Ser Gly Val Val Phe Gly Gly Gly Thr Lys Leu Thr Val Leu
             100                 105                 110
```

```
<210> SEQ ID NO 79
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Leu Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ala Phe Gly Gln Gly Thr Lys Leu Glu Ile Lys
            100                 105                 110

<210> SEQ ID NO 80
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Leu Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105

<210> SEQ ID NO 81
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30
```

```
Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Pro
                 85                  90                  95

Ile Thr Phe Gly Pro Gly Thr Lys Val Asp Ile Lys
            100                 105
```

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Glu Leu Val Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asn Tyr
                 20                  25                  30

Leu Asn Trp Tyr Gln Gln Lys Pro Gly Gln Ala Pro Arg Leu Leu Ile
            35                  40                  45

Tyr Gly Ala Ser Ser Arg Ala Thr Gly Ile Ala Asp Arg Phe Ser Gly
 50                  55                  60

Ser Gly Ser Gly Thr Asp Phe Thr Leu Ser Ile Ser Arg Leu Glu Pro
 65                  70                  75                  80

Glu Asp Phe Val Met Tyr Tyr Cys Gln Gln Tyr Asp Ser Ser Thr Pro
                 85                  90                  95

Thr Phe Gly Gln Gly Thr Lys Val Glu Ile Lys
            100                 105
```

<210> SEQ ID NO 83
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Glu Leu Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Pro Pro Lys Leu Leu Ile
            35                  40                  45

Tyr Trp Thr Ser Thr Arg Glu Ser Gly Val Pro Asp Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln Tyr Tyr Ser Ile Pro Leu
                 85                  90                  95

Thr Phe Gly Gln Gly Thr Lys Val Glu Ile Lys
            100                 105
```

<210> SEQ ID NO 84
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Ala
65                  70                  75                  80

Asp Asp Ser Ala Thr Tyr Tyr Cys Gln Gln Tyr Asn Thr Tyr Ser Thr
                85                  90                  95

Phe Gly Gln Gly Thr Lys Val Glu Ile Lys
            100                 105

<210> SEQ ID NO 85
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Leu Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Arg Thr Phe Gly Gln Gly Thr Lys Val Glu Ile Lys
            100                 105                 110

<210> SEQ ID NO 86
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Leu Val Leu Thr Gln Ser Pro Val Thr Leu Ser Val Ser Pro Gly
1               5                   10                  15

Glu Arg Ala Ser Leu Ser Cys Arg Ala Ser Gln Ser Val Gly Ser Arg
            20                  25                  30

Leu Ala Trp Tyr Glu His Lys Pro Gly Gln Ala Pro Arg Leu Leu Ile
        35                  40                  45

Tyr Asp Thr Ser Thr Arg Ala Thr Gly Ile Ser Ala Arg Phe Ser Gly
    50                  55                  60

Ser Gly Ser Gly Thr Asp Phe Thr Leu Thr Ile Asn Ser Leu Gln Ser
65                  70                  75                  80

Glu Asp Phe Ala Val Tyr Tyr Cys Gln His Arg Asp Asn Trp Pro Pro
                85                  90                  95

Ala Leu Thr Phe Gly Gly Gly Thr Lys Val Glu Ser Lys
            100                 105

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Leu Val Met Thr Gln Ser Pro Ala Thr Leu Ser Leu Ser Pro Gly
1               5                   10                  15

Glu Arg Val Thr Leu Ser Cys Arg Ala Ser Gln Ser Val Ser Gly Tyr
            20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Asp Arg Leu Glu Pro
65                  70                  75                  80

Glu Asp Phe Gly Val Tyr Phe Cys Gln Gln Tyr Glu Arg Ser Thr Leu
                85                  90                  95

Thr Phe Gly Gln Gly Thr Lys Leu Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

```
Thr Phe Gly Pro Gly Thr Lys Val Asp Ile Lys
            100                 105
```

<210> SEQ ID NO 89
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Glu Leu Val Met Thr Gln Ser Pro Asp Ser Leu Ala Val Ser Leu Gly
1               5                   10                  15

Glu Arg Ala Thr Ile Asn Cys Lys Ser Arg Gln Ser Val Leu Tyr Ser
            20                  25                  30

Ser Asn Asn Lys Asn Gly Ser Ser Arg Arg Ala Pro Thr Arg Glu Ser
            35                  40                  45

Gly Asp Arg Phe Ser Gly Ser Gly Ser Gly Thr Asp Phe Ser Leu Thr
        50                  55                  60

Ile Ser Ser Leu Gln Val Glu Gly Leu Leu Leu Ser Thr Lys Leu
65                  70                  75
```

<210> SEQ ID NO 90
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Ala Ala Glu Leu Val Met Thr Gln Ser Pro Asp Ser Leu Ala Val Ser
1               5                   10                  15

Leu Gly Glu Arg Ala Thr Ile Asn Cys Lys Ser Ser Gln Ser Ile Leu
            20                  25                  30

Tyr Ala Ser Asn Tyr Tyr Leu Ala Trp Tyr Gln Gln Lys Pro Gly Gln
            35                  40                  45

Pro Pro Lys Leu Leu Ile Tyr Trp Ala Tyr Thr Arg Ala Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Glu Lys Leu Pro Ser Thr Phe Gly Gln Gly Thr Arg Leu Glu Ile
            100                 105                 110

Lys
```

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Glu Leu Gln Met Thr Gln Ser Pro Ser Ser Leu Ser Ala Ser Val Gly
1               5                   10                  15

Asp Arg Val Thr Ile Thr Cys Arg Ala Ser Leu Asn Leu Gly Ser Tyr
            20                  25                  30
```

Leu Asn Trp Tyr Gln Gln Lys Pro Gly Lys Ala Pro Ser Leu Leu Ile
            35                  40                  45

Tyr Ala Ala Ser Ser Leu Pro Ile Gly Val Pro Ser Arg Phe Arg Gly
        50                  55                  60

Gly Gly Ser Gly Thr Asp Phe Thr Leu Thr Ile Ile Gly Leu Leu Pro
65                  70                  75                  80

Glu Asp Leu Ala Thr Tyr Tyr Cys Gln Gln Ser Tyr Ser Pro Pro Gln
                85                  90                  95

Ser Phe Gly Gln Gly Thr Lys Leu Glu Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Leu Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Val Phe Ile Ile
            35                  40                  45

Gln Glu Ala Thr Asn Leu Val Pro Gly Ile Ser Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Phe Gly Gln Gly Thr Arg Leu Glu Ile Lys
            100                 105

<210> SEQ ID NO 93
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Leu Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Arg Thr
                85                  90                  95

Phe Gly Gln Gly Thr Lys Val Glu Ile Lys
            100                 105

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Leu Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Thr Pro Trp
                85                  90                  95

Thr Phe Gly Gln Gly Thr Lys Val Glu Val Lys
            100                 105

<210> SEQ ID NO 95
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Leu Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Trp Thr Phe Gly Gln Gly Thr Lys Val Glu Ile Lys
            100                 105

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Leu Thr Leu Thr Gln Ser Pro Gly Thr Leu Ser Leu Ser Pro Gly
1               5                   10                  15

Glu Gly Ala Thr Leu Ser Cys Arg Ala Ser Gln Ser Val Ser Gly Lys
                20                  25                  30

Phe Leu Thr Trp Tyr Gln Gln Lys Ser Gly Gln Ala Pro Arg Leu Leu
            35                  40                  45

Ile Tyr Gly Thr Ser Thr Arg Ala Pro Gly Ile Pro Asp Arg Phe Ile
        50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
                100                 105

<210> SEQ ID NO 97
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
                20                  25                  30

Tyr Trp Ser Trp Ile Arg Gln Pro Pro Gly Lys Gly Leu Glu Trp Ile
            35                  40                  45

Gly Asn Ile Tyr Tyr Ile Gly Asn Thr Asn Tyr Asn Pro Ser Leu Lys
        50                  55                  60

Ser Arg Val Thr Ile Ser Leu Asp Thr Ser Lys Asn Gln Phe Ser Leu
65                  70                  75                  80

Lys Val Thr Ser Val Thr Ala Ala Asp Thr Ala Met Tyr Tyr Cys Ala
                85                  90                  95

Ser Asp Ala Ala Gly Leu Gly Tyr Trp Gly Gln Gly Thr Leu Val Thr
                100                 105                 110

Val Ser Pro
        115

<210> SEQ ID NO 98
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Val Gln Ser Gly Ala Glu Val Lys Lys Pro Gly Ala
1               5                   10                  15

Ser Val Met Val Ser Cys Lys Ala Ser Gly Tyr Thr Phe Thr Arg Tyr
                20                  25                  30

Gly Ile Thr Trp Val Arg Gln Ala Pro Gly Gln Gly Pro Gln Tyr Met
            35                  40                  45

Gly Trp Thr Asn Thr Asp Ser Gly Arg Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Tyr Asn Gly Ser Tyr Ser Pro Phe Asp Tyr Trp
            100                 105                 110

Gly Gln Gly Thr Leu Val Thr Val Ser Pro
        115                 120

<210> SEQ ID NO 99
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Gln Glu Ser Gly Pro Gly Leu Val Lys Pro Ser Gln
1               5                   10                  15

Thr Leu Ser Leu Thr Cys Ser Val Ser Gly Gly Ser Ile Ser Gly Ser
            20                  25                  30

Ser Tyr Tyr Trp Gly Trp Ile Arg Gln Pro Pro Gly Lys Gly Leu Glu
        35                  40                  45

Trp Val Gly Ser Ile Tyr Tyr Arg Gly Ser Thr Tyr Tyr Asn Pro Ser
    50                  55                  60

Leu Thr Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Met Tyr Tyr
                85                  90                  95

Cys Ala Arg His Gly Tyr Ser Tyr Asp Ser Ser Gly Ser Ser Pro Leu
            100                 105                 110

Asp Ser Trp Gly Pro Gly Thr Leu Val Thr Val Ser Ser
        115                 120                 125

<210> SEQ ID NO 100
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Ala Trp Ile Arg Gln Pro Pro Gly Lys Ala Leu Glu
        35                  40                  45

Trp Leu Ala Leu Val Tyr Trp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Gly Thr Tyr Tyr
                85                  90                  95

Cys Ala His Arg Ser Pro Val Val Thr Gly Thr Ala Pro His Lys Trp
            100                 105                 110

Phe Asp Pro Trp Gly Gln Gly Ala Leu Val Thr Val Ser Pro
        115                 120                 125

<210> SEQ ID NO 101
<211> LENGTH: 124
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 101

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Arg Gly Arg Ile Ala Ala Arg Leu Arg Ala Thr Arg Phe Asp
            100                 105                 110

Tyr Trp Gly Gln Gly Thr Leu Val Thr Val Ser Ser
        115                 120

<210> SEQ ID NO 102
<211> LENGTH: 123
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 102

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Val Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Pro Gly Ser Gly Ser Phe Leu Val Tyr Gly Met Asp Val
            100                 105                 110

Trp Gly Gln Gly Thr Leu Val Thr Val Ser Pro
        115                 120

<210> SEQ ID NO 103
<211> LENGTH: 127
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 103

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Gly Tyr Ser Tyr Gly Leu Gly Leu Leu Arg Trp Thr Val
            100                 105                 110

Arg Phe Asp Tyr Trp Gly Gln Gly Thr Leu Val Thr Val Ser Ser
        115                 120                 125

<210> SEQ ID NO 104
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Gln Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Gly Ile Asn Ser Gly Pro Phe Asp Tyr Trp Gly Gln
            100                 105                 110

Gly Thr Leu Val Thr Val Ser Ser
        115                 120

<210> SEQ ID NO 105
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Ile Thr Leu Lys Glu Ser Gly Pro Val Leu Val Lys Ala Thr Glu
1               5                   10                  15

Thr Leu Thr Leu Thr Cys Thr Val Ser Gly Phe Ser Asp Ser Ser Ala
            20                  25                  30

Arg Val Gly Val Ser Trp Ile Arg Gln Pro Pro Gly Lys Ala Leu Glu

```
                35                  40                  45

Trp Leu Ala His Ile Ser Ser Lys Asp Glu Lys Ser Tyr Ser Pro Ser
     50                  55                  60

Leu Lys Asn Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg Thr Ser Val Thr Leu Phe Glu Asn Trp Gly Gln Gly
                100                 105                 110

Thr Leu Val Thr Val Ser Pro
            115

<210> SEQ ID NO 106
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Val Gln Ser Gly Ala Glu Val Lys Lys Pro Gly Glu
1               5                  10                  15

Ser Leu Thr Ile Ser Cys Lys Ala Ser Gly Tyr Asn Phe Ala Asp Tyr
            20                  25                  30

Trp Ile Gly Trp Val Arg Gln Met Pro Gly Lys Gly Leu Glu Trp Met
        35                  40                  45

Ala Ile Val Tyr Pro Glu Asp Ser Asp Ala Arg Tyr Ser Pro Ser Phe
     50                  55                  60

Glu Gly His Ile Thr Ile Ser Ala Asp Arg Ser Ile Gly Thr Ala Tyr
 65                  70                  75                  80

Leu Gln Trp Thr Ser Leu Lys Ala Ser Asp Thr Ala Met Tyr Phe Cys
                 85                  90                  95

Val Arg Pro Pro Thr Thr Val Thr Pro Pro Asp Tyr Trp Gly Gln Gly
                100                 105                 110

Thr Leu Val Thr Val Ser Pro
            115

<210> SEQ ID NO 107
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Ser Ser Leu Arg Ser Glu Asp Thr Ala Val Tyr Tyr Cys
```

```
                         85                  90                  95

Ala Arg Asp Pro Ser Tyr Gly Ser Gly Ser Tyr Arg Gly Gly Asp Phe
                100                 105                 110

Asp Tyr Trp Gly Gln Gly Thr Leu Val Thr Val Ser Pro
        115                 120                 125

<210> SEQ ID NO 108
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Phe
            20                  25                  30

Asp Met His Trp Val Arg Gln Ala Thr Gly Lys Gly Leu Glu Trp Val
        35                  40                  45

Ser Ala Ile Gly Leu Ala Gly Asp Thr Tyr Tyr Pro Ala Ser Val Lys
    50                  55                  60

Gly Arg Phe Thr Ile Ser Arg Glu Asp Ala Lys Asn Thr Leu Tyr Leu
65                  70                  75                  80

Gln Met Asp Ser Leu Arg Ala Glu Asp Thr Ala Val Tyr Tyr Cys Ala
                85                  90                  95

Arg Glu Gly Ser Thr Gly Arg Ser Ser Trp Asn Asn Trp Tyr Phe Asp
                100                 105                 110

Leu Trp Gly Arg Gly Thr Leu Val Thr Val Ser Ser
        115                 120

<210> SEQ ID NO 109
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Trp Arg Asp Cys Ser Gly Gly Ser Cys Ala Asp Ala
                100                 105                 110

Phe Asp Ile Trp Gly Gln Gly Thr Leu Val Thr Val Ser Ser
        115                 120                 125
```

```
<210> SEQ ID NO 110
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Leu Glu Ser Gly Gly Gly Leu Gly Arg Pro Gly Glu
1               5                   10                  15

Ser Leu Arg Leu Ser Cys Ala Ala Ser Gly Phe Ser Phe Asn Asn Ala
                20                  25                  30

Trp Met Ser Trp Val Arg Gln Ala Pro Gly Gly Leu Glu Trp Val
            35                  40                  45

Gly Leu Ile Lys Ser Arg Asp Tyr Gly Gly Thr Ile Asp Tyr Ala Ala
        50                  55                  60

Pro Val Lys Gly Arg Phe Thr Ile Ser Arg Asp Asp Ser Lys Asn Met
65                  70                  75                  80

Leu Tyr Leu Asn Met Tyr Ser Leu Lys Ser Glu Asp Thr Ala Val Tyr
                85                  90                  95

Tyr Cys Thr Ser Ser Gly Ser Phe Tyr Val Asn Gly Tyr Trp Gly Gln
            100                 105                 110

Gly Thr Leu Val Thr Val Ser Pro
        115                 120

<210> SEQ ID NO 111
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Gly Ser Ser Ile Asp Tyr Trp Gly Gln Gly Thr Leu Val
            100                 105                 110

Thr Val Ser Ser
        115

<210> SEQ ID NO 112
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112
```

Glu Val Gln Leu Val Glu Ser Gly Ala Glu Val Lys Pro Gly Glu
1               5                   10                  15

Ser Leu Lys Ile Ser Cys Lys Gly Ser Gly Tyr Gly Phe Thr Gly His
            20                  25                  30

Trp Ile Gly Trp Val Arg Gln Met Pro Gly Lys Gly Leu Glu Trp Met
            35                  40                  45

Gly Ile Ile His Pro Val Asp Ser Asp Thr Arg Tyr Ser Pro Ser Phe
        50                  55                  60

Arg Gly Gln Val Thr Met Ser Ile Asp Lys Ser Thr Arg Thr Ala Tyr
65                  70                  75                  80

Leu Gln Trp Asp Thr Leu Lys Ala Ser Asp Thr Ala Val Tyr Tyr Cys
                85                  90                  95

Ala Arg Leu Gly Asp Ser Gly Met Leu His Phe Asp His Trp Gly Gln
                100                 105                 110

Gly Thr Leu Val Thr Val Ser Ser
        115                 120

<210> SEQ ID NO 113
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Met Gly Leu Glu Trp
            35                  40                  45

Ile Gly Ser Ile His His Gly Thr Thr Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Arg Ser Val Thr Ala Ala Asp Thr Ala Val Phe Tyr Cys
                85                  90                  95

Ala Arg Val Ser Gly Glu Ala Ala Ala Gly Trp Ala Asn Trp Phe Asp
                100                 105                 110

Pro Trp Gly Gln Gly Thr Leu Val Thr Val Ser Ser
        115                 120

<210> SEQ ID NO 114
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

```
Ala Phe Ile Arg Tyr Asp Gly Ser Asn Lys Tyr Tyr Ala Asp Ser Val
        50                  55                  60

Lys Gly
65
```

<210> SEQ ID NO 115
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Gln Ile Thr Leu Lys Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Glu Glu Ser Ser Trp Met Gly Trp Gly Pro Asn Trp Phe
            100                 105                 110

Asp Pro Trp Gly Gln Gly Thr Leu Val Thr Val Ser Ser
        115                 120                 125
```

<210> SEQ ID NO 116
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Glu Leu Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Tyr Ser Thr Pro Tyr
                85                  90                  95

Thr Phe Gly Gln Gly Thr Lys Leu Glu Ile Lys
            100                 105
```

<210> SEQ ID NO 117
<211> LENGTH: 106
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 117

Glu Leu Thr Leu Thr Gln Ser Pro Ser Thr Leu Ser Ala Ser Val Gly
1               5                   10                  15

Asp Arg Val Ala Ile Thr Cys Arg Ala Ser Gln Asp Ile Val Thr Trp
            20                  25                  30

Leu Ala Trp Tyr Gln His Lys Pro Gly Gln Ser Pro Lys Leu Leu Ile
        35                  40                  45

Tyr Lys Ala Ser Thr Leu Gln Ile Gly Val Pro Ser Arg Phe Ser Gly
50                  55                  60

Ser Arg Ser Gly Arg Asp Phe Ser Leu Phe Ile Ser Gly Leu Gln Pro
65                  70                  75                  80

Asp Asp Val Ala Thr Tyr Tyr Cys Gln Gln Tyr Lys Ala Phe Trp Thr
                85                  90                  95

Ser Gly Gln Gly Thr Lys Val Asp Val Asn
            100                 105

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Gly Ser
            20                  25                  30

Leu Ala Trp Tyr Gln Gln Lys Pro Gly Arg Ala Pro Lys Leu Leu Val
        35                  40                  45

Tyr Ala Thr Ser Arg Leu Glu Thr Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Ser Thr Phe Pro
                85                  90                  95

Thr Phe Gly Gly Gly Thr Lys Val Glu Ile Lys
            100                 105

<210> SEQ ID NO 119
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Leu Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Arg Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Gln
                85                  90                  95

Trp Thr Phe Gly Gln Gly Thr Lys Val Glu Ile Lys
                100                 105
```

<210> SEQ ID NO 120
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Glu Leu Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Arg Leu Glu Ile Lys
                100                 105
```

<210> SEQ ID NO 121
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Glu Leu Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Ser Trp
                20                  25                  30

Leu Ala Trp Tyr Gln Gln Lys Pro Gly Lys Ala Pro Asn Leu Leu Ile
            35                  40                  45

Tyr Lys Ala Ser Ala Leu Glu Ser Gly Val Pro Ser Arg Phe Ser Gly
        50                  55                  60

Ser Gly Ser Gly Thr Asp Phe Thr Leu Thr Ile Ser Asp Leu Gln Pro
65                  70                  75                  80

Glu Asp Phe Ala Thr Tyr Tyr Cys Gln Gln Phe Lys Ser Tyr Pro Leu
                85                  90                  95

Thr Phe Gly Gly Gly Thr Lys Val Glu Ile Lys
                100                 105
```

<210> SEQ ID NO 122
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Ser Phe Gly Gln Gly Thr Lys Leu Glu Ile Lys
            100                 105

<210> SEQ ID NO 123
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Leu Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

<210> SEQ ID NO 124
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Leu Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
```

```
                35                  40                  45
Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
                100                 105                 110

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Leu Pro Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Asn Ser
            20                  25                  30

Gln Leu Ala Trp Tyr Gln Gln Lys Pro Gly Gln Pro Arg Leu Leu
        35                  40                  45

Ile Tyr Asp Ala Thr Thr Arg Ala Thr Gly Ile Pro Asp Arg Phe Ser
        50                  55                  60

Gly Ser Gly Ser Gly Ala Asp Phe Thr Leu Thr Ile Ser Arg Leu Glu
65                  70                  75                  80

Pro Glu Asp Phe Ala Val Tyr Tyr Cys Gln Gln His Gly His Ser Ile
                85                  90                  95

Thr Phe Gly Gly Gly Thr Lys Val Glu Val Lys
                100                 105

<210> SEQ ID NO 126
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Leu Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Trp Val Phe Gly Gly Gly Thr Lys Leu Thr Val Leu
                100                 105                 110
```

```
<210> SEQ ID NO 127
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Leu Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp His Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Ile Ile Ser Arg Val Glu Ala Gly
65                  70                  75                  80

Asp Glu Ala Asp Tyr Tyr Cys Gln Val Trp Asp Ser Ser Asp His
                85                  90                  95

Pro Leu Phe Gly Gly Gly Thr Lys Leu Thr Val Leu
            100                 105

<210> SEQ ID NO 128
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Leu Val Met Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Ser Gly Ser Val Phe Gly Gly Gly Thr Lys Leu Thr Val Leu
            100                 105                 110

<210> SEQ ID NO 129
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Leu Met Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30
```

Tyr Tyr Pro Ser Trp Tyr Gln Gln Thr Pro Gly Gln Ala Pro Arg Thr
                35                  40                  45

Leu Ile Tyr Ser Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Ser
                 85                  90                  95

Gly Ile Ser Val Phe Gly Gly Gly Thr Lys Leu Thr Val Leu
                100                 105                 110

<210> SEQ ID NO 130
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Leu Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Ser
                20                  25                  30

Tyr Tyr Pro Ser Trp Tyr Gln Gln Thr Pro Gly Gln Ala Pro Arg Thr
                35                  40                  45

Leu Ile Tyr Ser Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Ser
                 85                  90                  95

Gly Ile Ser Val Phe Gly Gly Gly Thr Lys Leu Thr Val Leu
                100                 105                 110

<210> SEQ ID NO 131
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Leu Val Leu Thr Gln Ser Pro Ser Ala Ser Ala Ser Leu Gly Ala
 1               5                  10                  15

Ser Val Lys Leu Thr Cys Thr Leu Ser Ser Gly His Ser Ser Tyr Ala
                20                  25                  30

Ile Ala Trp His Gln Gln Pro Glu Lys Gly Pro Arg Tyr Leu Met
                35                  40                  45

Lys Leu Asn Ser Asp Gly Ser His Ser Lys Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gln Thr Trp Gly
                 85                  90                  95

Thr Gly Ile Trp Val Phe Gly Gly Gly Thr Lys Leu Thr Val Leu
                100                 105                 110

<210> SEQ ID NO 132
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Leu Val Met Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Val
        35                  40                  45

Leu Ile Tyr Ala Thr Thr Asn Arg Leu Ser Gly Val Pro Asp Arg Phe
    50                  55                  60

Ser Gly Ser Lys Ser Gly Thr Ser Ala Thr Leu Gly Ile Thr Gly Leu
65                  70                  75                  80

Gln Thr Gly Asp Glu Ala Asp Tyr Tyr Cys Gly Thr Trp Asp Ser Ser
                85                  90                  95

Leu Ser Ala Val Val Phe Gly Gly Gly Thr Lys Leu Thr Val Leu
            100                 105                 110

<210> SEQ ID NO 133
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Leu Ala Leu Thr Gln Pro Pro Ser Ala Ser Gly Ser Pro Gly Glu
1               5                   10                  15

Ser Val Thr Ile Phe Cys Thr Gly Thr Ser Ser Asp Val Gly Arg Tyr
            20                  25                  30

Asp Tyr Val Ser Trp Tyr Gln Gln Tyr Pro Gly Asn Ala Pro Lys Leu
        35                  40                  45

Ile Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu
            100                 105                 110

<210> SEQ ID NO 134
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Leu Val Met Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110

<210> SEQ ID NO 135
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Leu Val Leu Thr Gln Ser Pro Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Gln Pro Glu Lys Gly Pro Arg Tyr Leu Met
        35                  40                  45

Lys Leu Asn Ser Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Thr Gly Ile Gln Val Phe Gly Gly Gly Thr Lys Leu Thr Ile Leu
            100                 105                 110

<210> SEQ ID NO 136
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

```
Cys Ala His Asn Arg Tyr Ser Ser Gly Trp Tyr Phe Asp Tyr Trp Gly
            100                 105                 110

Gln Gly Thr Leu Val Thr Val Ser Ser
        115                 120

<210> SEQ ID NO 137
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Arg Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Gly Gly Thr Asp Tyr Trp Tyr Phe Asp Leu Trp Gly Arg
            100                 105                 110

Gly Thr Leu Val Thr Val Ser Pro
        115                 120

<210> SEQ ID NO 138
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Ile Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Gly Asp Pro Pro Tyr Tyr Phe Asp Tyr Trp Gly Gln
            100                 105                 110

Gly Thr Leu Val Thr Val Ser Pro
        115                 120

<210> SEQ ID NO 139
<211> LENGTH: 118
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Met Gly Thr Gly Leu Val Asp Tyr Trp Gly Gln Gly Thr
            100                 105                 110

Leu Val Thr Val Ser Pro
        115

<210> SEQ ID NO 140
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Gly Gly Glu Trp Leu Phe Phe Asp Tyr Trp Gly Gln
            100                 105                 110

Gly Thr Leu Val Thr Val Ser Pro
        115                 120

<210> SEQ ID NO 141
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Val Gln Ser Gly Ala Glu Val Lys Lys Pro Gly Ser

```
              1               5                  10                 15
Ser Val Lys Val Ser Cys Lys Ala Ser Gly Gly Thr Phe Ser Ser Tyr
              20                 25                 30

Ala Ile Ser Trp Val Arg Gln Ala Pro Gly Gln Gly Leu Glu Trp Met
              35                 40                 45

Gly Gly Ile Ile Pro Ile Phe Gly Thr Ala Asn Tyr Ala Gln Lys Phe
              50                 55                 60

Gln Gly Arg Val Thr Ile Thr Ala Asp Glu Ser Thr Ser Thr Ala Tyr
65                70                 75                 80

Met Glu Leu Ser Ser Leu Arg Ser Glu Asp Thr Ala Val Tyr Tyr Cys
              85                 90                 95

Ala Arg Asp Arg Arg Ile Thr Met Val Arg Gly Val Ile Thr Asn Trp
              100                105                110

Phe Asp Pro Trp Gly Gln Gly Thr Leu Val Thr Val Ser Ser
              115                120                125
```

<210> SEQ ID NO 142
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

```
Gln Val Gln Leu Gln Glu Ser Gly Pro Gly Leu Val Lys Pro Ser Glu
1               5                  10                 15

Thr Leu Ser Leu Thr Cys Thr Val Ser Gly Gly Ser Ile Ser Ser Tyr
              20                 25                 30

Tyr Trp Ser Trp Ile Arg Gln Pro Pro Gly Lys Gly Leu Glu Trp Ile
              35                 40                 45

Gly Tyr Ile Tyr Tyr Ser Gly Ser Thr Asn Tyr Asn Pro Ser Leu Lys
              50                 55                 60

Ser Arg Val Thr Ile Ser Val Asp Thr Ser Lys Asn Gln Phe Ser Leu
65                70                 75                 80

Lys Leu Ser Ser Val Thr Ala Ala Asp Thr Ala Val Tyr Tyr Cys Ala
              85                 90                 95

Arg Asp His His Ser Gly Trp Phe Asp Pro Trp Gly Gln Gly Thr Leu
              100                105                110

Val Thr Val Ser Ser
              115
```

<210> SEQ ID NO 143
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

```
Gln Val Gln Leu Gln Glu Ser Gly Pro Gly Leu Val Lys Pro Ser Glu
1               5                  10                 15

Thr Leu Ser Leu Thr Cys Thr Val Ser Gly Gly Ser Ile Asn Ala His
              20                 25                 30

Asp Phe Tyr Trp Ala Trp Val Arg Gln Pro Pro Gly Lys Gly Leu Glu
              35                 40                 45

Trp Leu Gly Ser Ile Ser His Thr Gly Ser Thr Tyr Leu Asn Pro Ser
```

```
                50                  55                  60

Leu Arg Ser Arg Val Thr Leu Ser Ile Asp Ile Ser Asn Asn Gln Phe
 65                  70                  75                  80

Ser Leu Lys Leu Ser Ser Val Thr Ala Ala Asp Thr Ala Ile Tyr Tyr
                 85                  90                  95

Cys Ala Gly Pro Pro Gly Tyr Cys Thr Ala Thr Thr Cys Tyr Glu Trp
                100                 105                 110

Tyr Phe Asp Phe Trp Gly Arg Gly Thr Leu Val Thr Val Ser Pro
            115                 120                 125

<210> SEQ ID NO 144
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Asn Ala His
                 20                  25                  30

Asp Phe Tyr Trp Ala Trp Val Arg Gln Pro Pro Gly Lys Gly Leu Glu
             35                  40                  45

Trp Leu Gly Ser Ile Ser His Thr Gly Ser Thr Tyr Leu Asn Pro Ser
 50                  55                  60

Leu Arg Ser Arg Val Thr Leu Ser Ile Asp Ile Ser Asn Asn Gln Phe
 65                  70                  75                  80

Ser Leu Lys Leu Ser Ser Val Thr Ala Ala Asp Thr Ala Ile Tyr Tyr
                 85                  90                  95

Cys Ala Gly Pro Pro Gly Tyr Cys Thr Ala Thr Thr Cys Tyr Glu Trp
                100                 105                 110

Tyr Phe Asp Phe Trp Gly Arg Gly Thr Leu Val Thr Val Ser Pro
            115                 120                 125

<210> SEQ ID NO 145
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Gln Glu Ser Gly Pro Gly Leu Val Lys Pro Ser Gly
  1               5                  10                  15

Thr Leu Ser Leu Thr Cys Ala Val Ser Gly Gly Ser Ile Ser Ser Ser
                 20                  25                  30

Asn Trp Trp Ser Trp Val Arg Gln Pro Pro Gly Lys Gly Leu Glu Trp
             35                  40                  45

Ile Gly Glu Ile Asn His Ser Gly Ser Thr Asn Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Leu Phe Trp Phe Asp Pro Trp Gly Gln Gly Thr Leu Val
```

```
                  100                 105                 110

Thr Val Ser Ser
            115

<210> SEQ ID NO 146
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Gln Gln Trp Gly Ala Gly Leu Leu Lys Pro Ser Glu
1               5                   10                  15

Thr Leu Ser Leu Thr Cys Ser Val Ser Gly Gly Ser Phe Gly Asp Tyr
            20                  25                  30

Gln Trp Thr Trp Ile Arg Gln Pro Pro Gly Lys Gly Leu Glu Trp Ile
        35                  40                  45

Gly Lys Ile Ser Gly Thr Gly Gly Ala Thr Tyr Ser Pro Ser Leu Lys
    50                  55                  60

Thr Arg Val Ala Ile Ser Ile Asp Gly Ser Lys Asn Gln Phe Tyr Leu
65                  70                  75                  80

Glu Leu Ser Ser Leu Thr Ala Ala Asp Thr Ala Leu Tyr Tyr Cys Ala
                85                  90                  95

Arg Gly Asp Tyr Asp Gly Ser Ser Tyr Glu Gly Gly Trp Tyr Tyr Phe
            100                 105                 110

Asp His Trp Gly Gln Gly Thr Leu Val Thr Val Ser Ser
        115                 120                 125

<210> SEQ ID NO 147
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gln Ile Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Arg Ala Gly Gln Leu Asp Phe Asp Tyr Trp Gly Gln
            100                 105                 110

Gly Thr Leu Val Thr Val Ser Pro
        115                 120

<210> SEQ ID NO 148
<211> LENGTH: 117
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Gly Val Phe Asp Tyr Trp Gly Gln Gly Thr Leu
            100                 105                 110

Val Thr Val Ser Ser
            115

<210> SEQ ID NO 149
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Tyr Gly Ser Gly Ser Asn Trp Phe Asp Pro Trp Gly
            100                 105                 110

Gln Gly Thr Leu Val Thr Val Ser Ser
        115                 120

<210> SEQ ID NO 150
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Ile Thr Leu Lys Glu Ser Gly Ala Glu Val Lys Lys Pro Gly Ser
1               5                   10                  15

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Phe Phe Asp Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Lys Gly Leu
            100

<210> SEQ ID NO 151
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Gly Tyr
            20                  25                  30

Tyr Trp Ser Trp Ile Arg Gln Pro Pro Gly Lys Gly Leu Glu Trp Ile
        35                  40                  45

Gly Asp Val Tyr Tyr Ser Gly Ser Thr Lys Asp Asn Pro Ser Leu Lys
 50                  55                  60

Ser Arg Val Thr Met Ser Val Asp Pro Ser Lys Asn Glu Phe Phe Leu
65                  70                  75                  80

Lys Val Asn Ser Val Thr Ala Ala Asp Thr Ala Val Tyr Tyr Cys Ala
                85                  90                  95

Arg Val Asn Gly Gly Gly Val Asp Tyr Trp Gly Gln Gly Thr Leu Val
            100                 105                 110

Thr Val Ser Pro
        115

<210> SEQ ID NO 152
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
 50                  55                  60

Leu Lys Ser Arg Leu Thr Ile Thr Lys Asp Thr Ser Lys Asn Gln Val
65                  70                  75                  80
```

```
Val Leu Thr Met Thr Asn Met Asp Pro Val Asp Thr Ala Thr Tyr Tyr
                85                  90                  95

Cys Ala His Ser Arg Gly Tyr Tyr Gly Ser Gly Ser Tyr Tyr Asn Phe
            100                 105                 110

Asp Tyr Trp Gly Gln Gly Thr Leu Val Thr Val Ser Ser
        115                 120                 125

<210> SEQ ID NO 153
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Gln Leu Gln Gln Trp Gly Ala Gly Leu Leu Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Ile Val Val Arg Gly Val Pro Phe Asp Tyr Trp Gly Gln
            100                 105                 110

Gly Met Leu Val Thr Val Ser Pro
        115                 120

<210> SEQ ID NO 154
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Lys Trp Gly Glu Leu Pro Tyr Tyr Phe Asp Tyr Trp Gly
            100                 105                 110

Gln Gly Thr Leu Val Thr Val Ser Pro
        115                 120
```

```
<210> SEQ ID NO 155
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Ile Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Arg Tyr Cys Ser Gly Gly Ser Cys Arg Asn Tyr Tyr
                100                 105                 110

Phe Asp Tyr Trp Gly Gln Gly Thr Leu Val Thr Val Ser Pro
            115                 120                 125

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 156

His His His His His His
1               5

<210> SEQ ID NO 157
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Leu Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Tyr Tyr Ser Thr Pro Pro Thr Phe Gly Gly Thr Lys Val Glu Ile
            100                 105                 110
Lys

<210> SEQ ID NO 158
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Leu Val Leu Thr Gln Ser Pro Gly Thr Leu Ser Val Ser Pro Gly
1               5                   10                  15

Glu Arg Ala Thr Leu Ser Cys Arg Ala Ser Gln Asn Ile Asn Asn Asn
            20                  25                  30

Tyr Leu Ala Trp Tyr Gln Gln Lys Pro Gly Gln Gly Leu Arg Leu Leu
        35                  40                  45

Ile Ser Gly Ala Ser Ser Arg Ala Thr Gly Ile Pro His Arg Phe Val
50                  55                  60

Gly Ser Gly Ser Trp Thr Asp Phe Thr Leu Thr Ile Ile Arg Leu Glu
65                  70                  75                  80

Pro Glu Asp Phe Ala Val Tyr Phe Cys Gln Gln Tyr Gly Ser Ser Pro
                85                  90                  95

Asn Thr Phe Gly Gln Gly Thr Lys Leu Glu Ile Lys
            100                 105

<210> SEQ ID NO 159
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Leu Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Leu
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Ser Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ile Gln Ala
                85                  90                  95

Leu Gln Thr Tyr Thr Phe Gly Gln Gly Thr Lys Leu Glu Ile Arg
            100                 105                 110

<210> SEQ ID NO 160
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

```
Glu Leu Gln Met Thr Gln Ser Pro Ala Thr Leu Ser Ala Ser Val Gly
1               5                   10                  15

Asp Arg Val Thr Ile Thr Cys Arg Ala Ser Gln Ser Val Ser Arg Tyr
            20                  25                  30

Ile Asn Trp Tyr Gln Gln Lys Ser Gly Lys Ala Pro Lys Leu Leu Ile
        35                  40                  45

Tyr Arg Ala Ser Thr Leu Gln Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Thr Tyr Trp Thr
                85                  90                  95

Phe Gly Gln Gly Thr Lys Val Glu Ser Lys
            100                 105

<210> SEQ ID NO 161
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Glu Leu Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Asn Phe Ser
50                  55                  60

Gly Ser Gly Ser Gly Arg Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 162
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Leu Val Leu Thr Gln Ser Pro Gly Thr Leu Ser Leu Ser Pro Gly
1               5                   10                  15

Asp Arg Ala Thr Leu Ser Cys Arg Ala Ser Gln Ser Val Ser Gly Asn
            20                  25                  30

Tyr Leu Ala Trp Tyr Gln Gln Lys Pro Gly Gln Ala Pro Arg Leu Leu
        35                  40                  45

Ile Phe Gly Thr Ser Ser Arg Ala Thr Asp Ile Pro Asp Arg Phe Ser
50                  55                  60

Gly Ser Val Ser Gly Thr Asp Phe Thr Leu Thr Ile Gly Ser Leu Glu
65                  70                  75                  80
```

```
Pro Glu Asp Phe Ala Leu Tyr Tyr Cys His Gln Tyr Gly Thr Ala Pro
                85                  90                  95

His Thr Phe Gly Gln Gly Thr Lys Leu Glu Ile Lys
            100                 105

<210> SEQ ID NO 163
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Leu Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Thr Asn Phe Pro Pro
                85                  90                  95

Thr Phe Gly Gly Gly Thr Lys Val Glu Ile Lys
            100                 105

<210> SEQ ID NO 164
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Leu Val Leu Thr Gln Ser Pro Gly Ala Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln His Lys Pro Gly Gln Ala Pro Arg Leu Leu
        35                  40                  45

Ile Tyr Asp Ala Ser Asn Arg Ala Thr Gly Ile Pro Asp Arg Phe Ser
    50                  55                  60

Gly Thr Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Pro Gly Thr Lys Leu Glu Ile Lys
            100                 105

<210> SEQ ID NO 165
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 165

```
Glu Leu Val Met Thr Gln Ser Pro Ser Ser Leu Ser Ala Ser Val Gly
1               5                   10                  15

Asp Arg Val Thr Ile Ala Cys Arg Thr Ser Gln Ser Ile Thr Thr Tyr
            20                  25                  30

Leu Asn Trp Tyr Gln Gln Ile Pro Gly Lys Ala Pro Lys Leu Leu Ile
        35                  40                  45

Tyr Ala Ala Ser Ser Leu Gln Thr Gly Val Pro Ala Arg Phe Thr Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Arg Asp Ile Pro Asp
                85                  90                  95

Thr Phe Gly Gln Gly Thr Lys Leu Glu Ile Lys
            100                 105
```

<210> SEQ ID NO 166
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

```
Glu Leu Gln Met Thr Gln Ser Pro Gly Ser Ser Ala Ser Val Gly
1               5                   10                  15

Asp Thr Val Thr Ile Thr Cys Arg Ser Ser Gln Asn Ile Arg Lys Phe
            20                  25                  30

Leu Asn Trp Tyr Gln Gln Lys Pro Gly Lys Ala Pro Arg Leu Leu Ile
        35                  40                  45

Tyr Gly Ala Ser Asn Leu Gln Ser Asp Val Pro Ser Arg Phe Arg Gly
    50                  55                  60

Ser Gly Ser Gly Thr Gln Phe Ser Leu Thr Ile Thr Asp Leu Arg Pro
65                  70                  75                  80

Glu Asp Phe Ala Thr Tyr Tyr Cys Gln Gln Ser Phe Lys Thr Pro Pro
                85                  90                  95

Tyr Thr Phe Gly Gln Gly Thr Lys Val Glu Ile Arg
            100                 105
```

<210> SEQ ID NO 167
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

```
Glu Leu Thr Leu Thr Gln Ser Pro Asp Ser Leu Ser Leu Ser Pro Gly
1               5                   10                  15

Glu Arg Ala Thr Leu Ser Cys Arg Ala Ser Gln Ser Ile Ser Arg Asn
            20                  25                  30

Ser Leu Val Trp Tyr Gln Gln Lys Pro Gly Gln Ala Pro Ser Leu Leu
        35                  40                  45

Ile Tyr Asp Ala Ser Thr Arg Ala Ala Gly Thr Pro Asp Arg Phe Ser
    50                  55                  60
```

-continued

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 168
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Thr Val Ser Gly Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Tyr Thr Phe Gly Gln Gly Thr Lys Leu Glu Ile Lys
            100                 105

<210> SEQ ID NO 169
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Glu Leu Val Met Thr Gln Ser Pro Asp Ser Leu Ala Val Ser Leu Gly
1               5                   10                  15

Glu Arg Ala Thr Ile Thr Cys Lys Ser Ser Gln Ser Val Phe Phe Ser
            20                  25                  30

Pro Asn Ser Lys Asn Tyr Leu Ala Trp Tyr Gln Leu Lys Pro Gly Gln
        35                  40                  45

Ala Pro Lys Leu Leu Ile Ser Trp Ala Ser Ala Arg Glu Phe Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Leu Tyr Tyr Cys Gln Gln
                85                  90                  95

Tyr Phe Asn Leu Pro Arg Thr Phe Gly Gln Gly Thr Lys Leu Glu Ile
            100                 105                 110

Lys

<210> SEQ ID NO 170
<211> LENGTH: 112
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 170

Glu Leu Val Met Thr Gln Ser Pro Val Ser Leu Ser Val Thr Pro Gly
1               5                   10                  15

Gln Pro Ala Ser Ile Ser Cys Lys Ser Ser Gln Ser Leu Leu His Arg
            20                  25                  30

Asp Gly Lys Thr Tyr Phe Phe Trp Tyr Leu Gln Lys Pro Gly Gln Pro
        35                  40                  45

Pro Gln Leu Leu Val Tyr Glu Val Ser Lys Arg Phe Ser Gly Val Pro
    50                  55                  60

Asp Arg Phe Arg Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Thr
                85                  90                  95

Ile Gln Leu Pro His Thr Phe Gly Gln Gly Thr Lys Leu Glu Ile Lys
            100                 105                 110

<210> SEQ ID NO 171
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Leu Thr Leu Thr Gln Ser Pro Ala Thr Leu Ser Val Ser Pro Gly
1               5                   10                  15

Gln Arg Ala Thr Leu Ser Cys Arg Ala Ser Gln Ser Val Ser Ser Ser
            20                  25                  30

Tyr Val Ala Trp Tyr Gln Gln Lys Pro Gly Gln Thr Pro Arg Leu Leu
        35                  40                  45

Ile Tyr Gly Ala Ser Ser Arg Ala Thr Gly Ile Pro Ala Arg Phe Ser
    50                  55                  60

Gly Ser Gly Ser Gly Thr Glu Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 172
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Glu Leu Thr Leu Thr Gln Ser Pro Asp Thr Leu Ser Val Ser Pro Gly
1               5                   10                  15

Glu Arg Val Thr Leu Ser Cys Arg Ala Ser Gln Ser Val Ser Thr Asn
            20                  25                  30

Leu Ala Trp Tyr Gln Gln Arg Pro Ala Gln Pro Pro Arg Leu Leu Ile
        35                  40                  45
```

Tyr Gly Ala Ser Ser Arg Ala Thr Gly Ile Pro Asp Arg Phe Ser Gly
            50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His His Tyr Gly Ser Ser Pro Pro
                85                  90                  95

Trp Thr Phe Gly Gln Gly Thr Lys Val Glu Ile Lys
            100                 105

<210> SEQ ID NO 173
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Glu Leu Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asp
            20                  25                  30

Leu Ala Trp Tyr Gln Gln Arg Pro Gly Gln Ala Pro Arg Leu Phe Ile
        35                  40                  45

Tyr Gly Ala Ser Ser Arg Ala Thr Gly Ile Pro Asp Arg Phe Arg Gly
            50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Tyr Gly Ser Ser Pro Met
                85                  90                  95

Tyr Thr Phe Gly Gln Gly Thr Lys Leu Glu Ile Lys
            100                 105

<210> SEQ ID NO 174
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ile Asn Tyr
            20                  25                  30

Leu Thr Trp Tyr Gln Phe Lys Pro Gly Lys Ala Pro Lys Leu Leu Ile
        35                  40                  45

His Thr Thr Ser Ser Leu Gln Asn Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Glu Gln Thr Lys Ile Ala Pro Tyr
                85                  90                  95

Thr Phe Gly Gln Gly Thr Lys Leu Glu Ile Lys
        100                 105

<210> SEQ ID NO 175

```
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Leu Thr Leu Thr Gln Ser Pro Ala Thr Leu Ser Val Ser Pro Gly
1               5                   10                  15

Gly Arg Ala Thr Leu Ser Cys Arg Thr Ser Gln Ser Val Asn Ser Lys
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Gly Ser Pro Val
                85                  90                  95

Tyr Thr Phe Gly Gln Gly Thr Lys Leu Glu Ile Lys
            100                 105

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Leu Val Leu Thr Gln Ser Pro Gly Thr Leu Ser Leu Ser Pro Gly
1               5                   10                  15

Gln Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Val Pro Gly Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Ser Gln Asp Arg Ala
                85                  90                  95

Ser Phe Gly Gln Gly Thr Lys Val Glu Ile Lys
            100                 105

<210> SEQ ID NO 177
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Ser Ser Asn Ile Arg Ser Asn Thr Val Asn Trp Tyr Gln Gln Phe Pro
1               5                   10                  15

Gly Thr Ala Pro Lys Leu Leu Ile Tyr Ser Asn Asn Gln Arg Pro Ser
            20                  25                  30
```

Gly Val Pro Asp Arg Phe Ser Gly Ser Lys Ser Gly Thr Ser Ala Ser
            35                  40                  45

Leu Ala Ile Ser Gly Leu Gln Ser Glu Asp Glu Ala Asp Tyr Tyr Cys
 50                  55                  60

Ala Ala Trp Asp Asp Ser Leu Asn Gly Pro Val Phe Gly Gly Gly Thr
 65                  70                  75                  80

Lys Leu Thr Val Leu
                85

<210> SEQ ID NO 178
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Ser Ser Asn Ile Gly Ser Asn Thr Val Asn Trp Tyr Gln Gln Leu Pro
 1               5                  10                  15

Gly Thr Ala Pro Lys Leu Leu Ile Tyr Ser Asn Asn Gln Arg Pro Ser
            20                  25                  30

Gly Val Pro Asp Arg Phe Ser Gly Ser Lys Ser Gly Thr Ser Ala Ser
            35                  40                  45

Leu Ala Ile Ser Gly Leu Gln Ser Glu Asp Glu Ala Asp Tyr Tyr Cys
 50                  55                  60

Ala Ala Trp Asp Asp Ser Leu Asn Gly Pro Val Phe Gly Gly Gly Thr
 65                  70                  75                  80

Lys Leu Thr Val Leu
                85

<210> SEQ ID NO 179
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Val Ser Asn Ile Gly Ser Asn Ile Val Ser Trp Tyr Gln Gln Phe Pro
 1               5                  10                  15

Gly Lys Ala Pro Lys Leu Leu Ile Tyr Asn Asp Ser Gln Arg Pro Ser
            20                  25                  30

Gly Val Pro Asp Arg Phe Ser Gly Ser Lys Ser Gly Thr Ser Ala Ser
            35                  40                  45

Leu Ala Ile Ser Gly Leu Gln Ser Glu Asp Glu Ala Glu Tyr Tyr Cys
 50                  55                  60

Ala Thr Trp Asp Asp Ile Leu Arg Gly Arg Val Phe Gly Gly Gly Thr
 65                  70                  75                  80

Lys Leu Ser Val Leu
                85

<210> SEQ ID NO 180
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 180

Ser Ser Asn Ile Gly Arg Asn Ser Val His Trp Tyr Gln Gln Phe Pro
1               5                   10                  15

Gly Thr Ala Pro Lys Leu Leu Leu Tyr Thr Asn Asn Gln Arg Pro Ser
            20                  25                  30

Gly Val Pro Asp Arg Phe Ser Gly Ser Arg Ser Gly Thr Ser Ala Ser
        35                  40                  45

Leu Ala Ile Ser Gly Leu Arg Ser Glu Asp Glu Ser Asp Tyr Tyr Cys
    50                  55                  60

Ala Ala Trp Asp Asp Ser Leu Arg Gly Val Val Phe Gly Gly Gly Thr
65                  70                  75                  80

His Leu Thr Val Leu
            85

<210> SEQ ID NO 181
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Ser Gly Ser Ile Ala Ser Asn Tyr Val Gln Trp Ser Gln Gln Arg Pro
1               5                   10                  15

Gly Ser Ser Pro Thr Thr Val Ile Tyr Glu Asp Asn Gln Arg Pro Ser
            20                  25                  30

Gly Val Pro Asp Arg Phe Ser Gly Ser Ile Asp Ser Ser Asn Ser
        35                  40                  45

Ala Ser Leu Thr Ile Ser Gly Leu Lys Thr Glu Asp Glu Ala Asp Tyr
    50                  55                  60

Tyr Cys Gln Ser Ser Asp Ser Ser Asn Trp Val Phe Gly Gly Gly Thr
65                  70                  75                  80

Lys Leu Thr Val Leu
            85

<210> SEQ ID NO 182
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (71)..(71)
<223> OTHER INFORMATION: Any amino acid

<400> SEQUENCE: 182

Ser Ser Asn Ile Gly Ser Asn Pro Val Asn Trp Tyr Gln Gln Leu Pro
1               5                   10                  15

Gly Thr Ala Pro Arg Leu Leu Val Tyr Ser Asn Asp Gln Arg Pro Ser
            20                  25                  30

Gly Val Pro Ala Arg Phe Ser Ala Ser Arg Tyr Ala Ser Ser Val Ser
        35                  40                  45

Leu Ser Ile Arg Gly Leu Arg Ser Glu Asp Glu Ala Val Tyr His Cys
    50                  55                  60

Ser Ser Trp Asp Asp Ser Xaa Asp Gly Arg Val Phe Asp Gly Gly Thr
65                  70                  75                  80

Arg Leu Thr Val Leu
            85

<210> SEQ ID NO 183
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Any amino acid

<400> SEQUENCE: 183

Ser Ser Asn Ile Gly Ser Thr Phe Asp Val Asn Trp Tyr Gln Gln Leu
1               5                   10                  15

Pro Gly Thr Ala Pro Lys Val Leu Ile Tyr Gly Asn Asn Arg Pro
            20                  25                  30

Ser Gly Val Pro Asp Xaa Phe Ser Gly Ser Lys Ser Gly Ala Ser Ala
            35                  40                  45

Ser Leu Ala Ile Asn Gly Leu Gln Ala Glu Asp Glu Ala Asp Tyr Tyr
50                  55                  60

Cys Gln Ser Phe Asp Ser Ser Leu Arg Gly Ser Val Phe Gly Gly Gly
65                  70                  75                  80

Thr Arg Leu Thr Val Leu
            85

<210> SEQ ID NO 184
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Arg Ser Asn Ile Gly Ser Ser Asn Val Tyr Trp Tyr Gln Gln Phe Pro
1               5                   10                  15

Gly Thr Ala Pro Lys Leu Leu Ile Tyr Arg Asn Asn Gln Arg Pro Ser
            20                  25                  30

Gly Val Pro Asp Arg Phe Ser Gly Ser Arg Ser Gly Thr Ser Ala Ser
            35                  40                  45

Leu Ala Ile Ser Asp Leu Arg Ser Asp Glu Ala Asp Tyr Tyr Cys
50                  55                  60

Ala Ala Trp Asp Ala Ser Leu Asn Gly Val Ala Phe Gly Gly Gly Thr
65                  70                  75                  80

Lys Val Thr Val Leu
            85

<210> SEQ ID NO 185
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gly Gly Ser Ile Ala Ser Lys Tyr Val Gln Trp Tyr Gln Leu Arg Pro
1               5                   10                  15

Gly Ser Ala Pro Thr Thr Val Ile Tyr Glu Asn Asn Gln Arg Pro Ser
            20                  25                  30

Gly Val Pro Ala Arg Phe Ser Gly Ser Leu Asp Thr Ser Ser Asn Ser
        35                  40                  45

Ala Ser Leu Thr Ile Ser Gly Leu Lys Thr Glu Asp Glu Ala Asp Tyr
 50                  55                  60

Tyr Cys Gln Ser Ser Thr Ser Thr Asn Asp Arg Ile Phe Gly Gly Gly
 65                  70                  75                  80

Thr Lys Leu Thr Val Leu
                85

<210> SEQ ID NO 186
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Ser Arg Asp Ile Gly Ser Asp Asn Tyr Val Ser Trp Tyr Gln Tyr Arg
1               5                   10                  15

Pro Gly Arg Ala Pro Lys Ile Ile Ile Tyr Glu Val His Lys Arg Pro
            20                  25                  30

Ser Gly Val Pro Asp Arg Phe Ser Gly Ser Lys Ser Gly Asn Thr Ala
        35                  40                  45

Ser Leu Thr Val Ser Gly Leu Gln Ala Glu Asp Glu Ala Asp Tyr Tyr
 50                  55                  60

Cys Ser Ser Asn Gly Gly Gly Leu Leu Val Phe Gly Gly Gly Thr
 65                  70                  75                  80

Lys Leu Thr Val Leu
                85

<210> SEQ ID NO 187
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Ser Ser Asn Ile Gly Arg Asn Ser Val Asn Trp Tyr His Gln Phe Pro
1               5                   10                  15

Gly Thr Ala Pro Asn Leu Leu Ile Tyr Gly Ser Asn Gln Arg Pro Ser
            20                  25                  30

Gly Val Pro Asp Arg Phe Ser Gly Ser Lys Ser Gly Thr Ser Ala Ser
        35                  40                  45

Leu Ala Ile Ser Gly Leu Gln Ser Glu Asp Glu Ala Asp Tyr Tyr Cys
 50                  55                  60

Ala Ala Trp Asp Asp Ser Leu Arg Gly Arg Leu Phe Gly Gly Gly Thr
 65                  70                  75                  80

Lys Val Thr Val Leu
                85

<210> SEQ ID NO 188
<211> LENGTH: 85
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 188

Asn Ser Asn Ile Gly Ser His Thr Gly Asn Trp Tyr Gln Gln Leu Pro
1               5                   10                  15

Gly Ala Ala Pro Arg Leu Leu Ile Tyr Met Asn Asn Lys Arg Pro Ser
            20                  25                  30

Gly Ile Pro Glu Arg Phe Ser Gly Ser Lys Ser Gly Asn Thr Ala Thr
        35                  40                  45

Leu Thr Ile Asp Arg Val Glu Pro Gly Asp Glu Ala Asp Phe Phe Cys
50                  55                  60

Gln Val Trp Asp Ser Asp Thr Tyr His Trp Val Phe Gly Gly Gly Thr
65                  70                  75                  80

Lys Leu Thr Val Leu
                85

<210> SEQ ID NO 189
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Asn Ser Asn Ile Gly Ser Asn Thr Val Asn Trp Tyr Gln Gln Leu Pro
1               5                   10                  15

Gly Thr Ala Pro Lys Leu Leu Ile Tyr Ser Asp Asp Gln Arg Pro Ser
            20                  25                  30

Gly Val Pro Asp Arg Phe Ser Gly Ser Lys Ser Gly Thr Ser Ala Ser
        35                  40                  45

Leu Ala Ile Gly Gly Leu Gln Ser Glu Asp Glu Ala Asp Tyr Tyr Cys
50                  55                  60

Ser Ala Trp Asp Asp Ser Leu Asp Gly Pro Leu Phe Gly Gly Gly Thr
65                  70                  75                  80

Arg Val Thr Val Leu
                85

<210> SEQ ID NO 190
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asn Leu Trp Asp Lys Tyr Val Ser Trp Tyr Gln Gln Arg Pro Gly Gln
1               5                   10                  15

Pro Pro Val Leu Leu Leu Tyr Arg Asp Asn Met Arg Pro Ser Gly Ile
            20                  25                  30

Pro Glu Arg Phe Ser Gly Ser Asn Ser Asp Asn Thr Ala Thr Leu Thr
        35                  40                  45

Ile Ser Gly Thr Gln Ala Met Asp Glu Ala Asp Tyr Tyr Cys Gln Val
50                  55                  60

Trp Gly Thr Asp Ser Tyr Val Phe Gly Thr Gly Thr Lys Leu Ser Val
65                  70                  75                  80

Leu

<210> SEQ ID NO 191
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Ser Ser Asn Ile Gly Ser Asn Tyr Val Ser Trp Tyr Gln Gln Leu Pro
1               5                   10                  15

Gly Thr Ala Pro Lys Leu Leu Ile Tyr Asp Asn Asn Lys Arg Pro Ser
            20                  25                  30

Gly Ile Pro Asp Arg Phe Ser Gly Ser Lys Ser Gly Thr Ser Ala Thr
        35                  40                  45

Leu Ala Ile Ser Gly Leu Gln Thr Gly Asp Glu Ala Asp Tyr Tyr Cys
    50                  55                  60

Ala Thr Trp Asp Asp Ile Leu Arg Gly Arg Val Phe Gly Gly Gly Thr
65                  70                  75                  80

Lys Leu Ser Val Leu
                85

<210> SEQ ID NO 192
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Ser Gly Ser Ile Ala Gly Asn Tyr Val Gln Trp Tyr Gln Gln Arg Pro
1               5                   10                  15

Gly Ser Ser Pro Thr Thr Val Met Tyr Glu Asp Asn Gln Arg Pro Ser
            20                  25                  30

Gly Val Pro Asp Arg Phe Ser Gly Ser Ile Asp Ser Ser Ser Asn Ser
        35                  40                  45

Ala Ser Leu Thr Ile Ser Gly Leu Arg Ala Glu Asp Glu Ala Asp Tyr
    50                  55                  60

Tyr Cys Gln Ser Tyr Asp Ser Asn Asn His Val Val Phe Gly Gly Gly
65                  70                  75                  80

Thr Lys Leu Thr Val Leu
                85

<210> SEQ ID NO 193
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Ser Ser Asn Ile Gly Ser Asn Thr Val Asn Trp Tyr Gln Gln Leu Pro
1               5                   10                  15

Gly Thr Ala Pro Lys Leu Leu Ile Tyr Ser Asn Asn Gln Arg Pro Ser
            20                  25                  30

Gly Val Pro Asp Arg Phe Ser Gly Ser Lys Ser Gly Thr Ser Ala Ser
        35                  40                  45

-continued

Leu Ala Ile Ser Gly Leu Gln Ser Glu Asp Glu Ala Asp Tyr Tyr Cys
        50                  55                  60

Ala Ala Trp Asp Asp Ser Leu Asn Gly Pro Val Phe Gly Gly Gly Thr
 65                  70                  75                  80

Lys Leu Thr Val Leu
                85

<210> SEQ ID NO 194
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Ser Asp Val Asn Val Asp Asn Tyr Asn Ile Tyr Trp Tyr Gln Gln Lys
  1               5                  10                  15

Pro Gly Ser Pro Pro Arg Tyr Leu Leu Tyr Tyr Tyr Ser Asp Ser Asp
                 20                  25                  30

Lys Gly Gln Gly Ser Gly Val Pro Ser Arg Phe Ser Gly Ser Lys Asp
             35                  40                  45

Ala Ser Ala Asn Thr Gly Ile Leu Leu Ile Ser Gly Leu Gln Ser Glu
         50                  55                  60

Asp Glu Ala Asp Tyr Tyr Cys Met Ile Trp Pro Ser Asn Ala Trp Val
 65                  70                  75                  80

Phe Gly Gly Gly Thr Lys Leu Thr Val Leu
                 85                  90

<210> SEQ ID NO 195
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:

```
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (63)..(65)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (73)..(73)
<223> OTHER INFORMATION: Any amino acid

<400> SEQUENCE: 195

Lys Leu Gly Asp Lys Tyr Ala Cys Trp Tyr Xaa Xaa Lys Pro Gly Gln
1               5                   10                  15

Ser Pro Val Leu Val Ile Tyr Xaa Asp Xaa Lys Xaa Pro Ser Xaa Ile
            20                  25                  30

Pro Glu Arg Phe Ser Gly Ser Xaa Ser Gly Asn Thr Ala Thr Leu Thr
        35                  40                  45

Xaa Ser Gly Thr Gln Xaa Met Asp Glu Xaa Asp Tyr Tyr Cys Xaa Xaa
50                  55                  60

Xaa Asp Ser Xaa Thr Ala Val Val Xaa Gly Gly Thr Lys Leu Thr
65                  70                  75                  80

Val Leu

<210> SEQ ID NO 196
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Ser Ser Asn Ile Gly Ser Asn Thr Val Asn Trp Tyr Gln Gln Leu Pro
1               5                   10                  15

Gly Thr Ala Pro Lys Leu Leu Ile Tyr Asn Ser Asn Gln Arg Pro Ser
            20                  25                  30

Gly Val Pro Asp Arg Phe Ser Gly Ser Lys Ser Gly Thr Ser Ala Ser
        35                  40                  45

Leu Ala Ile Ser Gly Leu Gln Ser Glu Asp Glu Ala Asp Tyr Asp Cys
50                  55                  60

Ala Ala Trp Asp Asp Ser Leu Asn Gly Tyr Val Phe Gly Thr Gly Thr
65                  70                  75                  80

Lys Val Thr Val Leu
            85

<210> SEQ ID NO 197
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gln Val Gln Leu Val Gln Ser Gly Ala Glu Leu Lys Gln Pro Gly Glu
1               5                   10                  15

Ser Leu Lys Ile Ser Cys Lys Gly Ser Glu Tyr Ile Phe Thr Asn Tyr
```

```
            20                  25                  30
Trp Ile Val Trp Val Arg Gln Met Pro Gly Lys Gly Leu Glu Trp Met
        35                  40                  45

Gly Val Ile Tyr Pro Gly Asp Ser His Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Glu Ala Ser Asp Thr Ala Ile Tyr Tyr Cys
                85                  90                  95

Ala Thr Ser Pro Leu Thr Tyr Gly Tyr Tyr Leu Asp Tyr Trp Gly Gln
            100                 105                 110

Gly Thr Leu Val Thr Val Ser Ser
        115                 120

<210> SEQ ID NO 198
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Ile Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Gln Arg Leu Gly Tyr Ser Tyr Thr Trp Ala Ala Glu
            100                 105                 110

Tyr Phe Gln His Trp Gly Gln Gly Thr Leu Val Thr Val Ser Pro
        115                 120                 125

<210> SEQ ID NO 199
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Val Glu Ser Gly Gly Gly Leu Val Arg Pro Gly Gly
1               5                   10                  15

Ser Leu Thr Leu Ser Cys Ala Ala Ser Gly Phe Thr Phe Pro Asp Ala
            20                  25                  30

Trp Met Ser Arg Val Arg Gln Ser Pro Gly Thr Gly Leu Glu Trp Val
        35                  40                  45

Gly Arg Ile Gln Ser Lys Lys Asp Gly Gly Ala Ala Val Phe Ala Ala
    50                  55                  60

Pro Val Lys Gly Arg Phe Ser Ile Ser Arg Asp Asp Ser Lys Thr Thr
```

```
                65                  70                  75                  80
Pro Phe Phe Gln Met Asn Ser Met Lys Pro Glu Glu Ser Ala Val Tyr
                    85                  90                  95

Phe Cys Thr Ser His Leu Asp Tyr Gly Asp Tyr Glu Gly Trp Tyr Phe
                    100                 105                 110

Asp Leu Trp Gly His Gly Thr Arg Val Thr Val Ser Pro
                115                 120                 125

<210> SEQ ID NO 200
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Thr Phe Ser Arg Tyr
                20                  25                  30

Trp Ile His Trp Val Arg Leu Val Pro Gly Lys Gly Leu Val Trp Val
            35                  40                  45

Ser Arg Ile Ser Pro Asp Gly Asn Ser Ile Ser Tyr Ala Asp Ser Val
        50                  55                  60

Lys Gly Arg Phe Thr Ile Ser Arg Asp Asn Ala Glu Asn Thr Leu Tyr
65                  70                  75                  80

Leu Gln Met Asn Gly Leu Arg Ala Glu Asp Thr Ala Val Tyr Tyr Cys
                85                  90                  95

Val Ile Trp Pro Thr Pro Met Ile Thr Asp Leu Asp Val Trp Gly Gln
                100                 105                 110

Gly Thr Ala Val Thr Val Ser Pro
            115                 120

<210> SEQ ID NO 201
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Ala
                20                  25                  30

Tyr His Trp Gly Trp Ile Arg Gln Pro Pro Gly Lys Gly Leu Glu Trp
            35                  40                  45

Ile Gly Asn Ile Tyr His Ser Gly Ser Thr Ser Tyr Asn Pro Ser Leu
        50                  55                  60

Lys Ser Arg Val Thr Ile Leu Ile Asp Thr Ser Lys Ser Gln Phe Ser
65                  70                  75                  80

Leu Lys Leu Ser Ser Val Thr Ala Ala Asp Thr Ala Val Tyr Tyr Cys
                85                  90                  95

Ala Thr Val Ala Val Ala Gly Thr Lys Trp Phe Gly Pro Trp Gly Gln
                100                 105                 110

Gly Thr Leu Val Thr Val Ser Ser
```

```
                115                 120

<210> SEQ ID NO 202
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Phe Ser Ala Arg
            20                  25                  30

Asp Val Gly Val Gly Trp Ile Arg Gln Pro Pro Gly Lys Ala Leu Glu
        35                  40                  45

Trp Leu Ala Leu Ile Tyr Trp Asp Asp Ala Lys Tyr Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Gly His Lys Gly Val Ile Ala Val Arg Tyr Phe Asp Tyr Trp Gly
            100                 105                 110

Gln Gly Thr Leu Val Thr Val Ser Pro
        115                 120

<210> SEQ ID NO 203
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gln Val Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Asn Leu Thr Ser Val Thr Ala Ala Asp Thr Ala Val Tyr Tyr
                85                  90                  95

Cys Ala Arg His Tyr Lys Gly Phe Asp Leu Trp Gly Gln Gly Thr Leu
            100                 105                 110

Val Thr Val Ser Ser
        115

<210> SEQ ID NO 204
<211> LENGTH: 120
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 204

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Lys Gly Leu Glu Trp Val
        35                  40                  45

Ala Leu Ile Ser Tyr Asp Gly Thr Asn Lys His Tyr Ala Asp Ser Val
    50                  55                  60

Lys Gly Arg Phe Thr Val Ser Arg Asp Asp Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Val Arg Ala Leu Leu Thr Ala Ala Gly Pro Glu Asp Val Trp Gly Gln
            100                 105                 110

Gly Thr Thr Val Thr Val Ser Ser
        115                 120

<210> SEQ ID NO 205
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Glu Gly Arg Phe Thr Ile Ser Arg Asp Asn Ala Arg Asn Ser Leu Phe
65                  70                  75                  80

Leu Gln Met Asn Ser Leu Arg Ala Glu Asp Thr Ala Thr Tyr Phe Cys
                85                  90                  95

Ala Ala Lys Val Gly Leu Asp Phe Trp Gly Arg Gly Thr Leu Val Thr
            100                 105                 110

Val Ser Pro
        115

<210> SEQ ID NO 206
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Tyr Met His Trp Val Arg Gln Ala Pro Gly Gln Gly Leu Glu Trp Met
            35                  40                  45

Gly Ile Ile Asn Pro Ser Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Gly Asp Thr Gly Phe His Asp Pro Phe Asp Ile Trp Gly
             100                 105                 110

Gln Gly Thr Leu Val Thr Val Ser Ser
         115                 120
```

<210> SEQ ID NO 207
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

```
Glu Val Gln Leu Val Glu Ser Gly Gly Ala Leu Ala Gln Pro Gly Gly
  1               5                  10                  15

Ser Leu Arg Leu Ser Cys Ala Ala Ser Gly Phe Ile Phe Asp Asp Tyr
             20                  25                  30

Gly Met His Trp Val Arg Gln Val Pro Arg Lys Gly Leu Glu Trp Val
         35                  40                  45

Ser Gly Ile Ser Gly Asn Ser Val Asp Ile Gly Tyr Ala Asp Ser Val
 50                  55                  60

Asp Gly Arg Phe Thr Ile Ser Arg Asp Asn Ala Lys Asn Ser Leu Tyr
 65                  70                  75                  80

Leu Glu Met Asn Ser Leu Arg Pro Glu Asp Thr Ala Leu Tyr Tyr Cys
                 85                  90                  95

Val Lys Ala Trp Thr Val Val Gly Ala Thr Thr Asp Ser Phe Asp Phe
             100                 105                 110

Trp Gly Gln Gly Thr Leu Val Thr Val Ser Pro
         115                 120
```

<210> SEQ ID NO 208
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

```
Gln Val Gln Leu Val Gln Ser Gly Gly Asp Leu Val Gln Pro Gly Gly
  1               5                  10                  15

Ser Leu Arg Leu Ser Cys Ala Ala Ser Gly Phe Thr Phe Ser Asn His
             20                  25                  30

Trp Ile Asn Trp Val Arg Gln Ala Pro Gly Lys Gly Leu Glu Trp Val
         35                  40                  45

Ala Asn Ile Asn Glu Asp Gly Thr Ile Lys Tyr Tyr Val Asp Ser Val
 50                  55                  60

Lys Gly Arg Phe Thr Ile Ser Arg Asp Tyr Ala Lys Asn Ser Val Tyr
 65                  70                  75                  80
```

```
Leu Gln Met Asn Ser Leu Arg Ala Glu Asp Thr Ala Val Tyr Tyr Cys
                85                  90                  95

Ala Arg Arg Ser Gly Gly Pro Phe Asp Tyr Trp Gly Gln Gly Thr Leu
            100                 105                 110

Val Thr Val Ser Pro
        115

<210> SEQ ID NO 209
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ala Thr Val Thr Pro Leu Tyr Tyr Tyr Tyr Met Asp Val
            100                 105                 110

Trp Gly Lys Gly Thr Leu Val Thr Val Ser Ser
            115                 120

<210> SEQ ID NO 210
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Glu Pro Arg Ser Trp Glu Tyr Ser Ser Ser Tyr Tyr Phe
            100                 105                 110

Asp Tyr Trp Gly Gln Gly Thr Leu Val Thr Val Ser Pro
            115                 120                 125
```

<210> SEQ ID NO 211
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Val Gln Leu Gln Glu Ser Gly Pro Gly Leu Val Lys Pro Ser Glu
1               5                   10                  15

Thr Leu Ser Leu Ile Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Thr Gly Ser Ser Glu Tyr Asn Pro Ser Leu Lys
    50                  55                  60

Ser Arg Val Thr Ile Ser Ile Asp Thr Pro Lys Asn Gln Phe Ser Val
65                  70                  75                  80

Lys Leu Thr Ser Val Thr Ala Ala Asp Thr Ala Ile Tyr Tyr Cys Ala
                85                  90                  95

Arg Ser Arg Ser Pro Tyr Tyr Tyr Pro Glu Ala Phe Asp Pro Trp Gly
            100                 105                 110

Gln Gly Thr Leu Val Thr Val Ser Ser
        115                 120

<210> SEQ ID NO 212
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Arg Ser Gly Tyr Pro Thr Cys Asp Tyr Trp Gly Gln
            100                 105                 110

Gly Thr Leu Val Thr Val Ser Pro
        115                 120

<210> SEQ ID NO 213
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Thr Gly Ser Gly Tyr Thr Ile Tyr Ala Asp Ser Val
    50                  55                  60

Lys Gly Arg Phe Thr Ile Ser Arg Asp Asn Ala Lys Lys Leu Leu Tyr
65                  70                  75                  80

Leu Gln Met Asp Ser Leu Arg Ala Glu Asp Thr Ala Val Tyr Tyr Cys
                85                  90                  95

Ala Leu Gly Tyr Asp Tyr Trp Gly Gln Gly Thr Leu Val Thr Val Ser
            100                 105                 110

Pro

<210> SEQ ID NO 214
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ile Met Ser Trp Val Arg Gln Ala Pro Gly Lys Gly Pro Glu Trp Val
        35                  40                  45

Ser Ser Ile Gly Ala Ser Gly Leu Asn Thr Phe Tyr Ala Asp Ser Val
    50                  55                  60

Lys Gly Arg Phe Thr Ile Ser Arg Asp Ile Pro Lys Asn Thr Leu Tyr
65                  70                  75                  80

Leu Gln Met Asn Gly Leu Arg Val Glu Asp Thr Ala Ile Tyr Tyr Cys
                85                  90                  95

Ala Lys Ala Leu Val Val Gly Lys Asn Trp Phe Asp Pro Trp Gly Gln
            100                 105                 110

Gly Thr Leu Val Thr Val Ser Ser
        115                 120

<210> SEQ ID NO 215
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gln Val Gln Leu Val Glu Ser Gly Gly Gly Leu Val His Pro Gly Arg
1               5                   10                  15

Ser Leu Arg Leu Ser Cys Ala Thr Ser Gly Phe Ile Phe Asp Asp Tyr
            20                  25                  30

Ala Met His Trp Val Arg Gln Ala Pro Gly Lys Gly Leu Glu Trp Val

```
                35                  40                  45
Ser Gly Ile Ser Trp Asn Gly Gly Arg Ile Gly Tyr Glu Asp Ser Val
 50                  55                  60

Lys Gly Arg Phe Thr Ile Ser Arg Asp Asn Ala Lys Asn Ser Leu Tyr
 65                  70                  75                  80

Leu Glu Met Asn Ser Leu Arg Ala Glu Asp Thr Ala Leu Tyr Tyr Cys
                 85                  90                  95

Ala Lys Gly Pro Thr Ala Gly Tyr Tyr Asn Tyr Met Asp Val Trp Gly
            100                 105                 110

Lys Gly Thr Leu Val Asn Val Ser Ser
        115                 120

<210> SEQ ID NO 216
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gln Val Gln Leu Gln Gln Trp Gly Ala Gly Leu Leu Lys Pro Ser Glu
 1               5                  10                  15

Thr Leu Ser Leu Thr Cys Gly Val Tyr Asp Gly Ser Phe Ser Gly Tyr
                 20                  25                  30

Ser Trp Ser Trp Val Arg Gln Ser Pro Gly Lys Gly Leu Glu Trp Ile
             35                  40                  45

Gly Glu Ile Ser His Arg Gly Val Thr Asp Tyr Asn Pro Phe Leu Lys
 50                  55                  60

Ser Arg Val Thr Ile Ser Leu Asp Val Ser Lys Arg Gln Phe Ser Leu
 65                  70                  75                  80

Gln Leu Thr Ser Leu Thr Ala Ala Asp Thr Ala Thr Tyr Tyr Cys Ala
                 85                  90                  95

Arg Leu Glu Pro Gly Asn Phe Trp Phe Asp Pro Trp Gly Gln Gly Thr
            100                 105                 110

Leu Val Thr Val Ser Ser
        115

<210> SEQ ID NO 217
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Asn Trp Ile Arg Gln Pro Pro Gly Lys Gly Leu Glu Trp Ile
             35                  40                  45

Gly Glu Asn Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Arg Leu Arg Ser Val Thr Ala Ala Asp Thr Ala Val Tyr Tyr Cys Ala
```

```
                    85                  90                  95

Arg Gly Phe Leu Gly Gly Met Asp Val Trp Gly Gln Gly Thr Leu Val
                100                 105                 110

Thr Val Ser Ser
        115

<210> SEQ ID NO 218
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Met Ser Ser Tyr
            20                  25                  30

Tyr Trp Ser Trp Ile Arg Gln Pro Ala Gly Lys Gly Leu Glu Trp Ile
        35                  40                  45

Gly Arg Phe Tyr Ser Ser Ala Ser Ile Ser Tyr Asn Pro Ser Leu Gln
    50                  55                  60

Ser Arg Val Thr Met Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Val
                85                  90                  95

Ser Gly Trp Tyr Arg Ala Phe Val Ser Tyr Trp Gly Gln Gly Thr Leu
                100                 105                 110

Val Thr Val Ser Ser
        115

<210> SEQ ID NO 219
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Ser Phe Thr Asp Tyr
            20                  25                  30

Phe Ile His Trp Val Arg Gln Ala Pro Gly Gln Gly Leu Glu Trp Met
        35                  40                  45

Gly Trp Ile Asn Pro Asn Ser Gly Ala Thr Lys Tyr Ala Gln Lys Phe
    50                  55                  60

Gln Gly Arg Val Thr Met Thr Arg Asp Thr Ser Ile Ser Thr Ala Phe
65                  70                  75                  80

Met Asp Leu Ser Ser Leu Thr Ser Asp Asp Thr Ala Val Tyr Phe Cys
                85                  90                  95

Ala Arg Phe Glu Gly Val Val Pro Thr Ile Leu His Ser Gly Tyr Asp
                100                 105                 110

Tyr Trp Gly Gln Gly Thr Leu Val Thr Val Ser Ser
            115                 120
```

```
<210> SEQ ID NO 220
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Ser Ser Leu Ser Thr Ser
            20                  25                  30

Gly Glu Ala Leu Gly Trp Ile Arg Gln Pro Pro Gly Lys Ala Leu Glu
        35                  40                  45

Trp Leu Ala Leu Ile Phe Trp Asp Gly Asp Lys Arg Tyr Arg Pro Ser
    50                  55                  60

Leu Lys Ser Arg Leu Ser Ile Thr Lys Asp Thr Ser Lys Asn Gln Val
65                  70                  75                  80

Val Leu Lys Met Thr Asn Met Asp Pro Val Asp Thr Ala Thr Tyr His
                85                  90                  95

Cys Ala His Arg Leu Phe Tyr Gln Ser Ile Thr Ser Tyr Gly Asn Pro
            100                 105                 110

Phe Asp Ile Trp Gly Gln Gly Thr Met Val Thr Val Ser Ser
        115                 120                 125

<210> SEQ ID NO 221
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Ile Thr Leu Lys Glu Ser Gly Pro Thr Leu Val Lys Pro Thr Gln
1               5                   10                  15

Thr Leu Thr Leu Ala Cys Thr Phe Ser Ala Phe Ser Leu Ser Thr Ser
            20                  25                  30

Gly Val Gly Val Gly Trp Phe Arg Gln Pro Pro Gly Lys Ala Leu Glu
        35                  40                  45

Trp Leu Ala Leu Ile Tyr Trp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Pro Arg Pro Asp Tyr Phe Gly Ser Gly Ser Tyr Met
            100                 105                 110

Ala Phe Asp Pro Trp Gly Gln Gly Thr Leu Val Thr Val Ser Ser
        115                 120                 125

<210> SEQ ID NO 222
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222
```

-continued

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Asn Tyr
            20                  25                  30

Ala Ile Asn Trp Val Arg Gln Ala Pro Gly Gln Gly Leu Glu Trp Met
        35                  40                  45

Gly Trp Ile Asn Ala Tyr Asn Gly His Thr Asn Tyr Ala Gln Lys Leu
    50                  55                  60

Gln Gly Arg Val Thr Met Thr Thr Asp Thr Ser Thr Ser Thr Ala Tyr
65              70                  75                  80

Met Glu Leu Arg Ser Leu Arg Ser Asp Asp Thr Ala Val Tyr Tyr Cys
                85                  90                  95

Ala Arg Asp Met Val Arg Gly Val Ile Leu Trp Phe Asp Pro Trp Gly
                100                 105                 110

Gln Gly Thr Leu Val Thr Val Ser Ser
            115                 120

<210> SEQ ID NO 223
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Glu Ser Phe Ser Gly His
            20                  25                  30

Tyr Trp Ala Trp Ile Arg Gln Pro Pro Gly Lys Gly Leu Glu Trp Ile
        35                  40                  45

Gly Glu Ile Glu Tyr Ser Gly Pro Thr Asn Tyr Asn Pro Ser Leu Lys
    50                  55                  60

Ser Arg Val Ser Met Ser Val Tyr Thr Ser Lys Lys Arg Phe Phe Leu
65              70                  75                  80

Lys Leu Thr Ser Val Thr Ala Ala Asp Thr Ala Val Tyr Tyr Cys Ala
                85                  90                  95

Arg Ala Pro Met Val Arg Gly Val Pro Phe Asp Phe Asp Tyr Trp Gly
                100                 105                 110

Gln Gly Thr Leu Val Thr Val Ser Ser
            115                 120

<210> SEQ ID NO 224
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Gln Val Gln Leu Gln Gln Trp Gly Ser Gly Leu Leu Lys Pro Ser Glu
1               5                   10                  15

Thr Leu Ser Leu Thr Cys Ala Val Tyr Gly Gly Ser Phe Ser Gly His
            20                  25                  30

Tyr Trp Ser Trp Ile Arg Gln Pro Pro Gly Arg Gly Leu Glu Trp Ile
        35                  40                  45

```
Gly Glu Ile Asn His Gly Gly Ser Thr Ser Tyr Asn Pro Ser Leu Lys
            50                  55                  60

Ser Arg Val Ser Ile Ser Val Asp Thr Ser Lys Glu Gln Phe Ser Leu
 65                  70                  75                  80

Thr Leu Ser Ser Val Thr Ala Ala Asp Thr Ala Val Tyr Tyr Cys Ala
                    85                  90                  95

Arg Gly Gly Asp Tyr Tyr Asp Asp Tyr Ile Ala Asp Trp Gly Gln Gly
                100                 105                 110

Thr Leu Val Thr Val Ser Ser
            115
```

<210> SEQ ID NO 225
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Gly Arg Gly Thr Ile Ser Leu Asp Thr Ser Lys Asn Gln Phe Ser Leu
 65                  70                  75                  80

Arg Leu Ser Ser Met Thr Ala Ala Asp Thr Ala Val Tyr Tyr Cys Ala
                85                  90                  95

Arg Glu Ser Thr Thr Tyr Gly Tyr Gly Arg Phe Asp Leu Trp Gly Arg
                100                 105                 110

Gly Thr Leu Val Thr Val Ser Pro
            115                 120
```

<210> SEQ ID NO 226
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 226

```
Pro Xaa Glu Leu Xaa Glu Ser Gly Pro Gly Leu Val Lys Pro Ser Glu
 1               5                  10                  15

Thr Leu Ser Leu Thr Cys Ser Val Ser Gly Gly Ser Leu Asn Ser Ser
                20                  25                  30

Thr Asn Phe Trp Gly Trp Ile Arg Gln Pro Pro Gly Lys Gly Leu Glu
            35                  40                  45
```

```
Trp Ile Ala Thr Ile Tyr Trp Ser Gly Tyr Thr Gln Tyr Asn Pro Ser
    50                  55                  60

Leu Lys Ser Arg Val Thr Thr Ser Glu Asp Thr Ser Lys Asn Gln Phe
65                  70                  75                  80

Ser Leu Lys Met Thr Ser Val Thr Ala Ala Asp Thr Ala Ile Tyr Tyr
                85                  90                  95

Cys Ala Arg Leu Asn Phe Gly Val Glu Arg Leu Asp Tyr Trp Gly Gln
            100                 105                 110

Gly Thr Leu Val Thr Val Ser Pro
        115                 120

<210> SEQ ID NO 227
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Phe
            20                  25                  30

Tyr Trp Thr Trp Ile Arg Arg His Pro Gly Lys Gly Leu Glu Trp Ile
        35                  40                  45

Gly Glu Ile Asn Asp Arg Gly Ser Thr Ser Tyr Asn Pro Ser Leu Lys
    50                  55                  60

Ser Arg Val Thr Ile Ser Ile Asp Thr Ser Lys Ser Leu Phe Ser Leu
65                  70                  75                  80

Lys Leu Thr Ser Val Thr Ala Ala Asp Thr Ala Val Tyr Tyr Cys Ala
                85                  90                  95

Arg Gly Gly Leu Asp Gly Asp Tyr Ala Ser Leu Trp Gly Gln Gly Ala
            100                 105                 110

Leu Val Thr Val Ser Ser
        115

<210> SEQ ID NO 228
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95
```

Ser Arg Arg Arg Ser Tyr Asp Glu Ile Leu Thr Pro Tyr Ile Leu Val
            100                 105                 110

Asp Ser Gly Gln Gly Asn Leu Val Thr Val Ser Pro
        115                 120

<210> SEQ ID NO 229
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gln Val Gln Leu Val Gln Ser Gly Ala Glu Val Lys Lys Pro Gly Glu
1               5                   10                  15

Ser Leu Lys Ile Ser Cys Lys Ala Ser Gly Tyr Ile Phe Thr Asn Tyr
            20                  25                  30

Trp Ile Gly Trp Val Arg Gln Met Pro Gly Lys Gly Leu Glu Trp Met
        35                  40                  45

Gly Leu Ile His Pro Gly Asp Ser Asp Thr Arg Tyr Ser Pro Phe Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Gln Gly Ser Asp Thr Ala Met Tyr Phe Cys
                85                  90                  95

Ala Ser Gly Gly Lys Tyr Tyr Phe Asp His Trp Gly Gln Gly Thr Leu
            100                 105                 110

Val Thr Val Ser Ser
        115

<210> SEQ ID NO 230
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gln Val Gln Leu Val Gln Ser Gly Ala Glu Val Lys Lys Ser Gly Glu
1               5                   10                  15

Ser Leu Lys Ile Ser Cys Arg Gly Ser Gly Tyr Arg Phe Ala Thr Tyr
            20                  25                  30

Trp Ile Gly Trp Val Arg Gln Leu Pro Gly Lys Gly Leu Glu Trp Met
        35                  40                  45

Gly Ile Ile Tyr Pro Gly Asp Thr Thr Ser Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Thr Leu Lys Ala Ser Asp Thr Ala Met Tyr Tyr Cys
                85                  90                  95

Ala Arg Leu Glu Arg Val Val Ser Arg Asn Leu Tyr Ile Gly Met Asp
            100                 105                 110

Val Trp Gly Gln Gly Thr Thr Val Thr Val Ser Pro
        115                 120

<210> SEQ ID NO 231
<211> LENGTH: 125

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Phe Ser Thr Tyr
            20                  25                  30

Tyr Trp Ser Trp Ile Arg Gln Pro Pro Gly Lys Gly Leu Glu Trp Ile
        35                  40                  45

Gly Glu Ile Ser His Ile Gly Tyr Thr Asn Tyr Ser Pro Ser Leu Lys
    50                  55                  60

Gly Arg Val Thr Ile Ser Leu Ala Thr Ser Lys Asn Glu Phe Ser Leu
65                  70                  75                  80

Arg Leu Asn Ser Val Thr Ala Ala Asp Thr Ala Met Tyr Tyr Cys Ala
                85                  90                  95

Arg Gly Leu Arg Val Gly Gly Cys Ser Gly Gly Tyr Cys Asp Pro Phe
            100                 105                 110

Ser Tyr Trp Gly Gln Gly Ala Leu Val Thr Val Ser Ser
        115                 120                 125

<210> SEQ ID NO 232
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Tyr Trp Ser Trp Ile Arg Gln Pro Ala Gly Lys Gly Leu Glu Trp Ile
        35                  40                  45

Gly Arg Phe Tyr Ala Ser Gly Gly Thr His Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ile Ser Val Thr Ala Ala Asp Thr Ala Val Tyr Tyr Cys Thr
                85                  90                  95

Arg Ala Ser Gly Thr Gly Thr Thr Gly Phe Asp Tyr Trp Gly Gln Gly
            100                 105                 110

Thr Leu Val Thr Val Ser Ser
        115

<210> SEQ ID NO 233
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Val Gln Leu Gln Glu Ser Gly Pro Gly Leu Val Lys Pro Ser Glu

-continued

```
                1               5                  10                  15
Thr Leu Ser Leu Thr Cys Thr Val Ser Gly Asp Ser Met Ser Ser Tyr
                20                  25                  30

Tyr Trp Ser Trp Ile Arg Gln Pro Ala Gly Lys Gly Leu Glu Trp Ile
            35                  40                  45

Gly Arg Phe Tyr Ser Ser Ala Ser Ile Ser Tyr Asn Pro Ser Leu Gln
        50                  55                  60

Ser Arg Val Thr Met Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Val
                85                  90                  95

Ser Gly Trp Tyr Arg Ala Phe Val Ser Tyr Trp Gly Gln Gly Thr Leu
            100                 105                 110

Val Thr Val Ser Ser
            115
```

<210> SEQ ID NO 234
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Asn Tyr
                20                  25                  30

Ala Ile Asn Trp Val Arg Gln Ala Pro Gly Gln Gly Leu Glu Trp Met
            35                  40                  45

Gly Trp Ile Asn Ala Tyr Asn Gly His Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Met Val Arg Gly Val Ile Leu Trp Phe Asp Pro Trp Gly
            100                 105                 110

Gln Gly Thr Leu Val Thr Val Ser Ser
        115                 120
```

<210> SEQ ID NO 235
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
```

```
                50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Pro Arg Gly Tyr Ser Gly Tyr Asp Phe Asp Tyr Trp Gly Gln Gly
            100                 105                 110

Thr Leu Val Thr Val Ser Ser
        115
```

<210> SEQ ID NO 236
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

```
Gln Val Gln Leu Val Gln Ser Gly Ala Glu Val Lys Lys Pro Gly Ala
 1               5                  10                  15

Ser Val Lys Val Ser Cys Lys Ala Phe Gly Tyr Ser Phe Thr Asp Tyr
             20                  25                  30

Phe Ile His Trp Val Arg Gln Ala Pro Gly Gln Gly Leu Glu Trp Met
         35                  40                  45

Gly Trp Ile Asn Pro Asn Ser Gly Ala Thr Lys Tyr Ala Gln Lys Phe
     50                  55                  60

Gln Gly Arg Val Thr Met Thr Arg Asp Thr Ser Ile Ser Thr Ala Phe
 65                  70                  75                  80

Met Asp Leu Ser Ser Leu Thr Ser Asp Asp Thr Ala Val Tyr Phe Cys
                 85                  90                  95

Ala Arg Phe Glu Gly Val Val Pro Thr Ile Leu His Ser Gly Tyr Asp
            100                 105                 110

Tyr Trp Gly Gln Gly Thr Leu Val Thr Val Ser Ser
        115                 120
```

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ggcccaggcg gccgagctcg tgc                                              23

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ggcccaggcg gccgagctcg tgc                                              23

<210> SEQ ID NO 239
<211> LENGTH: 23
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 239
ggcccaggcg gccgagctcg tgt                                            23

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ggcccaggcg gccgagctcg tgc                                            23

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ggcccaggcg gccgagctcg tgg                                            23

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ggcccaggcg gccgagctcg ccc                                            23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ggcccaggcg gccgagctcg ccc                                            23

<210> SEQ ID NO 244
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggcccaggcg gccgagctca tgc                                            23

<210> SEQ ID NO 245
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 245
ggcccaggcg gcccgagctc gtgc                                              24

<210> SEQ ID NO 246
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ggcccaggcg gccgagctcg tgc                                               23

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ggcccaggcg gccgagctcg tgg                                               23

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ggcccaggcg gccgagctcg ccc                                               23

<210> SEQ ID NO 249
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ggcccaggcg gccgagctcg ccc                                               23

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ggcccaggcg gccgagctcg tgc                                               23

<210> SEQ ID NO 251
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 251
ggcccaggcg gccgagctcg tgc                                              23

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ggcccaggcg gccgagctcg tgc                                              23

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ggcccaggcg gccgagctca tgc                                              23

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ggcccaggcg gccgagctcg tgg                                              23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
ggcccaggcg gccgagctcg tgg                                              23

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ggcccaggcg gccgagctcg tgg                                              23

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 257
ggcccaggcg gccgagctca cac                                            23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ggcccaggcg gccgagctcg tgc                                            23

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
ggcccaggcg gccgagctcg tgc                                            23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ggcccaggcg gccgagctca cac                                            23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ggcccaggcg gccgagctcg ccc                                            23

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
ggcccaggcg gccgagctcg tgg                                            23

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ggcccaggcg gccgagctca cac                                              23

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ggcccaggcg gccgagctcg tgg                                              23

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ggcccaggcg gccgagctcg tgg                                              23

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ggcccaggcg gccgagctca cac                                              23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ggcccaggcg gccgagctcg tgc                                              23

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ggcccaggcg gccgagctca cgc                                              23

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 269
ggcccaggcg gccgagctcg tgc                                           23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ggcccaggcg gccgagctca cac                                           23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ggcccaggcg gccgagctcg agc                                           23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ggcccaggcg gccgagctca tgc                                           23

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
ggcccaggcg gccgagctca cac                                           23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ggcccaggcg gccgagctcg tgc                                           23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
```

```
ggcccaggcg gccgagctcg tgc                                              23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
ggcccaggcg gccgagctcg tgc                                              23

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ggcccaggcg gccgagctcg tgc                                              23

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ggcccaggcg gccgagctcg cca                                              23

<210> SEQ ID NO 279
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ggccaggccg gccagcacca tca                                              23

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ggccaggccg gccagcacca tca                                              23

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
```
ggccaggccg gccagcacca tca                                              23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
ggccaggccg gccagcacca tca                                              23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ggccaggccg gccagcacca tca                                              23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ggccaggccg gccagcacca tca                                              23

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ggccaggccg gccagcacca tca                                              23

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ggccaggccg gccagcacca tca                                              23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ggccaggccg gccagcacca tca                                              23

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
ggccaggccg gccagcacca tca                                           23

<210> SEQ ID NO 289
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ggccaggccg gccagcacca tca                                           23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ggccaggccg gccagcacca tca                                           23

<210> SEQ ID NO 291
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ggccaggccg gccagcacca tca                                           23

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
ggccaggccg gccagcacca tca                                           23

<210> SEQ ID NO 293
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ggccaggccg gccagcacca tca                                           23

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
ggccaggccg gccagcacca tca                                              23

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
ggccaggccg gccagcacca tca                                              23

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
ggccaggccg gccagcacca tca                                              23

<210> SEQ ID NO 297
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
ggccaggccg gccagcacca tca                                              23

<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
ggccaggccg gccagcacca tca                                              23

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ggccaggccg gccagcacca tca                                              23

```
<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
ggccaggccg gccagcacca tca                                              23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
ggccaggccg gccagcacca tca                                              23

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
ggccaggccg gccagcacca tca                                              23

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
ggccaggccg gccagcacca tca                                              23

<210> SEQ ID NO 304
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
ggccaggccg gccagcacca tca                                              23

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
ggccaggccg gccagcacca tca                                              23

<210> SEQ ID NO 306
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
ggccaggccg gccagcacca tca                                             23

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ggccaggccg gccagcacca tca                                             23

<210> SEQ ID NO 308
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ggccaggccg gccagcacca tca                                             23

<210> SEQ ID NO 309
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
ggccaggccg gccagcacca tca                                             23

<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
ggccaggccg gccagcacca tca                                             23

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
ggccaggccg gccagcacca tca                                             23

<210> SEQ ID NO 312
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
ggccaggccg gccagcacca tca                                              23

<210> SEQ ID NO 313
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ggccaggccg gccagcacca tca                                              23

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
ggccaggccg gccagcacca tca                                              23

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
ggccaggccg gccagcacca tca                                              23

<210> SEQ ID NO 316
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ggccaggccg gccagcacca tca                                              23

<210> SEQ ID NO 317
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
ggccaggccg gccagcacca tca                                              23

<210> SEQ ID NO 318
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 318
ggccaggccg gccagcacca tca                                            23

<210> SEQ ID NO 319
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
ggccaggccg gccagcacca tca                                            23

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
ggccaggccg gccagcacca tca                                            23

<210> SEQ ID NO 321
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Ala Glu Asp Glu Ala Asp Tyr Tyr Cys Ser Ser Tyr Thr Ser Ser Ser
1               5                   10                  15
Thr Tyr Val Leu Phe Gly Gly Gly Thr Lys Leu Thr Val Leu
            20                  25                  30

<210> SEQ ID NO 322
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Ser Ser Ile His Phe Arg Pro Trp Asp Gln Ser Gly Tyr Gln Thr Asn
1               5                   10                  15
Cys Gly Cys Thr Ile Cys Leu His Leu Pro Ala Ile
            20                  25

<210> SEQ ID NO 323
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323
```

```
Ala Val Glu Ile Trp Asn Cys Leu Cys Cys Val Pro Ala Glu
1               5                   10
```

<210> SEQ ID NO 324
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

```
Leu Leu Ser Gln Arg Gly Gln Ser Thr Val Glu Gly Gly
1               5                   10
```

<210> SEQ ID NO 325
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

```
Arg Pro Pro Ile Gly
1               5
```

<210> SEQ ID NO 326
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

```
Leu Pro Gly Glu Cys His Arg Ala Gly Gln Gln Gly Gln His Tyr Ser
1               5                   10                  15

Leu Ser Ser Thr Leu Thr Leu Ser
            20
```

<210> SEQ ID NO 327
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

```
Phe Thr Ile Ser Arg Asp Asn Ser Lys Asn Thr Leu Tyr Leu Gln Met
1               5                   10                  15

Asn Ser Leu Arg Ala Glu Asp Thr Ala Val Tyr Tyr Cys Ala Lys Asp
            20                  25                  30

Ser Asn Tyr Cys Ser Gly Gly Ser Cys Tyr Gly Ser Phe Leu Ile Tyr
        35                  40                  45

Tyr Tyr Tyr Gly Met Asp Val Trp Gly Gln Gly Thr Thr Val Ile Val
    50                  55                  60

Ser Pro
65
```

<210> SEQ ID NO 328
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 328

Tyr Gln Leu Leu Trp Pro Arg Asp Thr Ile Phe
1               5                   10

<210> SEQ ID NO 329
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Leu Val Leu Leu Glu Gly Thr Leu Val Thr Val Ser Pro
1               5                   10

<210> SEQ ID NO 330
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tttttttttt tttttttt                                                   18
```

ANTIBODY PHAGE DISPLAY LIBRARY

RELATED APPLICATIONS

The present application claims priority under 37 U.S.C. § 371 to International Patent Application No. PCT/IN2017/050257, filed Jun. 23, 2017, which claims priority to and the benefit of Indian Patent Application Nos. 201621006661, filed on Jun. 26, 2016, and 201621019380, filed on Jul. 3, 2016. The contents of these applications are hereby incorporated by reference in their entireties.

SEQUENCE LISTING

The instant application contains a Sequence Listing which has been filed electronically in ASCII format and is hereby incorporated by reference in its entirety. Said ASCII copy, created on Feb. 28, 2019, is named 120174-0107_SL.txt and is 242,366 bytes in size.

FIELD OF THE INVENTION

The present invention relates to the field of biotechnology. In particular, the present invention relates to a large antibody phage display library, a process for arriving at the library and a method of producing antigen-specific Fabs through the said library.

BACKGROUND OF THE INVENTION

Antibody discovery was enabled by immunizing a non-human host species to generate polyclonal antibodies from serum or generate monoclonal antibodies by the hybridoma technology (Köhler G and Milstein C, 1975). The process of antibody discovery by immunization is however dependent on the uncertainties in the biology of immunization and results in full length non-human IgGs only. Further, such non-human IgGs are recognized as foreign by our immune system resulting in anti-species antibodies. The advent of technologies of grafting the antigen-recognizing rodent variable domains on human constant domains (-ximAbs) or grafting the complementarity-determining regions from rodents on human variable region frameworks (-zumabs) as well as the technology of mice transgenic for human Ig loci have reduced the problem of generating anti-species antibodies. Nonetheless, this method of human antibody generation, particularly when it comes to toxic antigens or protein targets that are highly conserved in amino acid sequence between humans and rodents, is not preferred.

Another alternative to this technology is Antibody Phage Display Library (APDL). Antibody phage display is a technique that can be used for the production of antigen-specific antibodies. One of the early references of APDL pertains to George P Smith (1985), who first described the phage display concept. APDL uses in vitro recombinant antibody synthesis techniques that rely on cloning of immunoglobulin gene segments to create libraries of antibodies. In this technique, antibody genes or gene fragments are fused to phage genes, thus allowing the antibody genes to be expressed and displayed as fusions to coat proteins on phage surfaces.

The ability to generate large repertoires of human antibodies combined with total display of the expressed repertoire allows the selection of individual antibodies with a desired specificity after biopanning against a target molecule. With this technique, tailor-made antibodies can be synthesized and selected to acquire the desired affinity of binding and specificity for in vitro and in vivo diagnosis, or for immunotherapy of human disease. This technique is particularly useful for production of antibodies for difficult antigens such as proteins homologous to human proteins, an area where conventional antibody producing methods of immunization often fail.

The antibody format commonly used for phage display include single-chain variable fragment (scFv) and Fragment antibody binding (Fab) fragments. scFv are monovalent structures that comprises the V region of the heavy and light chains of antibody molecules fused into a single polypeptide chain via a short flexible linker. Each Fab displays a single antigen binding site and consists of an Fd chain ($V_H$-$C_H1$-hinge fragment) and a light chain ($V_L$-$C_L$) bonded to each other at the C-terminus by a disulfide bond.

Prior art discloses certain scFv libraries and synthetic libraries. For instance, WO1992/001047 A1 discloses an antibody library in scFv format. Libraries with sizes of $10^7$ and $2 \times 10^7$ cfu constructed from a naïve human IgM source, and $5 \times 10^7$ cfu from naïve human IgG source cloned in phagemid vector pHEN1 in scFv format are disclosed. Secretion of scFv and Fab antibody fragments from a phagemid vector transformed in amber suppressor host HB2151 and their detection in Westerns using polyclonal or tag-specific antibodies is disclosed. However, WO'047 does not disclose as to whether such secreted scFvs or Fabs from bacterial cultures can bind to an antigen of interest or not.

U.S. Pat. No. 6,794,128 B2 discloses a scFv phage antibody library of $7.0 \times 10^9$ members. It further discloses selection of library on antigens and confirmation of the binders by phage ELISA. However, it appears that there are significant differences between the number of samples screened for such antigen-specific ELISA and the number of corresponding hits. Furthermore, the proportion of conversion of hits to water-soluble scFvs capable of recognizing the cognate antigen is very low.

U.S. Pat. No. 6,696,248 B1 discloses a fully synthetic human combinatorial antibody library (HuCAL) based on consensus sequences of the human immunoglobulin repertoire. The format used is the scFv format and the size of the libraries varied between $10^7$ and greater than $10^8$ members. US'248 discloses yields of 5-10 mg/L of purified scFvs but affinities of such scFvs are not disclosed.

US2005/0119455 A1 discloses (i) single chain Fv (scFv); (ii) single chain Fv with zipper domain (scFvzip); (iii) Fab fragment (Fab); and (iv) Fab fragment with zipper domain (Fabzip) fused to the C-terminal domain of the minor coat protein (gIII). Further, the polypeptide is expressed as a fusion protein on the surface of viral particle where the heavy chain variable domain is fused to a portion of a viral coat protein. US'455 further discloses display of $10^{11}$ polypeptide sequences or antibody variable sequence in the scFv format. Construction of F(ab')$_2$ libraries with L3/H3 diversity and both Fab and F(ab')$_2$ libraries with H1/H2/H3 diversities are also disclosed but it does not provide any method to arrive at such libraries and size of the libraries are also not set out in this document.

US2005/0164180 A1 discloses a method for generating a dAB (single heavy domain antibody fragment) phage library derived from human monoclonal antibody BT32/46 having $V_H$ portion of the said monoclonal antibody mutated in the CDR regions for enhanced expression. The description discloses a library size of $2.4 \times 10^8$ cfu.

KR2009/100961392 discloses a method for producing an antibody phage surface display library using the $V_H$3-23/$V_L$1g gene as a framework, and the phage display vector pFDV. The scFv gene library consisting of sublibraries of AE ($2.1\times10^9$ cfu), BE($2.7\times10^9$ cfu), CF($1.1\times10^9$ cfu) and DF($1.7\times10^9$ cfu) was obtained by sequential polymerisation between the cleaved sublibraries and pFDV vector at SfiI sites. Borate extracts of periplasm from single colonies of strain ER2537 from panning rounds for performing ELISA and declaring hits are disclosed, however score ratio and affinity estimates for such hits are not disclosed.

US2009/0054254 A1 provides a method for generating immunoglobulin libraries by isolating RNA from a subset of B cells. It discloses a method for generating an immunoglobulin library, comprising the steps of: a) isolating a subset of B cells essentially of IgM memory B origin; b) isolating RNA from this subset of B cells; c) converting the isolated RNA into cDNA; d) amplifying immunoglobulin sequences of cDNA; e) inserting the amplified immunoglobulin sequences into vector, and f) transforming a host cell with the vector containing the amplified sequences to obtain an immunoglobulin library. The format disclosed is both scFv and Fab, although the size of the library disclosed is for the scFv format only ($10^7$ cfu).

US2011/236372 A1 discloses synthetic antibody libraries in scFv format. The description discloses total library size to be higher than $10^9$ individual clones, of which ~80% were determined to be capable of secreting scFv in bacterial supernatant.

Thus, the prior arts are predominantly drawn to methods of producing antibody phage display library in scFv format. However, these methods do not disclose an ultra-large naive library in the Fab format. Using Fab format for producing antibody phage display library offer certain advantages when compared to the other formats of phage display such as single chain Fv (scFv). The advantage of Fab phage display library is that antigen-selected Fabs out of such libraries have high stability as water-dissolved proteins. In contrast, antibodies in single chain fragment variable (scFv) format have the tendency to form aggregates and are relatively unstable over longer periods of time (Weidner K M et al., 1992; Holliger P et al., 1993; Kortt et al., 1997; Quintero-Hernandez V et al., 2007). Furthermore, the scFvs may show a reduced affinity of up to one order of magnitude compared to the corresponding Fab fragments.

Certain prior art disclose naïve human Fab libraries. For instance, EP2067788 A2 discloses a naïve human Fab library with $4.3\times10^{10}$ individual clones. EP'788 further discloses scoring antigen-specific hits using periplasmic extracts, although the method cited for hit screening from periplasmic extracts is not designed to allow periplasmic extraction of Fabs but scFvs.

From the available citations, it is evident that while it is easy to get libraries of a small size ($10^8$-$10^9$ clones), it is not at all easy to obtain a library of a size that is the theoretical limit of mammalian immune diversity ($10^{14}$ permutations). Furthermore, the chances of generating false positives or no binders at all remain very high due to the inherent flaws of the recombinant antibody assembly and discovery process, and also due to the biology of phages that tend to propagate non-recombinant (wild type) or partially recombinant phages (parasite phages) over the recombinant ones. Therefore, the present invention is drawn so as to overcome this disadvantage.

Regardless of the library format, biopanning may be employed to select binders from antibody libraries. Biopanning may be conducted in vitro by immobilizing pure antigens on solid surfaces such as polystyrene, or by biotinylating the pure antigens and immobilizing them on streptavidin-coated polystyrene surfaces, followed by exposure to phages displaying the Fv domains in various formats. Biopanning may also be conducted in vitro by capturing the biotinylated antigens on streptavidin coated magnetic microbeads, followed by exposure to phages displaying the Fv domains in various formats. The latter approach has the advantage of being able to carry out panning in liquid phase, where the laws governing reaction equilibrium and kinetics may be applied far more confidently to pull out binders with desirable affinity and thermodynamic characteristics. Biopanning may also be carried out against target antigens present on the surface or inside a living cell, or against antigens such as cell surface receptors stabilized in lipid bilayers.

During the process of biopanning, the number of specific binders (binders) to a given antigen is a minuscule proportion of the entire gamut of non-specific binders (background) present in the phage population. Several rounds of panning are therefore required to enrich the specific binding subpopulation over the background. Furthermore, the small proportion of specific binders captured at each round of panning does require amplification of these binders by transduction in $F^+$ hosts to be able to conduct the next round of panning. These amplification cycles however have the potential to propagate any genome (with phage replication ori) that has a growth advantage—phages containing a shorter length of genomes or translational stop codons within open reading frames appear to possess such an advantage. This biological fact can complicate the retrieval and analysis of genuine binders, particularly in case of phages derived from phagemid libraries where most phages are bald to begin with.

The various methods of biopanning discussed in prior art involves incubation of phage clones with target antigen followed by recovery of the bound phage to the target antigen by various elution strategies. Further, methods for affinity assessment by ELISA, Westerns and SPR has been disclosed in the prior art, but the exact method for obtaining optimal yield of the antibodies against the target antigen with desired manufacturability characteristics is not disclosed.

Thus, the various existing antibody phage display libraries and the method of their production are described with diversity capture as their major goal, with little or no attention paid to the problems inherent in monoclonal lead identification or manufacturability aspects. Therefore, large antibody phages display libraries and the methods to produce antibodies reproducibly, confidently, and speedily out of them needs to be developed. The present invention provides methods to produce large and high diverse antibody phage display libraries which are commercially viable and could be produced in a short span of time period. The present invention provides novel methods of making large antibody phage display libraries as well as antibody retrieval from such libraries that are suitable for manufacture using established tools of biotechnology.

OBJECT OF THE INVENTION

The object of the invention is to create large antibody phage display library for its use as therapeutic and diagnostic purposes.

SUMMARY OF THE INVENTION

The present invention discloses a naïve antibody phage display library (APDL) having a size ranging between $8.86\times10^{10}$ to $9.13\times10^{11}$ ($3.06\times10^{11}$) cfu, that includes 5.38×

$10^{10}$ to $2.55 \times 10^{11}$ ($1.26 \times 10^{11}$) cfu kappa library and $7.33 \times 10^{10}$ to $3.59 \times 10^{11}$ ($1.79 \times 10^{11}$) cfu lambda library.

The present invention discloses a process for producing the APDL, wherein the immune repertoire capture comprises the steps of:
  i) RNA isolation and cDNA synthesis;
  ii) amplification of $V_L$ (lambda and kappa) and $V_H$ domains using primers comprising the SEQ ID 1-23 and 42-54;
  iii) amplification of C domains using SEQ ID 24-26 and using primers comprising the SEQ ID 27-31;
  iv) overlap PCR of light chains by fusion of $V_\kappa$ and $C_\kappa$ domains and $V_\lambda$ and $C_\lambda$ domains obtained from step (ii) and (iii), respectively, using primers comprising the SEQ ID 30, 32, 35-37 and 55;
  v) overlap PCR of heavy chains obtained from fusion of $V_H$ and $C_H1$ obtained from step (ii) and (iii) using primers comprising the SEQ ID 28 & 33;
  vi) overlap PCR of light chains and heavy chains obtained from steps (iv) and (v) respectively to obtain Fabs using primers comprising the SEQ ID 32, 34, 35-37 and 55;
  vii) purifying the amplicons at each step.

The present invention also discloses a method of obtaining manufacturable antibodies as soluble Fabs from the antibody phage display library in a defined order comprising the steps of:
  i) target specific panning;
  ii) periplasmic quantitative ELISA (qELISA);
  iii) kinetic ranking;
  iv) bioassay;
  v) manufacturability assessment;
resulting in a phenotype to genotype correlation of >90% so obtained after kinetic ranking.

BRIEF DESCRIPTION OF FIGURES

FIG. 26 depicts sequences and paired alignment of the two final overlap primers SEQ ID 32 and SEQ ID 34. The upper panel shows the primer sequences and orientation along with SEQ ID. The portion aligning to the $V_L$-$C_L$ or $V_H$-$C_H1$ template is in bold. The overhangs are in regular font. The SfiI and SacI sites in SEQ ID 32 are italicized. The bottom panel shows a paired alignment of the two sequences using the Martinez-Needleman-Wunsch algorithm with a similarity index of 66.7%.

FIG. 35 depicts antigen-specific ELISA. Four 96-well plates are shown in this screenshot. Odd-numbered wells were coated with 2 µg/ml human serum albumin while even-numbered wells were coated with the same amount of target antigen. Whole cell extracts prepared as described in the text from monoclonal recombinants were incubated at optimized dilutions in these pre-coated wells in duplicates, such that one aliquot of the dilution is pipetted into the odd-numbered well while the other aliquot is pipetted into the even-numbered well of the pair. Bound Fabs were detected with a human Fab-specific polyclonal serum (Jackson ImmunoResearch 309-036-003). Clones that show antigen-specific reactivity at least 2-folds over the paired non-specific antigen well are highlighted and bolded.

FIG. 51 depicts schematic of design and results of epitope binning of 10 anti-TNFα SPR positive clones. In the first experiment, five Fabs viz. bT1, bT16, bT38, bT59 and bT75 were immobilized on horizontal channels 1 to 5 of a NLC chip, respectively. Surfaces were saturated using three consecutive injections of test Fabs for 300s at 25 μl/min. Analyte (sTNFα) was injected next in vertical direction to interact with these Fabs and to block the respective target epitopes. Lastly, same five Fabs were flown again over these surfaces, but this time vertically to see the interaction pattern. Second experiment was performed similarly using set of next five clones viz. bT76, bT77, bT84, bT86 and bT88. In the third and final experiment, previous two sets of five clones were tested similarly with each other. (✓) mark indicates positive SPR response while (X) mark indicates negative SPR response. Tables below each experimental schematic show bins generated for respective combination of clones.

FIG. 60 depicts summarized view of SPR profiles and parameters of anti-PfCSP monoclonal Fabs. The 1:1 mixture of biotinylated bivalent anti-$C_H$1/anti-κ and anti-$C_H$1/anti-λ capture antibodies were immobilized at three different concentrations (10, 3 and 1 µg/ml) in duplicate on a NLC chip in the vertical direction. 1:5 dilutions of test Fabs were captured on five vertical channels (L1 to L5) for 300s at 25 µl/min flow rate. Two to three consecutive captures were performed to saturate the capture surface. Reference surface (L6) was saturated using non-specific (non-PfCSP binder) commercial human Fab to exactly mimic the test surfaces. Before the analyte injection, baseline was stabilized using three consecutive injections of running buffer at 100 µl/min for 60s. The system was paused for 5 min after first buffer injection followed by the remaining two—this helps to stabilize the signal rapidly. Five concentrations (reciprocal dilution) of PfCSP ranging between 500 nM-31.25 nM were injected in the horizontal direction for 600s (10 min). Dissociation of bound Fabs to target antigens was carried out for 900s (15 min) with running buffer. Surfaces were regenerated using glycine pH 2.0 for 60s followed by second injection for 30s. For data analysis, the sensorgrams were referenced appropriately and analyzed using Langmuir 1:1 fitting models. Resultant affinity constant values ($k_a$, $k_d$, $K_D$) were noted as required.

DETAILED DESCRIPTION

Figure 1:
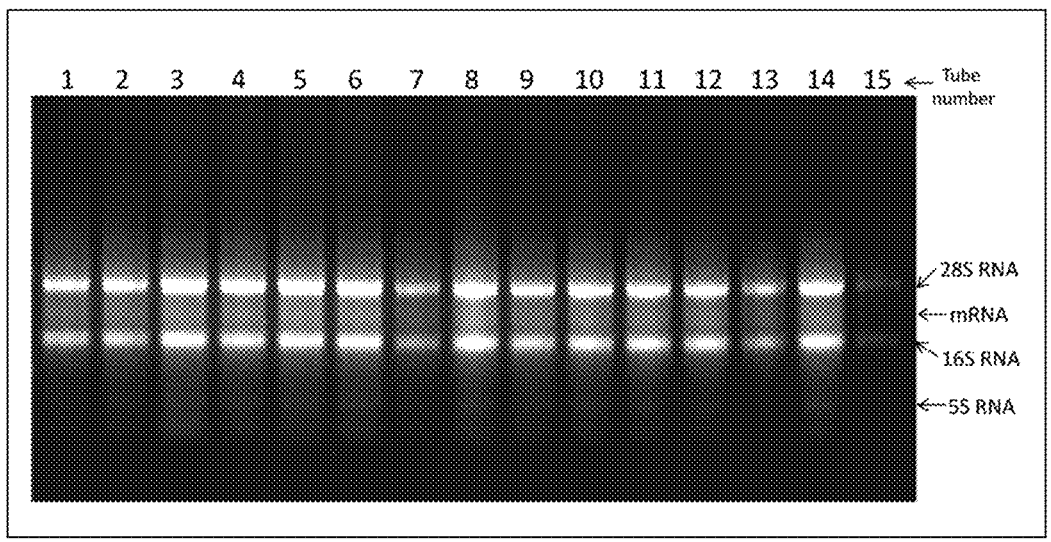
FIG. 1 depicts quality check of total RNA extracted from isolated PBMC's.

The present invention discloses a large antibody phage display library, a method for producing the antibody phage display library and a method of screening various antigens to obtain manufacturable antibodies against the said antigens.

The present invention discloses a large and diverse library in the Fab format which significantly increases the chances of identifying binding compounds with high affinity and high specificity for the target. Further, the invention offers easy isolation of target-specific soluble Fabs with minimal sequence engineering. The Fabs in the present invention are expressed as self-folded proteins in *E. coli* periplasm as output which is easier to detect and manufacture and further use for clinical or diagnostic purposes. The present invention offers the advantage of speed and cost-effectiveness as the process of constructing the library to panning and identification of lead monoclonal can be done in few weeks. The present invention is thus a high fidelity productive process for obtaining manufacturable antibodies and establishes a method of screening of various antigens to obtain such antibodies in a controlled manner.

The present invention discloses a process of antibody discovery that matches pre-set critical quality attributes for manufacturing arranged as a series of staged assessments starting from a large repertoire of antibody fragments displayed on phages—this process is exemplified and discussed in the Examples that follow. The benefits of this invention include phage displayed antibody fragments and are possible to extend to other in vivo display systems such as yeast display or bacterial display that also use antibody fragments for display and that are subject to the same stringent requirements of staged assessments, especially in high throughput format as water soluble proteins.

CQAs in Antibody Discovery: Industrial antibody discovery and manufacture necessitates monitoring of the protein product throughout the process (Alt N et al., 2016; Kepert J F et al., 2016). In other words, the binding, activating, agonistic or conjugating phenotypes that are predefined for a therapeutic target (reviewed in Labrijn A F et al., 2008) should be assignable to the protein moiety, so that the Critical Quality Attributes (CQA's) responsible for such phenotypes can be defined as early as possible. Such definitions usually include assessment of affinity, specificity against the target, and biological functionality as common aims, and may include additional assessment of productivity, tendency to aggregate, thermodynamic stability (Thiagarajan G et al., 2016) and potential immunogenicity (Hai S-H et al., 2009. Immunogenicity screening using in silico methods: Correlation between T-Cell epitope content and clinical immunogenicity of monoclonal antibodies. In: *Therapeutic Monoclonal Antibodies: From Bench to Clinic*), all of which are properties directly assignable to the behaviour of an antibody as a protein dissolved in water, or are inherent in its structural features. The intent of defining such early stage CQAs is therefore to mitigate the risks innate in the mismatch between targeted and observed phenotype as well as the observed phenotype and the underlying genotype as early as possible. This invention demonstrates how to achieve this aim for antibodies discovered from naïve human phage display library platforms.

Therapeutic or diagnostic antibody usage has very much depended upon the format available for discovering antibodies. Historically, antibody discovery was enabled by immunizing a non-human host species to generate polyclonal antibodies from serum (von Behring E A and Kitasato S, 1890), or generate monoclonal antibodies by the hybridoma technology (Köhler G and Milstein C, 1975). The process of antibody discovery by immunization is therefore dependent on the uncertainties in the biology of immunization and results in full length non-human IgGs only. Such non-human IgGs are usually not suitable for human use as they are recognized as foreign by our immune system, resulting in anti-species antibodies that neutralize the therapeutic benefit after repeated use (Chester K A and Hawkins R E, 1995; Glennie M J and Johnson P W M, 2000). Antibodies generated by the non-human immunization path therefore remained useful only as research or diagnostic reagents for many years until the technologies of grafting the antigen-recognizing variable domains on human constant domains (-ximabs; Liu A Y et al., 1987) or grafting the complementarity-determining regions on human variable region frameworks (-zumabs; Jones P T et al., 1986; Carter P et al., 1992) were developed by industry pioneers. Use of mice transgenic for human Ig loci (Brüggemann M and Taussig M J, 1997; Green L L, 1999; Lonberg N, 2008; Dechiara T M et al., 2009) has today largely bypassed the non-human Ig origin problem for generating therapeutic monoclonal antibodies from immunization and several antibodies have now been marketed from this technology (Panitumumab aka Vectibix®, Golimumab aka Simponi®, Canakinumab aka Ilaris®, Ustekinumab aka Stelara®, Ofatumumab aka Arzerra®, and Denosumab aka Xgeva/Prolia®). Nonetheless, this method of human antibody generation remains subject to the uncertainties of immunization, particularly when it comes to toxic antigens or protein targets that are highly conserved in amino acid sequence between humans and rodents (Frenzel A et al., 2016).

Full length IgGs have the in-built benefit of long half-life of circulation in blood or capability to engage immune effector cells or both by virtue of features encoded with the Fc domain, and therefore have a structural CQA advantage by design in many therapeutic scenarios. An additional advantage is embedded in the fact that as such IgGs are discovered as secreted proteins, attribution of the phenotypic qualities to the protein per se and assignment of CQAs to such proteins is straightforward. Linking the phenotypes to the underlying genotypes, which is a critical knowledge for manufacturing constancy, is also technically feasible for antibodies secreted by hybridomas on a routine basis (Bradbury A, 2010. Cloning hybridoma cDNA by RACE. In: *Antibody Engineering*; Vol. 1), although it remains a formidable technical challenge for polyclonal species secreted by a multitude of B-cells in vivo for routine use (Meijer P J et al., 2006; Tiller T et al., 2008).

With the advent of systems capable of displaying antibody fragments in vivo or in vitro, bypassing the vagaries of immunization (antigen toxicity, antigen homology, lack of response) has become possible and the format for discovery is no longer confined to full length IgG alone. These systems depend upon the power of recombinant DNA technology, which in essence utilizes the modularity inherent in Ig protein structure as well as their genomic origin to recombine the antigen recognizing elements of immunoglobulin genes in vitro in a variety of forms. The source of such genes may be natural or synthetic. Upon appropriate capture of these diverse V-domain permutations in host cells of prokaryotic or eukaryotic origin and subsequent expression and display, these recombinant formats can bind to antigens in vitro, and such binders can then be isolated and sequenced easily to assign the binding phenotype to a finite genotype. The possibility of easy phenotype-to-genotype linkage therefore allows possibility of assignment of gross CQA's to the binders as proteins. Examples cited herein document that when it comes to obtaining antibodies from phage display, such assignment is not obvious and needed to be invented.

The present invention discloses a process in which immunoglobulin fragments may be discovered as secreted proteins in *E. coli* periplasm, and allows attribution of the phenotypic qualities to the protein per se. The present invention links the phenotypes to the underlying genotypes, which is a critical knowledge for manufacturing constancy.

The present invention also discloses a method of obtaining manufacturable antibodies as soluble Fabs from the antibody phage display library in a defined order comprising the steps of:
  i) target specific panning;
  ii) periplasmic qELISA;
  iii) kinetic ranking;
  iv) bioassay;
  v) manufacturability assessment;
resulting in a phenotype to genotype correlation of >90% in the antibodies so obtained after kinetic ranking.

Phage display technology rests on five key ideas: (a) bacteriophages can express heterologous peptides or polypeptides fused to their coat proteins when transduced in host bacteria; (b) given a multitude of such peptides or polypeptides, a library of recombinant phages can be created that display all these variants on a coat protein of choice; (c) such a library of phages can be screened as a population for ability to bind (recognize) a target molecule in vitro; (d) the binders can be separated from the non-binders by washing them away in a process akin to washing sand away from gold dust (panning), and (e) the isolated binders can be analyzed for the sequence of the variant encoded within its genome. Since its conceptualization (Smith G P, 1985), this technology has proven invaluable for a variety of investigations that includes antibody discovery, epitope mapping, protein interaction site mapping, enzyme substrate discovery and molecular evolution (reviewed in Burton D R, 1995; Azzazy H M and Highsmith W E, 2002).

The present invention discloses a method of obtaining antibodies from the antibody phage display library, wherein the panning is conducted in solid or solution phase at various temperatures ranging between 4 and 37° C. and for various lengths of time ranging between 1 h and 16 h. The solid phase panning may comprise the steps of:

i) optimizing the maximal coating concentration for a given antigen on a solid surface such as charged polystyrene;
ii) conversion of the phagemid library to phage format;
iii) coating the selected surface with the optimal concentration of the antigen as determined at step (i) followed by blocking with protein or non-protein molecules to block non-specific sites;
iv) pre-adsorption of phage pool as obtained at step (ii) on unblocked polystyrene surface to eliminate plastic binders;
v) incubation of pre-adsorbed phages from step (iv) with immobilized target antigen (step iii) for defined periods of time;
vi) multiple rounds of washings to eliminate unbound phages from step (v);
vii) elution of bound phages from step (v) by trypsin digestion and concurrent transduction in amber suppressor as well as non-amber suppressor hosts to obtain phage titers;
viii) amplification of eluted phages from step (vii) by transducing in amber suppressor host for next round of panning;
ix) performing the next round of panning by using reduced antigen concentration and repeating steps (iii) to (viii) to enrich the target specific antibody population;
x) repetition of steps (vii) to (ix);
xi) evaluation of eluted phages from step (vii) and (x) for enrichment of binding over rounds of panning using target specific ELISA.

The solution phase panning may comprise the steps of:
xii) optimizing the reaction conditions for optimal biotinylation of a given antigen to achieve a biotin to protein molar ratio of <10, preferable 1-5;
xiii) conversion of the phagemid library to phage format;
xiv) blocking the phages obtained at step (ii) with protein or non-protein molecules to block non-specific sites for defined periods of time simultaneous with streptavidin bead washing followed by blocking the beads with protein or non-protein molecules to block non-specific sites;
xv) incubation of blocked phages from step (xiii) with soluble target biotinylated antigen (step xii) for defined periods of time;
xvi) incubation of phage-antigen complex obtained at step (xiv) with pre-blocked streptavidin beads;
xvii) multiple rounds of washings of the beads bound to antigen-phage conjugates at step (xv) to eliminate unbound phages;
xviii) elution of bound phages at step (xvi) by DTT or trypsin digestion and concurrent transduction in amber suppressor as well as non-amber suppressor hosts to obtain phage titers;
xix) amplification of eluted phages from step (xviii) by transducing in amber suppressor host for next round of panning;
xx) performing the next round of panning by using reduced antigen concentration and repeating steps (xiv) to (xviii) to enrich the target specific antibody population;
xxi) repetition of step (xix) to step (xx);
xxii) evaluation of eluted phages from step (xviii) and (xxi) for enrichment of binding over rounds of panning using target specific ELISA.

A very important concept embedded within the phage display technology is the physical linkage of the binding phenotype to the encoded genotype within the recombinant phage. In contrast, cDNA expression libraries can also encode a multitude of polypeptides, but the phenotype of a particular clone after a population-based screening can only be linked to its encoded genotype after a separate investigative step conducted on a parallel master set of clones (hybridization with radiolabeled probe and colony picking, for example; Sambrook J and Russell D W, 2001a. Preparation of cDNA libraries and gene identification. In: *Molecular Cloning: A Laboratory Manual; Vol.* 2). The speed and throughput that can be obtained from phage display libraries are therefore incomparably faster and higher compared to screening cDNA libraries.

When it comes to assessing antibodies as a protein however, the display technology loses its power, for in principle; the industrial proposition of must-assess-discovered-entity-as-protein puts it at a same advantage or disadvantage level as a cDNA library. Furthermore, the high throughput that is possible today for assessment of individuals of a variant population of proteins and that are applied to secreted IgGs from hybridomas on a routine basis for antibody discovery (Hay F C and Westwood O M R, 2002. Preparation of human B-cell hybridoma. In: *Practical Immunology*), are not possible to apply for phage displayed antibodies. The primary obstacle to high throughput with phage display technology is the necessity for transducing the growing bacterial cultures with infective phages and then harvesting the amplified phages, which involves centrifugation to separate the bacteria from the phages, a second step of polyethylene glycol (PEG) mediated precipitation to concentrate the phages, and then repeated washes to eliminate any bacterial contamination before beginning to assess any binding phenotype. To put this process in contrast, hybridomas can be cultured in 96-well plates and centrifuged to collect the supernatant, which can be directly assessed for binding phenotype (Green L L, 1999).

A secondary but critical obstacle rests on the fact that by design, phage displayed antibodies are linked N- or C-terminally to a much larger phage particle. The presence of such a large "tag" to the discovered antibody fragment can most certainly be predicted to influence the basic phenotype of binding, as has been documented in several reports (Lou J et al., 2001; Chowdhury P S, 2002. Targeting random mutations to hotspots in antibody variable domains for affinity improvement. In: *Methods in Molecular Biology, Vol.* 178: *Antibody Phage Display: Methods and Protocols*; Pavoni E et al., 2007). The inbuilt limitations of phage biology result in propagation of a majority of clones that (a) do not display the antibody fragments at all (Winter G et al., 1994; Azzazy H M and Highsmith W E, 2002; Hust M et al., 2009. Antibody phage display. In: *Therapeutic Monoclonal Antibodies: From Bench to Clinic*), (b) that are shorter in size compared to the expected size of the recombinant genomes (de Bruin R et al., 1999; Lowe D and Vaughan T J, 2009. Human antibody repertoire libraries; In: *Therapeutic Monoclonal Antibodies: From Bench to Clinic*), and that (c) have the greatest growth advantage as opposed to the experimental objective of amplifying the antibody displaying recombinants only (de Bruin R et. al., 1999; Løset G Å et al., 2005; Lowe D and Vaughan T J, 2009. Human antibody repertoire libraries; In: *Therapeutic Monoclonal Antibodies: From Bench to Clinic*). These inbuilt errors can result in situations where binding ability of a monoclonal phage to a target antigen is not mirrored by the binding ability of the protein antibody produced from the same clone (Vaughan T J et al., 1996; Chowdhury P S, 2002. Targeting random mutations to hotspots in antibody variable domains for affinity improvement. In: *Methods in Molecular Biology, Vol. 178: Antibody Phage Display: Methods and Protocols*; U.S. Pat. No. 6,794,128; Pavoni E et al., 2007), as would be expected from the principle of genotype-phenotype linkage. Examples cited herein document such phenomenon in great detail, and necessitate inventing methods that recognize the pitfalls of the process and therefore, can bypass them.

A common method of mitigating the risk that the binding phenotype shown by a phage-antibody fusion may not be mirrored by the antibody as a protein when expressed minus the phage tag is by inquiring whether the genome of the binder represents an expressible open reading frame (ORF)—usually achieved by sequencing (Buckler D R et al., 2008). Despite major advances in automation, such an approach, although invaluable in clone assessment, remains labor-intensive and cannot be construed as a high throughput method. Furthermore, sequencing per se does not guarantee whether an antibody ORF will be expressible. Rules for what kinds of antibody ORFs might be expressible in bacteria and mammalian cells have been suggested (Ewert S et al., 2004; Röthlisberger D et al., 2005) and synthetic antibodies libraries today depend upon such rules for their success (Knappik A et al., 2000; Rothe C et al., 2008; Prassler J et al., 2011; Tiller T et al., 2013). No such deterministic rules are obviously possible for binders derived out of a random combination of V-domains that represent a naïve or immune phage display library. Therefore the present invention discloses a method that would allow assessment of antibody fragments as proteins secreted out from bacteria akin to the high throughput assessment of IgGs secreted out of hybridoma cultures. Such method as disclosed herein is one of the factors in enabling high throughput. Certain prior art discloses such methods (Winter G et. al.., 1994, Kirsch M et al., 2005; Løset G Å et al., 2005; Petropoulos K, 2012. Phage display. In: *Methods in Molecular Biology Vol. 901: Antibody Methods and Protocols*; Rader C, 2012a. Selection of human Fab libraries by phage display. In: *Methods in Molecular Biology Vol. 901: Antibody Methods and Protocols*), but these methods do not suggest further resolution of the genotype-phenotype dissociation expected from this approach. Examples cited herein therefore document a novel staged assessment system that continues to harnesses the essential power of the phage display technology (phenotype-linked-to-genotype) when screening en masse, but employs biochemical principles of analyzing antibodies as proteins when screening the phenotype of each clone (phenotype delinked from genotype), while maintaining the capability to assign the observed phenotype to the underlying genotype.

The process of the present invention achieves the objectives by examining and establishing the theory and process pertaining to the format of the antibody that can be displayed by the phages but that is also stable as an isolated protein in water, and the ability of the host bacteria to secrete such forms as protein, amongst other factors and processes. scFvs as proteins are known to be generally less stable and more prone to aggregation compared to Fabs when in an aqueous environment (Weidner K M et al., 1992; Holliger P et al., 1993; Kortt A A et al., 1997; Quintero-Hernández V et al., 2007), although careful studies suggest that this an epiphenomenon directed by the given combination of $V_L$- and $V_H$-domains (Röthlisberger D et al., 2005) as well as the fact that the unfolding kinetics of Fabs is slower rather than any intrinsically enhanced thermodynamic stability (Honegger A, 2008). Since Fabs have higher intrinsic stability then scFvs, the present invention discloses the use of Fabs for construction of the said library. The use of Fabs is further advantageous since Fabs or pegylated Fabs can directly serve as therapeutic structures, which is preferred when considering the gain in reducing the time between discovery and manufacture. In contrast, scFvs can only serve as diagnostic or conjugated therapeutics due to their short life in blood circulation (Chames P et al., 2009) and therefore, generally need to be re-formatted for alternative therapeutic use. The loss of speed between discovery and manufacture can therefore be considerable. Furthermore, when considering the structural elements of Fab, the paratope (binding surface) created by the $V_L$-$V_H$ interface in a Fab is a natural protein interaction domain while that created by the $V_L$-$V_H$ interface in a scFv is constrained by linker length and therefore, artificial (Kortt A A et al., 1997). Therefore, the affinity shown by a Fab towards a particular antigen would be driven by a natural $V_L$-$V_H$ interface while that shown by a scFv by an unnatural one, which may have unpredictable consequences during reformatting of a candidate scFv to Fab or IgG formats. Fab reformatting to a therapeutic IgG format, on the other hand, would actually benefit from a stability gain (Casadevall A and Janda A, 2012).

In order to enable the host bacteria to secrete these stable forms as proteins, the present invention advantageously utilizes the design inherent in phage display technology that uses periplasmic space to direct phage production (Webster R, 2001. Filamentous phage biology. In: *Phage Display: A Laboratory Manual*). The present invention discloses a hybridoma-like screen in which periplasmic extracts from growing bacteria recombinant for antibody fragments may be examined for the presence, absence and relative yield of Fabs—enabling high throughput without the loss in fidelity of the present process. The application of a periplasmic Western for qualitative analysis of expressed scFvs has been reported in prior art (Løset G Å et al., 2005; Eisenhardt S U and Peter K, 2010. Phage display and subtractive selection on cells. In: *Antibody Engineering; Vol. 1*), but the present application for the first time discloses such a process for screening Fabs as proteins out of a panned Fab display library. This approach also allows the crucial validation of whether the standard Fab design of two different periplasmic leaders for two different cistrons (light and heavy chains) have actually resulted in a heterodimeric Fab protein expressed in the periplasm. The advantage with this approach therefore is that it focuses attention and efforts to obtain functional Fab proteins that exist at a reasonable level of detection, and rejects clones that are at a low detection level, at an early discovery stage. However, this approach of expressing human Fabs as soluble proteins in *E. coli* periplasm can cause low yields (Better M et al., 1993; Humphreys D P, 2003). The proximate cause for low yields include misfolding in the periplasm (Skerra A and Plückthun A, 1991; Humphreys D P, 2003) and presence of periplasmic proteases that are able to digest such misfolded polypeptides, light chains in particular (Chen C et al., 2004). The distal causes of misfolding may include the inbuilt limitation of differential codon usage between the host and guest species, as well as the family-specific $V_L$-$V_H$ interface stability properties (Ewert S et al., 2004, Tiller T et al., 2013).

Certain methods are available for increasing Fab or Fab' yields in *E. coli* periplasm for synthetic library building or making grams of proteins for downstream purposes, however most of the methods in prior art have certain limitations (Humphreys D P and Bowering L, 2009. Production of antibody Fab' fragments in *E. coli*. In: *therapeutic Monoclonal Antibodies: from Bench to Clinic*; U.S. Pat. No. 8,062,865; Tiller T et al., 2013), and none exist that can be applied for screening hundreds of Fabs as proteins from a naïve library at an early discovery stage. The present invention discloses for the first time such assessment as a primary phenotypic screen to weed out clones that do not produce heterodimeric Fabs in the periplasm at the limit of detection for enhanced chemiluminescence based Westerns (1-3 pg/band). Hence the present invention advantageously benefits in terms of time and cost and overcomes the disadvantages of the need to handle poorly expressed clones, even though there is a possibility of losing some antigen specific binders. Another advantage of this gate is that one can type these periplasmic hits by simultaneous immunoblotting with anti-human kappa and lambda-specific antibodies, thus avoiding the need to sequence these clones when panning is done with mixed kappa and lambda libraries.

The present invention discloses methods/process to arrive at optimum set of methods and protocols to overcome the limitations in getting antigen-specific Fab protein binders with high fidelity. A limitation of the initial approach described above was that antibodies discovered as present in the periplasm and assumed to be heterodimeric were actually homodimeric for the light or heavy chains in many cases. The said limitation was overcome by utilizing the 2-site concept for ELISA development (Harlow E and Lane D, 1988. Immunoassays. In: *Antibodies: A Laboratory Manual*; Lawson A D G et al., 1997) to identify clones that are likely to produce heterodimeric Fabs. Examples included herein demonstrate that the present application has extended the basic 2-site concept to develop a novel chain-switch ELISA system that is not only able to distinguish clones producing heterodimeric Fabs away from clones producing homodimeric Fabs, but also allows to achieve a very crucial aim of estimating yields quantitatively in mass Fab/volume terms. This breakthrough improvement is a major step forward from the initial system of qualitative assessment by Westerns and demonstrates one of the inventive merits of the present application. The present invention discloses a method of obtaining antibodies from the panned antibody phage display library, wherein the periplasmic qELISA comprises the steps of:
 i) obtaining soluble Fabs from single bacterial colonies from eluate titer plates;
 ii) coating the surface of 96-well charged polystyrene plates with a capture antibody against heavy chain;
 iii) capturing the soluble Fab from step (i) on the coated surface of step (ii)
 iv) detection of light chain by utilization of light chain specific antibody to identify full length, tandem in-frame, heterodimeric, soluble Fabs.

Furthermore, development of Fab protein assessment in an ELISA format immediately allows high throughput as potential binder clones out of a pool of binders from a panning campaign can be grown in 96-well plates, such cultures induced to produce Fabs in the periplasm (Kontermann R E, 2010. Immunotube selections. In: *Antibody Engineering*; Vol. 1; Hust M and Mersmann M, 2010. Phage display and selection in microtitre plates. In: *Antibody Engineering*; Vol. 1; Petropoulos K, 2012. Phage display. In: *Methods in Molecular Biology Vol. 901: Antibody Methods and Protocols*), the periplasm harvested by simple lysis in situ (W01/94585; Humphreys D P and Bowering L, 2009. Production of antibody Fab' fragments in *E. coli*. In: *Therapeutic Monoclonal Antibodies: From Bench to Clinic*), and the supernatants harvested for assessment of Fabs as proteins in the same 96-well format akin to hybridoma culture supernatants. Replicas of these master cultures can be stored frozen as glycerol stocks (Petropoulos K, 2012. Phage display. In: *Methods in Molecular Biology Vol. 901: Antibody Methods and Protocols*; Protocol: Use of Glycerol Stocks and Preparation of Transfection-Quality Plasmid DNA; Broad Institute, Boston, Mass., 2015.), and clones with desirable protein properties regrown and interrogated most easily. None of these steps require further involvement of phage display.

The present invention discloses a method of obtaining soluble Fabs from the panned antibody phage display library, wherein obtaining the soluble Fabs comprises the steps of:
 i) picking single clones from titer plates of non-amber suppressor hosts and liquid culture in 96-well deepwell plates for overnight growth at 37° C. and 250 rpm;
 ii) diluting the overnight cultures 10-folds and allowing growth to log phase under conditions identical to (i);
 iii) inducing the log phase cultures at step (ii) with 1 mM IPTG and allowing overnight growth at 30° C. and 250 rpm;
 iv) centrifuging the cultures at step (iii) in 96-well plates to pellet down the induced cells;
 v) periplasmic extraction of the pelleted cells at step (iv) by using high concentrations of EDTA in a buffered solution while slowly shaking the buffer-suspended cells in the same 96-well plate overnight at 30° C.;
 vi) centrifugation to isolate the diffused periplasmic fraction at step (v) away from the spheroplast and cell debris.

Prior art discloses certain high throughput screening of monoclonal Fabs as soluble proteins after obtaining binder pools from a solution panning campaign (Petropoulos K, 2012. Phage display. In: *Methods in Molecular Biology Vol. 901: Antibody Methods and Protocols*; Rader C, 2012a. Selection of human Fab libraries by phage display. In: *Methods in Molecular Biology Vol. 901: Antibody Methods and Protocols*). However, a major disadvantage with the protocol described by Petropoulos K, 2012, is that it requires re-cloning of the phagemid DNA of potential monoclonal binders as a pool into an expression vector before screening as soluble Fabs. Such a requirement will surely result in significant slowdown in speed, plus the potential of losing binders during the subcloning process. Furthermore, the protocol makes no effort to isolate the periplasmic fraction away from the cytoplasmic fraction, which is a disadvantage insofar as the periplasmic translocation property of the Fab cannot be validated. Lastly, the prior art protocol uses an anti-Fab polyclonal antibody for detecting but not quantifying the Fab yield. In contrast, the invention of the present application (a) does not require re-cloning of binder pools by taking advantage of the amber stop codon in between the heavy chain and the gIII and use of non-amber suppressor hosts (also see the section on pSSY1 in this context), (b) utilizes a gentle periplasmic isolation method that allows separation of the periplasmic fraction away from the remainder of the *E. coli* fractions, and (c) uses the chain switch concept to unambiguously qualify and quantify heterodimeric Fabs only.

The protocol set out in the Rader C, 2012a, uses the concept of 2-site ELISA by immobilizing light chain polyclonal antibodies on polystyrene plates, capturing crude Fab preparations on such antibodies, and detecting with a heavy chain C-terminal tag. However, the process is not developed into a quantitative assay. As described, the process is low throughput (14 ml tubes used for sampling 32 clones), and actually samples Fab-pIII fusions isolated from a simple centrifugation of induced cultures that is unlikely to isolate a fraction enriched in periplasmic proteins. In contrast, the present application exemplified herein (a) uses a high throughput culture, induction and storage method very similar to that described (Petropoulos K, 2012. Phage display. In: *Methods in Molecular Biology Vol. 901: Antibody Methods and Protocols*), (b) takes advantage of the amber stop codon in between the heavy chain and the gIII and use of non-amber suppressor hosts to produce Fabs without the pIII (also see the section on pSSY1 in this context), (c) takes care to use a gentle periplasmic isolation method that allows separation of the periplasmic fraction away from the remainder of the *E. coli* fractions and (d) uses the chain switch concept to unambiguously qualify and quantify heterodimeric Fabs only without any pIII fusion.

The present application further discloses a method of obtaining antibodies from the antibody phage display library, wherein the surface may be charged polystyrene surface such as MaxiSorp™ or PolySorp™, or may be coated with avidin or streptavidin or neutravidin, preferably the Maxisorp™ surface is coated with streptavidin at a concentration ranging between 20 and 100 µg/ml, most preferably 100 µg/ml.

The capture antibody is selected from the group comprising goat anti-human IgG (goat anti-Human IgG (H+L); F(ab')2 fragment) or Capture Select Biotin Anti-IgG-$C_H1$ Conjugate, preferably the biotinylated anti-$C_H1$ antibody at a concentration of 1000-100 ng/ml, most preferably 250 ng/ml).

The light chain specific antibody is selected from the group comprising goat anti-human lambda LC specific peroxidase conjugate, goat anti-human kappa LC specific peroxidase conjugate, goat anti-human F(ab')2-HRP, mouse anti-human kappa light chain peroxidase conjugate, mouse anti-human kappa light chain monoclonal and rabbit anti-human kappa chain monoclonal, preferably at a dilution ranging between 1-20000, most preferably 1:10000 for anti-lambda and 1:2000 for anti-kappa.

Development of the quantitative chain switch ELISA as set out herein permits direct linking in series to an industry-standard assessment method—kinetic screening or affinity ranking for high throughput antibody discovery (Schräml M and Biehl M, 2012. Kinetic screening in the antibody development process. In: *Methods in Molecular Biology Vol. 901: Antibody Methods and Protocols*; Drake A W and Papalia G A, 2012. Biophysical considerations for development of antibody-based therapeutics. In: *Development of Antibody-based Therapeutics*). The practical reasons for affinity ranking are set out in literature (Tabrizi M A. 2012. Considerations in establishing affinity design goals for development of antibody-based therapeutics. In: *Development of Antibody-based Therapeutics*). It is one of the best predictor of antibody dose required for the maximum therapeutic benefit (potency) at a manageable cost-of-goods. Higher affinity antibodies will generally result in higher potency primarily determined by antigen concentration and turnover in vivo. Ability to rank antibodies in terms of their kinetic parameters early in the discovery phase enables the process of the present invention to match the capabilities of the phage display system to that of the hybridoma system in this aspect. The other benefits of kinetic ranking are high throughputs and possibility of assessment of thermodynamic stability (Schräml M and von Proff L, 2012. Temperature-dependent antibody kinetics as a tool in antibody lead selection. In: *Methods in Molecular Biology Vol. 901: Antibody Methods and Protocols*), which in turn is often a predictor of protein aggregation (Thiagarajan G et al., 2016)—a very important concern for manufacturing antibodies.

Affinity ranking can be done using competition ELISA or Surface Plasmon Resonance. Competition ELISA requires a labeled antigen that can be used as a detection handle. Due to this additional and often difficult-to-achieve requirement, such assays are used more for validation rather than a primary method of data generation today. SPR, in contrast, is a label-free method, and along with continuous improvements in software and hardware, has emerged to become the method-of-choice today for generating antibody affinity data. An SPR surface that is desirable for kinetic analysis is where the Fabs are oriented with their Fv surfaces (paratopes) facing the flowing water phase (with or without antigen) in the SPR flow cell. This requires a surface that would allow quantitative capture of crude Fab candidates in an oriented manner and allow kinetic ranking. Such oriented surfaces for full length IgGs are well described in literature (Canziani G A et al., 2004; Schräml M and Biehl M, 2012. Kinetic screening in the antibody development process. In: *Methods in Molecular Biology Vol. 901: Antibody Methods and Protocols*), but for Fabs (that lack the Fc domain by definition) such literature is indeed sparse (Leonard P et al., 2007). Pioneers therefore had no option but to immobilize the antigen itself on the surface of the SPR chip to determine kinetic parameters (de Haard H J et al., 1999; Steukers M et al., 2006). Such an approach mimics a direct ELISA with the distinct possibility of masking interesting epitopes. New reagents have now become commercially available that allow creation of such oriented surfaces even for Fabs, although detailed protocols are not available in the prior art. The present invention investigates several such surfaces, and examples presented herein.

The present invention discloses a method of obtaining antibodies from the antibody phage display library, wherein the kinetic ranking comprises the steps of:
  i) obtaining soluble Fabs from qELISA positive clones in 50 ml individual cultures;
  ii) dialyzing the obtained Fabs from step (i) against 1×PBS;
  iii) use of running buffer of physiological strength and pH for kinetic analysis—the buffer could be phosphate or HEPES, more preferably phosphate, containing NaCl or KCl concentration of 0.1 to 1.0M, preferably 0.25 to 0.75M, more preferably 0.4 to 0.6M, and Tween-20 concentration of 0.005 to 0.05%;
  iv) selecting the SPR (surface plasmon resonance) chip immobilization surface—such surface could be charged dextran, charged alginate, nickel nitrilotetraacetic acid coated on charged dextran or alginate surface, or streptavidin or neutravidin coated on charged dextran or alginate surface;
  v) selecting the immobilization chemistry for the SPR surface at step (iv)—such chemistry could be amine coupling using EDAC(1-Ethyl-3-(3-dimethylaminopropyl)carbodiimide) and sulfo-NHS (N-hydroxysuccinimide), $Ni^{2+}$ charging using 10 mM nickel sulfate, or streptavidin-biotin recognition chemistry;

vi) immobilizing the anti-Fab capture antibody on the chip surface from step (v)—capture antibodies may include anti-Fab IgG, anti-tag antibodies such as anti-His, anti-HA or biotinylated anti-$C_H$1 or biotinylated bivalent anti-$C_H$1/anti-$C_\lambda$ or biotinylated anti-$C_H$1/anti-$C_\kappa$ or a 50:50 mixture of both biotinylated bivalent anti-$C_H$1/anti-$C_\lambda$ and biotinylated anti-$C_H$1/anti-$C_\kappa$;

vii) capturing the crude periplasmic Fabs obtained from step (ii) on the capture antibody-coated surface of the chip from step (vi);

viii) signal stabilization by 1-3 rounds of running buffer injection over the chip surface with intermediate pause of 2-15 min;

ix) testing the analyte response on captured Fabs of step (vii) at an optimal concentration of analyte to distinguish between target antigen binders and non-binders;

x) removing the Fab-analyte complex using regenerating reagent for the surface to be re-used for the next round of screening—regenerating agent could include 2M $MgCl_2$, 0.85% $H_3PO_4$, 50 mM NaOH or 10 mM glycine, pH 2.0.

The combination of methods for Fab discovery as described in the preceding paragraphs achieves two aims. The first is that extension of the concept of manufacturability to antibody discovery from phage libraries is enabled as demonstrated herein from the initial step—Fabs discovered from such a system can be confidently assessed as quantifiable heterodimeric molecules expressed in the periplasm by design, with a range of yields that is not by design but on which a gating system can be applied. The second is that establishment of a consistent method for crude Fab capture on SPR chips allows us to interrogate binding of a target antigen to the captured Fab on the chip itself—a function conventionally carried out by direct/indirect ELISA where the antigen is immobilized on polystyrene surface. The latter approach can mask interesting and relevant epitopes as discussed earlier. In other words, the novel crude Fab capture system on SPR chips of the present invention is doubly advantageous in that it not only bypasses antigen-specific ELISA that is error prone, but also allows obtaining kinetic parameters directly for Fabs that do recognize the antigen, thus shortening the time required for discovery. Examples included herein demonstrate that Fabs assessed in this manner are also genotype true—that is, the combination of chain switch ELISA on periplasmic extracts and on-chip kinetic ranking (phenotyping) picks up only those clones that have intact ORFs in their tandem in-frame light chain-heavy chain Fab structure as determined by post hoc sequence analysis (genotyping).

Creating an Ultra-Large Naïve Phage Display Library as a Source of Antibodies

The staged assessment system described in the previous sections suggests that Fabs are the preferred format for antibody discovery for stability reasons, and can be assessed successfully as proteins in a high throughput manner. This design decision, added to the reality that a large number of potential binders will be lost due to the constraints of phage amplification, poor expression in E. coli, as well as the stringencies imposed by the staged assessment process itself, therefore necessitates that an ultra-large library of Fabs be created to compensate for the losses, and be made available for antigen recognition by a display method.

The primary rationale for creating large libraries is capturing as many diverse combinations of V-domains as possible to retrieve antibodies in the therapeutic range ($K_D$ in sub-nM to pM range). Library size therefore represents this diversity—the underlying assumption being that each recombinant clone represents a different $V_L$-$V_H$ combination (Hoogenboom H R et al., 1991; Waterhouse P et al., 1993). This assumption is difficult to verify without sequencing a very large number of clones. Digesting plasmid DNA with frequent cutting enzymes (BstNI, BstOI, AluI etc.) and running the digests on agarose gels to study the resultant fingerprints is conventional for assessing diversity but most certainly a weak substitute of sequence information. Sanger sequencing, because of its power to read long fragment lengths, is highly suitable to read the $V_L$-$V_H$ pairings embedded in scFv or Fab formats, but the throughput of sample preparation, sequencing and analysis does not allow it to be executed for more than a few hundred clones. Next-Generation Sequencing (NGS) has been applied to resolve this problem (Geyer C R et al., 2012. Recombinant antibodies and in vitro selection technologies. In: *Methods in Molecular Biology Vol. 901: Antibody Methods and Protocols*; Glanville J et al., 2015), but limitations in read lengths do not allow it to read $V_L$-$V_H$ pairs of a scFv library unambiguously for more than $10^6$ clones. The procedure is therefore more successful for enriching binders after the diversity of the library has been reduced after at least one round of panning (Ravn U et al., 2013; Glanville J et al., 2015). The limitation in read lengths implies that Fab libraries, where other than $V_L$-$V_H$ pairings, one also needs to confirm tandem in-frame nature of the light chain and heavy chain cassettes, are not currently amenable to verification by NGS. Recent developments in de novo assembly of short reads to construct maps of complex libraries (Cho N et al., 2015) may solve this problem. Regardless of this verification problem, the core principle of maximal paratope coverage is the key to the phage display libraries' ability to find antibodies against almost any antigen including self-antigens that are nearly impossible to obtain from immunizations. Furthermore, there exists an almost linear correlation between library size and affinities of binders—larger the library, greater the chances of finding therapeutic range antibodies (Hust M et al., 2009. Antibody phage display. In: *Therapeutic Monoclonal Antibodies: From Bench to Clinic*; Lowe D and Vaughan T J, 2009. Human antibody repertoire libraries; In: *Therapeutic Monoclonal Antibodies: From Bench to Clinic*). Making a large library is therefore advantageous from this respect as well.

While building an ultra large naïve library, the present invention and the process utilized herein balance the diversity in the library, while ensuring the size, rapid throughput and the economic advantage.

The present invention discloses a naïve antibody phage display library (APDL) having a size ranging between $8.86 \times 10^{10}$ to $9.13 \times 10^{11}$ ($3.06 \times 10^{11}$) cfu, that includes $5.38 \times 10^{10}$ to $2.55 \times 10^{11}$ ($1.26 \times 10^{11}$) cfu kappa library and $7.33 \times 10^{10}$ to $3.59 \times 10^{11}$ ($1.79 \times 10^{11}$) cfu lambda library.

Several attempts have been made earlier to overcome the disadvantage of the prior art by building alternative display systems. Alternative display systems may be categorized as in vivo systems that include yeast display (Boder E T and Wittrup K D, 1997; Weaver-Feldhaus J M et al., 2004), bacterial display (van Blarcom T J and Harvey B R, 2009. Bacterial display of antibodies. In: *Therapeutic Monoclonal Antibodies: From Bench to Clinic*) and mammalian display (Tomimatsu K et al., 2013; Horlick R A et al., 2013), and in vitro systems that include ribosome display (Hanes J and Plückthun A, 1997), DNA display (Sumida T et al., 2009), mRNA display (Roberts R W and Szostak J W, 1997) and bead display (Diamante L et al., 2013). In vivo systems usually rely on anchoring the expressed antibody format (scFv, Fab) on a cell surface protein to maintain the phenotype-genotype linkage. Similarly, in vitro systems anchor the transcription unit through a linker to the anchor (ribosome, puromycin or polystyrene beads) to maintain the phenotype-genotype linkage. However, similar to the phage display system, in vivo systems are limited by transformation efficiencies that do not allow library sizes to usually exceed $10^9$ variants, thus limiting their utility for capturing a naïve immune repertoire. In contrast, in vitro systems can display as many as $10^{12}$-$10^{14}$ variants, but are limited both by the difficulties in manipulation as well as inability to produce heterodimeric proteins by design (the only exception being the difficult-to-optimize DNA display system). These systems are therefore most useful in scenarios where molecular evolution of a candidate protein, such as affinity maturation of a parent Fab template, is desired. Phage display libraries, for their simplicity, robustness and track record in discovering multiple therapeutic or diagnostic antibodies, therefore remain as the method of choice for first-pass retrieval of a $V_L$-$V_H$ combination that has ability to recognize a given antigen (Hust M et al., 2009. Antibody phage display. In: *Therapeutic Monoclonal Antibodies: From Bench to Clinic*; Lowe D and Vaughan T J, 2009. Human antibody repertoire libraries; In: *Therapeutic Monoclonal Antibodies: From Bench to Clinic*).

Phage display libraries can be created either on phage or phagemid vector backbones with consequent advantages and disadvantages (Scott J K and CF Barbas III. 2001. Phage-display vectors. In: *Phage Display: A Laboratory Manual*). Phagemids are preferred both for monovalent display of antibody fragments that allow selection by true affinity as well for the fact that transformation efficiencies in *E. coli* are far superior compared to the phage vectors. Nonetheless, even this superior efficiency is limited by the maximum transformation efficiencies usually achievable for restriction digested plasmid vectors ligated to insert fragments, which is about $10^9$ cfu/µg. In contrast, the maximum efficiencies achievable for supercoiled plasmid preparations are at least a log higher ($10^{10}$ cfu/µg; Hoogenboom H R et al., 1991; Sambrook J and Russell D W. 2001b. The Hanahan method for preparation and transformation of competent *E. coli*: High efficiency transformation. In: *Molecular Cloning: A Laboratory Manual; Vol.* 1). However, as set out herein above, these limits of transformation efficiency limit the number of random $V_L$-$V_H$ permutations that can be captured in *E. coli* to create libraries, and have therefore forced the antibody community to create such large libraries in two steps or two independent cassettes transformed simultaneously (Waterhouse P et al., 1993; Griffiths A D et al., 1994; de Haard H J et al., 1999; Ostermeier M and Benkovic S J, 2000; Hoet R M et al., 2005) to ensure capture of both $V_L$ and $V_H$ diversity. It is therefore advantageous for building large Fab-phage display libraries if these limits can be pushed higher. Examples presented herein demonstrate that exceeding these limits is indeed possible, and can be applied to build large Fab-phage display libraries in one step wherein the only limitation is the maximum number of *E. coli* that can reside in one liter of bacterial culture ($10^{12}$/L; Hoogenboom H R et al., 1991).

The present invention discloses process for producing the APDL, wherein transformation is carried out at a DNA to cell volume ratio of 25 to 400, preferably 100 to 350, more preferably, 200 to 300 ng per 50 µl of ultracompetent cells.

The present invention further discloses a process for producing the APDL, wherein transformation is carried out at a voltage in the range of 1500 to 3500 volts, preferably 2500 to 3200 volts, capacitance in the range of 10 to 30 µF, preferably 20 to 28 µF and resistance of 100 to 400 ohms, preferably 250 to 350 ohms in a cuvette of 0.1, 0.2, 0.4 cm inter-electrode distance, preferably 0.2 cm. The host is an amber suppressor t-RNA encoding host selected from the group comprising TG1, XL-1 Blue and ER2537, preferably TG1 of ultrahigh competence ($4\times10^{10}$ cfu/µg).

The present invention discloses the use of higher rated transformation efficient cell (procured from Lucigen). Hence the present invention reports higher transformation efficiencies of restriction digested phagemid vectors ligated to Fab insert fragments. This advantageous utilization enables the present invention to arrive at a large naïve library as set out herein utilizing lesser number of transformations.

The present invention also discloses that the transformation efficiency of vector and insert ligations depends upon DNA quality and adequacy of ligation. While the problem of DNA quality has been focused upon and improved earlier (Martineau P, 2010. Synthetic antibody libraries. In: *Antibody Engineering*; Rader C, 2012b. Generation of human Fab libraries by phage display. In: *Methods in Molecular Biology Vol.* 901: *Antibody Methods and Protocols*), the problem of adequacy of ligation has not. To elaborate, most antibody cloning formats use a cassette cloning approach in which the $V_L$, $V_H$, $C_L$ or $C_H1$ fragments are treated modularly for PCR-based amplification, fusion, restriction digestion with enzymes that cut rarely within V-domains (Persic L et al., 1997), and ligation to a vector. The present invention discloses that highest transformation efficiencies may be obtained when the sticky ends generated after restriction digestion of a population of PCR amplified/fused fragments have the minimum number of mismatch with the compatible sticky ends in the vector. Other improvements such as the importance of salt removal from ligation mixes for achieving higher transformation efficiencies by electroporation have been described (Chowdhury P S, 2002. Targeting random mutations to hotspots in antibody variable domains for affinity improvement. In: *Methods in Molecular Biology, vol.* 178: *Antibody Phage Display: Methods and Protocols*), and the present invention demonstrates a similar beneficial effect using ultrafiltration through microconcentrators (de Haard H J W, 2002. Construction of large naïve Fab libraries. In: *Methods in Molecular Biology, Vol.* 178: *Antibody Phage Display: Methods and Protocols*; Green M R and Sambrook J, 2012a. Concentrating and desalting nucleic acids with microconcentrators. In: *Molecular Cloning: A Laboratory Manual; Vol.* 1) in the examples. The beneficial effect of high fidelity amplification and seamless fusion of these fragments for increasing potential translatability of the captured Fab that advantageously improves on the utility is also disclosed in the present application.

The present invention discloses a process for producing the APDL, wherein displaying the captured immune repertoire in a vector comprises the steps of:
i) ligating the Fabs in a phagemid vector;
ii) transforming the ligated mixture into a suitable host.

The present invention discloses a process for producing the APDL, wherein the ligation of Fab repertoires obtained using the SEQ ID 32 and 34 is conducted by
i) blunting the Fabs using the 3'-5' exonuclease property of T4 DNA polymerase at 11-37° C., preferably 11° C., and phosphorylation of the 5' ends of blunted Fabs using T4 polynucleotide kinase at 37° C. for 1-1.5 h, preferably 1.5 h;
ii) by self-ligation of Fabs obtained at step (i) at a temperature range of 4-16° C., preferably 16° C. for 16 h followed by 25° C. for 1 h, with a concentration range of 50-400 ng/μl of total DNA, preferably 200 ng/μl, in the presence of additives selected from the group comprising polyethylene glycol of molecular weight 6000-32000 Daltons, preferably 8000 Daltons, in a final percentage ranging between 1.5-9% w/v, preferably 4-7% w/v, more preferably 6% w/v;

iii) restriction digestion of the self-ligated Fab population from (ii) with 32 U/μg SfI at 50° C. for 16 h to release linear Fabs with sticky ends followed by agarose gel purification;

iv) by sticky end ligation of linear Fabs to pCOMB3XSS obtained at step (iii) at a temperature of 16° C. for 16 h followed by 37° C. for 1 h and heat-inactivation at 70° C. for 15 min.

The present invention further discloses a process for producing the APDL, wherein the ligation of Fab repertoires obtained using SEQ ID 34 and 35-37 to the pCOMB3XSS vector is conducted by i) restriction digestion of the linear Fab population with 32 U/μg SfiI at 50° C. for 16 h to release linear Fabs with sticky ends followed by agarose gel purification;

ii) by sticky end ligation of linear Fabs obtained at step (i) at a temperature of 16° C. for 16 h followed by 37° C. for 1 h and heat-inactivation at 70° C. for 15 min.

The present invention discloses a process for producing the APDL, wherein the ligation of Fab repertoires obtained using SEQ ID 34 and 55 to the pSSY1 vector is conducted by i) restriction digestion of the linear Fab population with 32 U/μg SfiI at 50° C. for 16 h to release linear Fabs with sticky ends followed by agarose gel purification;

ii) by sticky end ligation of linear Fabs obtained at step (i) at a temperature of 16° C. for 16 h followed by 37° C. for 1 h and heat-inactivation at 70° C. for 15 min.

The present invention also discloses vide examples a maximum amount of DNA that can be transformed into a fixed volume of high transformation efficiency TG1 cells without any decrease in efficiency. Although it seems obvious that building a library is a compromise between size and efficiency of transformation, a library having optimum size, diversity and balance of cost has not been found in prior art as of now. The present application discloses such a number by utilizing the principle of titration. Examples included herein demonstrate that this determination allowed the process of the present invention as set out herein in reducing the number of transformations drastically. Such reduction resulted in a very large library size, with a comparatively small amount of ligated DNA as well with much shorter turnaround times. The gain in library-making speed can be advantageous when immune libraries may be required to be created to discover pathogen-specific antibodies rapidly in biodefense-like scenarios. Similarly, significant cost savings in reagent use may be achieved by using smaller amounts of PCR-amplified and fused DNA. The present invention discloses a process to reduce the number of transformations thereby increasing the size, with benefits of time and cost and is one of the several advantages of the library and the process of arriving at the library as set out herein.

In the present invention, the APDL is obtained from 15-160 μg of ligated DNA, preferably 20-100 μg, more preferably 40 to 50 μg of ligated DNA in a single step of transformation. The present invention discloses a process for producing the kappa subtype APDL, wherein the APDL is obtained from 10 to 70 μg of ligated DNA, preferably 20 to 50n, more preferably 25 to 30 μg of ligated DNA as obtained in a single step of transformation. The present invention discloses a process for producing the lambda subtype APDL, wherein the APDL is obtained from 5 to 60 μg of ligated DNA, preferably 8 to 50 μg, more preferably 10 to 20 μg of ligated DNA as obtained in steps 15-20 in a single step of transformation.

The present invention discloses a process for producing the APDL, wherein the kappa APDL is obtained with an efficiency of $1.92 \times 10^9$ to $1.98 \times 10^{10}$ cfu/μg and the lambda APDL is obtained with an efficiency of $1.92 \times 10^9$ to $9.1 \times 10^9$ cfu/μg.

pSSY1—A new phagemid display vector: The present invention discloses a new phagemid vector for making ultra-large libraries (pSSY1; SEQ ID 38 and FIG. 28). As illustrated in the Examples, creation of this vector was necessitated by the inherent defects in the parental vector pCOMB3XSS (FIG. 12; Barbas C F III et al., 1991; Andris-Widhopf J et al., 2001. Generation of antibody libraries: PCR amplification and assembly of light- and heavy-chain coding sequences. In: *Phage Display: A Laboratory Manual*) that did not allow creation of ultra-large libraries due to inefficient ligations. The present invention discloses the re-design of the vector based on the design intent of the parental vector, but this effort also introduced major changes in the overall sequence and provided significant advantages that are illustrated in the Examples herein. Further features of this plasmid, and similarities as well as dissimilarities with pCOMB3XSS are illustrated in Example 24.

Producing recombinant antibodies by PCR amplification and fusion of V- and C-genes: This invention designs and utilizes an optimized set of PCR conditions for high fidelity amplification of human V-genes and their fusion with human C-genes for creating a combinatorial human immunoglobulin repertoire for subsequent cloning and display with the phagemid display vector pSSY1. For this purpose, it utilizes a set of 35 primers set out in the prior art (Andris-Widhopf J et al., 2001. Generation of antibody libraries: PCR amplification and assembly of light- and heavy-chain coding sequences. In: *Phage Display: A Laboratory Manual*) that were subsequently modified to allow efficient ligation to the pSSY1 vector. The present invention discloses a novel process for amplification of the said 35 primers and their subsequent ligation in the pCOMB3XSS vector. The present invention also discloses modified primers and their amplification and subsequent ligation into the novel vector pSSY1.

Recombinant antibody generation depends on the modularity inherent in how an immunoglobulin is assembled in vivo. Briefly, both the light and heavy chains of an immunoglobulin molecule are composed of variable (V), hinge (H) and constant (C) regions in a N-terminal-C-terminal direction that originate from their respective gene clusters (loci) within the chromosomes in a mirrored 5'-3' exon-intron fashion. The chromosomal location of these gene clusters do differ—while the human heavy chain locus is on chromosome 14 (IGH locus; 14q32.33), the human light chain loci are on chromosomes 2 (kappa or IGK locus; 2p11.2) and 22 (lambda or IGL locus; 22q11.2). Each locus can contain multiple genes—the overall number of all human Ig genes is estimated to range between 371 and 422. Diversity in the repertoire of heavy chains is primarily generated by recombination of the germline V, Diversity (D) and Junctional (J) exons, while diversity in the repertoire of light chains is primarily generated by recombination of the germline V and J exons. Three additional mechanisms contribute to the immunoglobulin chain diversity. The first is called the N diversity (N, for Nucleotides) which results from the deletion and/or addition of nucleotides at random by terminal deoxynucleotidyl transferase (TdT) at the V-D-J junction, resulting in a region that is not encoded in the germline DNA. The second mechanism is called somatic hypermutation (SHM), which specifically affects the V-D-J rearranged genes, and is believed to be controlled either by activation-induced cytidine deaminase-uracil DNA glycosylase-DNA polymerase eta enzyme complex, or an error prone RNA-directed DNA polymerase. Regardless of mechanism, the end result is change of nucleotides at "hot-spots" that therefore differ from the germline code, and generally result in improvements of affinity to a target antigen. The third mechanism is called class switch, which joins the rearranged V-D-J clusters of heavy chains to various hinge and constant exons. Class switch does not impact on the antigen recognition ability of the immunoglobulin, but allows differential interaction of immune effector cells to the constant regions that provides final functionality to the molecule.

The immunoglobulin genes are expressed only in the cells from B-lineage, first as membrane-bound receptors followed by secretion as immunoglobulin proteins. The type of recombination, SHM or class switch that a B-cell light and heavy chain combination might contain depends on the stage in its life cycle. The source of immune tissues for recombinant antibody generation therefore depends on the project goal—building a naïve library requires harvesting of B-cells that have undergone minimum re-arrangement of the germline, preferably without N-addition or SHM. In contrast, building an immune library requires harvesting of B-cells that have preferentially undergone SHM to retrieve the affinity matured V-D-J or V-J combinations. Different compartments of the human body encase B-cells at different stages of their life cycle, and therefore care must be exercised for appropriate tissue harvest (Dobson C L et al., 2012. Naïve antibody libraries from natural repertoires. In: *Phage Display in Biotechnology and Drug Discovery*). As exemplified herein, the ultra-large naïve Fab library described in this invention use B-cells harvested from human peripheral blood mononuclear cell population, tonsil and bone marrow.

The present invention discloses a process for producing the APDL comprising the steps of:
 i) immune repertoire capture to obtain a Fab;
 ii) displaying the captured immune repertoire of as above in a suitable vector.

The present invention further discloses a process for producing the APDL, wherein the immune repertoire capture comprises the steps of:
 i) RNA isolation and cDNA synthesis;
 ii) amplification of $V_L$ (lambda and kappa) and $V_H$ domains using primers comprising the SEQ ID 1-23 and 42-54;
 iii) amplification of C domains using SEQ ID 24-26 and using primers comprising the SEQ ID 27-31;
 iv) overlap PCR of light chains by fusion of $V_\kappa$ and $C_\kappa$ domains and $V_\lambda$ and $C_\lambda$ domains obtained from step (ii) and (iii), respectively, using primers comprising the SEQ ID 30, 32, 35-37 and 55;
 v) overlap PCR of heavy chains obtained from fusion of $V_H$ and $C_H1$ obtained from step (ii) and (iii) using primers comprising the SEQ ID 28 & 33;
 vi) overlap PCR of light chains and heavy chains obtained from steps (iv) and (v) respectively to obtain Fabs using primers comprising the SEQ ID 32, 34, 35-37 and 55.
 vii) purifying the amplicons at each step.

In contrast, synthetic or semi-synthetic libraries either depend upon a fixed natural Ig template or fixed synthetic framework regions of the variable domains on which the core antigen-recognizing amino acids of the variable domains (the complementarity determining region or CDR) are subcloned after in vitro synthesis.

Recombinant antibody generation from natural sources begins after harvesting the transcriptome (mRNA) of the target B-cell population and then reverse transcribing it to create complementary DNA (cDNA). Domain specific primers are then used to amplify the subtype-specific (kappa or lambda) V-gene repertoire from the cDNA templates by PCR. The amplified V-domains of one subtype are then allowed to pair randomly with the opposite subtype in vitro to allow creation of a multitude of paratopes. Further in vitro manipulations that are recombinase or DNA polymerase based allow joining of H- or C-regions to create Ig fragments or full length Igs that can be displayed. As should be obvious, V-domain specific amplification and random pairing destroys the inherent paratope information. To some extent, this is intentional for one of the design goals of recombinant antibody generation is to generate new paratopes that can recognize self-antigens or have very high affinities for a target antigen. Such paratopes would normally be deselected in vivo and therefore, would be not found in a B-cell immune repertoire (Foote J and Eisen H N, 1995; Hai S-H et al., 2009. Immunogenicity screening using in silico methods: Correlation between T-Cell epitope content and clinical immunogenicity of monoclonal antibodies. In: *Therapeutic Monoclonal Antibodies: From Bench to Clinic*). However, for some applications, it is important to capture the paratope information. A system of linked PCR has been described (Meijer P J et al., 2006) for such purposes.

Regardless whether the design intent is to capture the paratopes as they are or recombine the V-domains randomly, PCR primers are required to specifically amplify the V-domains. Both due to the multiplicity of V-gene families that further encode allelic variations, as well as the fact that a particular class of V-D-J or V-J combination needs to be captured depending on whether one wishes to create a naïve or immune library, a variety of thoughtful primer sets have been designed and successfully used to create antibody phage display libraries (Marks J D et al., 1991; de Boer M et al., 1994; Sblattero D and Bradbury A, 1998). All such primers incorporate degenerate nucleotides at specific positions to accommodate the variations in amino acids at those positions as revealed by sequences available in the antibody databases (http://www.bioinf.org.uk/abs/simkab.html; http://www.vbase2.org/; http://www.imgt.org/). The present invention discloses a process utilizing the primer set described by a Scripps group (Andris-Widhopf J et al., 2001. Generation of antibody libraries: PCR amplification and assembly of light- and heavy-chain coding sequences. In: *Phage Display: A Laboratory Manual*). The design intent and method used to design these primers is available (Burton D R, 2001. Overview: Amplification of antibody genes. In: *Phage Display: A Laboratory Manual*).

The present invention also discloses a set of novel primers as the earlier primers set out in the prior art when progressed to the recipient phagemid display vector pCOMB3XSS did not allow for efficient cassette cloning of the V-domains amplified by these primers. This re-design involved the restriction ends of the primers. In particular, the re-design involved changing the core pentanucleotide sequence of the SfiI sites that were built in all the $V_\kappa$ and $V_\lambda$ forward primers, as well as the final overlap forward primer. Further re-design involved reducing the homology between the final overlap forward and reverse primers. As exemplified herein, these design changes were crucial for high efficiency ligation of the amplified Fabs to the new phagemid display vector pSSY1. As discussed earlier and as exemplified herein, highly efficient ligation combined with parameter-controlled high efficiency transformation as disclosed herein enables for the first time a single step transformation to create a >$10^{11}$ cfu Fab-phage display library.

PCR primers alone are not sufficient in themselves to ensure high fidelity amplification of templates, particularly templates encoding multiple variations such as those encoded by the V-domains. Prior art primarily discloses use of Taq polymerase, partly because that was the only thermostable DNA polymerase available for a long time. Taq polymerase however has a fairly high error rate (Tindall K R and Kunkel T A, 1988; Gelfand D H and White T J, 1990) that results in introduction of stop codons and frameshifts in V-domains or V-C fusions (reviewed in Lowe D and Vaughan T J, 2009. Human antibody repertoire libraries; In: *Therapeutic Monoclonal Antibodies: From Bench to Clinic*; Azzazy H M and Highsmith W E, 2002). In recognition of this problem, more recent practitioners of this art have used thermostable polymerase blends (Andris-Widhopf J et al., 2001. Generation of antibody libraries: PCR amplification and assembly of light- and heavy-chain coding sequences. In: *Phage Display: A Laboratory Manual*; Rader C, 2012b. Generation of human Fab libraries by phage display. In: *Methods in Molecular Biology Vol. 901: Antibody Methods and Protocols*) based on the LA-PCR principle (Barnes W M, 1994), although this still does not ensure amplification of all V-domains (Løset G Å et al., 2005; Rader C, 2012b. Generation of human Fab libraries by phage display. In: *Methods in Molecular Biology Vol. 901: Antibody Methods and Protocols*). Regardless whether Taq or Taq blends are used, almost all practitioners have used conservative annealing temperatures (~56° C.) in order to allow the degenerate primers to amplify maximally (Marks J D et al., 1991; de Boer M et al., 1994; Sblattero D and Bradbury A, 1998; Andris-Widhopf J et al., 2001. Generation of antibody libraries: PCR amplification and assembly of light- and heavy-chain coding sequences. In: *Phage Display: A Laboratory Manual*; Rader C, 2012b. Generation of human Fab libraries by phage display. In: *Methods in Molecular Biology Vol. 901: Antibody Methods and Protocols*). As exemplified herein, our detailed analysis of the templates suggests that most of human $V_H$ and $V_\lambda$ family genes are GC-rich for most of their amplicon length, particularly in the $1^{st}$ framework (FR1) regions where all forward V-domain primers are designed to anneal, including the Scripps primers described in prior art. The $V_\kappa$ family genes, in contrast, have average GC content (~50%) for most of the length of their amplicons, including the FR1 region, although GC-rich stretches also exist within these gene families. The present invention discloses through extensive experimentation that neither the DNA polymerase combinations nor the low annealing temperature suggested in the prior art are appropriate for efficient amplification from such templates regardless of the accuracy of primer design. As exemplified herein, specific buffer-polymerase combinations were designed that follow the current standard of amplifying through such GC-rich regions (Green M R and Sambrook J. 2012b. PCR amplification of GC-Rich Templates. In: *Molecular Cloning: A Laboratory Manual; Vol. 1*). Furthermore, analysis of a limited number of clones from the resultant ultra-large library suggest that no loss of diversity has resulted from this inventive stratagem and the library was able to produce different binder sequences against each of the three tested antigens as determined by detailed analysis. In contrast to most published data, all of these binders were also kinetically stable with off-rates in the $10^{-4}$ to $10^{-5} \cdot s^{-1}$ range. This suggests that the inventive amplification system has captured the desired diversity of a naïve B-cell immune repertoire with high fidelity and efficiency. Examples illustrating these principles are presented herein.

The present application discloses a process for producing the APDL, wherein the amplification of variable lambda domains is conducted in a two-step PCR using primers comprising the SEQ ID 14-23 and 46-54 and comprising the steps of:
i) obtaining a mixture of cDNA template, polymerase enzyme, primers, buffer and dNTP mix in an aqueous solution;
ii) subjecting the mixture of step (i) to a temperature range of 90 to 96° C. to denature the templates;
iii) simultaneous annealing and extension of the denatured templates from (ii) at a temperature of 65 to 72° C. to obtain variable lambda domains such that it results in a diverse $V_\lambda$ repertoire capture.

Considering the fact that $T_m$ for variable kappa reverse primer was different, the 2-step PCR further was optimized to a 3-step PCR. The amplification of variable kappa domains is conducted by a three-step PCR using primers comprising the SEQ ID 9-13 and 42-45 and comprising the steps of:
i) obtaining a mixture of cDNA template, polymerase enzyme, primers, buffer and dNTP mix in an aqueous solution;
ii) subjecting the mixture of step (i) to a temperature range of 90 to 96° C. to denature the templates;
iii) annealing the primers to the denatured templates from step (ii) at a temperature range of 55 to 70° C.;
iv) extension of the primers on annealed templates from step (iii) at temperature of 65 to 72° C. to obtain variable kappa domains such that it results in a diverse $V_\kappa$ repertoire capture.

The present application discloses a process for producing the APDL, wherein the amplification of all variable heavy domains is conducted in a three-step PCR using primers comprising the SEQ ID 1-8 and comprising the steps of:
i) obtaining a mixture cDNA template, polymerase enzyme, primers, buffer and dNTP mix in an aqueous solution;
ii) subjecting the mixture of step (i) to a temperature range of 90 to 96° C. to denature the templates;
iii) annealing the primers to the denatured templates from step (ii) at a temperature range of 55 to 70° C.;
iv) extension of the primers on annealed templates from step (iii) at a temperature of 65 to 72° C. to obtain variable heavy domains such that it results in a diverse $V_H$ repertoire capture.

Considering that the C-domain templates are plasmid based (synthetic constructs), and less complex in terms of target base pairs to be scanned and hybridized by the primers, the invention discloses both 3-step PCR ($C_H1$ domains) and 2-step PCR ($C_K$ and CA) for amplifications.

The present application discloses a process for producing the APDL, wherein the amplification of $C_H1$ domains is conducted as a three-step PCR using primers comprising the SEQ ID 27-28 and templates comprising the SEQ ID 24 and 39, and comprising the steps of:
i) obtaining a mixture of synthetic $C_H1$-domain templates, polymerase enzyme, primers, buffer and dNTP mix in an aqueous solution;
ii) subjecting the mixture of step (i) to a temperature range of 90 to 96° C. to denature the templates;
iii) annealing the primers to the denatured templates from step (ii) at a temperature range of 55 to 70° C.;

iv) extension of the primers on annealed templates from step (iii) at a temperature of 65 to 72° C. to obtain the constant heavy domain.

The present application discloses a process for producing the APDL, wherein the amplification of $C_\kappa$ and $C_\lambda$ domains are conducted in a two-step PCR using primers comprising the SEQ ID 29-31 and templates comprising the SEQ ID 25-26 and 40-41, and comprising the steps of:
i) obtaining a mixture of synthetic $C_\kappa$ and $C_\lambda$ domains, polymerase enzyme, primers, buffer and dNTP mix in an aqueous solution;
ii) subjecting the mixture of step (i) to a temperature range of 90 to 96° C. to denature the templates;
iii) simultaneous annealing and extension of the denatured templates from step (ii) at a temperature of 65 to 72° C. to obtain the constant kappa and lambda domains.

The fusions of $V_\kappa$ and $C_\kappa$ domains and $V_\lambda$ and $C_\lambda$ domains for producing the APDL are conducted in a two-step PCR using primers comprising the SEQ ID 30, 32, 35-37 and 55 and comprising the steps of:
i) obtaining a mixture of light chain variable and constant gene templates obtained as described above, polymerase enzyme, primers, buffer and dNTP mix in an aqueous solution;
ii) subjecting the mixture of step (i) to a temperature range of 90 to 96° C. to denature the templates;
iii) simultaneous annealing and extension of the denatured templates from step (ii) at a temperature of 65 to 72° C. to obtain lambda and kappa light chain repertoires.

The fusion of $V_H$ and $C_H1$ domains for producing the APDL is conducted in a three-step PCR using primers comprising the SEQ ID 28 and 33, and comprising the steps of:
i) obtaining a mixture of heavy chain variable and constant gene templates, respectively, polymerase enzyme, primers, buffer and dNTP mix in an aqueous solution;
ii) subjecting the mixture of step (i) to a temperature range of 90 to 96° C. to denature the templates;
iii) annealing the primers to the denatured templates from step (ii) at a temperature of 55 to 70° C.;
iv) extension of the primers on annealed templates from step (iii) at a temperature of 68 to 72° C. to obtain heavy chain repertoires.

The fusion of the light and heavy chains obtained from above mentioned steps were carried out by 2-step or 3-step PCR using optimal enzyme and buffer compositions. The fusion PCR of light and heavy chains for producing the APDL are conducted in a two-step PCR using primers comprising the SEQ ID 32, 34, 35-37 and 55, and comprising the steps of:
i) obtaining a mixture of light and heavy chain repertoires, polymerase enzyme, primers, buffer and dNTP mix in an aqueous solution;
ii) subjecting the mixture of step (i) to a temperature range of 90 to 96° C. to denature the templates;
iii) simultaneous annealing and extension of the denatured templates from step (ii) at a temperature of 65 to 72° C. to obtain lambda and kappa Fab repertoires.

Alternatively, the fusion PCR of light and heavy chains for producing the APDL are conducted in a three-step PCR using primers comprising the SEQ ID 32, 34, 35-37 and 55, and comprising the steps of:
i) obtaining a mixture of light and heavy chain repertoire, polymerase enzyme, primers, buffer and dNTP mix in an aqueous solution;
ii) subjecting the mixture of step (i) to a temperature range of 90 to 96° C. to denature the templates;
iii) annealing the primers to the denatured templates from step (ii) at a temperature of 55 to 70° C.;
iv) extension of the primers on annealed templates from step (iii) at a temperature of 65 to 72° C. to obtain lambda and kappa Fab repertoires.

The present application further discloses a process for producing the APDL wherein the buffer is selected from the group comprising AmpliTaq® Gold buffer, AmpliTaq® PCR buffer, AmpliTaq® PCR buffer II, Expand™ buffer 2, Expand™ buffer 3, Expand™ buffer 4, Thermopol® buffer, Pfu Ultra II buffer, Exact™ polymerase buffer, PCR Extender buffer, Tuning buffer, Vent® Buffer, Advantage®2 buffer, Advantage®2 SA buffer and the thermostable DNA polymerase enzyme is selected from the group comprising AmpliTaq® Gold DNA polymerase, Expand™ LT Taq DNA polymerase blend, Phusion® High Fidelity DNA polymerase, PfuUltra™ II HS DNA polymerase, PCR Extender™ DNA polymerase blend, Exact™ DNA polymerase, Vent® DNA polymerase, Deep Vent® DNA polymerase, and Advantage®2 DNA polymerase Mix.

EXAMPLES

The examples supporting the invention are described as below. The following example is given by the way of illustration of the present invention and therefore should not be construed to limit the scope of the present invention.

Example 1

RNA Isolation and cDNA Synthesis

Total RNA was isolated from human PBMCs using a combined TRIzol (Invitrogen/ThermoFisher) plus RNeasy kit (Qiagen) method. Freshly harvested PBMC's were sonicated in TRIzol and the lysates stored at −80° C. The lysates were extracted with 0.2 volumes of chloroform to isolate the nucleic acid fraction in the aqueous phase. The aqueous phase was immediately mixed with 70% ethanol and the RNeasy kit instructions followed thereafter. RNA was quantified at 260 nm, and quality checked by agarose gel electrophoresis at neutral pH. FIG. 1 shows the image of an ethidium-bromide stained gel that demonstrates presence of high quality intact RNA with characteristic 28S and 16S bands without any genomic DNA contamination.

cDNA prepared from this total RNA preparation allows amplification of the V-domains. cDNA was synthesized from this total RNA preparation using Superscript III first strand cDNA synthesis system (Invitrogen/ThermoFisher) using a mixture of oligo $dT_{18}$ (SEQ ID NO: 330) and random hexamer primers. 1 μg of RNA was added per 20 μl reaction and 20 reactions of the same were carried out. The reactions were pooled after completion. The pooled cDNA was dissolved in water, purified by phenol chloroform extraction and ethanol precipitated. The yield of cDNA was estimated by both Picogreen and Ribogreen methods after phenol-chloroform extraction and ethanol precipitation. Table 1 shows an example of differences in yields estimated by the two dyes.

TABLE 1

| Yield/μg of Total RNA | By Picogreen | By Ribogreen |
|---|---|---|
| cDNA Preparation, SSIII First strand cDNA synthesis kit | 57 ng | 135 ng |

Example 2

Amplification of V-Domains

Figure 2:
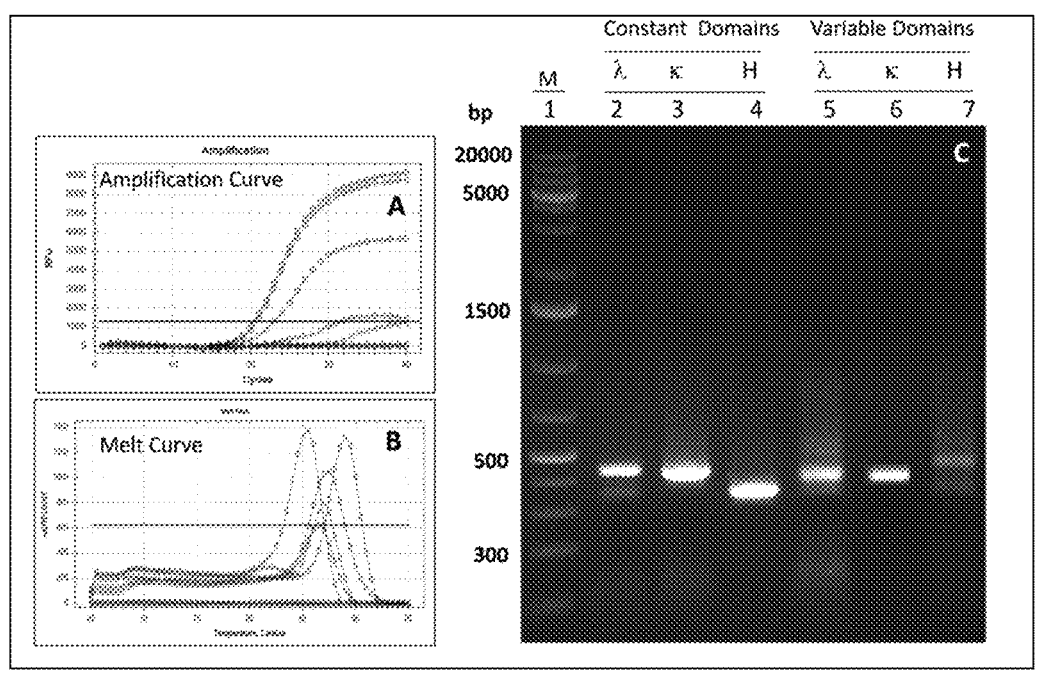
FIG. 2 depicts variable and constant gene amplifications in Sso Fast Evagreen. Panels A & B show amplification and melt curve peaks, respectively. Lanes 2, 3 and 4 of panel C contain PCR products of lambda, kappa and heavy constant synthetic genes as a template (20 ng/25 μl reaction) with respective constant gene primers viz. SEQ ID 29/SEQ ID 30, SEQ ID 31/SEQ ID 30 and SEQ ID 27/SEQ ID 28. Lanes 5, 6 and 7 contain PCR products of cDNA (20 ng/25 μl reaction) as a template with respective lambda, kappa and heavy variable primers viz. SEQ ID 14/SEQ ID 23, SEQ ID 9/SEQ ID 13 and SEQ ID 1/SEQ ID 7. Lane 1 contains 1 kb plus DNA marker from Fermentas. PCR products were run on 1.2% gels cast in 1×TBE containing 0.01 μg/ml ethidium bromide, and run at 5V/cm for 90 min.

A set of 23 primers (SEQ ID 1-23) were used to amplify $V_L$, $V_H$ and J regions of the human immunoglobulin families from the synthesized cDNA. Recommended PCR conditions (Andris-Widhopf J et al., 2001. Generation of antibody libraries: PCR amplification and assembly of light- and heavy-chain coding sequences. In: *Phage Display: A Laboratory Manual*), when applied, however, did not produce any amplicon. A highly efficient real time PCR cocktail using fast PCR amplification conditions (FIG. 2) was used to produce the amplicons. PCR reactions were cycled with the following protocol: hot start at 95° C. for 30s, followed by 40 cycles of denaturation at 95° C. for 5s, annealing at 58° C. for 5s, plate read, extension at 72° C. for 30s, followed by melt curve analysis of amplicons between 65° C. and 95° C. at 0.5° C. increments along with simultaneous plate read. The results are depicted at FIG. 2.

The present invention analyzes the GC content of all human variable gene families at 30 nucleotide windows based on sequence information available in the IMGT database (Lefranc M-P., 2001). Tables 2A-2C show that while the average % GC content of all the V-families is close to 50%, most $V_H$ and $V_\lambda$ families as well as a few $V_\kappa$ families have 60-70% GC content in many stretches, particularly in the first two 30 nt windows. The latter span encompasses the FR1 region where the forward V-domain amplification primers are designed to anneal.

TABLE 2A

% GC Content - IGHV Families

| Sr. No. | Sequence ID | Segment-1 30 | Segment-2 30 | Segment-3 30 | Segment-4 30 | Segment-5 30 | Segment-6 30 | Segment-7 30 | Segment-8 30 | Segment-9 30 | Segment-10 23-36 | Average |
|---|---|---|---|---|---|---|---|---|---|---|---|---|
| 1 | IGHV1-3 | 63 | 57 | 50 | 60 | 60 | 40 | 47 | 63 | 57 | 46 | 54 |
| 2 | IGHV1-18 | 60 | 60 | 50 | 60 | 60 | 37 | 60 | 57 | 57 | 54 | 55 |
| 3 | IGHV1-24 | 63 | 60 | 53 | 53 | 57 | 37 | 57 | 53 | 57 | 50 | 54 |
| 4 | IGHV1-45 | 63 | 50 | 57 | 67 | 63 | 40 | 47 | 57 | 57 | 38 | 54 |
| 5 | IGHV1-46 | 67 | 57 | 53 | 57 | 53 | 50 | 57 | 60 | 57 | 54 | 56 |
| 6 | IGHV1-58 | 67 | 60 | 60 | 60 | 63 | 40 | 53 | 60 | 57 | 54 | 57 |
| 7 | IGHV1-69 | 67 | 60 | 60 | 60 | 63 | 40 | 53 | 60 | 57 | 54 | 57 |
| 8 | IGHV2-5 | 53 | 60 | 56 | 60 | 67 | 40 | 57 | 50 | 50 | 48 | 54 |
| 9 | IGHV2-26 | 57 | 60 | 60 | 50 | 70 | 37 | 53 | 53 | 53 | 48 | 54 |
| 10 | IGHV2-70 | 63 | 57 | 57 | 50 | 70 | 37 | 53 | 50 | 50 | 48 | 54 |
| 11 | IGHV3-7 | 70 | 67 | 50 | 60 | 70 | 30 | 57 | 47 | 57 | 50 | 56 |
| 12 | IGHV3-9 | 67 | 60 | 50 | 57 | 67 | 37 | 60 | 50 | 50 | 39 | 54 |
| 13 | IGHV3-11 | 70 | 60 | 53 | 57 | 60 | 33 | 57 | 50 | 57 | 54 | 55 |
| 14 | IGHV3-13 | 70 | 63 | 53 | 60 | 53 | 43 | 63 | 37 | 60 | 43 | 55 |
| 15 | IGHV3-15 | 70 | 57 | 50 | 67 | 70 | 37 | 57 | 37 | 43 | 50 | 54 |
| 16 | IGHV3-20 | 67 | 70 | 50 | 57 | 67 | 37 | 57 | 50 | 53 | 54 | 56 |
| 17 | IGHV3-21 | 70 | 67 | 52 | 60 | 63 | 30 | 53 | 50 | 53 | 52 | 55 |
| 18 | IGHV3-23 | 67 | 63 | 53 | 63 | 67 | 43 | 63 | 43 | 57 | 46 | 57 |
| 19 | IGHV3-30 | 70 | 67 | 53 | 63 | 67 | 20 | 60 | 43 | 53 | 50 | 55 |
| 20 | IGHV3-33 | 70 | 67 | 53 | 63 | 67 | 23 | 60 | 43 | 57 | 50 | 55 |
| 21 | IGHV3-43 | 63 | 67 | 50 | 50 | 63 | 40 | 57 | 43 | 47 | 39 | 52 |
| 22 | IGHV3-48 | 70 | 63 | 53 | 57 | 60 | 30 | 57 | 43 | 53 | 50 | 54 |
| 23 | IGHV3-49 | 70 | 63 | 47 | 53 | 63 | 40 | 53 | 40 | 47 | 47 | 52 |
| 24 | IGHV3-53 | 67 | 63 | 60 | 60 | 63 | 43 | 60 | 40 | 57 | 52 | 57 |
| 25 | IGHV3-64 | 67 | 67 | 53 | 60 | 50 | 33 | 53 | 45 | 57 | 46 | 53 |
| 26 | IGHV3-66 | 67 | 63 | 63 | 60 | 63 | 40 | 60 | 40 | 53 | 48 | 56 |
| 27 | IGHV3-72 | 70 | 63 | 53 | 63 | 70 | 37 | 53 | 37 | 43 | 53 | 54 |
| 28 | IGHV3-73 | 73 | 63 | 57 | 67 | 67 | 40 | 57 | 43 | 47 | 50 | 56 |
| 29 | IGHV3-74 | 73 | 60 | 53 | 60 | 67 | 40 | 63 | 50 | 53 | 46 | 57 |
| 30 | IGHV4-4 | 70 | 63 | 57 | 60 | 67 | 47 | 57 | 53 | 67 | 52 | 59 |
| 31 | IGHV4-28 | 70 | 63 | 57 | 60 | 67 | 40 | 57 | 50 | 63 | 50 | 58 |
| 32 | IGHV4-31 | 70 | 60 | 57 | 57 | 63 | 50 | 53 | 40 | 63 | 55 | 57 |
| 33 | IGHV4-34 | 67 | 60 | 57 | 63 | 63 | 40 | 53 | 53 | 67 | 52 | 58 |
| 34 | IGHV4-39 | 70 | 63 | 60 | 53 | 67 | 47 | 57 | 47 | 63 | 52 | 58 |
| 35 | IGHV4-59 | 70 | 63 | 57 | 57 | 57 | 43 | 53 | 53 | 63 | 52 | 57 |
| 36 | IGHV4-61 | 70 | 63 | 63 | 57 | 63 | 47 | 57 | 57 | 63 | 55 | 60 |
| 37 | IGHV5-51 | 63 | 53 | 47 | 63 | 67 | 43 | 63 | 60 | 67 | 50 | 58 |
| 38 | IGHV6-1 | 62 | 60 | 63 | 50 | 63 | 50 | 33 | 40 | 57 | 53 | 53 |

TABLE 2B

% GC Content - IGKV Families

| Sr. No. | Sequence ID No. of bases | Segment-1 30 | Segment-2 30 | Segment-3 30 | Segment-4 30 | Segment-5 30 | Segment-6 30 | Segment-7 30 | Segment-8 30 | Segment-9 30 | Segment-10 15-33 | Ave GC % Content |
|---|---|---|---|---|---|---|---|---|---|---|---|---|
| 1 | IGKV1-6 | 60 | 53 | 53 | 40 | 53 | 50 | 57 | 57 | 30 | 33 | 49 |
| 2 | IGKV1-39 | 57 | 53 | 53 | 33 | 53 | 53 | 53 | 50 | 37 | 47 | 49 |
| 3 | IGKV1-33 | 57 | 53 | 53 | 30 | 53 | 50 | 50 | 50 | 33 | 33 | 46 |
| 4 | IGKV1-27 | 57 | 53 | 60 | 37 | 47 | 53 | 57 | 57 | 33 | 47 | 50 |
| 5 | IGKV1-17 | 57 | 53 | 53 | 40 | 57 | 53 | 57 | 53 | 33 | 33 | 49 |
| 6 | IGKV1-16 | 53 | 53 | 57 | 37 | 53 | 53 | 53 | 57 | 37 | 27 | 48 |
| 7 | IGKV1-13 | 60 | 53 | 57 | 43 | 47 | 57 | 57 | 57 | 33 | 20 | 48 |
| 8 | IGKV1-12 | 53 | 53 | 53 | 50 | 53 | 53 | 57 | 57 | 33 | 47 | 51 |
| 9 | IGKV1-9 | 53 | 53 | 53 | 60 | 53 | 53 | 57 | 53 | 33 | 33 | 50 |
| 10 | IGKV1-8 | 60 | 50 | 53 | 37 | 53 | 53 | 57 | 53 | 33 | 27 | 48 |
| 11 | IGKV1D-43 | 60 | 53 | 57 | 37 | 40 | 53 | 60 | 57 | 33 | 33 | 48 |
| 12 | IGKV1D-39 | 57 | 53 | 53 | 33 | 53 | 53 | 53 | 50 | 37 | 47 | 49 |
| 13 | IGKV1D-33 | 57 | 53 | 53 | 30 | 53 | 50 | 50 | 50 | 33 | 33 | 46 |
| 14 | IGKV1D-17 | 53 | 50 | 60 | 37 | 50 | 53 | 57 | 53 | 33 | 33 | 48 |
| 15 | IGKV1D-16 | 53 | 53 | 53 | 50 | 50 | 53 | 53 | 57 | 57 | 27 | 51 |
| 16 | IGKV1D-13 | 60 | 53 | 57 | 47 | 47 | 57 | 57 | 57 | 33 | 20 | 49 |
| 17 | IGKV1D-12 | 50 | 53 | 53 | 50 | 53 | 53 | 57 | 53 | 33 | 47 | 50 |
| 18 | IGKV1D-8 | 50 | 53 | 50 | 37 | 57 | 53 | 53 | 50 | 33 | 27 | 46 |
| 19 | IGKV2-30 | 50 | 73 | 50 | 40 | 57 | 43 | 60 | 47 | 60 | 47 | 53 |
| 20 | IGKV2-29 | 47 | 73 | 53 | 37 | 60 | 50 | 57 | 47 | 63 | 37 | 52 |
| 21 | IGKV2-28 | 47 | 77 | 57 | 33 | 60 | 50 | 63 | 40 | 57 | 40 | 52 |
| 22 | IGKV2-26 | 50 | 77 | 53 | 40 | 60 | 50 | 63 | 47 | 57 | 36 | 53 |
| 23 | IGKV2-24 | 50 | 67 | 50 | 47 | 63 | 33 | 57 | 50 | 60 | 37 | 51 |
| 24 | IGKV2D-40 | 50 | 77 | 53 | 40 | 60 | 50 | 63 | 47 | 57 | 36 | 53 |
| 25 | IGKV2D-30 | 50 | 73 | 50 | 40 | 57 | 40 | 60 | 47 | 60 | 47 | 52 |
| 26 | IGKV2D-29 | 47 | 73 | 53 | 37 | 63 | 47 | 57 | 47 | 63 | 37 | 52 |
| 27 | IGKV2D-28 | 47 | 77 | 57 | 33 | 60 | 50 | 63 | 40 | 57 | 41 | 52 |
| 28 | IGKV2D-26 | 53 | 60 | 60 | 57 | 37 | 57 | 47 | 57 | 57 | 40 | 52 |
| 29 | IGKV3-20 | 53 | 57 | 60 | 50 | 63 | 67 | 60 | 53 | 40 | 50 | 55 |
| 30 | IGKV3-15 | 53 | 60 | 60 | 50 | 63 | 67 | 60 | 53 | 37 | 33 | 54 |
| 31 | IGKV3-11 | 50 | 57 | 60 | 47 | 60 | 67 | 60 | 53 | 37 | 60 | 55 |
| 32 | IGKV3D-20 | 53 | 57 | 63 | 50 | 67 | 63 | 60 | 53 | 40 | 50 | 56 |
| 33 | IGKV3D-15 | 53 | 60 | 60 | 50 | 63 | 70 | 60 | 53 | 37 | 33 | 54 |
| 34 | IGKV3D-11 | 50 | 57 | 63 | 50 | 60 | 67 | 63 | 53 | 37 | 53 | 55 |
| 35 | IGKV3D-7 | 47 | 57 | 60 | 47 | 63 | 67 | 63 | 57 | 37 | 33 | 53 |
| 36 | IGK4-1 | 57 | 70 | 43 | 37 | 57 | 53 | 63 | 57 | 57 | 30 | 52 |
| 37 | IGK5-2 | 53 | 50 | 47 | 40 | 33 | 53 | 53 | 27 | 40 | 33 | 43 |

TABLE 2C

% GC Content - IGLV Families

| Sr. No. | Sequence ID No. of bases | Segment-1 30 | Segment-2 30 | Segment-3 30 | Segment-4 30 | Segment-5 30 | Segment-6 30 | Segment-7 30 | Segment-8 30 | Segment-9 30 | Segment-10 14-47 | Ave GC % Content |
|---|---|---|---|---|---|---|---|---|---|---|---|---|
| 1 | IGLV1-36 | 63 | 63 | 53 | 43 | 50 | 53 | 60 | 67 | 43 | 58 | 55 |
| 2 | IGLV1-40 | 67 | 70 | 63 | 50 | 57 | 57 | 60 | 67 | 50 | 55 | 60 |
| 3 | IGLV1-44 | 63 | 70 | 50 | 43 | 57 | 57 | 60 | 67 | 43 | 58 | 57 |
| 4 | IGLV1-47 | 63 | 70 | 50 | 40 | 57 | 57 | 60 | 70 | 47 | 62 | 57 |
| 5 | IGLV1-51 | 63 | 63 | 57 | 40 | 50 | 47 | 60 | 67 | 57 | 58 | 56 |
| 6 | IGLV2-8 | 70 | 60 | 57 | 43 | 53 | 60 | 60 | 67 | 50 | 44 | 56 |
| 7 | IGLV2-11 | 63 | 60 | 53 | 43 | 53 | 57 | 60 | 63 | 50 | 48 | 55 |
| 8 | IGLV2-14 | 67 | 57 | 57 | 43 | 53 | 53 | 53 | 63 | 53 | 48 | 55 |
| 9 | IGLV2-18 | 67 | 60 | 57 | 50 | 60 | 57 | 60 | 63 | 53 | 41 | 57 |
| 10 | IGLV2-23 | 67 | 57 | 57 | 43 | 53 | 60 | 53 | 60 | 53 | 44 | 55 |
| 11 | IGLV3-1 | 57 | 63 | 43 | 53 | 50 | 67 | 57 | 60 | 53 | 60 | 56 |
| 12 | IGLV3-9 | 53 | 63 | 43 | 57 | 57 | 67 | 63 | 67 | 50 | 60 | 58 |
| 13 | IGLV3-10 | 60 | 60 | 43 | 47 | 60 | 60 | 60 | 60 | 40 | 45 | 54 |
| 14 | IGLV3-12 | 53 | 60 | 43 | 60 | 53 | 67 | 63 | 60 | 50 | 45 | 55 |
| 15 | IGLV3-16 | 60 | 57 | 43 | 50 | 43 | 67 | 53 | 50 | 47 | 50 | 52 |
| 16 | IGLV3-19 | 57 | 57 | 50 | 53 | 47 | 63 | 53 | 60 | 50 | 50 | 54 |
| 17 | IGLV3-21 | 60 | 63 | 43 | 60 | 57 | 70 | 60 | 67 | 53 | 40 | 57 |
| 18 | IGLV3-22 | 57 | 60 | 50 | 57 | 50 | 57 | 60 | 60 | 50 | 50 | 55 |
| 19 | IGLV3-25 | 60 | 63 | 50 | 50 | 63 | 57 | 57 | 53 | 43 | 50 | 55 |
| 20 | IGLV3-27 | 53 | 60 | 43 | 60 | 50 | 67 | 63 | 63 | 47 | 43 | 55 |
| 21 | IGLV4-3 | 67 | 60 | 60 | 43 | 50 | 60 | 63 | 63 | 50 | 57 | 57 |
| 22 | IGLV4-60 | 57 | 60 | 60 | 53 | 57 | 53 | 60 | 63 | 43 | 48 | 55 |
| 23 | IGLV4-69 | 60 | 67 | 63 | 60 | 53 | 60 | 63 | 63 | 53 | 55 | 60 |
| 24 | IGLV5-37 | 63 | 60 | 50 | 47 | 63 | 47 | 67 | 43 | 53 | 43 | 54 |

TABLE 2C-continued

% GC Content - IGLV Families

| Sr. No. | Sequence ID No. of bases | Segment-1 30 | Segment-2 30 | Segment-3 30 | Segment-4 30 | Segment-5 30 | Segment-6 30 | Segment-7 30 | Segment-8 30 | Segment-9 30 | Segment-10 14-47 | Ave GC % Content |
|---|---|---|---|---|---|---|---|---|---|---|---|---|
| 25 | IGLV5-45 | 63 | 57 | 53 | 50 | 60 | 43 | 67 | 50 | 50 | 48 | 54 |
| 26 | IGLV5-52 | 57 | 50 | 53 | 50 | 63 | 47 | 63 | 50 | 60 | 47 | 54 |
| 27 | IGLV6-57 | 47 | 60 | 67 | 57 | 60 | 57 | 60 | 57 | 53 | 38 | 56 |
| 28 | IGLV7-43 | 60 | 60 | 60 | 47 | 53 | 43 | 70 | 60 | 57 | 54 | 56 |
| 29 | IGLV7-46 | 63 | 60 | 63 | 50 | 60 | 40 | 70 | 63 | 53 | 54 | 58 |
| 30 | IGLV8-61 | 60 | 60 | 53 | 53 | 70 | 53 | 60 | 63 | 37 | 46 | 56 |
| 31 | IGLV9-49 | 60 | 67 | 57 | 47 | 67 | 63 | 53 | 60 | 43 | 63 | 58 |

Figure 3:
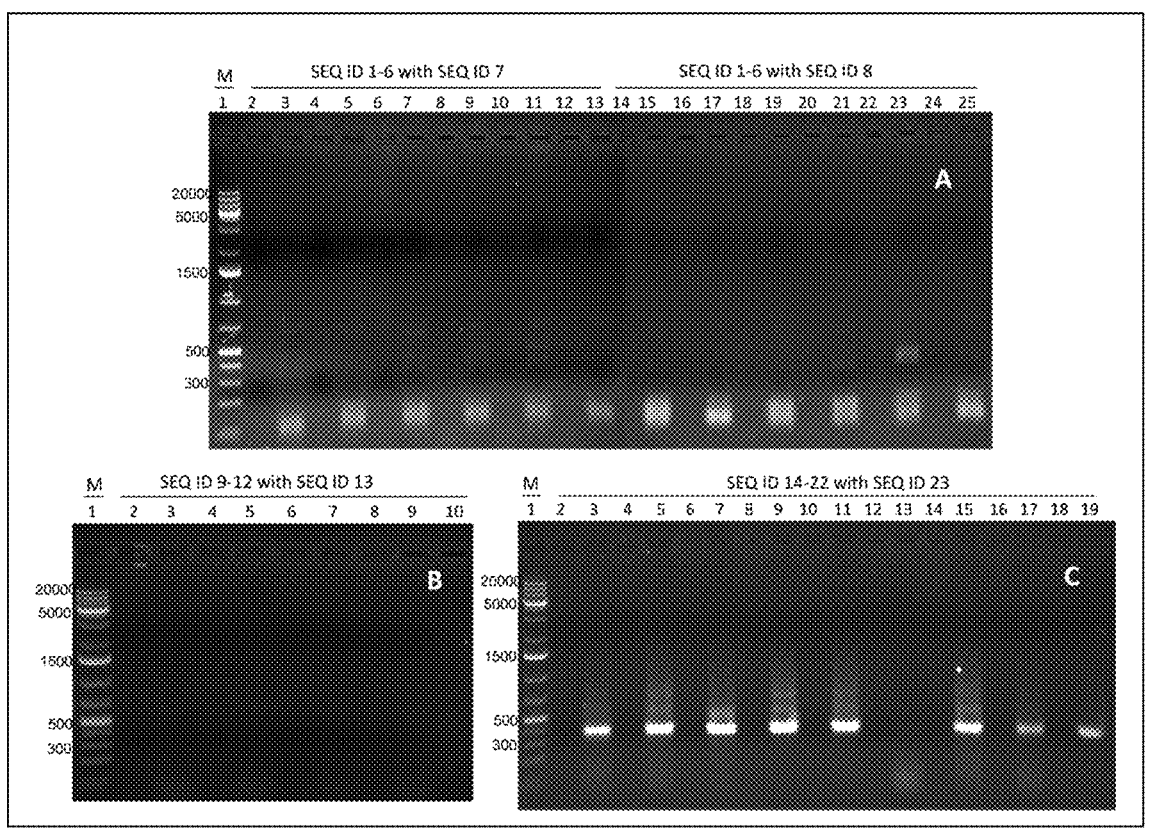
FIG. 3 depicts testing of amplifiability of human antibody variable genes using an optimized PCR buffer and DNA polymerase combination. After pre-heating at 94° C. for 5 min, reactions were cycled 30 times with a denaturation step at 94° C. for 15s, simultaneous annealing and extension step at 72° C. for 45s, followed by an extension and nick-sealing step at 72° C. for 10 min. Panel A: Heavy V-genes; Lanes 3, 5, 7, 9, 11 and 13 contain products from six forward primers (SEQ ID 1-6) with reverse primer SEQ ID 7, while lanes 2, 4, 6, 8, 10 and 12 contain their respective Negative (No Template) controls. Lanes 15, 17, 19, 21, 23 and 25 contain products from the same forward primer set with reverse primer SEQ ID 8. Lanes 14, 16, 18, 20, 22 and 24 contain their respective Negative (No Template) controls. Panel B: Kappa V-genes; Lanes 3, 5, 7 and 9 contain products from four kappa forward primers (SEQ ID 9-12) with reverse primer SEQ ID 13, while lanes 2, 4, 6, and 8 contain their respective Negative (No Template) controls. Lane 10 was empty. Panel C: Lambda V-genes; Lanes 3, 5, 7, 9, 11, 13, 15, 17 and 19 contain products from nine forward primers (SEQ ID 14-22) with reverse primer SEQ ID 23, while lanes 2, 4, 6, 8, 10, 12, 14, 16, and 18 contain their respective Negative (No Template) controls. Lane(s) 1 contains 1 kb plus DNA marker (Fermentas). All PCR products were run on 1.2% gels cast in 1×TBE containing 0.01 μg/ml ethidium bromide, and run at 5V/cm for 90 min.

Based on data from FIG. 2 and Tables 2A-C, the present invention discloses use of different buffers as well as blends of high fidelity Taq polymerase and proofreading polymerases which in combination are suitable for amplification of complex cDNA templates with long primers. In addition, the present invention utilizes a 2-step PCR with longer denaturation and combined annealing/extension cycles, or a 3-step PCR with high annealing temperatures, in alternate to the conditions described in prior art (Andris-Widhopf J et al., 2001. Generation of antibody libraries: PCR amplification and assembly of light- and heavy-chain coding sequences. In: *Phage Display: A Laboratory Manual*). In an experiment for a $V_\lambda$ primer set (SEQ ID 14 paired with SEQ ID 23), it was observed that the target amplicons were obtained for $V_\lambda$ domains. Based on these conditions, the experiments were conducted for all V domain primers (SEQ ID 1-23) with similar thermodynamic characteristics irrespective of their genomic origin. FIG. 3 demonstrates that the said conditions are optimum for majority of $V_\lambda$ domains but not suitable for kappa and heavy variable domains.

Example 3

Optimized Amplification of $V_\lambda$-Domains

Figure 4:
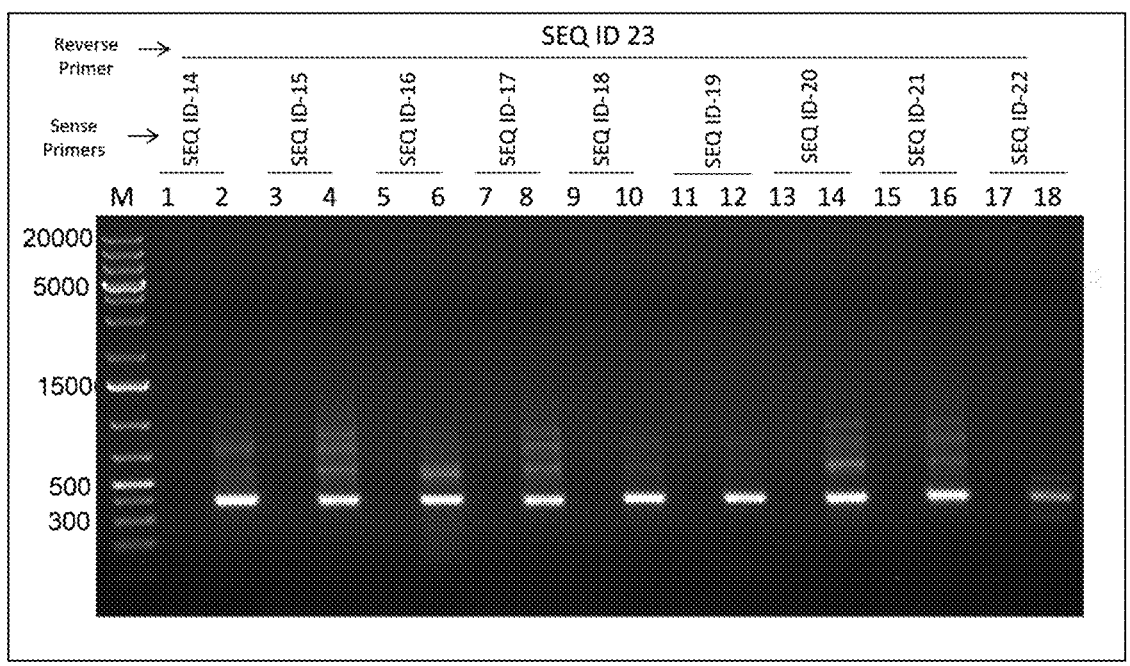
FIG. 4 depicts re-testing of optimized amplification conditions of all $V_\lambda$ primer pairs. All the amplifications were carried out using Pfu Ultra II HS and PCR Extender buffer. Primer pairs are SEQ ID 14-22 with reverse primer SEQ ID 23. Input cDNA was 50 ng per 50 μl reaction. After pre-heating at 94° C. for 5 min, reactions were cycled 30 times with a denaturation step at 94° C. for 15s, simultaneous annealing and extension step at 72° C. for 45s, followed by an extension and nick-sealing step at 72° C. for 10 min. Even numbered lanes contain products derived from respective $V_\lambda$ forward primers mentioned above the lanes with reverse primer SEQ ID 23. Odd numbered lanes contain their respective negative (No template) controls. M is the Generuler 1 kb plus DNA marker from Fermentas. All PCR products were run on 1.2% gels cast in 1×TBE containing 0.01 μg/ml ethidium bromide, and run at 5V/cm for 90 min.

Based on FIG. 3, it may be noted that 8 out of 9 $V_\lambda$ primer pairs provided good amplification. A forward primer that could not amplify with SEQ ID 23 was SEQ ID 19 (FIG. 3). In order to amplify all primers, further optimization of conditions was done by increasing the input cDNA per reaction from 20 ng to 50 ng. PCR reactions were carried out using conditions as set in FIG. 3. Results presented at FIG. 4 demonstrate amplification of $V_\lambda$ genes from the primer set SEQ ID 23/SEQ ID 19 along with the remainder $V_\lambda$-specific primer pairs.

Example 4

Optimized Amplification of $V_k$-Domains

Based on FIG. 3, it is understood that there is a need to amplify $V_\kappa$ domains with kappa-specific primers (SEQ ID 9-13) using a different protocol. It was observed that the $T_m$ for kappa reverse primer (SEQ ID 13) was 70.6° C. which is below 72° C., and since it was not too suitable for 2-step PCR's, the $V_\kappa$ amplification was performed with a 3-step cycling protocol using SEQ ID 9/SEQ ID 13 as a representative primer pair. Pfu Ultra II HS enzyme was used in this experiment, and the R×C design involved a series of PCR buffers and four different $T_a$ temperatures (56.2° C., 60.7° C., 67.3° C. and 70° C.). Optimal amplification from this primer pair was obtained at an annealing temperature of ~60° C. when the amplification buffer is Pfu buffer and the amplification enzyme is Pfu Ultra II HS enzyme.

When a similar 3-step PCR condition was applied to the remaining kappa primer pairs (total 4 including the representative pair), all produced amplicons of the expected size. Specifically, after pre-heating at 95° C. for 5 min, reactions were cycled 30 times with a denaturation step at 94° C. for 15s, annealing at 60° C. for 30s, extension at 72° C. for 30s, followed by an extension and nick-sealing step at 72° C. for 10 min. However, the primer pairs SEQ ID 9/SEQ ID 13 and SEQ ID 10/SEQ ID 13 amplified more efficiently (FIG. 5, panel A) when compared to the other two pairs i.e. SEQ ID 11/SEQ ID 13 and SEQ ID 12/SEQ ID 13.

Figure 5:
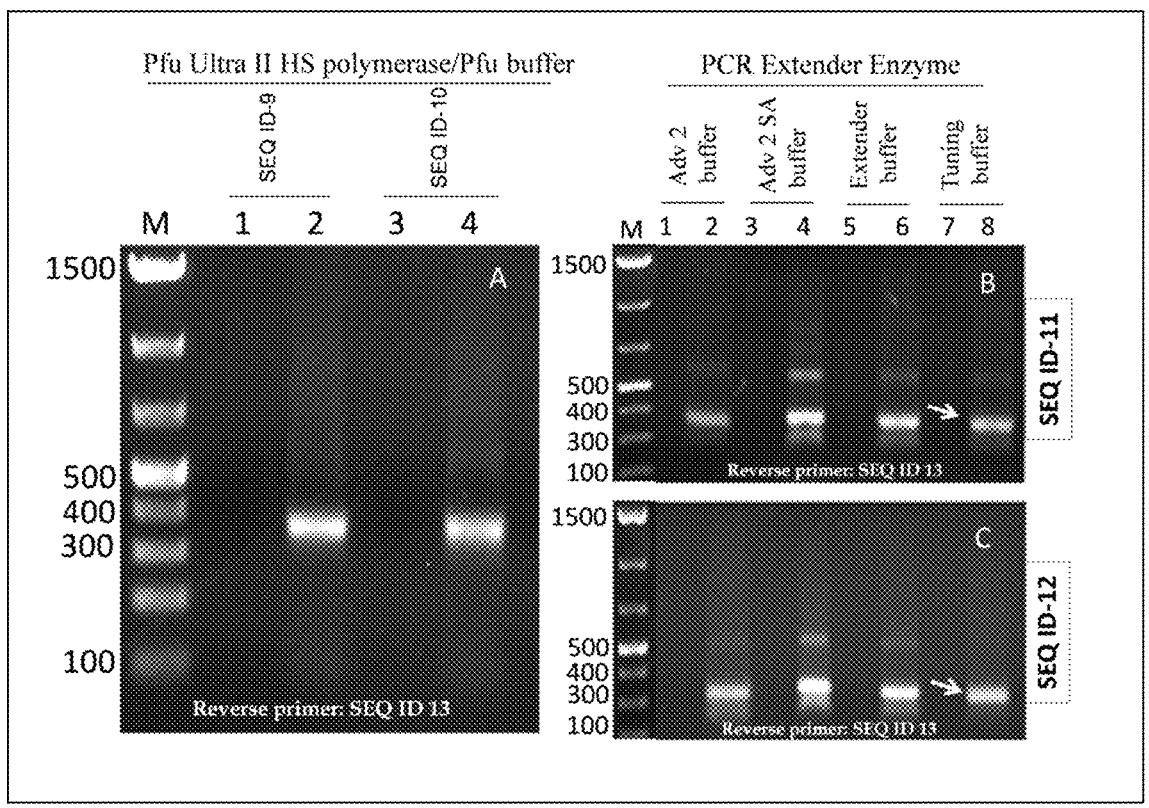
FIG. 5 depicts amplification by all $V_K$ primers. Reactions in Panel A were amplified using Pfu Ultra II HS polymerase and Pfu buffer. Lanes 2 and 4 contain products derived from primers SEQ ID 9 and 10 respectively with reverse primer SEQ ID 13, while lanes 1 and 3 contain their respective negative (No template) controls. Panel B and C show enzyme-buffer matrix to get better amplification by SEQ ID 11 and 12. Reactions in both panels were amplified using PCR Extender polymerase blend. Panel B shows amplification by SEQ ID 11 while Panel C shows amplification by SEQ ID 12, both paired with reverse primer SEQ ID 13. After pre-heating at 95° C. for 5 min, reactions were cycled 30 times with a denaturation step at 94° C. for 15s, annealing at 60° C. for 30s, extension at 72° C. for 30s, followed by an extension and nick-sealing step at 72° C. for 10 min. Lanes 2, 4, 6, and 8 contain PCR products with Advantage 2 buffer, Advantage 2 SA buffer, PCR Extender buffer and Tuning buffer respectively. Lanes 1, 3, 5, and 7 contains their respective negative (No template) controls. Input cDNA was 50 ng per 500 reaction for all panels. M is the Generuler 1 kb plus DNA marker from Fermentas. All PCR products were run on 1.2% gels cast in 1×TBE containing 0.01 μg/ml ethidium bromide, and run at 5V/cm for 90 min.

In the alternate, the invention also provides a further protocol in which optimal amplification of $V_\kappa$ genes are obtained with primer pairs SEQ ID 11/SEQ ID 13 and SEQ ID 12/SEQ ID 13 wherein the amplification buffer is Tuning Buffer and the amplification enzyme is PCR Extender blend (FIG. 5, panels B & C).

Example 5

Optimized Amplification of $V_H$-Domains

Based on FIG. 3, it is understood that there is a need to amplify $V_H$ families with family-specific primers (SEQ ID 1-9) with a different protocol. To get specific yields of $V_H$ domains, an R×C design of PCR buffers was performed at three different annealing temperatures (56° C., 60° C. and 68° C.) in a 3-step PCR protocol using Pfu Ultra II HS polymerase. The representative primer pair was SEQ ID 5/SEQ ID 8. Amplification was possible at all three temperatures using any of the buffers tested, but the buffers did differ in yield or specificity.

Figure 6:
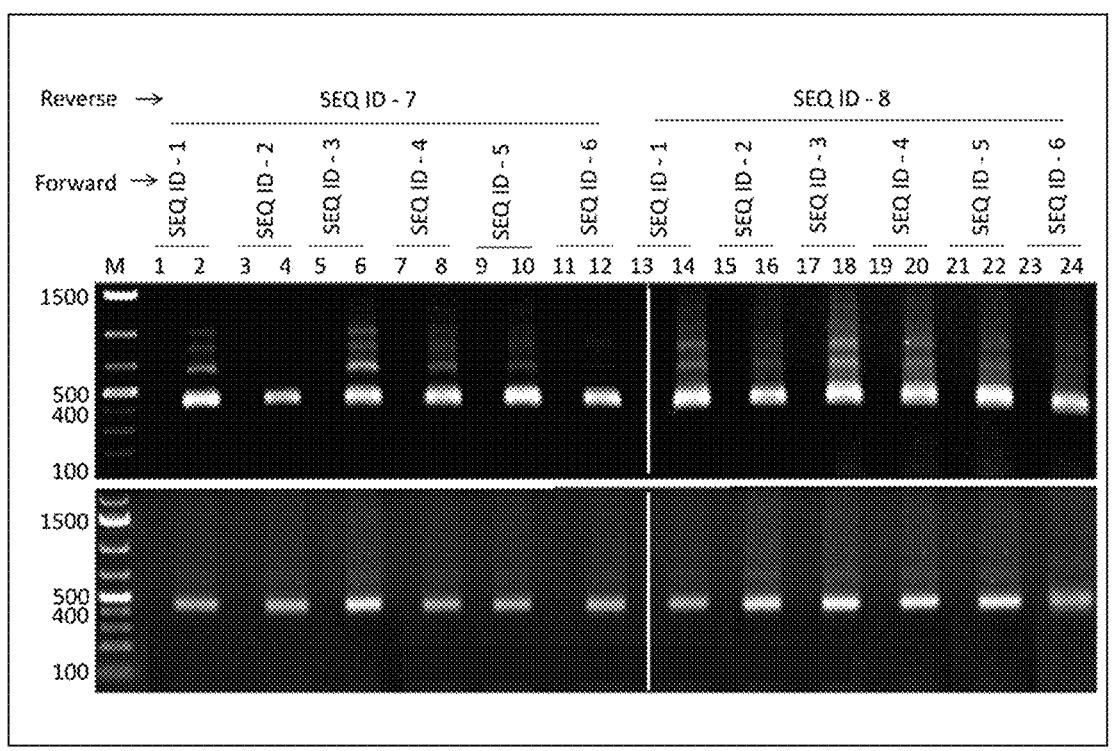
FIG. 6 depicts testing of amplification of $V_H$ genes using an optimized PCR buffer and DNA polymerase combination with all Scripps $V_H$ primer pairs. Top panel exhibits reactions carried out in Advantage 2 SA buffer, while the bottom panel exhibits reactions carried out in Tuning buffer. Enzyme used was Pfu Ultra II HS polymerase for all reactions. Lanes 1 to 12 contain all 6 $V_H$ sense primers (SEQ ID 1-6) with reverse primer SEQ ID 7. Lanes 13 to 24 contain all 6 $V_H$ sense primers with reverse primer SEQ ID 8. Input cDNA amount per 50 μl reaction was 50 ng. Even numbered wells contain products from respective primer pairs mentioned above them, while odd numbered wells contain their respective negative (No template) controls. M is the Generuler 1 kb plus DNA ladder from Fermentas.

The best conditions allowed amplification of all the remaining $V_H$ pairs using Pfu Ultra II HS enzyme with both the buffers i.e. Advantage 2 SA buffer and Tuning buffer. Specifically, after pre-heating at 95° C. for 5 min, reactions were cycled 30 times with a denaturation step at 94° C. for 15s, annealing at 68° C. for 30s, extension at 72° C. for 30s, followed by an extension and nick-sealing step at 72° C. for 10 min. The results are depicted at FIG. 6.

Example 6

Optimized Amplification of C-Domains

It was observed that the C domain-specific primers (SEQ ID 27-31) are shorter compared to the V domain-specific primers (SEQ ID 1-23), and do not have non-annealing overhangs (flat primers). The present invention also discloses use of C-domain templates that are plasmid based (synthetic constructs; SEQ ID 24-26), and therefore less complex in terms of target base pairs to be scanned and hybridized by the primers compared to the V domain-specific primers.

In one aspect of this invention, $MgCl_2$ and $T_a$ titrations were used to determine optimal conditions for these amplifications. AmpliTaq Gold polymerase in combination with AmpliTaq Gold buffer was used for such titrations. Specifically, after pre-heating at 95° C. for 5 min, reactions were cycled 30 times with a denaturation step at 94° C. for 15s, simultaneous annealing and extension step at 72° C. for 30s, followed by an extension and nick-sealing step at 72° C. for 10 min. All C domains ($C_H1$, $C_\kappa$ and $C_L$) could be amplified in abundance by this approach.

Figure 7:
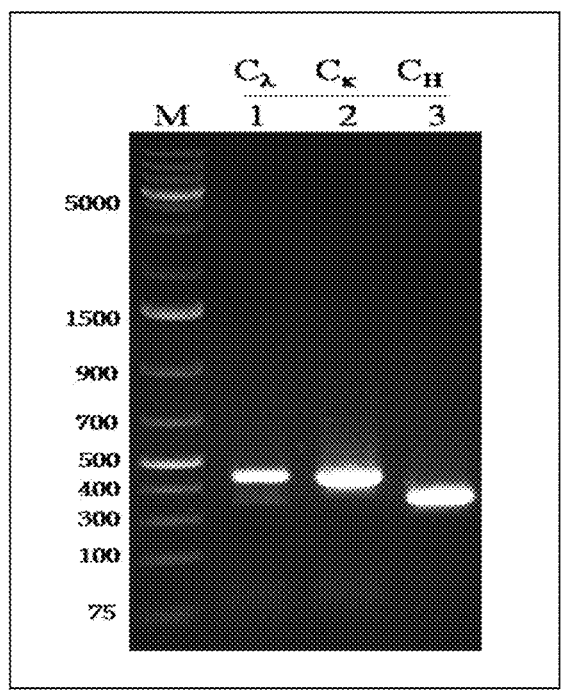
FIG. 7 depicts application of optimized enzyme-buffer matrix to check amplification of all constant domain primers ($C_\kappa$, $C_\lambda$, $C_H$). All reactions were amplified using Pfu Ultra II HS polymerase and PCR Extender buffer. Input DNA concentration was 50 ng per 50 μl reaction. Lane 1 contains product derived from SEQ ID 26 as template that was amplified using primer pair SEQ ID 29/SEQ ID 30, lane 2 contains product derived from SEQ ID 25 as template that was amplified using primer pair SEQ ID 31/SEQ ID 30, while lane 3 contains product derived from SEQ ID 24 as template that was amplified using primer pair SEQ ID 27/SEQ ID 28. M is the Generuler 1 kb plus DNA marker from Fermentas. All PCR products were run on a 1.2% gel cast in 1×TBE containing 0.01 μg/ml ethidium bromide, and run at 5V/cm for 90 min.

In another aspect of this invention, C domains were amplified using a combination of Pfu Ultra II HS polymerase and PCR Extender buffer. Specifically, after pre-heating at 95° C. for 5 min, reactions containing SEQ ID 24 as template were cycled 30 times with a denaturation step at 95° C. for 30s, annealing at 65° C. for 30s, extension at 72° C. for 30s, followed by an extension and nick-sealing step at 72° C. for 10 min. Similarly, after pre-heating at 95° C. for 5 min, reactions containing SEQ ID 25 or 26 as template were cycled 30 times with a denaturation step at 95° C. for 30s, simultaneous annealing and extension step at 72° C. for 30s, followed by an extension and nick-sealing step at 72° C. for 10 min. FIG. 7 demonstrates the utility of this approach in producing C-domain amplicons in abundance.

Example 7

First Overlap Assembly of $V_\lambda$ and $C_\lambda$ Domains

To fuse and amplify the $V_\lambda$ and $C_\lambda$ fusions unambiguously and in sufficient abundance, an R×C enzyme versus buffer design as exemplified in FIG. 5 was used. Equimolar concentrations of overlapping products were tested using enzyme-buffer combinations and PCR parameters as set in Table 3A and 3B.

TABLE 3A

| Polymerases | PCR Buffers |
| --- | --- |
| Advantage 2 Polymerase | Advantage 2 buffer |
| Pfu Ultra II HS polymerase | Advantage 2 SA buffer |
| Phusion HF polymerase | Exact polymerase buffer |
| PCR Extender Blend | PCR Extender buffer |
| Exact Polymerase | Pfu Ultra Buffer |
| — | Phusion HS buffer |
| — | Tuning buffer |
| Purified $V_\lambda$ | 50 ng |
| Purified $C_\lambda$ | 46 ng |
| dNTPs | 200 μM |
| Primers | 200 nM |

TABLE 4A

| 2-step PCR | | |
| --- | --- | --- |
| 95° C. | 5 min | 1x |
| 95° C. | 30 sec | 1x |
| 68° C. | 15, 30, 45 sec | 15, 20, 25, 30x |
| 68° C. | 1 min | 1x |
| 4° C. | ∞ | — |

TABLE 4B

| Polymerases | PCR Buffers |
| --- | --- |
| Advantage 2 Polymerase | Advantage 2 SA buffer |
|  | PCR Extender buffer |
| Purified $V_\lambda$ | 50 ng |
| Purified $C_\lambda$ | 46 ng |
| dNTPs | 200 μM |
| Primers | 200 nM |

Experiments conducted demonstrate that there is a significant decrease in non-specificity with reduced extension time but not number of cycles. Specificity of amplification can be further increased by use of an alternate protocol as set out in Tables 5A and 5B.

TABLE 5A

| 2-step PCR | | |
| --- | --- | --- |
| 95° C. | 5 min | 1x |
| 95° C. | 30 sec | 30x |
| 68° C. | 1 min | |
| 68° C. | 1 min | 1x |
| 4° C. | ∞ | — |

TABLE 5B

| Polymerases | PCR Buffers |
| --- | --- |
| Advantage 2 Polymerase (0.25x, 0.5x, 0.75x, 1x) | Advantage 2 SA buffer |
| Purified $V_\lambda$ | 10, 25 & 50 ng |
| Purified $C_\lambda$ | 9.2, 23 & 46 ng |
| dNTPs | 200 μM |
| Primers | 200 nM |

Figure 8:
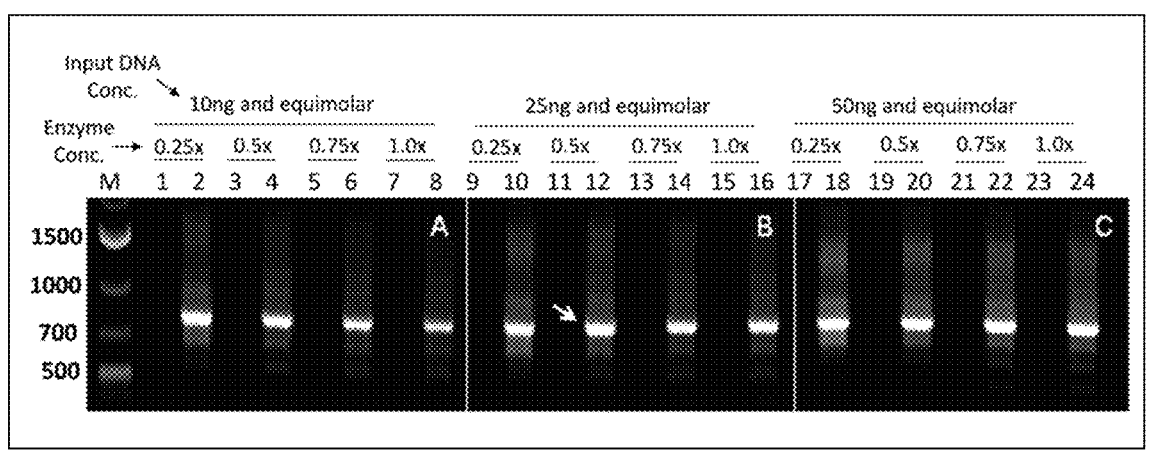
FIG. 8 depicts input DNA concentration versus varying polymerase concentration matrix to improve $1^{st}$ overlap PCR of $V_\lambda C_\lambda$. All the reactions were carried out using Advantage 2 polymerase and Advantage 2 SA buffer. Input DNA was equimolar for purified $V_\lambda$ and $C_\lambda$ product per 50 μl reaction. The primer pair was SEQ ID 32/SEQ ID 30. Panels A, B, and C show results for 10, 25, and 50 ng input DNA, respectively. Even numbered lanes contain products from respective enzyme concentrations (0.25×, 0.5×, 0.75× and 1.0×) mentioned above the lanes whereas odd numbered lanes contain their respective negative (No template) controls. M is the Generuler 1 kb plus DNA marker (Fermentas).

FIG. 8 demonstrates that the combinations of lower input DNA concentration (25 ng) and polymerase concentration (0.5x) resulted in sharp and abundant amplification of the desired PCR products (750-800 bp), with very little non-

TABLE 3B

| | Advantage 2 Pol Mix | | Pfu Ultra II HS | | Phusion HF Polymerase | | PCR Extender Enzyme | | Exact Polymerase | | Repeats |
| --- | --- | --- | --- | --- | --- | --- | --- | --- | --- | --- | --- |
| Initial Denaturation | 95° C. | 5 min | 95° C. | 5 min | 95° C. | 30 sec | 94° C. | 2 min | 95° C. | 5 min | 1x |
| Denaturation | 95° C. | 30 sec | 95° C. | 20 sec | 98° C. | 10 sec | 94° C. | 20 sec | 95° C. | 30 sec | 30x |
| Annealing | 68° C. | 1 min | 66° C. | 20 sec | 68° C. | 30 sec | 68° C. | 20 sec | 68° C. | 30 sec | |
| Extension | | | 72° C. | 15 sec | 72° C. | 30 sec | 72° C. | 45 sec | 72° C. | 1 min | |
| Final Extension | 68° C. | 1 min | 72° C. | 3 min | 72° C. | 10 min | — | — | — | — | 1x |
| Final Hold | 4° C. | ∞ | 4° C. | ∞ | 4° C. | ∞ | 4° C. | ∞ | 4° C. | ∞ | — |

Advantage 2 polymerase blend enabled amplification of PCR amplicons of the correct size in two buffers without significant non-specific amplifications. Specificity of amplification can be increased by use of an alternate protocol as set out in Tables 4A and 4B.

specific amplification. As the primer pair for $V_K$-$C_K$ fusion is exactly the same as for $V_\lambda$-$C_\lambda$ (SEQ ID 32/SEQ ID 30), therefore, the same conditions as optimized for $V_\lambda C_\lambda$ were used for $V_K$-$C_K$ fusions. This strategy worked at the first attempt, and no further optimizations were required.

Example 8

First Overlap Assembly of $V_H$ and $C_H1$ Domains $V_H$-$C_H1$ amplification was performed using protocols as described in Tables 6A and 6B.

TABLE 6A 3-step PCR

| | | |
|---|---|---|
| 95° C. | 5 min | 1x |
| 95° C. | 30 sec | 30x |
| 66° C. | 30 sec | |
| 72° C. | 1 min | |
| 72° C. | 1 min | 1x |
| 4° C. | ∞ | — |

TABLE 6B

| Polymerases | PCR Buffers |
|---|---|
| Advantage 2 Polymerase (0.25x, 0.5x, 0.75x, 1x) | Advantage 2 SA buffer |
| Pfu Ultra II HS polymerase | PCR Extender buffer |
| Purified $V_H$ | 10, 25 & 50 ng |
| Purified $C_H1$ | 7.4, 18.5 & 37 ng |
| dNTPs | 200 μM |
| Primers | 200 nM |

All the combinations tested enable amplification of the desired 750-800 bp overlap product of $V_H$-$C_H1$. Specificity of amplification can be further increased by use of an alternate protocol as set out in Tables 7A and 7B.

TABLE 7A 3-step PCR

| | | |
|---|---|---|
| 95° C. | 5 min | 1x |
| 95° C. | 30 sec | 30x |
| 66° C. | 30 sec | |
| 72° C. | 30 sec | |
| 72° C. | 1 min | 1x |
| 4° C. | ∞ | — |

TABLE 7B

| Polymerases | PCR Buffers |
|---|---|
| Advantage 2 Polymerase | Advantage 2 buffer |
| Pfu Ultra II HS polymerase | Advantage 2 SA buffer |
| PCR Extender Blend | Exact polymerase buffer |
| Exact Polymerase | PCR Extender buffer |
| Vent Polymerase | Vent Buffer |
| Deep Vent Polymerase | Tuning buffer |
| AmpliTaq Gold Polymerase | — |
| Purified $V_H$ | 50 ng |
| Purified $C_H1$ | 37 ng |
| dNTPs | 200 μM |
| Primers | 200 nM |

Figure 9:
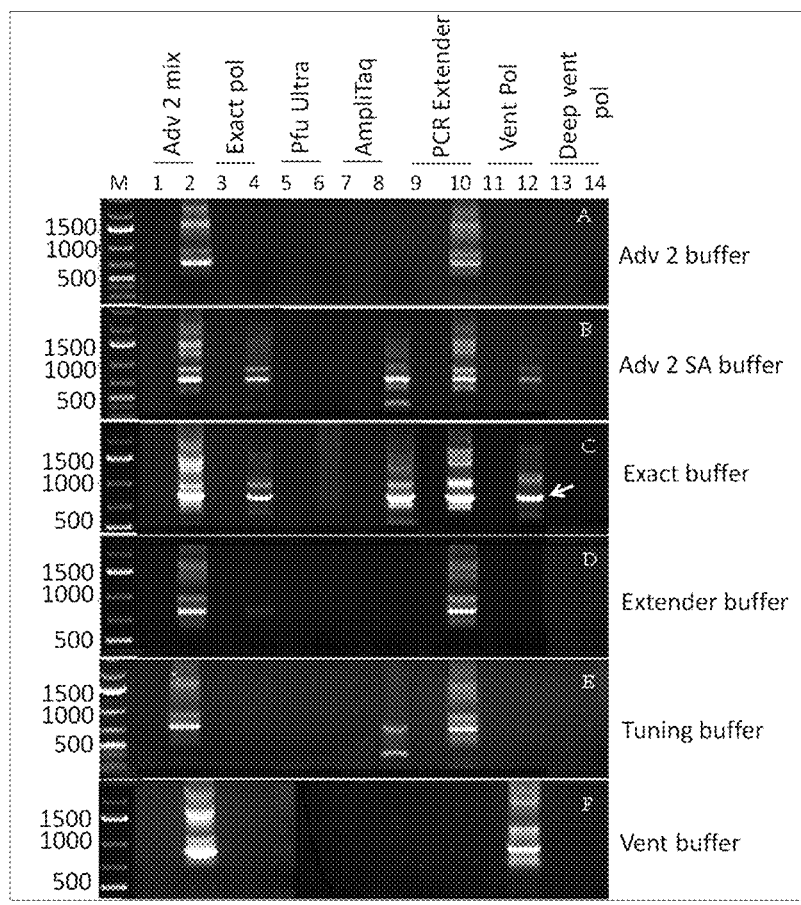
FIG. 9 depicts enzyme buffer matrix for the optimization of $1^{st}$ overlap product of $V_H C_H 1$. Panels A, B, C, D, E, and F show PCR products in Advantage 2 buffer, Advantage 2 SA buffer, Exact polymerase buffer, PCR Extender buffer, Tuning buffer and Vent buffer, respectively. Primer pair for $V_H C_H 1$ overlap is SEQ ID 33/SEQ ID 28. Input DNA concentration for $V_H$ was 50 ng, and equimolar amount of $C_H 1$ was used for the overlap reactions. Lanes 2, 4, 6, 8, 10, 12 and 14 contain products derived from Advantage 2 polymerase, Exact polymerase, Pfu Ultra II HS enzyme, AmpliTaq polymerase, PCR Extender, Vent polymerase and Deep Vent polymerase, respectively. Lanes 1, 3, 5, 7, 9, 11, and 13 contain their respective negative (No template) controls. M is the Generuler 1 kb plus DNA marker from Fermentas.

FIG. 9 demonstrates that the combination of high fidelity Vent Polymerase with Exact Polymerase buffer (panel C, lane 12) shows the desired sharp band with a minimum of smearing and non-specificity.

Example 9

Second Overlap Assembly of $V_L$-$C_L$ and $V_H$-$C_H1$ Domains to Create Fabs

Fusion of $V_L$-$C_L$ and $V_H$-$C_H1$ templates was performed as described in Tables 8A and 8B using the primer pair of SEQ ID 32/SEQ ID 34. In this experiment, only the $V_\lambda C_\lambda$ amplification product was used for fusion with the $V_H C_H1$ amplification product.

TABLE 8A 3-step $T_a$ Gradient PCR

| | | |
|---|---|---|
| 95° C. | 5 min | 1x |
| 95° C. | 30 sec | 30x |
| 62-72° C. | 30 sec | |
| 72° C. | 3 min | |
| 72° C. | 10 min | 1x |
| 4° C. | ∞ | — |

TABLE 8B

| Polymerases | PCR Buffers |
|---|---|
| Pfu Ultra II HS Polymerase | PCR Extender buffer |
| Purified $V_\lambda$-$C_\lambda$ | 50 ng |
| Purified $V_H$-$C_H1$ | 50 ng |
| dNTPs | 200 μM |
| Primers | 200 nM |

A very small amount of the desired (~1.5 kb) $2^{nd}$ overlap product was formed that was accompanied by smearing and nonspecific products very close to the target bands, without any clear temperature dependent trend. The most intense amplification was observed at 65.9° C., followed by 72° C. In an alternate protocol (Tables 9A and 9B), Expand LT Polymerase was used in $T_a$ titration format.

TABLE 9A 3-step $T_a$ Gradient PCR

| | | |
|---|---|---|
| 95° C. | 5 min | 1x |
| 95° C. | 30 sec | 30x |
| 40-65° C. | 30 sec | |
| 72° C. | 3 min | |
| 72° C. | 10 min | 1x |
| 4° C. | ∞ | — |

TABLE 9B

| Polymerases | PCR Buffers |
|---|---|
| Expand LT Polymerase | Expand buffer with $MgCl_2$ PCR Extender buffer |
| Purified $V_\lambda$-$C_\lambda$ | 50 ng |
| Purified $V_H$-$C_H1$ | 50 ng |
| dNTPs | 200 μM |
| Primers | 200 nM |

Expand LT enzyme blend was successful in fusing the $V_\lambda C_\lambda$-$V_H C_H1$ templates either in its own buffer or in PCR Extender buffer. However, the fusion product was ambiguous, and along with the 1.5 kb overlap product, smearing and nonspecific bands were also evident at all the annealing temperatures tested.

To improve the specificity of the amplification, Expand LT polymerase was further tested with several PCR buffers in an alternate protocol (Tables 10A and 10B) at a fixed $T_a$ of 56° C.

TABLE 10A

| 3-step PCR | | |
|---|---|---|
| 95° C. | 5 min | 1x |
| 95° C. | 30 sec | 30x |
| 56° C. | 30 sec | |
| 72° C. | 3 min | |
| 72° C. | 10 min | 1x |
| 4° C. | ∞ | — |

TABLE 10B

| Polymerases | |
|---|---|
| Expand LT Polymerase | |
| PCR Buffers | |
| Advantage 2 buffer | Tuning buffer |
| Advantage 2 SA buffer | Pfu Ultra II HS Buffer |
| PCR Extender buffer | Vent buffer |
| Exact polymerase buffer | Expand LT buffer |
| Purified $V_\lambda$-$C_\lambda$ | 50 ng |
| Purified $V_H$-$C_H1$ | 50 ng |
| dNTPs | 200 µM |
| Primers | 200 nM |

Although Expand LT could amplify the desired product in all the 8 buffers tested, high molecular weight smearing was common in all buffers. To improve the specificity of $V_L C_L$-$V_H C_H 1$ fusions, three strategies were designed (Higuchi R et al., 1988, Horton R M et al., 1989, Sarkar G and Sommer S S, 1990, Warrens A N et al., 1997, Heckman K L and Pease L R, 2007). Strategy A of asymmetric SOE-PCR (Warrens A N et al., 1997) was executed as in Tables 11A and 11B.

TABLE 11A

| 2-step PCR | | |
|---|---|---|
| 95° C. | 5 min | 1x |
| 95° C. | 30 sec | 15x |
| 72° C. | 1 min | |
| 72° C. | 10 min | 1x |
| 4° C. | ∞ | — |

TABLE 11B

| Asymmetric PCR | |
|---|---|
| Polymerases | PCR Buffers |
| AmpliTaq Gold Polymerase | GeneAmp 10X PCR Buffer |
| $V_L C_L$ or $V_H C_H 1$ | 50 ng |
| MgCl$_2$ | 2 mM |
| dNTPs | 250 µM |
| Primers | LeadB & Lead VH, 500 ng each |

After 15 cycles, 8 µl of each $V_\lambda C_\lambda$ and $V_H C_H 1$ PCR reactions were used as overlapping templates and an enzyme buffer matrix was carried out (Table 11C) for the overlap reaction. Specifically, the reactions were pre-heated at 95° C. for 5 min, and then cycled 30 times with a denaturation step at 95° C. for 30s, annealing at 56° C. for 30s, extension step at 72° C. for 3 min, followed by an extension and nick-sealing step at 72° C. for 10 min. Asymmetric PCR protocol as described (Warrens A N et al., 1997) did not form the desired product of 1.5 kb.

TABLE 11C

| Polymerases | PCR Buffers |
|---|---|
| PCR Extender Blend | PCR Extender buffer |
| Deep Vent Polymerase | 10x Thermo pol Buffer |
| Expand LT Polymerase | Expand buffer with MgCl$_2$ |
| Advantage 2 Polymerase | Advantage 2 SA buffer |
| $V_L C_L$ or $V_H C_H 1$ templates | 8 µl of 1$^{st}$ PCR |
| dNTPs | 250 µM |
| Primers | RSC-F or dp-EX; 500 ng each |

To execute strategy B of intermediate megaprimer formation (Sarkar G and Sommer S S, 1990), 50 ng each of $V_\lambda C_\lambda$ and $V_H C_H 1$ were mixed in 50 µl reactions without addition of any forward or reverse primers. The PCR reactions were then carried out as in Table 12. Forward and reverse primers (SEQ ID 32/SEQ ID 34) were then added, and the reactions cycled under the same 3-step conditions (Table 12) for 30 more times (FIG. 10).

TABLE 12

| 3-step PCR | | |
|---|---|---|
| 95° C. | 5 min | 1x |
| 95° C. | 30 sec | 15x |
| 56° C. | 30 sec | |
| 72° C. | 90 sec | |
| 72° C. | 10 min | 1x |
| 4° C. | ∞ | — |

Figure 10:
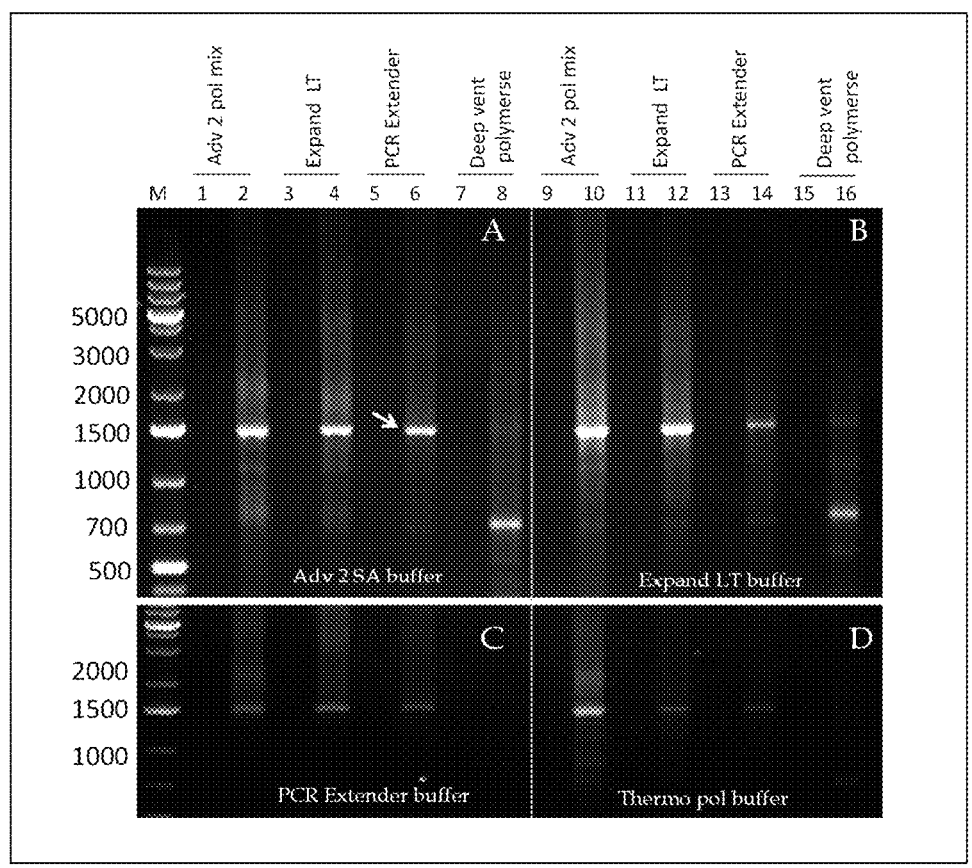
FIG. 10 depicts SOE PCR megaprimer strategy with enzyme buffer matrix for amplification of final Fab product. Initial 15 cycles were carried out without addition of primers with 50 ng each of the $1^{st}$ overlap products. After 15 cycles, 30 more cycles were carried out with addition of primer pair SEQ ID 32 and SEQ ID 34. Panels A, B, C, and D show amplification in Advantage 2 SA buffer, Expand LT buffer, PCR Extender buffer and Thermopol buffer respectively. Lanes 2, 4, 6 and 8 show amplification products derived by using Advantage 2 Polymerase mix, Expand LT Polymerase, PCR Extender Enzyme and Deep Vent Polymerase, respectively, while lanes 1, 3, 5 and 7 contain their respective negative (No template) controls. M is the Generuler 1 kb plus DNA marker from Fermentas.

FIG. 10 demonstrates that except for Deep Vent polymerase, all other enzyme-buffer combinations could form the desired 1.5 kb product, and the method of choice could be PCR Extender enzyme with Advantage 2 SA buffer. To execute Strategy C, a 2-step PCR protocol at 72° C. (Table 13) in an enzyme-buffer R×C design format.

TABLE 13

| 2-step PCR | | |
|---|---|---|
| 95° C. | 5 min | 1x |
| 95° C. | 30 sec | 30x |
| 72° C. | 1 min 45 sec | |
| 72° C. | 10 min | 1x |
| 4° C. | ∞ | — |

Figure 11:
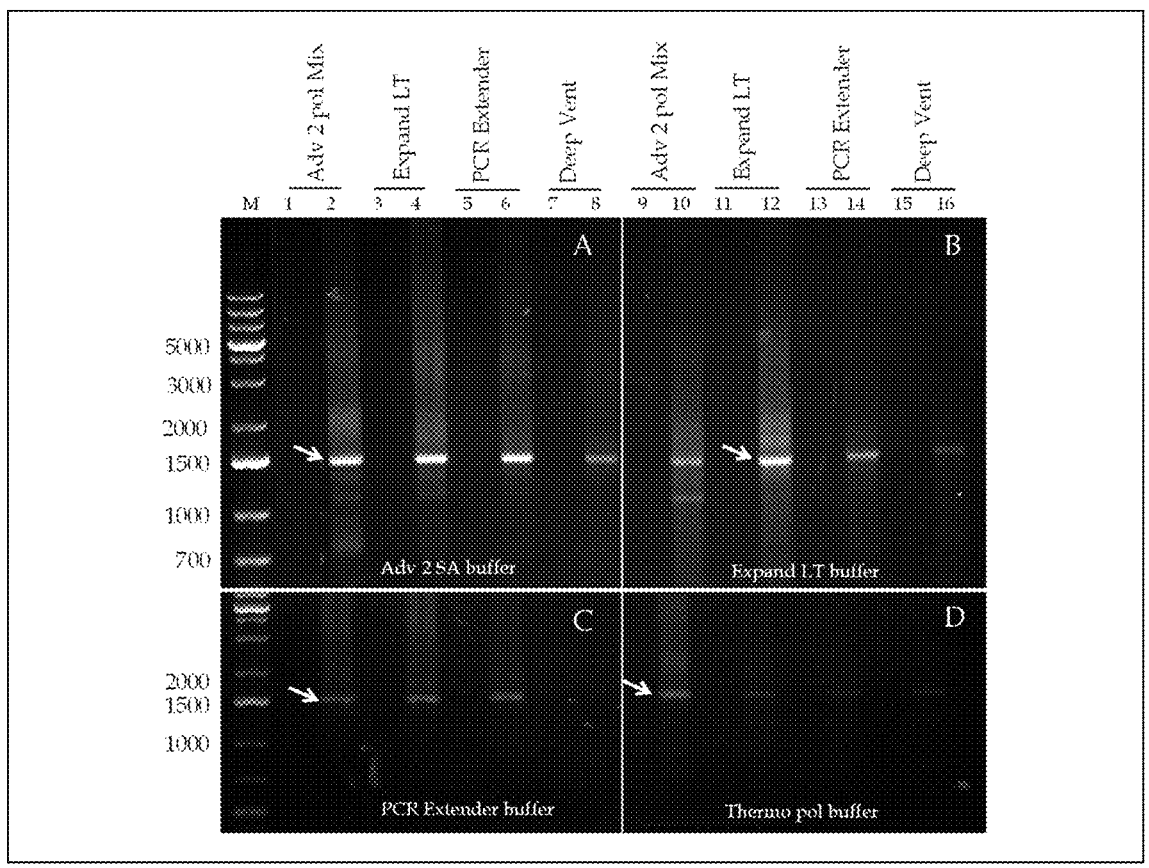
FIG. 11 depicts 2-step PCR strategy with enzyme buffer matrix for amplification of final Fab product. Primer pair was SEQ ID 32 and SEQ ID 34 with 50 ng each of the $1^{st}$ overlap products. Panels A, B, C, and D show amplification in Advantage 2 SA buffer, Expand LT buffer, PCR Extender buffer and Thermopol buffers, respectively. Lanes 2, 4, 6 and 8 show amplification products derived from Advantage 2 polymerase mix, Expand LT polymerase, PCR Extender Enzyme and Deep Vent polymerase respectively, while lanes 1, 3, 5 and 7 contain their respective negative (No template) controls. M is the Generuler 1 kb plus DNA marker from Fermentas.

FIG. 11 demonstrates that this strategy resulted into unambiguous 1.5 kb Fab fragments with substantially reduced smears. Therefore, for strategy C, the best conditions could be PCR Extender enzyme with Advantage 2 SA buffer.

Example 10

Vector Preparation

Figure 12:
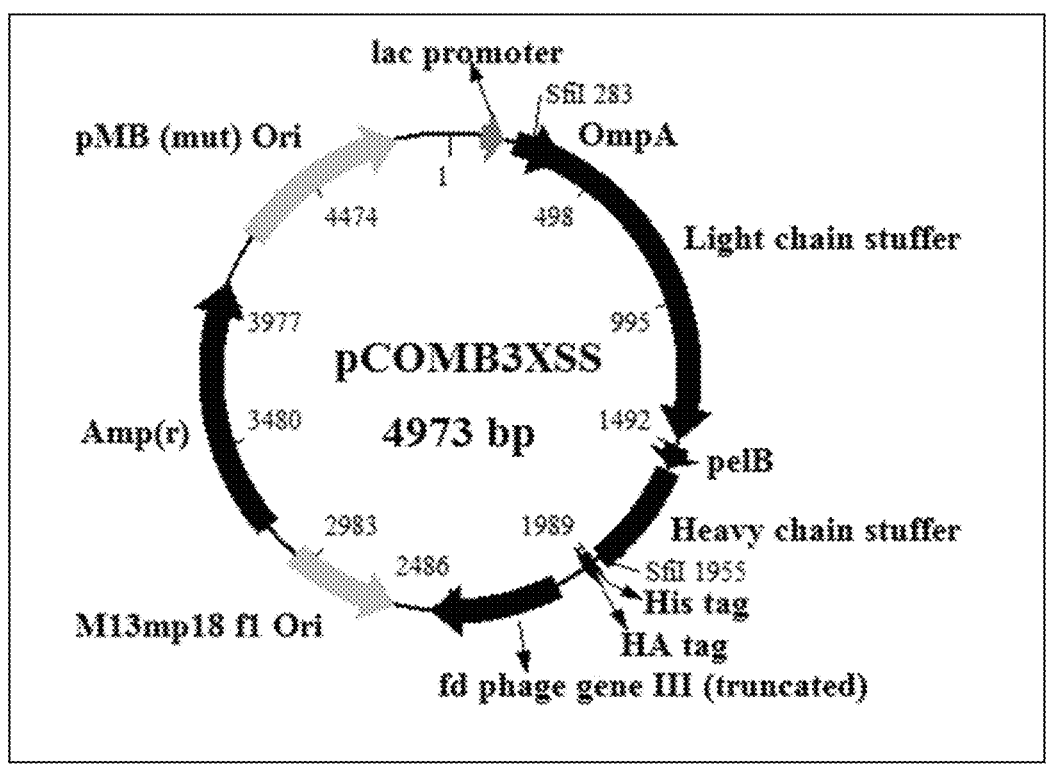
FIG. 12 depicts circular plasmid map of pCOMB3XSS.
Figure 13:
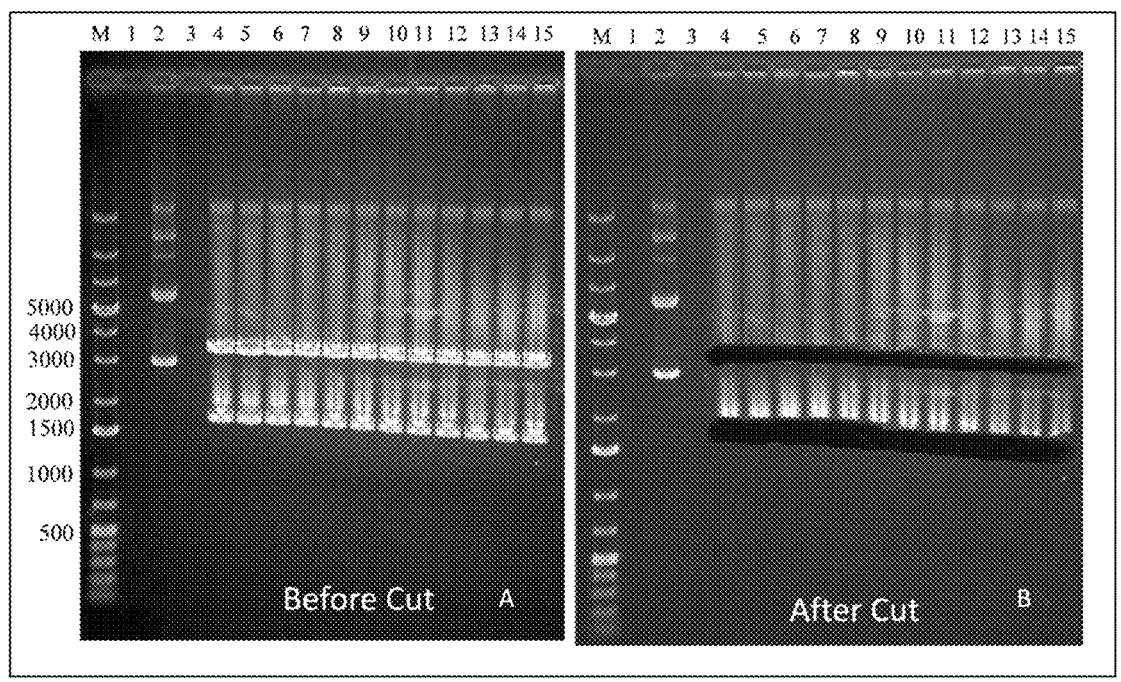
FIG. 13 depicts SfiI digestion of pCOMB3XSS vector. Panel A shows SfiI-digested pCOMB3XSS vector and stuffer fragments before band-cutting while Panel B shows the same gel after the desired bands were cut out. Lane 2 contains uncut pCOMB3XSS while lanes 4 to 15 contain SfiI-digested pCOMB3XSS. The upper band is the 3.3 kb vector backbone while lower band is the 1.6 kb stuffer fragment. 10 U/μg of SfiI enzyme was used for overnight digestion at 50° C. M is the 1 kb plus DNA marker from Fermentas.

For this purpose, sufficient amounts of the pCOMB3XSS (recreated in the lab; FIG. 12) vector backbone was prepared by digesting total 60 µg of the vector (3 reaction tubes; 20 µg/100 µl reaction) with SfiI (10 U/µg vector) in buffer M (Roche) overnight at 50° C. Reaction mixtures were pooled, phenolized and ethanol precipitated, and dissolved in TE. SfiI-digested vector was loaded into wells of a 0.8% preparative gel without ethidium bromide. The gel was run at 5V/cm for 2.5 h. After ethidium bromide staining, the ~3.3 kb pCOMB3XSS vector backbone was gel extracted and purified using QIAEXII gel extraction kit (FIG. 13). Simul taneously, the ~1.6 kb stuffer released from the vector after SfiI digestion was also isolated and gel purified (FIG. 13). Both the vector backbone and the stuffer were used in test ligations to optimize the ligation efficiency as well as to check for vector quality.

FIG. 13 shows that even after over-night over-digestion, a significant amount of vector cannot be digested, and the digestion pattern is smeary. Close examination of the two SfiI sites in the pCOMB3XSS suggest that this could be due to hemi-methylated nature of the plasmid at these sites, as both (5'-GGCCcaggcGGCC-3' (SEQ ID NO: 56) and 5'-GGCCaggccGGCC-3' (SEQ ID NO: 57)) are dcm methyltransferase sensitive (recognition sites underlined). Use of dam⁻/dcm⁻ E. coli strains could be useful to reduce cytosine methylation and improve digestion with SfiI. Examples of such strains include INV110 and ER2925.

Example 11

Test Ligation and Library Size Calculation

Test ligations were performed using the 1.6 kb stuffer fragment released from the vector after restriction digestion using SfiI (see FIGS. 12 and 13). The rationale underlying this test is that ligation conditions optimized for the 1.6 kb stuffer fragment can be applied directly to the similarly sized (~1.5 kb) Fab fragments without wasting the latter in optimizations.

In the first round of test ligation, a titration for optimum vector:insert ligation ratio was carried out in which a constant mass of 140 ng of SfiI-digested vector (386 fmoles) was ligated with appropriate molar ratios of SfiI-digested stuffer and Fab in half-log steps (1:0.35, 1:1 and 1:3.5 vector:insert molar ratio). For ligation, 1 U of T4 DNA ligase was used per 100 ligation mix, and ligations were incubated over-night at 16° C. The vector-alone (self-ligation) control was included to check the vector quality as well as for calculating background.

Along with optimization of ligation ratio, the effect of heat inactivation of the ligation mixtures on the efficiency of transformations was also tested. For this purpose, half of each 10 µl ligation mix was heat inactivated at 70° C. for 15 min. The remaining 5 µl was used as such. Transformation of both unheated and heat-treated ligation mixes was done by electroporation. Electroporation and recovery of transformed cells were carried out using manufacturer's protocol (Lucigen). Transformed cultures were incubated at 37° C. and 250 rpm for 1 h before spreading 1, 10 and 100 µl respectively on 90 mm LB plates containing 100 µg/ml carbenicillin. Plates were incubated overnight in 37° C. incubator.

Figure 14:
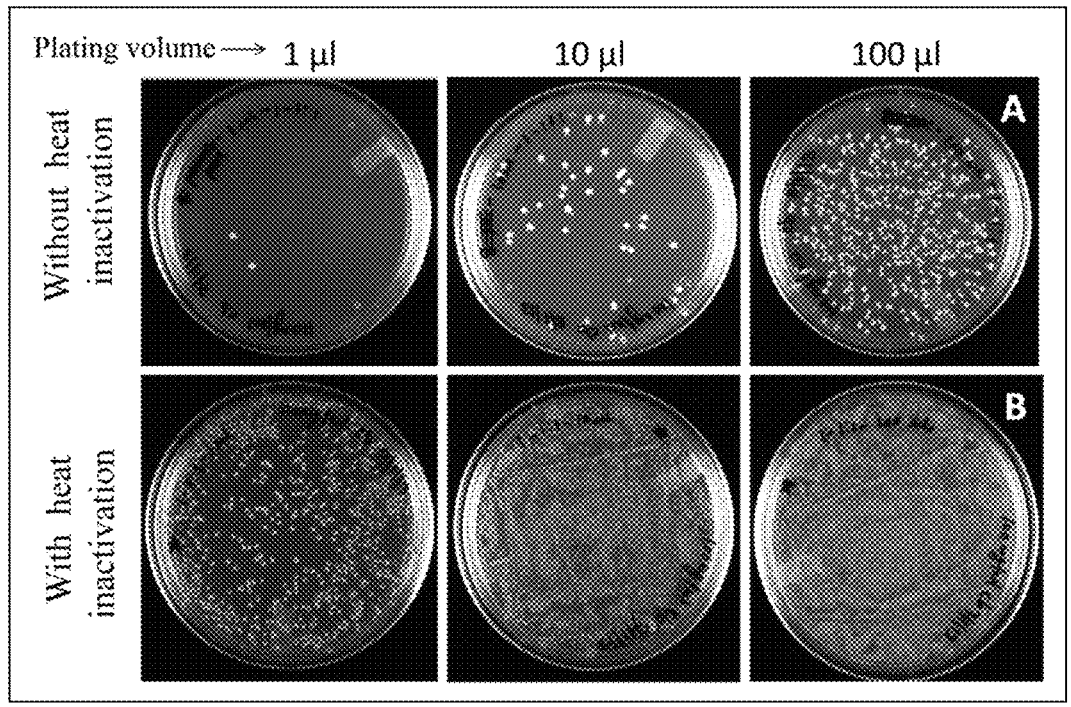
FIG. 14A depicts effect of heat inactivation of ligation mix. Panel A shows the number of transformants from the 1:0.35 ligation mix without any heat inactivation, while panel B shows the number of transformants for the same 1:0.35 ligation mix with heat inactivation treatment. For transformation, neat (undiluted) 1 μl from either the untreated or the heat inactivated ligation mixes were electroporated per 25 μl of TG1 cells, and 1, 10 and 100 μl of the culture was plated after electroporation. Data are shown only for the 1:0.35 ligation ratio for convenience. Other two ligation ratios (1:1 and 1:3.5) also follow the same trend but with much more matted growth.
FIG. 14B depicts calculation of vector background. Panel A shows vector control ligation in which only 140 ng vector was added without any insert, while panel B shows the plate of 1:1 heat inactivated ligation mix. Data are shown for the 1 μl plating volume only.
Figure 14:
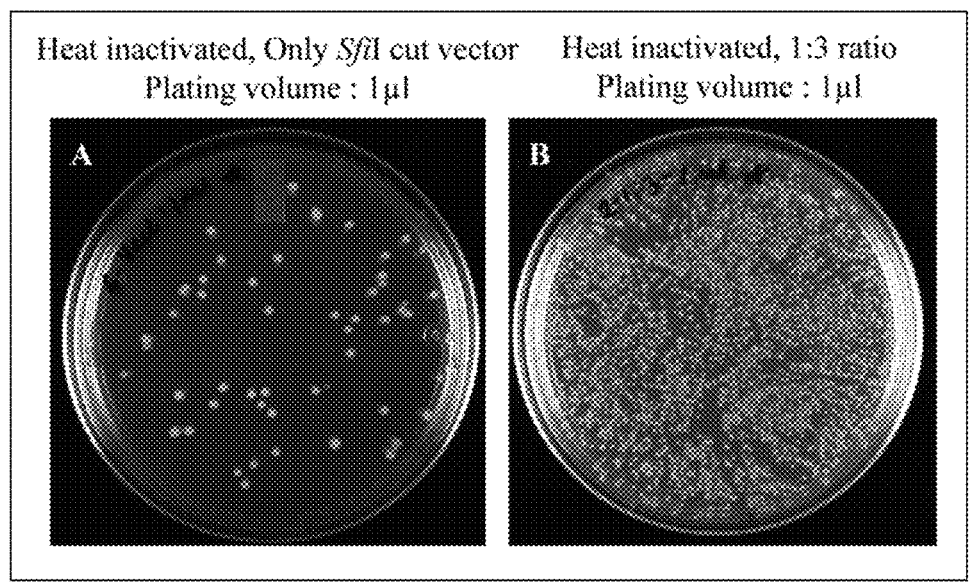

The effect of heat inactivation of ligation mixes was compared first. From FIG. 14A, it is evident that heat inactivation of ligation mix before electroporation has a drastic effect on the efficiency of transformation when using the electrocompetent TG1 cells (Lucigen). In the heat inactivated transformations, number of colonies were several times higher compared to the transformations done with unheated ligation mix. Results from only the heat inactivated samples were considered further for deciding the optimal ligation ratio. To calculate the vector background, the heat inactivated 1:1 ratio ligation mix was compared against the vector-alone plate (FIG. 14B; Table 14).

TABLE 14

| Vector:Insert ratio | No. of transformants, (plating volume 1 µl) | Transformation efficiency |
|---|---|---|
| 1:0.35 | 1114 | $7.8 \times 10^7$ |
| 1:1 | 2847 | $1.07 \times 10^8$ |
| 1:3.5 | 629 | $3.7 \times 10^6$ |
| Vector background | 54 | 1.8% |

The calculated vector background was 1.8% (Table 14), which was considered well within the range of quality check recommendations (Andris-Widhopf J et al., 2001. Generation of antibody libraries: PCR amplification and assembly of light- and heavy-chain coding sequences. In: *Phage Display: A Laboratory Manual*). Table 14 also shows that heat-treated ligation reactions follow a typical bell-shaped profile wherein the 1:1 ratio gives maximum number of colonies and therefore, can be considered as optimum ligation ratio. The calculated library size (efficiency) at this stage was therefore $1.07 \times 10^8$ per µg of transformed vector.

It was concluded from this first round of transformations that heat inactivation improves efficiency and that the 1:1 vector:insert ratio is optimum. The present invention discloses that the efficiency can be increased further by diluting the ligation mixtures before transformation. The present experiment was performed with both heat inactivated and native 1:1 mixes to re-confirm the results of heat inactivation.

To carry out this experiment, the 1:1 ligation mix was diluted 1:20 by mixing 2 µl of the ligation mix with 38 µl of water. 1, 3, 5, 7 and 10 µl of the diluted ligation mixes were then transformed as described previously. Volumes of all the diluted aliquots were made up to 10 µl with water to avoid effect of different volumes during electroporation (if any). 1, 10 and 100 µl of the transformants were then plated on 90 mm LB+ carbenicillin (100 µg/ml) plates as previous.

The present invention discloses that the number of transformants increases with a concomitant increase in the volume sampled from the diluted ligations. However, this increase reaches its maxima within 2 steps only (1 to 3 µl), after which transformation is not inhibited but remains at a plateau (Table 15).

TABLE 15

| Transformed ligation volume | No. of transformants | Efficiency/µg Vector |
|---|---|---|
| 1 µl | 295 | $4.2 \times 10^8$ |
| 3 µl | 1288 | $6.1 \times 10^8$ |
| 5 µl | 1239 | $3.5 \times 10^8$ |
| 7 µl | 1343 | $2.6 \times 10^8$ |
| 10 µl | 1397 | $2 \times 10^8$ |
| Vector Background | 3 | 0.23% |

Table 15 further shows that after diluting the ligation mixture, the vector background is reduced from 1.8% to 0.23%. This decrease in background contributes to 6-folds increase in library efficiency (from $1.07 \times 10^8$ to $6 \times 10^8$ cfu per µg of vector when 3 µl of the diluted 1:1 ratio is considered as the transforming volume; compare Table 15 to Table 14).

Example 12

Ligating the Different Domains of the Said Immunoglobulin or Fragment Comprising Both Light and Heavy Chains to SfiI Digested pCOMB3XSS A Fab test ligation was performed according to the conditions optimized (heat inactivation and dilution of ligation mixes) using stuffer control (Example 11). Fabs were prepared by optimum protocols as demonstrated in Example 9. The ligation mix was heat inactivated at 70° C. for 15 min and diluted 1:20 by mixing 2 μl of ligation mix with 38 μl of water. 3 μl of the ligation mix was transformed in 25 μl TG1 electro-competent cells. Cultures were incubated for 1 h at 250 rpm and 37° C. 1, 10 and 100 μl of the cultures were plated on LB plates containing 100 μg/ml carbenicillin. Plates were incubated overnight at 37° C. incubator. Colony counts from this experiment are shown in Table 16.

TABLE 16

| Barbas method | Number of colonies | | | Average number of colonies after normalization to 10 μl volume | Vector background | Efficiency |
|---|---|---|---|---|---|---|
| Plating volume | 1 μl | 3 μl | 10 μl | — | — | — |
| Only vector (140 ng) | 1 | 3 | 14 | 11 | — | — |
| Vector:stuffer (1:2) | 60 | 140 | 593 | 553 | 2% | $3.5 \times 10^6$/μg vector |
| Vector:Fab (1:2) | 6 | 28 | 83 | 79 | 14% | $5 \times 10^5$/μg vector |

A further experiment was conducted changing the amount of vector (50 ng) in the ligation mixes and changing the molar proportion of insert to vector (1:1, 1:3 and 1:10 vector:insert ratio; see Table 17).

TABLE 17

| JM_method | Number of colonies | | | Average number of colonies after normalization to 10 μl volume | Vector background | Efficiency |
|---|---|---|---|---|---|---|
| Plating volume | 1 μl | 3 μl | 10 μl | — | — | — |
| Only vector (50 ng) | 0 | 1 | 1 | 1 | — | — |
| Vector:stuffer (1:1) | 33 | 56 | 250 | 255 | 0.4% | $5.2 \times 10^6$/μg vector |
| Vector:stuffer (1:3) | 88 | 310 | 1215 | 1042 | 0.09% | $2.1 \times 10^6$/μg vector |
| Vector:stuffer (1:10) | 81 | 210 | 789 | 766 | 0.13% | $1.5 \times 10^7$/μg vector |
| Vector:Fab (1:1) | 6 | 28 | 83 | 41 | 2.4% | $8.0 \times 10^5$/μg vector |

From Table 16 and 17, it can be seen that the ligation efficiency for Fabs was not optimum to result in the formation of a large antibody library.

Example 13

Contaminating Supercoiled/Uncut Plasmid in SfiI Digested pCOMB3XSS Preparations The factor(s) responsible for low ligation efficiency of PCR-amplified Fabs to SfiI-digested pCOMB3XSS were examined. The colonies from the Fab ligation plates were examined for the presence of Fab fragments. 48 colonies were analyzed for their plasmid DNA for the presence of a 1.5 kb band after SfiI digestion.

Agarose gel analysis showed that 46 clones out of 48 were positive for a ~1.5 kb band. The positive clones with ~1.5 kb inserts were sequenced with vector-specific primers. It was observed that sequences of all 46 clones were identical to the 1.6 kb stuffer fragment of the phage display vector (pCOMB3XSS), demonstrating presence of vector alone in these recombinants.

It was surmised that the supercoiled vector is incompletely digested due to its inherent properties. A single-species vector band on an agarose gel will therefore contain both the SfiI digested 3.3 kb vector band as well as the supercoiled residual, and the latter species will dominate during transformation. The vector was therefore linearized by first cutting within the stuffer fragment so that when resolved on an agarose gel, the linear DNA will run at 5 kb position and the supercoiled position at 3.3 kb, enabling resolution in a gel. For the best results, two rounds of SacI digestion are preferred.

Using this triple-digested (SacI-SfiI-SacI) vector, the complete cycle of Fab making, SfiI digestion and ligations along with only vector and stuffer control was performed to reduce the vector background to 0.02%. The stuffer also ligated with an efficiency of $3\times10^8$/μg but again in the case of Fabs, efficiency was low.

Example 14

Incorrect Ends of Fabs as a Barrier to Successful Vector Ligation

Figure 15:
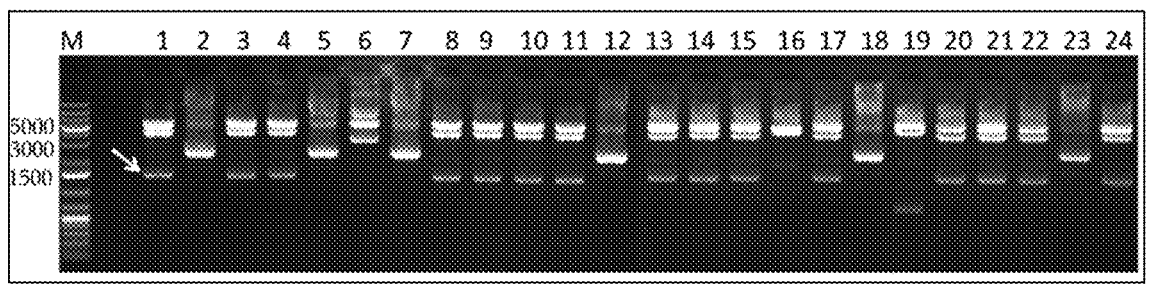
FIG. 15 depicts TOPO-Fab clone confirmation by SfiI digestion. All reactions contain 1 μg of miniprep plasmid from respective TOPO-Fab clones. Digestions were carried out in NEB buffer 4 with 5 U of SfiI per μg DNA in 200 reactions. Numbers above the lanes indicate the respective clone numbers. Samples were run in 1% analytical grade agarose gel in 1×TBE with 0.1 μg/ml ethidium bromide at 5V/cm for 1.5 h. M is the 1 kb plus DNA marker from Fermentas. Arrow indicates the 1.5 kb Fab band released after SfiI digestion.

To improve the ligation efficiency of Fabs, the SfiI recognition sequences at 5' and 3' ends of PCR amplified Fabs were further examined by sequencing. For this purpose, an aliquot of pooled Fab fragments prepared as per Example 9 and without any SfiI digestion were cloned by topoisomerase I mediated ligation using a kit and vector contained within the kit (TOPO-TA 4.0 kit; Life Technologies/ThermoFisher). 24 clones were picked from LB-carbenicillin plates, and plasmid DNA prepared at small scale. When the plasmids were digested with SfiI, 15 out of 24 (62.5%) showed SfiI release (FIG. 15). Sequencing of 8 clones demonstrated that clones which had intact SfiI sequence on both ends (c1, c3, c4, c8—Table 18) also released a 1.5 kb Fab band after restriction digestion (FIG. 15). Therefore, from this experiment it maybe surmised that 1 out of 5 (20%) of the pooled Fab fragments contain incorrect SfiI at either 5' or 3' ends.

TABLE 18

(Table 18 discloses SEQ ID NOS 56 and 58, respectively, in order of appearance)

| Sr. no. | Landmarks | Clone 1 | Clone 2 | Clone 3 | Clone 4 | Clone 5 | Clone 6 | Clone 7 | Clone 8 |
|---|---|---|---|---|---|---|---|---|---|
| 1 | SEQ ID 32 | 3' 20 bp including SfiI site is present; 5' 21 bp floppy tail which is basically GAG repeat is missing; | No | 100% binding | 100% binding | No | Binds with 1 mismatch in SfiI recognition site | No | 100% binding |
| 2 | 5' SfiI site | Yes_intact and correct | No | Yes_intact and correct | Yes_intact and correct | No | Yes_but modified. GGCCCAGGCGGCC has modified to GGCCCAGGCGA CC; could be a false base call | No | Yes_intact and correct |
| 3 | Vk forward primers | Yes | No | Yes | Yes | No | Yes | No | Yes |
|  | SEQ ID 9 | X |  | X | X |  | X |  | 100% binding |
|  | SEQ ID 10 | X |  | 100% binding | 100% binding |  | X |  | X |
|  | SEQ ID 11 | X |  | X | X |  | 100% binding |  | X |
|  | SEQ ID 12 | 100% binding |  | X | X |  | X |  | X |
| 4 | Vk Reverse primers | Yes | No | Yes | Yes | No | Yes | No | Yes |
|  | SEQ ID 13 | 100% binding |  | 100% binding | 100% binding |  | 100% binding |  | 100% binding |
| 5 | Ck forward primer | Yes | No | Yes | Yes | No | Yes | No | Yes |
|  | SEQ ID 31 | 100% binding |  | 1 mismatch. A is modified to G | 100% binding |  | 100% binding |  | 100% binding |
| 6 | Ck Reverse primer | Yes | No | Yes | Yes | No | Yes | No | Yes |
|  | SEQ ID 30 | 100% binding |  | 100% binding | 100% binding |  | 100% binding |  | 100% binding |
| 7 | Shine Dalgano sequence or RBS | Yes |  | Yes | Yes |  | Yes |  | Yes |
| 8 | PelB leader sequence | Yes |  | Yes | Yes |  | Yes |  | Yes |
| 9 | VH forward primers | Yes | No | Yes | Yes | No | Yes | No | Yes |
|  | SEQ ID 1 | X |  | X | X |  | X |  | X |
|  | SEQ ID 2 | X |  | X | X |  | X |  | X |
|  | SEQ ID 3 | X |  | X | X |  | X |  | X |
|  | SEQ ID 4 | 100% binding |  | X | X |  | X |  | X |
|  | SEQ ID 5 | X |  | 100% binding | 100% binding |  | X |  | 100% binding |
|  | SEQ ID 6 | X |  | X | X |  | 100% binding | X | X |
| 10 | VH Reverse primers | Yes | No | Yes | Yes | No | Yes | No | Yes |
|  | SEQ ID 7 | X |  | X | 100% binding |  | 100% binding |  | 100% binding |
|  | SEQ ID 8 | 100% binding |  | 100% binding | 100% binding |  | 100% binding |  | 100% binding |
| 11 | CH forward primer | Yes | No | Yes | Yes | No | Yes | No | Yes |
|  | SEQ ID 27 | 100% binding |  | 100% binding | 100% binding |  | 100% binding |  | 100% binding |
| 12 | CH Reverse primer | Yes | No | Yes | Yes | No | Yes | No | Yes |
|  | SEQ ID 28 | 1 mismatch. G is modified to A |  | 100% binding | 100% binding |  | 100% binding |  | 100% binding |
| 13 | 3' SfiI site | Yes_intact and correct | No | Yes_intact and correct | Yes_intact and correct | No | Yes_intact and correct | No | Yes_intact and correct |
| 14 | SEQ ID 34 | 100% binding | No | 1 mismatch. A is modified to G | 100% binding | No | With 1 mismatch from A to G | No | 3 mismatches and 1 base missing in annealing region |

Example 15

Fabs Released from Topo Vectors can be Re-Ligated FIG. 15 made it abundantly clear that Fab fragments could be released successfully from supercoiled TOPO vectors provided the SfiI site was intact at either end. In addition, the present invention examined whether the Fab fragments released from the TOPO vectors can be ligated back to the SfiI-digested TOPO vector (from a Fab positive clone) or to the triple-digested pCOMB3XSS vector.

SfiI released fragment from a single Fab positive clone was ligated with 140 ng each of triple-digested pCOMB3XSS vector as well as SfiI-digested and gel purified pCRTOPO4 vector in 10 μl reactions. The vector-only control was maintained both for the TOPO and pCOMB3XSS vectors while stuffer ligation control was used only for the pCOMB3XSS vector. When ligating with pCOMB3XSS vector, both phosphorylated and dephosphorylated versions of the vector were used (marked as CIP and non-CIP in Table 19).

The results of re-ligation of TOPO released Fab back to SfiI-digested pCRTOPO4 vector and pCOMB3XSS vector are shown in Table 19. This data clearly indicates that TOPO released Fab can re-ligate successfully back to the parental vector (pCR-TOPO4) as well as the triple-digested pCOMB3XSS vector with efficiency similar to that achieved for the stuffer fragment.

TABLE 19

| Ligation Reactions | Efficiency |
|---|---|
| Stuffer Control_pCOMB3XSS_CIP (1:2) | $3.2 \times 10^8$ |
| Stuffer Control_pCOMB3XSS_Non CIP (1:2) | $3.6 \times 10^8$ |
| Released Fab to TOPO vector (1:2) | $4 \times 10^8$ |
| Released Fab to pCOMB3XSS_CIP (1:2) | $2.6 \times 10^8$ |
| Released Fab to pCOMB3XSS_Non CIP (1:2) | $2.9 \times 10^8$ |
| Vector Background | |
| Vector Control_TOPO | 2% |
| Vector Control_pCOMB3XSS_CIP | 0.05% |
| Vector Control_pCOMB3XSS_Non CIP | 0.32% |

Therefore, the present invention discloses for the first time use of Fabs in a supercoiled form to enable efficient SfiI digestion and optimal use of SfiI to obtain high efficiency of ligation of Fabs.

Example 16

Circularization of a Fab by Self-Ligation to Facilitate SfiI Digestion

Figure 16:
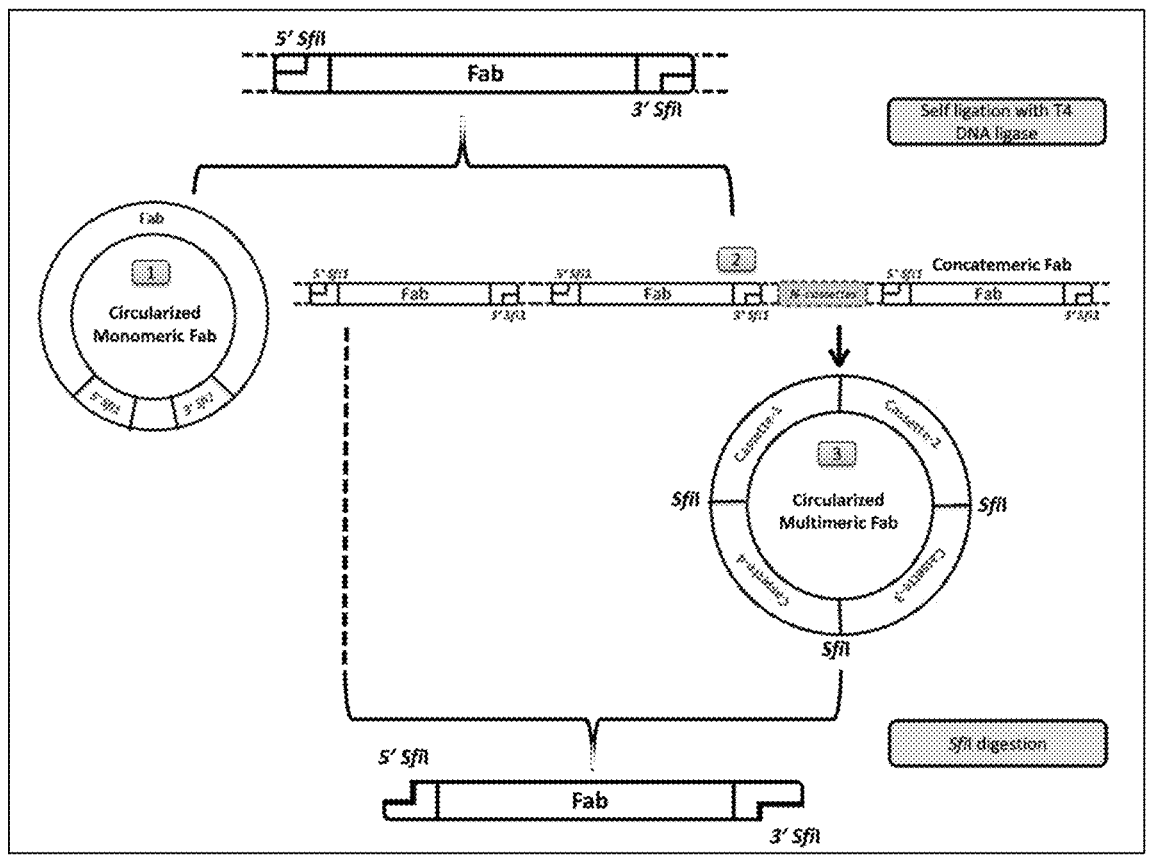
FIG. 16 depicts schematic illustrating the concept of self-circularization to release Fabs with ligatable SfiI ends.

To improve the Fab ligation efficiency, the present invention discloses an approach which is to create supercoiled Fabs by self-ligating the linear Fab fragments. After self-ligation, single linear Fabs can become circularized or multiple linear Fabs can ligate to each other to form linear concatemers. The latter can remain as such, or may further ligate to form larger circular molecules mimicking a supercoiled plasmid that will be more suitable substrates for SfiI. The concept is illustrated in FIG. 16.

10 µg of blunt end Fab was generated using Pfu Ultra II HS polymerase, and phosphorylated by incubating with T4 polynucleotide kinase at 37° C. for 2 h. The kinase reactions were heat inactivated at 65° C. for 20 min before phenolization and ethanol precipitation. Phosphorylated Fabs free from protein or salt contaminants (2.5 µg) were then self-ligated overnight at 16° C. by adding 2 units of T4 DNA ligase per µg of DNA in 30 µl reactions. Self-ligated circular or concatameric Fabs were then purified by phenolization followed by ethanol precipitation, and quantified by Picogreen assay.

Figure 17:
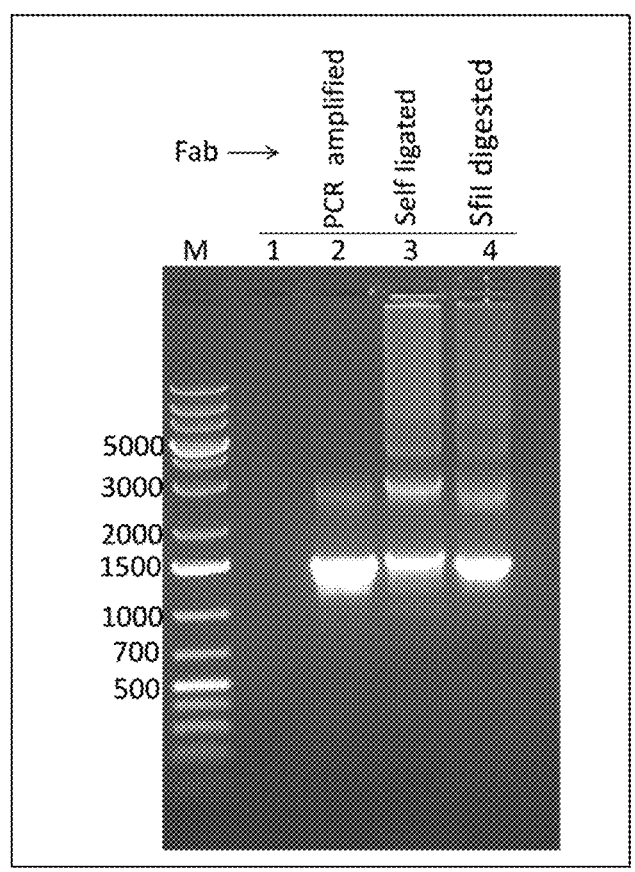
FIG. 17 depicts SfiI digestion of linear Fabs by self-ligation strategy. The Fab used was of single type amplified from plasmid isolated from a TOPO-Fab clone. Lanes 2, 3 and 4 contain 1 μg each of PCR amplified Fab product, Fab after self-ligation and Fab after SfiI digestion, respectively. Products were analyzed on a 1% agarose gel prepared in 1×TBE containing 0.1 μg/ml ethidium bromide and run at 5V/cm for 1.5 h. M is the 1 kb plus DNA marker from Fermentas. Numbers at the left show marker size in base pairs.

An aliquot of 1 µg of self-ligated Fabs was saved for agarose gel analysis and the remaining subjected to SfiI digestion (16 U/µg) overnight at 50° C. in a water bath. Following digestion, an aliquot of the digest was used for agarose gel analysis along with the original un-ligated PCR product and the aliquot of ligated Fab saved earlier. FIG. 17 demonstrates successful self-ligation with smears ranging between 3 kb and above with concomitant disappearance of the 1.5 kb Fab product. FIG. 17 also demonstrates efficient release of linear Fab fragments after SfiI digestion.

Figure 18:
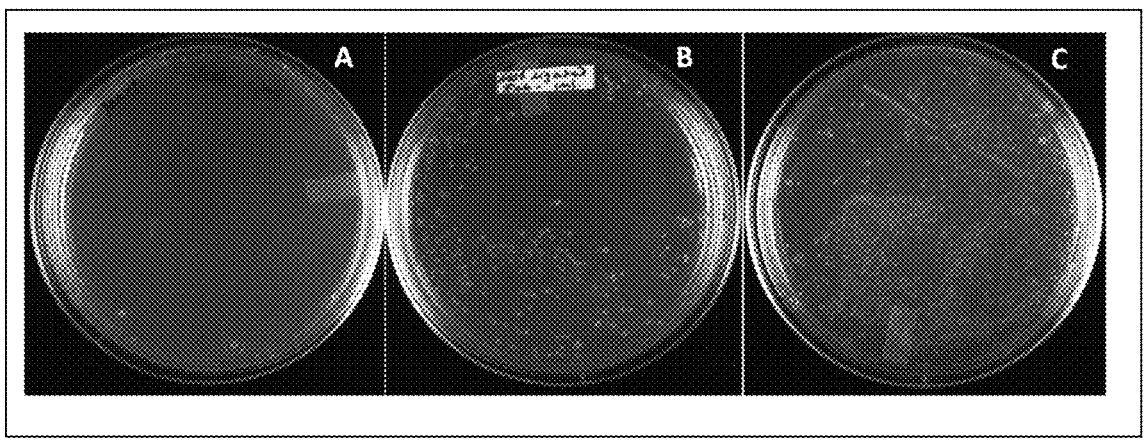
FIG. 18 depicts results of the first self-ligation test on a single population of Fab. Panel A shows Vector control plate while Panel B shows that for the self-ligated Fab. Panel C is the stuffer control. Plates from 1 μl plating volume are shown.

The 1.5 kb SfiI-digested self-ligated Fab band was gel purified using QiaQuik gel extraction kit (Qiagen GmBH, Hilden, Germany). After quantification by Picogreen, the Fab preparation was ligated to 140 ng of dephosphorylated pCOMB3XSS vector in a ~1:2 molar ratio. Ligation was carried out overnight at 16° C. The ligation mix was heat inactivated at 70° C. for 15 min and diluted 1:20 by mixing 2 µl heat inactivated ligation mix with 38 µl of water. 3 µl of the ligation mix was transformed in 25 µl TG1 electro-competent cells as illustrated in Example 11. After overnight incubation, colonies were observed on each plate. The plating volume of 1 µl showed well isolated colonies and considered for efficiency calculation (FIG. 18), while 10 and 100 µl plating volume plates showed crowded and matted growth, respectively.

With zero vector background, self-ligated and SfiI-digested Fabs showed an efficiency of $3.7 \times 10^8$ clones per µg vector (Table 20), thus increasing the efficiency by 3 logs over Example 12 (compare to Tables 16 and 17). The efficiency of self-circularization is further demonstrated on a diverse Fab pool at Example 17.

TABLE 20

| Data for plating volume 1 µl | No. of clones | Efficiency/µg vector |
|---|---|---|
| Vector control | 0 clones | 0 |
| Stuffer control | 2250 clones | $2.1 \times 10^9$ |
| Self ligated Fab SfiI | 392 clones | $3.7 \times 10^8$ |

Example 17

Circularization of Fab Pools by Self-Ligation to Facilitate SfiI Digestion

A kappa Fab pool was prepared by overlap PCR and gel purified as demonstrated in Example 9. As the final overlap PCR for Fabs is optimized with PCR Extender enzyme blend which generates "A" overhangs, an additional step of blunting by T4 polymerase was added before Fab ligation. The blunted Fabs were made free of contaminating proteins and salts by phenolization and ethanol precipitation before self-ligation. The self-ligation, SfiI digestion, vector ligation and transformation procedures were carried out as in Example 16. Results of this study are presented in Table 21.

TABLE 21

| Type of Fab | Efficiency per µg vector | earlier data | Vector background |
|---|---|---|---|
| Single population Fab | $6.6 \times 10^7$ | $3.7 \times 10^8$ | 0 |
| Kappa Fab pool | $3.8 \times 10^7$ | Not attempted | 0 |

Results of Table 21 demonstrate that the self-ligation strategy appears to work for pooled Fabs as well but with reduced efficiency (1 log lesser compared to the single population Fabs—compare Table 21 with Table 20). However, the same single population Fab control which earlier showed the $3.7 \times 10^8$/µg DNA efficiency also showed more than half log reduced efficiency in this experiment. Taking this into consideration, the true ligation efficiency of the self-ligated kappa pool was 5.6-folds higher ($2.1 \times 10^8$/µg vector DNA).

Figure 19:
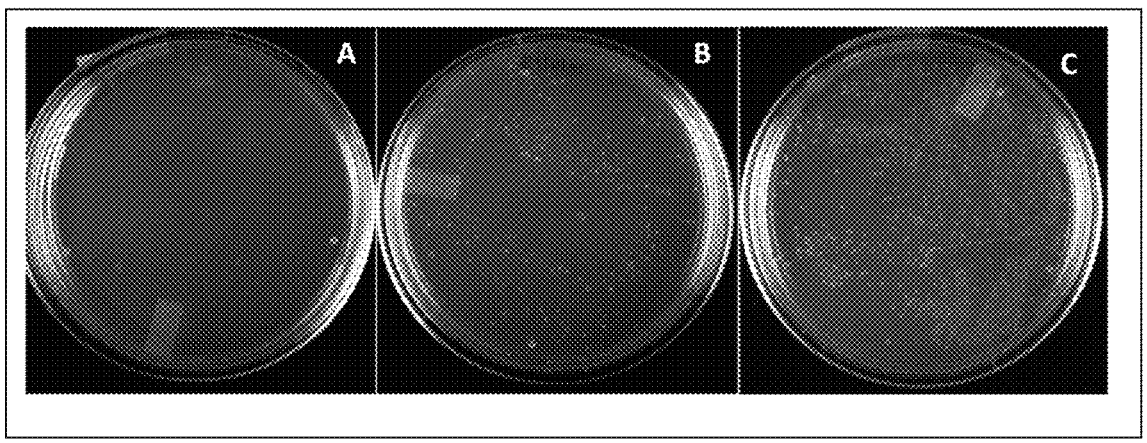
FIG. 19 depicts results of the self-ligation test on a diverse population of Fabs. Panel A shows vector control plate whereas Panel B shows the lambda Fab pool prepared by the self-ligation strategy. Panel C shows the stuffer control plate.

Similarly, a lambda Fab pool was prepared by overlap PCR and gel purified as demonstrated in Example 9. Results of the lambda Fab pool transformation are shown at FIG. 19, and the efficiency data presented in Table 22.

TABLE 22

| Type of Fab | Efficiency per µg vector | Vector background |
|---|---|---|
| Lambda Fab pool | $1.9 \times 10^8$ | 0% |
| Stuffer control | $1 \times 10^9$ | |

A summary of self-ligation is presented at Table 23, which demonstrates the ligation efficiency required to create a large naïve library of the present invention.

TABLE 23

| Vector | Fab type_self ligation | Vector background | Efficiency/μg Vector |
|---|---|---|---|
| pCOMB vector 1 | Kappa_Single_Clone Topo amplified | 0 | $3.7 \times 10^8$ |
| pCOMB vector 2 | Kappa_Fab_pool Overlap PCR | 0 | $2.1 \times 10^8$ |
| pCOMB vector 3 | Lambda_Fab_pool Overlap PCR | 0 | $1.9 \times 10^8$ |

Example 18

Analysis of Recombinant Clones from pCOMB3XSS Ligations to Self-Ligated and SfiI-Digested Fab Pools A total of 24 clones (12 each for kappa and lambda) were picked initially and plasmid DNA extracted at small scale. To confirm Fab identity, PCR was carried out with the plasmid DNA as templates and Fab end-specific primers SEQ ID 32/SEQ ID 34 using a 2-step PCR protocol as shown in Table 24. AmpliTaq Gold enzyme was used in combination with AmpliTaq Gold buffer containing 1.5 mM $MgCl_2$ for such amplifications.

TABLE 24

| | | |
|---|---|---|
| 95° C. | 5 min | 1x |
| 95° C. | 30 sec | 30x |
| 72° C. | 1.45 min | |
| 72° C. | 10 min | 1x |
| 4° C. | Infinity | — |

Figure 20:
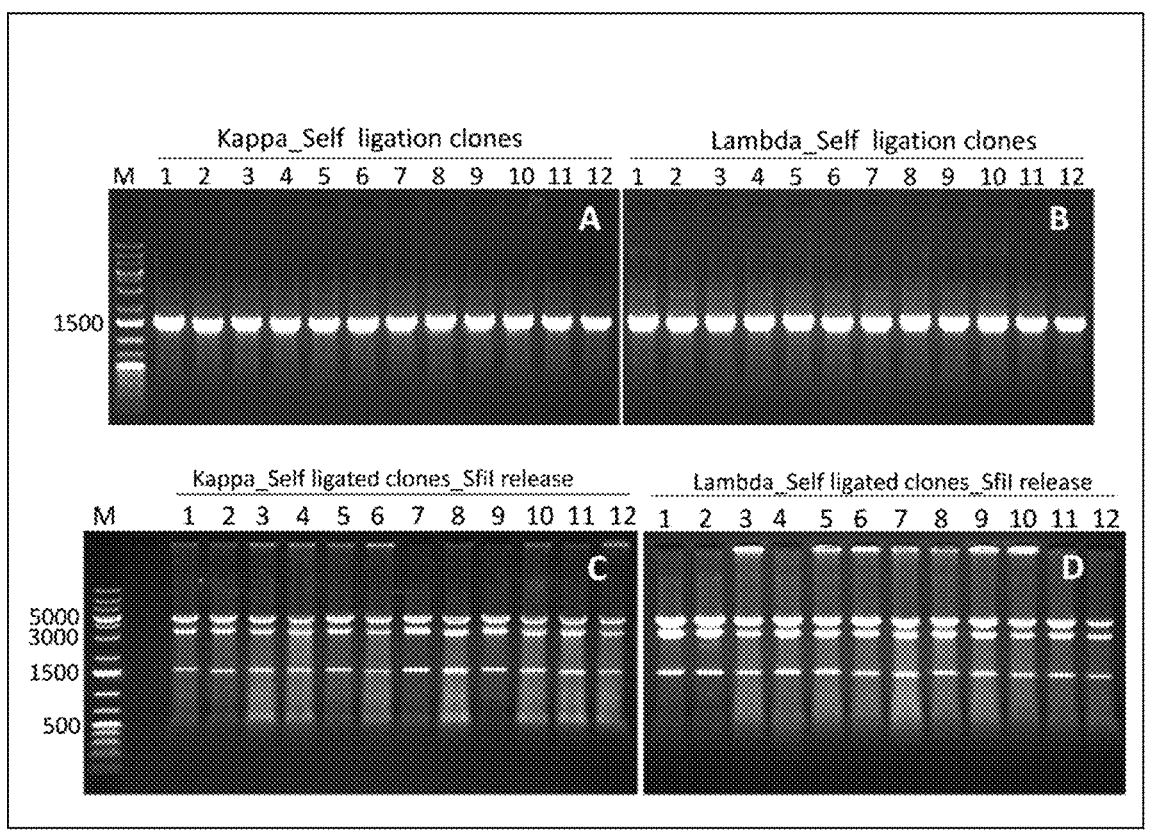
FIG. 20 depicts characterization of self-ligation library clones. Panel A shows PCR amplification for the kappa self-ligation clones while Panel B shows the same for lambda self-ligation clones. 10 μl of PCR products were loaded in each lane. Panel C shows SfiI digestion pattern for the kappa self-ligation clones while Panel D shows SfiI digestion pattern for the lambda self-ligation clones. All lanes in Panels C & D contain 1 μg of SfiI digested plasmid DNA isolated from respective clones. Numbers above the lanes indicate clone numbers. Analysis was done in 1% agarose gels prepared in 1×TBE containing 0.1 µg/ml ethidium bromide and run at 5V/cm for 1.5 h. M is the 1 kb plus DNA marker from Fermentas. Numbers on the left show marker size in base pairs.

Simultaneously, the plasmid DNA samples were digested with SfiI. If the clones were Fab positive, 1.5 kb bands would be expected out of both analyses. It was observed that all 12 kappa and 12 lambda clones were positive for Fab specific PCR amplification (FIG. 20, panels A and B) as well as for SfiI release (FIG. 20, panels C and D).

Upon confirmation that all the 12 clones are Fab positive, another 36 clones each for kappa and lambda ligation plates were further analyzed to answer the percentage and diversity questions. A total of 48 clones each for kappa and lambda Fabs were thus analyzed by PCR for the presence of Fab using Fab specific primers SEQ ID 32/SEQ ID 34 using a 2-step PCR protocol as shown in Table 24. 10 μl from each 50 μl PCR reaction was used for agarose gel analysis. The results demonstrate that all the 96 clones are positive for Fab inserts and show an unambiguous 1.5 kb band.

All 48 clones were then subjected to BstNI fingerprinting. To perform this analysis, the remaining 40 μl from each 50 μl PCR reaction was subjected to BstNI digestion. The digestion mixture is shown in Table 25.

TABLE 25

| Components | Volume (μl) | Final Concentration |
|---|---|---|
| PCR amplified Fab product | 40 | ~4-6μg |
| 10x Buffer 2; NEBL | 10 | 1x |
| 100x BSA | 1 | 1x |
| Bst NI (10U/μl); Roche | 2 | 20U/40μl PCR reaction |
| Nuclease free water | to make up to 100μl | — |
| Total volume | 100 | — |

Figure 21:
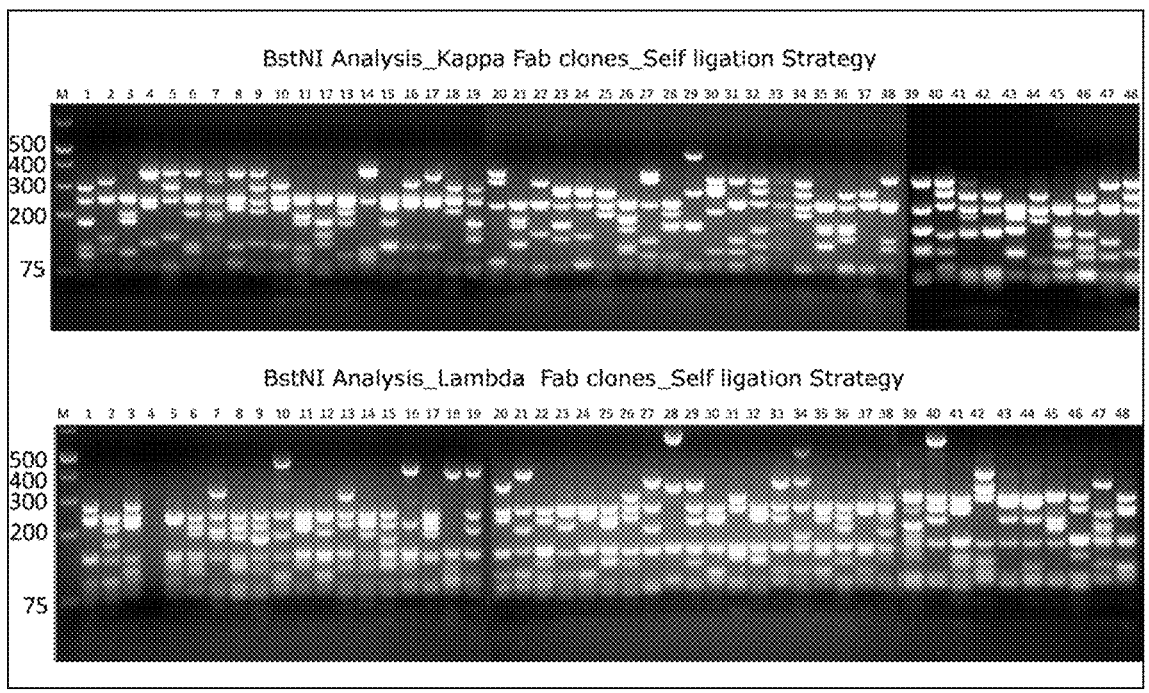
FIG. 21 depicts BstNI analysis of kappa and lambda Fab clones. All lanes contain 40 µl of the BstNI digestion reaction. Top panel shows the fingerprint of kappa Fabs while the lower panel shows lambda Fab fingerprint. Images represent ethidium bromide stained 3% agarose gels cast in 1×TBE, and run at 4V/cm for 3 h. Numbers above the lanes indicate the respective clone numbers. M is the 1 kb plus DNA marker (Fermentas). Numbers on the left indicate marker size in base pairs.

40 μl from each digestion mix was analyzed on 3% agarose gels. FIG. 21 shows that none of the kappa and lambda clones showed any repeat pattern and each clone is different.

Figure 22:
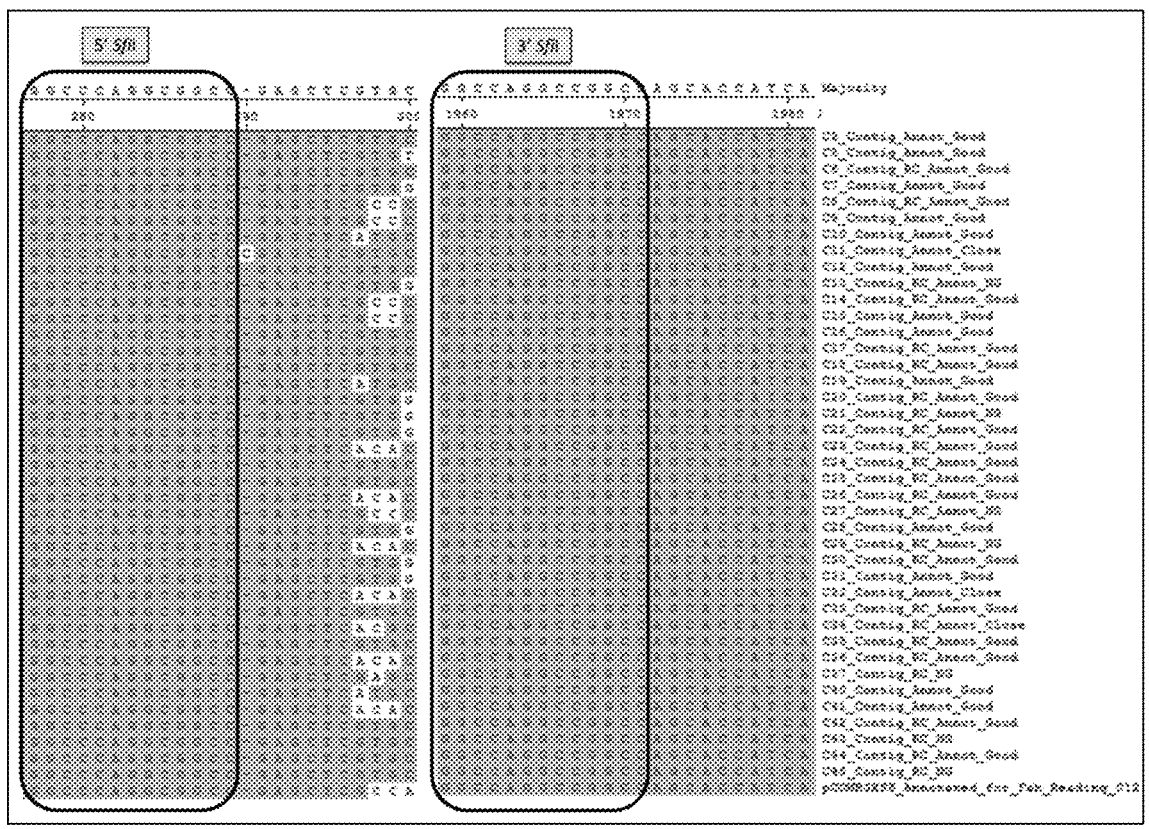
FIG. 22 depicts ClustalW report of all sequenced lambda Fabs. Nucleotide sequences of lambda Fabs were compared against pCOMB3XSS to verify presence and intactness of SfiI on both 5' and 3' ends. 5' SfiI discloses SEQ ID NOS 237-278 and 3' SfiI discloses SEQ ID NOS 279-320, respectively, in order of appearance

All 48 clones from each library were subjected to dideoxy sequencing using two vector backbone specific, two pelB adjacent region specific, and one $C_H1$ specific primers. The Fab sequence of each clone was analyzed following an algorithm of contig building from sequence chromatograms, and visual verification of anomalous base calls. Contigs were then manually annotated for landmarks such as the SfiI sites at 5' and 3' ends, the $V_L$, $V_H$, $C_L$ and $C_H1$ domains, and for completeness of the individual light and heavy chains from Start to the Stop codons. FIG. 22 is an example demonstrating verification of intact SfiI sites on both ends of all lambda clones.

The results of the manual analysis and annotation are summarized in Tables 26 and 27. Based on these tables, ~80% of the clones from either kappa or lambda Fab libraries prepared by the novel self-ligation method are full length translatable Fabs.

TABLE 26

| | $V_\kappa$-$C_\kappa$ | | | | | |
|---|---|---|---|---|---|---|
| Clone number | PCR +ve | Sequenced | Intact 5' and 3' SfiI ends | $V_\kappa$-$C_\kappa$ ORF | VH-CH ORF | Both ORFs |
| 1 | ✓ | ✓ | ✓ | ✗ | ✗ | ✗ |
| 2 | ✓ | ✓ | ✓ | ✓ | ✗ | ✗ |
| 3 | ✓ | ✓ | ✓ | ✓ | ✓ | ✓ |
| 4 | ✓ | ✓ | ✓ | ✓ | ✗ | ✗ |
| 5 | ✓ | ✓ | ✓ | ✓ | ✓ | ✓ |
| 6 | ✓ | ✓ | ✓ | ✓ | ✓ | ✓ |
| 7 | ✓ | — | — | — | — | — |
| 8 | ✓ | ✓ | ✓ | ✓ | ✓ | ✓ |
| 9 | ✓ | ✓ | ✓ | ✗ | ✓ | ✗ |
| 10 | ✓ | ✓ | ✓ | ✓ | ✓ | ✓ |
| 11 | ✓ | ✓ | ✓ | ✓ | ✓ | ✓ |
| 12 | ✓ | ✓ | ✓ | ✓ | ✓ | ✓ |
| 13 | ✓ | ✓ | ✓ | ✗ | ✓ | ✗ |
| 14 | ✓ | ✓ | ✓ | ✓ | ✓ | ✓ |
| 15 | ✓ | ✓ | ✓ | ✓ | ✓ | ✓ |
| 16 | ✓ | ✓ | ✓ | ✓ | ✓ | ✓ |
| 17 | ✓ | ✓ | ✓ | ✓ | ✓ | ✓ |
| 18 | ✓ | ✓ | ✓ | ✓ | ✓ | ✓ |
| 19 | ✓ | — | — | — | — | — |
| 20 | ✓ | ✓ | ✓ | ✓ | ✓ | ✓ |
| 21 | ✓ | ✓ | ✓ | ✓ | ✓ | ✓ |
| 22 | ✓ | ✓ | ✓ | ✓ | ✓ | ✓ |
| 23 | ✓ | ✓ | ✓ | ✓ | ✓ | ✓ |
| 24 | ✓ | ✓ | ✓ | ✗ | ✓ | ✗ |
| 25 | ✓ | ✓ | ✓ | ✓ | ✓ | ✓ |
| 26 | ✓ | ✓ | ✓ | ✓ | ✓ | ✓ |
| 27 | ✓ | ✓ | ✓ | ✓ | ✓ | ✓ |
| 28 | ✓ | ✓ | ✓ | ✓ | ✓ | ✓ |
| 29 | ✓ | ✓ | ✓ | ✓ | ✗ | ✗ |
| 30 | ✓ | ✓ | ✓ | ✗ | ✓ | ✗ |
| 31 | ✓ | ✓ | ✓ | ✓ | ✓ | ✓ |
| 32 | ✓ | ✓ | ✓ | ✓ | ✓ | ✓ |
| 33 | ✓ | — | — | — | — | — |
| 34 | ✓ | ✓ | ✓ | ✓ | ✓ | ✓ |
| 35 | ✓ | ✓ | ✓ | ✓ | ✓ | ✓ |
| 36 | ✓ | ✓ | ✓ | ✓ | ✓ | ✓ |
| 37 | ✓ | ✓ | ✓ | ✗ | ✓ | ✗ |
| 38 | ✓ | ✓ | ✓ | ✓ | ✓ | ✓ |
| 39 | ✓ | ✓ | ✓ | ✓ | ✓ | ✓ |
| 40 | ✓ | — | — | — | — | — |
| 41 | ✓ | ✓ | ✓ | ✓ | ✓ | ✓ |

TABLE 26-continued

$V_\kappa$-$C_\kappa$

| Clone number | PCR +ve | Sequenced | Intact 5' and 3' SfiI ends | $V_\kappa$-$C_\kappa$ ORF | VH-CH ORF | Both ORFs |
|---|---|---|---|---|---|---|
| 42 | ✓ | ✓ | ✓ | ✓ | ✓ | ✓ |
| 43 | ✓ | ✓ | ✓ | ✓ | ✓ | ✓ |
| 44 | ✓ | ✓ | ✓ | ✓ | ✓ | ✓ |
| 45 | ✓ | ✓ | ✓ | ✓ | ✓ | ✓ |
| Total score | 45 | 41 | 41 | 35 | 36 | 31 |
| No. obtained/total | 45/45 | 41/41 | 41/41 | 35/41 | 37/41 | 32/41 |
| Percentage | 100% | 100% | 100% | 85.40% | 90.20% | 78.60% |

TABLE 27

$V_\lambda$-$C_\lambda$

| Clone number | PCR +ve | Sequenced | Intact 5' and 3' SfiI ends | $V_\lambda$-$C_\lambda$ ORF | VH-CH ORF | Both ORFs |
|---|---|---|---|---|---|---|
| 1 | ✓ | — | — | — | — | — |
| 2 | ✓ | — | — | — | — | — |
| 3 | ✓ | ✓ | ✓ | ✓ | ✓ | ✓ |
| 4 | ✓ | — | — | — | — | — |
| 5 | ✓ | ✓ | ✓ | ✓ | ✓ | ✓ |
| 6 | ✓ | ✓ | ✓ | ✓ | ✓ | ✓ |
| 7 | ✓ | ✓ | ✓ | ✓ | ✓ | ✓ |
| 8 | ✓ | ✓ | ✓ | ✓ | ✓ | ✓ |
| 9 | ✓ | ✓ | ✓ | ✓ | ✓ | ✓ |
| 10 | ✓ | ✓ | ✓ | ✓ | ✓ | ✓ |
| 11 | ✓ | ✓ | ✓ | ✓ | ✓ | ✓ |
| 12 | ✓ | ✓ | ✓ | ✓ | ✓ | ✓ |
| 13 | ✓ | ✓ | ✓ | ✗ | ✗ | ✗ |
| 14 | ✓ | ✓ | ✓ | ✓ | ✓ | ✓ |
| 15 | ✓ | ✓ | ✓ | ✓ | ✓ | ✓ |
| 16 | ✓ | ✓ | ✓ | ✓ | ✓ | ✓ |
| 17 | ✓ | ✓ | ✓ | ✓ | ✓ | ✓ |
| 18 | ✓ | ✓ | ✓ | ✗ | ✓ | ✗ |
| 19 | ✓ | ✓ | ✓ | ✓ | ✓ | ✓ |
| 20 | ✓ | ✓ | ✓ | ✓ | ✓ | ✓ |
| 21 | ✓ | ✓ | ✓ | ✗ | ✓ | ✗ |
| 22 | ✓ | ✓ | ✓ | ✓ | ✓ | ✓ |
| 23 | ✓ | ✓ | ✓ | ✓ | ✓ | ✓ |
| 24 | ✓ | ✓ | ✓ | ✓ | ✓ | ✓ |
| 25 | ✓ | ✓ | ✓ | ✓ | ✓ | ✓ |
| 26 | ✓ | ✓ | ✓ | ✓ | ✓ | ✓ |
| 27 | ✓ | ✓ | ✓ | ✗ | ✓ | ✗ |
| 28 | ✓ | ✓ | ✓ | ✓ | ✓ | ✓ |
| 29 | ✓ | ✓ | ✓ | ✗ | ✗ | ✗ |
| 30 | ✓ | ✓ | ✓ | ✓ | ✓ | ✓ |
| 31 | ✓ | ✓ | ✓ | ✓ | ✓ | ✓ |
| 32 | ✓ | ✓ | ✓ | ✗ | ✓ | ✗ |
| 33 | ✓ | ✓ | ✓ | ✓ | ✓ | ✓ |
| 34 | ✓ | ✓ | ✓ | ✓ | ✓ | ✓ |
| 35 | ✓ | ✓ | ✓ | ✓ | ✓ | ✓ |
| 36 | ✓ | ✓ | ✓ | ✓ | ✓ | ✓ |
| 37 | ✓ | ✓ | ✓ | ✓ | ✗ | ✗ |
| 38 | ✓ | — | — | — | — | — |
| 39 | ✓ | — | — | — | — | — |
| 40 | ✓ | ✓ | ✓ | ✓ | ✓ | ✓ |
| 41 | ✓ | ✓ | ✓ | ✓ | ✓ | ✓ |
| 42 | ✓ | ✓ | ✓ | ✓ | ✓ | ✓ |
| 43 | ✓ | ✓ | ✓ | ✓ | ✗ | ✗ |
| 44 | ✓ | ✓ | ✓ | ✓ | ✓ | ✓ |
| 45 | ✓ | ✓ | ✓ | ✓ | ✗ | ✗ |
| Total sore | 45 | 40 | 40 | 33 | 35 | 30 |
| No. obtained/total | 45/45 | 40/40 | 40/40 | 34/40 | 35/40 | 31/40 |
| Pertentage | 100% | 100% | 100% | 85.00% | 87.50% | 77.50% |

The sequences of $V_L$ and $V_H$ domains of all clones were submitted to the IMGT database for detailed annotation on the germline family, framework and CDRs as well as differences in amino acids compared to reference human sequences. This analysis (Table 28) showed that except for one family each of $V_H$ (VH6) and $V_\lambda$ (VL10), all other families were represented in these clones (Table 28). As these missing families are represented by fewer variants as compared to the other families, it is possible that a clone belonging to such families has been missed both because of their rarity and low sampling number in this sequence dataset. 46% of all $V_H$ domains belonged to the VH4 family and 24% belonged to VH3, while other families (VH1, VH2 and VH5) were in the range of 5-18%. Similarly, 5 families of $V_\kappa$ and 8 families of $V_\lambda$ were represented. In kappa family, 50% of clones belonged to the VK3 family and 30% to the VK1 family. Representation of other families was between 2.5 and 10%. In lambda family, the representation was 33% for VL1, 31% for VL2, and remaining families (VL3, VL4, VL6, VL7, VL8 and VL9) were in the 3-13% range.

Remaining annotations from the IMGT database are summarized in Tables 29-31 for a subset of sequenced clones. 97% of all clones have V domains without any stop codons, and are therefore functional. This is a remarkable number, and suggests that our amplification strategy results in faithful capture of functional Ig mRNA.

TABLE 28

| Clone | Gene family | No. of clones analyzed | Total coverage in different gene family | Percentage (%) |
|---|---|---|---|---|
| VH (Kappa and Lambda both) | | | | |
| VH | VH1 | 79 | 14 | 18 |
|  | VH2 |  | 4 | 5 |
|  | VH3 |  | 19 | 24 |
|  | VH4 |  | 36 | 46 |
|  | VH5 |  | 6 | 8 |
|  | VH6 |  | 0 | 0 |
| $V_\kappa$ | | | | |
| VK | VK1 | 40 | 12 | 30 |
|  | VK2 |  | 3 | 7.5 |
|  | VK3 |  | 20 | 50 |
|  | VK4 |  | 4 | 10 |
|  | VK5 |  | 1 | 2.5 |
| $V_\lambda$ | | | | |
|  | VL1 | 39 | 13 | 33 |
|  | VL2 |  | 12 | 31 |
|  | VL3 |  | 5 | 13 |
|  | VL4 |  | 1 | 3 |

TABLE 28-continued

| Clone | Gene family | No. of clones analyzed | Total coverage in different gene family | Percentage (%) |
|---|---|---|---|---|
| | VL5 | 0 | | 0 |
| | VL6 | 3 | | 8 |
| | VL7 | 3 | | 8 |
| | VL8 | 1 | | 3 |
| | VL9 | 1 | | 3 |
| | VL10 | 0 | | 0 |

TABLE 29

(Table 29 discloses the full-length sequence of SEQ ID NOS 59-75, 321, and 76-78, respectively, in order of appearance)
Variable Lambda (V$_\lambda$)

| Clone | FR1 | CDR1 | FR2 | CDR2 | FR3 | CDR3 |
|---|---|---|---|---|---|---|
| 11 | ELVLTQPPSASGTPGQRVTISCSGS | TSNIERDT | VIWYQKVPGTAPKLLIY | GND | QRPSGVPDRFSGSRSGASASLAISGLQSDDEADYYC | AAWDDSLNGWV |
| 12 | ELVLTQPPSVSGTPGQKVTISCSGS | SSNIESNN | VNWYHQLPGRAPKLLLY | INN | QRPSGVPDRFSGSKSGTSASLAISGLQSEDEADYYC | AAWDDSLNGWV |
| 13 | ELVVTQPPSVSAAPGQKVTISCSGS | SSNIGNNY | VSWYQQLPGTAPKLLIY | ENN | KRPSGIPDRFSGSKSGTSATLGITGLQTGDEADYYC | |
| 14 | ELALTQPPSASGSPGQSVTISCTGT | SSDVGAYNY | VSWYQQHPGKAPKLMIY | DVS | NRPSGVSNRFSGSKSGNTASLTISGLQAEDEADYYC | SSYTSSSTLEV |
| 15 | ELALTQPPSASGSPGQSVTISCTGT | SSDVGGYNV | VSWYQQHPGKAPKLMIY | EVS | KRPSGVPDRFSGSKSGNTASLTVSGLQAEDEADYYC | SSYAGSNNLKV |
| 16 | ELVLTQPPSASGTPGQRVTISSSGS | SSNIGNNY | VFWYQQPPGTAPKLIIY | EVT | NRPSGVPDRFSGSKSGNTASLTITGLQAEDEANYYC | VSQSTTTTWV |
| 17 | ELVLTQPPSASASLGASVTLTCTLS | SGYSNYK | VDWYQQRPGKGPRFVMR | VGTGGIVG | SKGDGIPDRFSVLGSGLNRYLTIKNIQEEDESDYHC | GADHGSGSNFAYVV |
| 18 | ELVLTQEPSLTVSPGGTVTLTCGSS | TGAVTSGHY | PYWFQQKPGQAPRTLIY | DTS | NKHSWTPARFSGSLLGGKAALTLSGAQPGDEAEYYC | LLSYSGAGV |
| 19 | ELMLTQPHSVSESPGKTVTISCTRS | SGNIAGDY | VQWFQQRPGSVPTTVIY | EDD | RRPSGVPDRFSGSIDSSSNSATLTISGLTTEDEADYYC | QSYQTNSFWV |
| 20 | ELVVTQEPSFSVSPGGTVTLTCGLR | YGSVSTADY | PSWYQRTPGQAPRMLIY | TTN | TRSSGVPDRFSGSIIGNKAALTITGAQPDDESDYYC | LLYMGSGISV |
| 21 | ELVVTQPPSVSGAPGQRVTISCTGS | SSNIGAGYD | VHWYQQLPGTAPKLLIY | GNS | NRPSGVPDRFSGSKSGTSASLAISGLQSEDEADYYC | AAWDDSLNGWV |
| 22 | ELVVTQPPSVSGAPGQRVTISCTGS | SSNIGADYH | VHWYQQLPGTAPKLLIY | GNS | NRPSGVPDRFSGSKSGTSASLAITGLQAEDEADYYC | QSYDISLNGWV |
| 23 | ELTLTQSPSASGSPGQSVTISCTGT | SSDVGGYNY | VSWYQQHPGKAPKLMIY | EVT | KRPSGVPDRFSGSKSGNTASLTVSGLQAEDEADYYC | NSYAGSNNCV |
| 24 | ELVLTQPPSVSAAPGQRVTISCSGS | SSNIGENY | VSWYQQLPGTAPKLLIY | DNN | KRPSGIPDRFSGSKSGTSATLGVTGLQDEADYYC | GTWDSSLTAVV |
| 25 | ELVLTQPPSASGSPGQSVTISCTGT | SRDIGRYNY | VSWYQQHPGKAPKVMIY | EVS | KRPSGVPDRFTGSKSGNTASLTVSGLQVEDEADYYC | GSYGGNDNPVV |
| 26 | ELTLTQSSSASGSPGQSVAISCTGT | SSDVGGYNY | VSWYQQHPGKAPKLMIY | DVS | NRPSGVSNRFSGSKSGNTASLTISGLQAEDEADYYC | QSYDSNLSGWV |
| 27 | ELALTQPPSASGSPGQSVTISCTGT | SSDIGSYKY | VSWYQQHPGKVPKIMIY | DVS | DRPSGVSNRFSGSKSGNTASLTISGL*AEDEADYYC | SSYTSSSTYVL |
| 28 | ELVVTQEPSLTVSPGGTVTLTCGSS | SGAVTSGHY | PYWVQQKPGQAPRALIY | DVT | KKYSWTPARFSGSLLGGKAALTLSGAEPEDEAEYFC | FLSYSDGRV |
| 29 | SSHFTQSPSVSVSPGQTASITCSGD | KLGDKY | ACWYQQKPGQSPVLVIY | QDS | KRPSGIPERFSGSNSGNTATLTISGTQAMDEADYYC | QAWDSSVV |
| 30 | ELVVTQEPSVSAAPGQKVTISCSGS | SSNIGAGYD | VHWYQQLPGTAPKLLIY | GNS | NRPSGVPDRFSGSKSGTSASLAITGLQAEDEADYYC | QSYDSSLSGVV |

| Clone | FR4 | Germline | Amino acid different from germline | Family | Percentage Identity |
|---|---|---|---|---|---|
| 11 | FGGGTKLTVL | IGLV1-44*01 F | 14 | VL1 | 89.82% |
| 12 | FGGGTKLTVL | IGLV1-44*01 F | 10 | VL1 | 95.44% |
| 13 | FGGGTKLTVL | IGLV1-51*02 F | 3 | VL1 | 98.25% |
| 14 | FGGGTKLTVL | IGLV2-14*01 F | 7 | VL2 | 96.18% |
| 15 | FGGGTKLTVL | IGLV2-8*01 F | 2 | VL2 | 98.61% |
| 16 | FGGGTKVTVL | IGLV1-47*01 F | 23 | VL1 | 82.81% |
| 17 | FGGGTKLTVL | IGLV9-49*01 F | 3 | VL9 | 98.99% |
| 18 | FGGGTKLTVL | IGLV7-46*01 F | 4 | VL7 | 97.92% |
| 19 | FGGGTKLTVL | IGLV6-57*01 F | 11 | VL6 | 91.75% |
| 20 | FGGGTKLTVL | IGLV8-61*01 F | 12 | VL8 | 93.75% |
| 21 | FGGGTKLTVL | IGLV1-50*01 ORF | 8 | VL1 | 94.44% |
| 22 | FGGGTKLTVL | IGLV1-40*01 F | 7 | VL1 | 96.88% |
| 23 | FGGGTKLTVL | IGLV2-8*01 F | 6 | VL2 | 96.18% |
| 24 | FGGGTKLTVL | IGLV1-51*01 F | 6 | VL1 | 95.44% |
| 25 | LGGGTKVTVL | IGLV2-8*01 F | 13 | VL2 | 93.06% |
| 26 | FGGGTKLTVL | IGLV2-8*01 F | 11 | VL2 | 90.97% |

TABLE 29-continued

| | | | | | |
|---|---|---|---|---|---|
| 27 | FGGGTKLTVL | IGLV2-14*01 F | 13 | VL2 | 93.40% |
| 28 | FGGGTKLTVL | IGLV7-46*01 F | 13 | VL7 | 93.40% |
| 29 | FGGGTKLTVL | IGLV3-1*-01 F | 4  | VL3 | 96.06% |
| 30 | FGGGTKLTVL | IGLV1-40*01 F | 7  | VL1 | 95.49% |

TABLE 30

(Table 30 discloses the full-length sequence of SEQ ID NOS 79-89, 322-326, and 90-96, respectively, in order of appearance)
Variable Kappa ($V_\kappa$)

| Clone | FR1 | CDR1 | FR2 | CDR2 | FR3 | CDR3 |
|---|---|---|---|---|---|---|
| 1 | ELQMTQSPDSLAVSLGERATINCKSS | QSVLYSSNNKNY | LAWYQQKPGQPPKLLIY | WAS | TRESGVPDRFSGSGSGTDFTLTISSLQAEDVAVYYC | QQYYSTPA |
| 2 | ELVMTQSPATLSVSPGERATLSCRAS | QSVSSN | LAWYQQKPGQAPRRLIY | DAD | TRATGIPDRFSGSGSGTDFTLTISRLEPEDEDFAVYYC | QQYGSSPWT |
| 3 | ELQMTQSPSSLSASVGDRVTITCRAS | QDISNY | LAWYQQKPGKVPKLLIY | AAS | TLQSGVPSRFSGSGSGTDFTLTISSLQPEDVATYYC | QKYNSAPPIT |
| 4 | ELVMTQSPSTLSASVGDRVTITCRAS | QSISNY | LNWYQQKPGQAPRLLIY | GAS | SRATGIADRFSGSGSGTDFTLSISRLEPEDFVMYYC | QQYDSSTPT |
| 5 | ELVMTQSPATLSVSPGERATLSCRAS | QSVSSN | LAWYQQKPGQPPKLLIY | WTS | TRESGVPDRFSGSGSGTDFTLTISSLQAEDVAVYYC | QQYYSIPLT |
| 6 | ELVMTQSPSSLSASVGDRVTITCRAS | QSISSW | LAWYQQKPGKAPKLLIY | DAS | NLQSGVPSRFSGSGSGTEFTLTISSLQADDSATYYC | QQYNTYST |
| 8 | ELVLTQSPLSLPVTPGEPASISCRSS | QSLLHSNGYNY | LDWYLQKPGQSPQLLIY | LGS | NRASGVPDRFSGSGSGTDFTLKISRVEAEDVGVYYC | MQALQTRT |
| 10 | ELVLTQSPVTLSVSPGERASLSCRAS | QSVGSR | LAWYEHKPGQAPRLLIY | DTS | TRATGISARFSGSGSGTDFTLTINSLQSEDFAVYYC | QHRDNWPPALT |
| 11 | ELVMTQSPATLSLSPGERVTLSCRAS | QSVSGY | LAWYQQRPGQAPRLLIY | DAS | NRATGIPARFSGSGSGTDFTLTIDRLEPEDFGVYFC | QQYERSTLT |
| 12 | ELVMTQSPSSLSASVGDRVTITCRAS | QSISSY | LNWYQQKPGKAPKLLIY | AAS | SLQSGVPSRFSGSGSGTDFTLTISSLQPEDFATYYC | QQSYSTPRT |
| 13 | ELVMTQSPDSLAVSLGERATINCKSR | QSVLYSSNNKNG | SSRRAPTRESGDRFSGS | GSG | TDFSLTISSLQVEGLLLSTKLSSIHFRPWDQSGY | QTNCGCTICLHLPAIAVEIWNCLCCVPAE*LLSQRGQSTVEGG*RPPIG*LPGECHRAGQQGQH |
| 14 | AAELVMTQSPDSLAVSLGERATINCK | SSQSILYASNYY | LAWYQQKPGQPPKLLIY | WAY | TRASGVPDRFSGSGSGTDFTLTISSLQAEDVAVYYC | QQYEKLPST |
| 15 | ELQMTQSPSSLSASVGDRVTITCRAS | LNLGSY | LNWYQQKPGKAPSLLIY | AAS | SLPIGVPSRFRGGSGTDFTLTIIGLLPEDLATYYC | QQSYSPPQS |
| 16 | ELTLTQSPAFMSATPGDKVTISCKAS | QDIDDD | MNWYQQKPGEAAVFIIQ | EAT | NLVPGISPRFSGSGYGTDFTLTINNIESEDAAYYFC | LQHDNFPLT |
| 17 | ELVLTQSPATLSLSPGERATLSCRAS | QSVSSY | LAWYQQKPGQAPRLLIY | GAS | SRATGIPDRFSGSGSGTDFTLTISRLEPEDFAVYYC | QQYGSSRT |
| 18 | ELVMTQSPATLSVSPGERATLSCRAS | QSVSSN | LAWYQQKPGQAPRLLIY | DAS | NRATGIPARFSGSGSGTDFTLTISSLEPEDFAVYYC | QQSDNTPWT |
| 20 | ELVMTQSPATLSLSPGERATLSCRAS | QSVSSSY | LAWYQQKPGQAPRLLIY | GAS | SRATGIPDRFSGSGSGTDFTLTISRLEPEDFAVYYC | QQYGSSPRWT |
| 21 | ELTLTQSPGTLSLSPGEGATLSCRAS | QSVSGKF | LTWYQQKSGQAPRLLIY | GTS | TRAPGIPDRFIGSGSGTDFTLTITRLEPEDFAVYYC | QQYGSSYT |

| Clone | FR4 | Germline | Amino acid different from germline | Family | Percentage Identity |
|---|---|---|---|---|---|
| 1 | FGQGTKLEIK | IGKV4-1*01 F | 3 | VK4 | 98.32% |
| 2 | FGQGTKVEIK | IGKV3-20*01 F | 7 | VK3 | 96.06% |
| 3 | FGPGTKVDIK | IGKV1-27*01 F | 3 | VK1 | 98.92% |
| 4 | FGQGTKVEIK | IGKV3-20*01 F | 18 | VK3 | 87.46% |
| 5 | FGQGTKVEIK | IGKV4-1*01 F | 15 | VK4 | 89.93% |
| 6 | FGQGTKVEIK | IGKV1-5*01 F | 9 | VK1 | 94.62% |
| 8 | FGQGTKVEIK | IGKV2-28*01 F | 3 | VK2 | 98.30% |
| 10 | FGGGTKVESK | IGKV3-15*01 F | 16 | VK3 | 90.68% |
| 11 | FGQGTKLEIK | IGKV3-20*01 F | 15 | VK3 | 91.76% |
| 12 | FGPGTKVDIK | IGKV3-39*01 F | 3 | VK1 | 98.21% |
| 13 | TSLSSTLTLS | IGKV4-3*01 F | 54 | VK4 | 48.82% |
| 14 | FGQGTRLEIK | IGKVF-1*01 F | 41 | VK4 | 72.05% |
| 15 | FGQGTKLEIK | IGKV1-39*01 F | 16 | VK1 | 90.32% |
| 16 | FGQGTRLEIK | IGKV5-2*01 F | 5 | VK5 | 96.06% |

TABLE 30-continued

| | | | | | |
|---|---|---|---|---|---|
| 17 | FGQGTKVEIK | IGKV3-20*01 F | 2 | VK3 | 97.85% |
| 18 | FGQGTKVEVK | IGKV3-11*01 F | 7 | VK3 | 94.98% |
| 20 | FGQGTKVEIK | IGKV3-20*01 F | 3 | VK3 | 97.87% |
| 21 | FGQGTKLEIK | IGKV3-28*01 F | 13 | VK3 | 91.13% |

TABLE 31

(Table 31 discloses the full-length sequence of SEQ ID NOS 97-114, 327, and 115, respectively, in order of appearance)
Variable Heavy chain (V$_H$)

| Clone | FR1 | CDR1 | FR2 | CDR2 | FR3 | CDR3 |
|---|---|---|---|---|---|---|
| 11 | QVQLQESGPGLVKPSETLSLTCTVS | GGSISGYY | WSWIRQPPGKGLEWIG | IYYIGNT | NYNPSLKSRVTISLDTSKNQFSLKVTSVTAADTAMYYC | ASDAAGLGY |
| 12 | QVQLVQSGAEVKKPGASVMVSCKAS | GYTFTRYG | ITWVRQAPGQGPQYMGW | TNTDSGRT | NYAQKLQGRVTMTTDTSTATAYMELRSLRSDDTAVYYC | ARDLRYNGSYSPFDY |
| 13 | QVQLQESGPGLVKPSQTLSLTCSVS | GGSISGSSYY | WGWIRQPPGKGLEWVGGS | IYYRGST | YYNPSLTSRVTISVDTSKNQFSLKLSSVTAADTAMYYC | ARHGYSYDSSGSSPLDS |
| 14 | QITLKESGPTLVKPTQTLTLTCTFS | GFSLSTSGVG | VAWIRQPPGKALEWLAL | VYWDDDK | RYSPSLKSRLTITKDTSKNQVVLTMTNMDPVDTGTYYC | AHRSPVVTGTAPHKWFDP |
| 15 | QVQLQQWGAGLLKPSETLSLTCAVY | GGSFSGYY | WSWIRQPPGKGLEWIGE | INHSGST | NYNPSLKSRVTISVDTSKNQFSLKLSSVTAADTAVYYC | ARVRGRIAARLRATRFDY |
| 16 | QVQLQQWGAGLLKPSETLSLTCAVY | GGSFSGYY | WSWIRQPPGKGLEWIGE | INHSGST | NYNPSLKSRVTVSVDTSKNQFSLKLSSVTAADTAVYYC | ARWGPGSGSGLVYGMDV |
| 17 | QVQLQQWGAGLLKPSETLSLTCAVY | GGSFSGYY | WSWIRQPPGKGLEWIGE | INHSGST | NYNPSLKSRVTISVDTSKNQFSLKLSSVTAADTAVYYC | ARGRGYSYGLGLLRWTVRFDY |
| 18 | QVQLQESGGGVVQPGGSLRLSCAAS | GFTFSSYG | MYWVRQAPGKGLEWVAF | IRYDGSNK | YYADSVKGRFTISRDNSKNTLYLQMNSLRAEDTAVYYC | AKGWGINSGPFDY |
| 20 | QITLKESGPVLVKATETLTLTCTVS | GFSDSSARVG | VSWIRQPPGKALEWLAH | ISSKDEK | SYSPSLKNRLTITKDTSKNQVVLTMTNMDPVDTATYYC | AHRTSVTLFEN |
| 21 | QVQLVQSGAEVKKPGESLTISCKAS | GYNFADYWI | IGWVRQMPGKGLEWMA | VYPEDSDA | RYSPSFEGHITISADRSIGTAYLQWTSLKASDTAMYFC | VRPPTTVTPPDY |
| 22 | QVQLVQSGAEVKKPGASVKVSCKAS | GYTFTSYG | ISWVRQAPGQGLEWMG | ISAYNGNT | NYAQKLQGRVTMTTDTSTATAYMELSSLRSEDTAVYYC | ARDPSYGSGSYRGGDPFDY |
| 23 | EVQLVESGGGLVQPGGSLRLSCAAS | GFIFSSFD | MHWVRQATGKGLEWVSA | IGLAGDT | YYPASVKGRFTISREDAKNTLYLQMDSLRAEDTAVYYC | AREGSTGRSSWNNWYFDL |
| 24 | EVQLLESGAEVKKPGASVKVSCKAS | GYTFTSYY | MHWVRQAPGQGLEWMGI | INPSGGGT | NYAQKFQGWVTMTRDTSISTAYMELSSLRSDDTAVYYC | ARESWRDCSGGSCADAFDI |
| 25 | EVQLLESGGGLGRPGESLRLSCAAS | GFSFNNAW | MSWVRQAPGGGLEWVGL | IKSRDYGGTI | DYAAPVKGRFTISRDDSKNMLYLNMYSLKSEDTAVYYC | TSSGSFYVNGY |
| 26 | QVQLQQWGAGLLKPSETLSLTCAVY | GGSFSGYY | WSWIRQPPGKGLEWIGE | INHSGST | NYNPSLKSRVTISVDTSKNQFSLKLSSVTAADTAVYYC | ARGRGSSIDY |
| 27 | EVQLVESGAEVKKPGESLKISCKGS | GYGFTGHWI | IGWVRQMPGKGLEWMGI | IHPVDSDT | RYSPSFRGQVTMSIDKSTRTAYLQWDTLKASDTAVYYC | ARLGDSGMLHFDH |
| 28 | QVQLQESGPGLVKPSETLSLTCAVS | GYSISSGYS | WGWIRQPPGMGLEWIGS | IHHGGTT | YYNPSLKSRVTISVDTSKNQFSLKLRSVTAADTAFYC | ARVSGEAAAGWANWFDP |
| 29 | EVQLVESGGGLVQPGRSLRLSCTAS | GFTFSSYG | MHWVRQAPGKGLEWVAF | IRYDGSNK | YYADSVKG*FTISRDNSKNTLYLQMNSLRAEDTAVYYC | AKDSNYCSGGSCYGSFLIYYYYGMPDV |
| 30 | QITLKESGGGVVQPGRSLRLSCAAS | GFTFSSYG | MHWVRQAPGKGLEWVAV | ISYDGSNK | YYADSVKGRFTISRDNSKNTLYLQMNSLRAEDTAVYYC | AKQEESSWMGWGPNWFDP |

| Clone | FR4 | Germline | Amino acid different from germline | Family | Percentage Identity |
|---|---|---|---|---|---|
| 11 | WGQGTLVTVSP | IGHV4-59*01 F | 8 | VH4 | 97.19% |
| 12 | WGQGTLVTVSP | IGHV1-18*01 F | 12 | VH1 | 93.75% |
| 13 | WGPGTLVTVSS | IGHV4-39*03 F | 8 | VH4 | 95.52% |
| 14 | WGQGALVTVSP | IGHV2-5*04 F | 4 | VH2 | 97.94% |
| 15 | WGQGTLVTVSS | IGHV4-34*01 F | 0 | VH4 | 100.00% |
| 16 | WGQGTLVTVSP | IGHV4-34*01 F | 1 | VH4 | 99.30% |
| 17 | WGQGTLVTVSS | IGHV4-34*01 F | 0 | VH4 | 100.00% |
| 18 | WGQGTLVTVSS | IGHV3-30*02 F | 2 | VH3 | 98.61% |
| 20 | WGQGLTVTVSP | IGHV2-26*01 F | 11 | VH2 | 93.81% |
| 21 | WGQGLTVTVSP | IGHV5-51*01 F | 18 | VH5 | 90.28% |
| 22 | WGQGTLVTVSS | IGHV1-18*01 F | 2 | VH1 | 98.96% |
| 23 | WGRGTLVTVSS | IGHV3-13*04 F | 8 | VH3 | 96.49% |
| 24 | WGQGLTVTVSS | IGHV1-2*04 F | 7 | VH1 | 95.83% |
| 25 | WGQGLTVTVSP | IGHV3-15*05 F | 16 | VH3 | 91.84% |
| 26 | WGQGLTVTVSS | IGHV4-34*01 F | 0 | VH4 | 100.00% |
| 27 | WGQGLTVTVSS | IGHV5-51*01 F | 14 | VH5 | 93.06% |
| 28 | WGQGTLVTVSS | IGHV4-b*01 F | 6 | VH4 | 97.22% |
| 29 | WGQGTTVTVSP | IGHV3-30*02 F | 5 | VH3 | 96.88% |
| 30 | WGQGLTVTVSS | IGHV1-18*01 F | 0 | VH1 | 99.65% |

Example 19

Improving the Self-Circularization Process and Recovery Calculations

Data in FIG. 17 shows that when SfiI digested Fabs were prepared from self-ligated linear Fabs, a discernible proportion of un-ligated Fabs do remain. In the protocol that was created initially, this undigested Fab population is carried over along with the released (SfiI digested and ligatable) Fabs during agarose gel fractionation (FIG. 17). This undigested Fab population is likely to reduce the efficiency of the library as well as dilute the proportion of ligatable Fabs. The optimization process of self-circularization of linear Fabs is set out herein below:

Approach 1—Improving self-ligation (smear formation) by crowding the ligating DNA: The Fabs were ligated as per Examples 16 and 17. ~83 ng/µl DNA was used in 20 µl of the ligation reaction. Crowding of linear Fabs was attempted by increasing the concentration to 200 ng/µl. Both concentrations of Fabs were self-ligated in the presence as well as absence of the molecular crowding agent PEG 8000 at final concentration 6% per reaction (Green M R and Sambrook J, 2012c. Cloning in plasmid vectors: Blunt end cloning; In: *Molecular Cloning: A Laboratory Manual, Vol.* 1). Ligation reactions were incubated overnight at 16° C., and purified by organic extraction prior to agarose gel analysis (FIG. 23).

Figure 23:
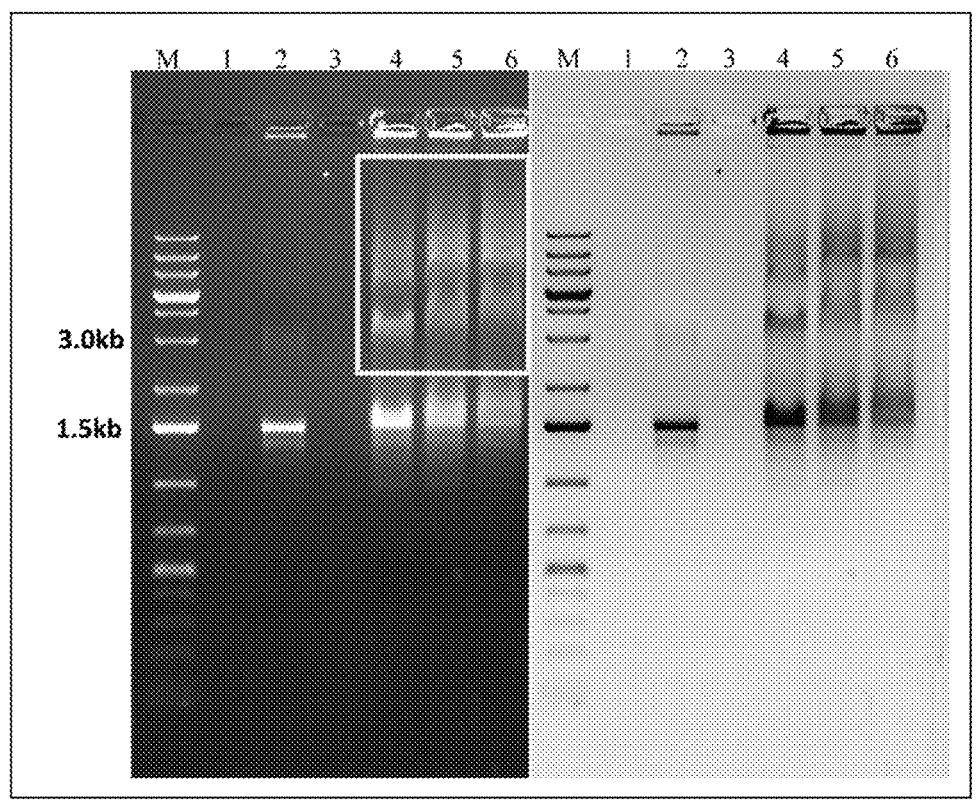
FIG. 23 depicts the process of improving the self-ligation method by increasing DNA concentration per unit volume and use of PEG 8000. Lane 2 contains the phosphorylated Fab pool alone, while lanes 4, 5 and 6 contain samples of ligation mixtures after 16 h of incubation at 16° C. Equal amounts (2.5 µs) of all were loaded for visual comparison. Lane 4 contains sample from the standard 83 ng/µl ligation reaction, while lane 5 contains the standard reaction supplemented with 6% PEG. Lane 6 samples a ligation reaction that contained 200 ng/µl of DNA, supplemented with 6% PEG. Lanes 1 and 3 are empty. M is the 1 kb plus DNA marker from Fermentas. Numbers on the left show marker size in base pairs. Panel on the left shows the epifluorescent image of a 1% agarose gel prepared in 1×TBE containing 0.1 µg/ml ethidium bromide and run at 5V/cm for 1.5 h. Image on the right is the photographic negative of the same.

It is evident from FIG. 23 that the presence of PEG 8000 and increasing the DNA concentration per unit volume has significantly improved the self-ligation, as indicated by decreased amount of residual 1.5 kb un-ligated Fab.

Approach 2—Obtaining 100% ligatable Fab by gel purification and digestion of the HMW smear population: Another approach to avoid non-ligatable Fabs from SfiI digested ligatable Fab preparation would be to gel extract only the high molecular weight (HMW) DNA smear (see boxed area in FIG. 23), thus excluding the 1.5 kb band before SfiI digestion. The recovery of HMW smears from agarose gels were conducted by various methods as below:
  a. Gel extraction of smear using standard QIAEXII protocol (3 volumes of QX1 per unit gram of agarose gel piece).
  b. Gel extraction of smear using modified QIAEXII protocol (de Haard H J W, 2002. Construction of large naïve Fab libraries. In: *Methods in Molecular Biology, vol.* 178: *Antibody Phage Display: Methods and Protocols;* 30 volumes of QX1 per unit gram of agarose gel piece and 100 µl of beads per 5 µg of DNA).
  c. Gel extraction by electro-elution method (Sambrook J and Russell D W, 2001c. Recovery of DNA from agarose gels: electroelution in dialysis bags; In: *Molecular Cloning: A Laboratory Manual; Vol.* 1).
  d. Without gel extraction—instead of gel extraction, clean up and buffer exchange the self-ligation mixture with water using Nanosep (Pall) or Microcon (Millipore) spin filters, and directly digest with SfiI.

To execute experiments a. to d., a total of 75 µg of Fab was generated using PCR Extender polymerase blend as per Example 9. After blunting and phosphorylation, ~23 µg of Fab was recovered. There was always a huge loss during these processes, especially while recovering after blunting by T4 DNA polymerase. Blunting is, however, mandatory for self-ligation of linear Fab fragments if the thermostable DNA polymerase or blend used for creating Fabs by the final SOE PCR step does not generate blunt ends. 23 µg of Fabs was ligated as per the self-ligation protocol and loaded evenly (~5.6 µg/gel) into three different preparative mini gels to execute experiments a. to c. The fourth aliquot of 5.6 µg was saved for experiment d.

Starting with 5.6 µg each, recoveries were 230 ng (4.1%—standard QIAEX II protocol), 180 ng (3.2%—modified QIAEX II protocol), 900 ng (16%—electroelution), and 4.6 µg (~82%—buffer exchange only in spin filters) respectively, as measured using PicoGreen assay. To check the SfiI digestion pattern of these HMW smeared Fabs, recovered material from methods a. to c. were pooled and digested in buffer M (Roche Diagnostics, Indianapolis, Ind., USA) overnight at 50° C. using 16 U/µg of SfiI (Roche Diagnostics). Similarly, Fabs recovered from experiment d. (~4.6 µg) were divided into three parts (1.5 µg each). One part was kept as such to check the self-ligation while other two were digested using 16 U and 32 U of SfiI per µg of Fab in buffer M (Roche) at 50° C. overnight. SfiI was able to unambiguously release 1.5 kb Fab bands from HMW smears regardless whether they were obtained through gel extraction or simple buffer exchange.

In a second round of optimization starting again with 50 µg of PCR-amplified Fabs from a SOE PCR Fab pool, the exact yields at each step were computed before creating a large library (Table 32).

TABLE 32

| Steps | Input DNA (µg) | Output DNA (µg) | Recovery/step (in %) | Overall recovery (in %) |
|---|---|---|---|---|
| Starting DNA amount | 50 | — | — | — |
| Blunting | 50 | 21 | 42.0 | 42 |
| Kinasing | 21 | 16 | 76.2 | 32 |
| Sell ligation After cleanup by column | 16 | 12.8 | 80 | 25.6 |
| Sfi I digestion and gel extraction | 12.8 | 3.8 | 29.7 | 7.6 |

Example 20

Electroporation Parameters in Ultracompetent TG1 Cells

To reach a target library size of $2 \times (5 \times 10^8) = 10^9$ clones, the present invention utilises electrocompetent cells that had transformation efficiency 2 logs higher with the supercoiled plasmid control (i.e. $4\text{-}5 \times 10^{10}$ cfu/µg; Lucigen, Madison, Wis., USA).

Transformation was carried out in 1 mm gap cuvettes in triplicates using pUC control (10 pg/25 µl TG1 cells; electroporation pulse set for 1800V, 25 µF, 600Ω). The efficiencies ranged between $1\text{-}1.6 \times 10^{10}$ cfu/µg DNA (Table 33)—contrary to the reported product literature ($\geq 4 \times 10^{10}$ cfu/µg) for pUC control for such cells. The present invention concludes that the new TG1 cells had the preferred $10^{10}$ cfu/µg scale efficiency in 1 mm gap cuvettes and could be used for large scale Fab library making.

TABLE 33

| Cuvette | Plating Volume (µl) | Set I No. of Colonies | Set I Efficiency | Set II No. of colonies | Set II Efficiency | Set III No. of colonies | Set III Efficiency | Average No. of colonies | Average Efficiency |
|---|---|---|---|---|---|---|---|---|---|
| BioRad Cuvette (1 mm) | 10 | 902 | $9 \times 10^9$ | 1071 | $1.1 \times 10^{10}$ | 936 | $9.4 \times 10^9$ | 970 | $9.7 \times 10^9$ |
|  | 5 | 768 | $1.6 \times 10^{10}$ | 274 | $5.5 \times 10^9$ | 253 | $5 \times 10^9$ | 432 | $8.7 \times 10^9$ |
|  | 2 | 82 | $4.1 \times 10^9$ | 236 | $1.2 \times 10^{10}$ | 69 | $3.5 \times 10^9$ | 129 | $6.5 \times 10^9$ |

As a 1 mm gap cuvette has a recommended maximum fill volume of 40 µl only, and would therefore be too tedious to use for making a large library, the present invention then examines the efficiencies of the same cells but double the volume in a larger 2 mm cuvette. This scalability question was crucial in order to understand the reproducibility and comparability between historical results when shifting optimizations from 1 mm to 2 mm cuvettes.

To execute this experiment, different electroporation protocols were tested for 2 mm cuvettes by varying voltage, capacitance and resistance to find the optimum parameters. Two pre-set protocols are suggested for 2 mm cuvettes in the available electroporator (Genepulser Xcell, BioRad)—a) 2500V, 25 µF, 200Ω, and b) 3000V, 25 µF, 200Ω. One more protocol was designed by proportionally increasing the parameters for 1 mm to 2 mm cuvette. The first change to try would be to double the voltage to compensate for the doubling of distance between the electrode plates, along with a proportional increase in amperage to compensate for the increased cell mass. As this electroporator would not allow setting up a 3600V condition, a setting of 3000V, 25 µF and 300Ω was conducted. 20 pg of pUC19 plasmid was electroporated per 50 µl cells, using the abovementioned protocols.

TABLE 34

| Cuvette | Plating Volume (µl) | 2500 V_25 µF_200 Ω No. of Colonies | 2500 V_25 µF_200 Ω Efficiency | 3000 V_25 µF_200 Ω No. of colonies | 3000 V_25 µF_200 Ω Efficiency | 2500 V_25 µF_300 Ω No. of colonies | 2500 V_25 µF_300 Ω Efficiency |
|---|---|---|---|---|---|---|---|
| BioRad Cuvette (2 mm) | 1:10 dil, 100 µl | 1818 | $9.1 \times 10^9$ | 1432 | $7.2 \times 10^9$ | 1958 | $9.8 \times 10^9$ |
|  | 1:10 dil, 20 µl | 73 | $1.8 \times 10^9$ | 45 | $1.2 \times 10^9$ | 341 | $8.5 \times 10^9$ |

It was observed that efficiency for the given lot of TG1 cells remained at ~$1 \times 10^{10}$/µg of DNA (Table 34). It was concluded that optimizations are linearly scalable from 1 mm to 2 mm gap BioRad cuvettes. All optimizations from this point were therefore performed in 2 mm cuvettes with the protocol 3000V, 25 µF, 300Ω, unless mentioned otherwise.

Example 21

Transformation Parameters in Ultracompetent TG1 Cells

As per the optimized procedure for test ligations and electroporations (see Table 15), 3 µl of heat inactivated and 1:20 diluted ligation mix needs to be transformed per 25 µl of TG1 cells, which is equivalent to 2.2 ng (1.1 ng each of vector and Fabs) per transformation. It follows therefore that to reach a library size of $10^9$/µg of vector DNA, it is required to perform ~1000 individual transformations. The present invention discloses reduction in the number of transformations by removing salts by precipitation or by buffer exchange, and by accurately titrating the saturation point for a fixed volume of TG1 cells vis-à-vis the amount of input total ligated DNA as demonstrated herein below.

Example 21a

Effect of Salt Removal of Ligation Mix on Transformation Efficiencies:

Stuffer-pCOMB3XSS ligations were used for this experiment. A total of 22 ligation reactions were set up (140 ng vector+140 ng stuffer/20 µl reaction) to get ~6 µg of ligated DNA mixture. The linearized vector and stuffer DNA mix was heated at 45° C. for 5 min and immediately chilled on ice before adding ligase buffer and ligase enzyme in order to prevent unwarranted cohesive end ligations. After overnight ligation at 16° C., the ligations were heat inactivated at 70° C. for 15 min. The 6 µg ligation pool was divided into 2 parts (3 µg each). One part was subjected to salt removal by ethanol precipitation while the second part was subjected to salt removal by using Microcon DNA Fast Flow spin-filters. Supercoiled pCOMB3XSS plasmid alone was kept as a positive control, wherein it was added to the ligation mix and treated in exactly the same way as the stuffer-pCOMB3XSS ligations. Supercoiled pUC19 control was also included to ensure that the experimental procedure and cells were working as expected. The amounts of input DNA and recovery at each step was recorded while performing this experiment (Table 35).

TABLE 35

| DNA | Purification | Final sample volume (µl) | DNA conc. (ng/µl) by Picogreen assay | Final yield (µg) | Recovery (%) |
|---|---|---|---|---|---|
| Supercoiled pCOMB3XSS | EtOH ppt | 25 | 116.33 | 2.9 | 96.9 |
| Stuffer + pCOMB3XSS | EtOH ppt | 25 | 109.72 | 2.74 | 91.4 |
| Supercoiled pCOMB3XSS | Microcon DNA fast flow | 21.5 | 138.52 | 2.97 | 99.3 |
| Stuffer + pCOMB3XSS | Microcon DNA fast flow | 20.5 | 128.12 | 2.62 | 87.5 |

DNA cleaned up by ethanol precipitation or by Microcon spin-filters were transformed at the quantum of 4.4 ng (total DNA) for every 50 µl of TG1 cells in 2 mm BioRad cuvette. The transformed cells were regenerated in 950 µl of Recovery Buffer (Lucigen) before plating 2, 5 and 10 µl on 90 mm LB agar plates containing 2% glucose and 50 µg/ml carbenicillin. Table 36 shows the efficiency calculations.

Figure 24:
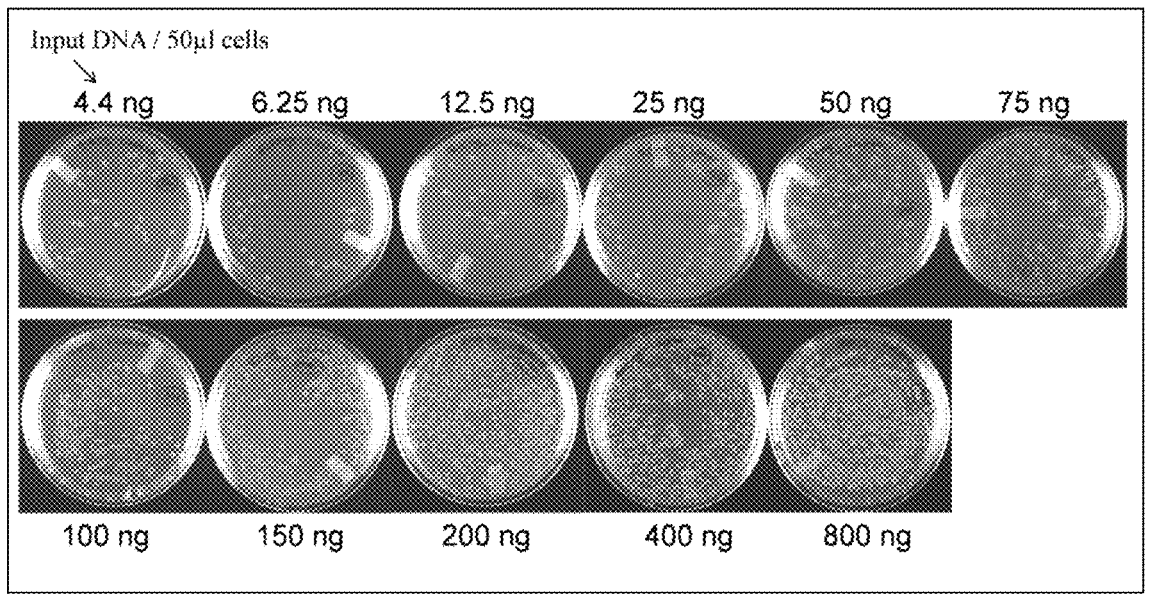
FIG. 24A depicts photographic evidence of the Cell to DNA ratio titration experiment. Plates from the 1:25000 dilutions are shown.
FIG. 24B depicts graphical representation of the cell to DNA ratio titration experiment listed in Table 37.
Figure 24:
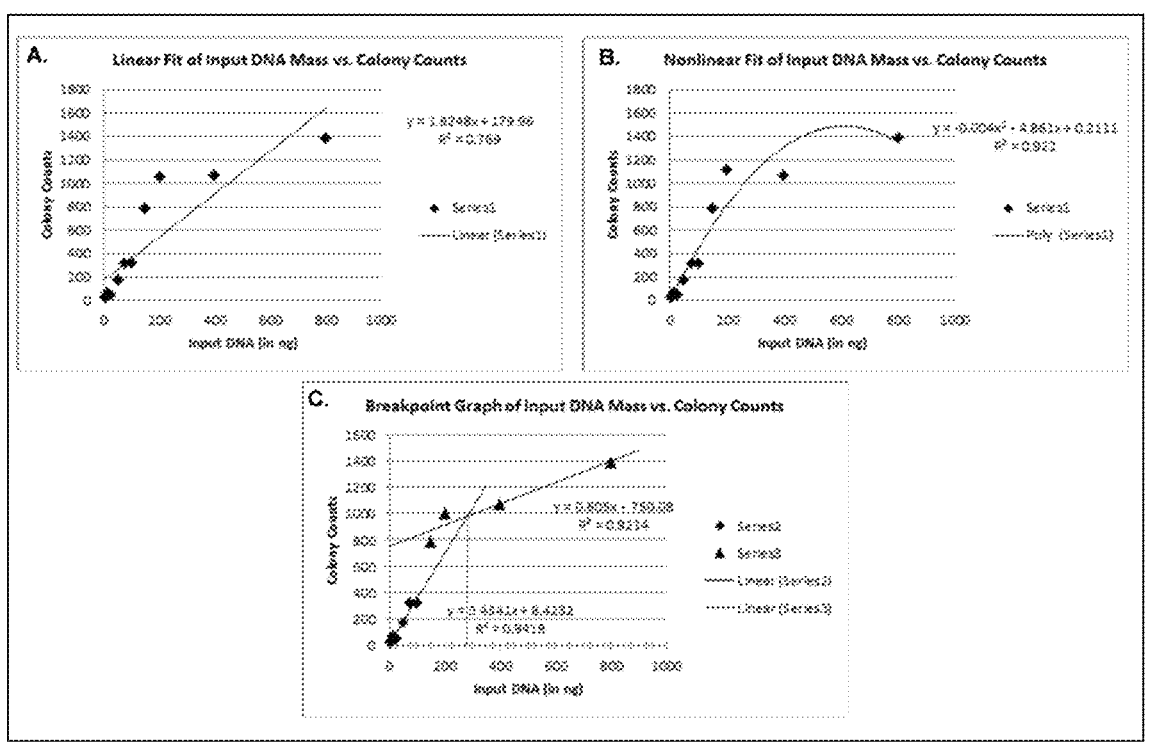

~$10^{10}$/µg efficiency was repeated for supercoiled pUC control, and Microcon spin-filter purified sample gave slightly better efficiency than ethanol precipitated sample. Plating data is shown for the stuffer-pCOMB3XSS ligations for Microcon spin-filter purified samples only.

insert) as per the protocol set in Example 21a, following DNA amounts were transformed per 50 µl of TG1 cells: 6.25, 12.5, 25, 50, 75, 100, 150, 200, 400 and 800 ng. The transformed cells were regenerated in 950 µl of Recovery Buffer (Lucigen) before plating 100 µl each from 1:1000, 1:5000, 1:25000 and 1:50000 dilutions on 90 mm LB agar plates containing 2% glucose and 50 µg/ml carbenicillin. 1:100000 dilutions were carried out only for the 400 and 800 ng samples. FIG. 24A shows the transformed plates from this ligation, and Table 37 shows the counted and processed data.

TABLE 36

LB agar + 2% Glucose_2 mm BioRad cuvette_3000 V/25 µF/300 Ω_TG1: Lot# 6940

| Ligation | Plating volume_Neat_2 µl | | Plating volume_Neat_5 µl | | Plating volume_Neat_10 µl | | 1:1000 dil_100 µl | |
|---|---|---|---|---|---|---|---|---|
| | No. of colonies | Efficiency/µg | No. of colonies | Efficiency/µg | No. of colonies | Efficiency/µg | No. of colonies | Efficiency/µg |
| pCOMB3XSS + Stuffer (Salt removal by Microcon filter) | Not countable | — | Not countable | — | Not countable | — | 636 | 2.89 × $10^9$ |
| pUC control | 3280 | 1.65 × $10^{10}$ | 1120 | 1.1 × $10^{10}$ | 253 | 6.3 × $10^9$ | | |
| Only vector control (VC) | 15 | | Vector background: <0.2% | | | | | |
| Only insert (Stuffer) control | 0 | | — | | | | | |

Table 36 demonstrates that the stuffer ligates successfully as indicated by crowded growth with less than 0.2% vector background, and with a transformation efficiency of 2.89× $10^9$/µg of vector. From Table 36, it can also be concluded that the removal of salts from ligation mix by dilution (1:20), which leads to a large number of transformations, can be replaced as a method by salt removal using Microcon spin-filter device with more than 90% recovery of ligated DNA, and transformation efficiency equal to or better than simple dilution.

Example 21b

Optimal Cell-to-DNA Ratio for Transforming TG1 Cells of Efficiency ≥$10^{10}$ cfu/µg:

Another potential approach to reduce the number of transformations in order to reach a library size of $10^9$ clones is to find out the maximum amount of DNA that can be transformed into a fixed volume (50 µl) of TG1 cells without any decrease in efficiency. A total of 18 standard ligation reactions i.e. 20 µl reaction each containing 140 ng vector+ 140 ng stuffer=280 ng total DNA were set up to obtain ~5 µg of ligated DNA exactly as described in Example 21a. All the reactions were pooled, and ~3.5 µg of ligated DNA was recovered after cleaning the pooled ligation mix using Microcon spin-filters. Starting with total 4.4 ng (vector+

TABLE 37 pCOMB3XSS + stuffer_clean up by Microcon filter_2mm BioRad cuvette 3000V/25µF/300Ω_Plating volume 100 µl

| Total (vector + insert) DNA (in ng) transformed per 50 µl of cells | Dilution plated | Total DNA amount plated (in fg) | No. of colonies | Efficiency per µg | Average efficiency per µg |
|---|---|---|---|---|---|
| 4.4 | 1000 | 220 | 180 | 8.18 × $10^8$ | 1.9 4× $10^9$ |
| | 5000 | 44 | 115 | 2.61 × $10^9$ | |
| | 25000 | 8.8 | 32 | 3.64 × $10^9$ | |
| | 50000 | 4.4 | 3 | 6.82 × $10^8$ | |
| 6.25 | 1000 | 312.5 | 765 | 2.45 × $10^9$ | 2.22 × $10^9$ |
| | 5000 | 62.5 | 141 | 2.26 × $10^9$ | |
| | 25000 | 12.5 | 26 | 2.08 × $10^9$ | |
| | 50000 | 6.25 | 13 | 2.08 × $10^9$ | |
| 12.5 | 1000 | 625 | 565 | 9.04 × $10^8$ | 3.14 × $10^9$ |
| | 5000 | 125 | 197 | 1.58 × $10^9$ | |
| | 25000 | 25 | 74 | 2.96 × $10^9$ | |
| | 50000 | 12.5 | 89 | 7.12 × $10^9$ | |
| 25 | 1000 | 1250 | Not countable | — | 8.83 × $10^9$ |
| | 5000 | 250 | 352 | 1.41 × $10^9$ | |
| | 25000 | 50 | 50 | 1.0 × $10^9$ | |
| | 50000 | 25 | 6 | 2.4 × $10^8$ | |
| 50 | 1000 | 2500 | Not countable | — | 2.73 × $10^9$ |
| | 5000 | 500 | 1408 | 2.82 × $10^9$ | |
| | 25000 | 100 | 172 | 1.72 × $10^9$ | |
| | 50000 | 50 | 183 | 3.66 × $10^9$ | |

TABLE 37-continued pCOMB3XSS + stuffer_clean up by Microcon filter_2mm BioRad cuvette 3000V/25μF/300Ω_Plating volume 100 μl

| Total (vector + insert) DNA (in ng) transformed per 50 μl of cells | Dilution plated | Total DNA amount plated (in fg) | No. of colonies | Efficiency per μg | Average efficiency per μg |
|---|---|---|---|---|---|
| 75 | 1000 | 3750 | Not countable | — | 1.63 × 10⁹ |
|  | 5000 | 750 | 1600 | 2.13 × 10⁹ |  |
|  | 25000 | 150 | 318 | 2.12 × 10⁹ |  |
|  | 50000 | 75 | 48 | 6.4 × 10⁸ |  |
| 100 | 1000 | 5000 | Not countable | — | 2.46 × 10⁹ |
|  | 5000 | 1000 | 2504 | 2.5 × 10⁹ |  |
|  | 25000 | 200 | 325 | 1.63 × 10⁹ |  |
|  | 50000 | 100 | 325 | 3.25 × 10⁹ |  |
| 150 | 1000 | 7500 | Not countable | — | 1.99 × 10⁹ |
|  | 5000 | 1500 | 3000 | 2 × 10⁹ |  |
|  | 25000 | 300 | 790 | 2.63 × 10⁹ |  |
|  | 50000 | 150 | 200 | 1.33 × 10⁹ |  |
| 200 | 1000 | 10000 | Not countable | — | 1.62 × 10⁹ |
|  | 5000 | 2000 | Not countable | — |  |
|  | 25000 | 400 | 1123 | 2.81 × 10⁹ |  |
|  | 50000 | 200 | 88 | 4.4 × 10⁸ |  |
| 400 | 25000 | 800 | 1070 | 1.34 × 10⁹ | 8.83 × 10⁸ |
|  | 50000 | 400 | 91 | 2.28 × 10⁸ |  |
|  | 100000 | 200 | 217 | 1.09 × 10⁹ |  |
| 800 | 25000 | 1600 | 1388 | 8.68 × 10⁸ | 1.28 × 10⁹ |
|  | 50000 | 800 | 1260 | 1.58 × 10⁹ |  |
|  | 100000 | 400 | 555 | 1.39 × 10⁹ |  |

Graphical analysis of the input DNA mass versus colony count data (Table 37) showed that the linear fit was poor ($R^2$ of 0.769; FIG. 24B, panel A), but a non-linear (second order polynomial) fit proved much better ($R^2$ of 0.922; FIG. 24B, panel B). The non-linear fit clearly suggests that the dependence of colony counts on input DNA mass is not rectilinear, and that the asymptote of the non-linear fitted curve is the saturation point. The present invention also discloses an alternative graphical approach as set in FIG. 24B (segmented regression; Jones R H and Mollitoris B A, 1984; Küchenhoff H, 1996) to break the overall linear fit into two individual linear fits that have much better Coefficients of Determination ($R^2$) than the overall fit (FIG. 24B, panel C), and considered the intersection of the two individual fits as the saturation point. This value is ~272 ng of total ligated DNA per 50 μl of TG1 cells.

The present invention also examines the effect of transformation efficiency with respect to increase in volume of cells. 400 ng input DNA was transformed per 100 μl of TG1 cells in the same 2 mm cuvettes. The efficiency was examined by proportional increase in the input DNA mass from 200 to 400 ng. Based on the data, it can be concluded that the efficiency is reduced by half (9.13×10⁸ cfu/μg) with increase in volume.

Example 22

Making a Large Phagemid Library by the Self-Circularization Protocol

RNA was isolated from a pool of 12 donors using characterized PBMC's from CTL (Cellular Technologies Ltd., Cleveland, Ohio, USA) and by following steps detailed in Example 1. cDNA was prepared as detailed in Example 1. To test the quality of the prepared cDNA, one primer pair each specific for $V_H$, $V_\kappa$ and $V_\lambda$ domains was used on the pooled cDNA with 50 ng template per 50 μl reaction. Use of optimum PCR cycling protocols as described in Examples 3-5 resulted in unambiguous amplification of the respective V-families from this cDNA preparation.

Based on this result, the RNA samples were pooled at this point (~900 μg), aliquoted, and stored at −80° C. For maxi-cDNA preparation from pooled total RNA of human PBMC's, 120 reactions were assembled with 1 μg of total RNA per reaction. Yield was estimated by the RiboGreen method. The total yield of 13.6 μg cDNA (Table 38) was pooled with 4.2 μg cDNA that was prepared earlier from uncharacterized PBMCs from CTL (3 donors; Table 1).

TABLE 38

Maxi-cDNA Preparation

| | |
|---|---|
| Total RNA used from 12 donors | 120 μg |
| cDNA yield | 13.6 μg |
| Earlier cDNA (from 3 donors) | 4.2 μg |
| Total cDNA | 17.8 μg |

PCR amplifications to make final kappa and lambda Fab fragments were carried out using methods as described in Examples 3-9.

On the basis of the recovery chart (Tables 32 and 35) for the self-ligation process, it was computed that to generate 5 μg each of final ligatable kappa and lambda Fabs, 100 μg of each type of Fab is needed to start the self-ligation process. First overlap (SOE) PCR's were performed using equimolar amounts of V and C genes. Total 50 SOE reactions for each light chain and 100 SOE reactions for heavy chain were set up. The final yields by QIAEXII gel extraction kits were 27 μg for $V_\lambda C_\lambda$, 31 μg for $V_\kappa C_\kappa$ and 53 μg for $V_H C_H 1$. Second overlap (SOE) PCR's were similarly performed using equimolar amounts of $V_L C_L$ and $V_H C_H 1$ amplicons. A total of 500 PCRs were performed each for kappa and lambda chains. The final yields by QIAEXII gel extraction kits were 96 μg for λ-Fab and 99 μg for κ-Fab.

Following blunting and kinasing, samples were adjusted to ~500 ng/μl, and 3.0 μg of Fabs were ligated per 15 μl reaction using 1 U/μg of T4 DNA Ligase. The DNA concentration was adjusted such that the final concentration in a 15 μl reaction volume would reach 200 ng/μl. As illustrated in Example 19, PEG 8000 was added to a final concentration of 6%. Reactions were incubated at 16° C. in PCR block for 14-16 h. Ligations were left at room temperature for 1 h following the overnight incubation before proceeding further.

Aliquots (1-2 μg) of self-ligated Fabs (smear) were saved for analysis. The remaining ligation reactions were pooled and cleaned up first by phenolization and then subjected to three rounds of buffer exchange with water using Microcon spin-filters. The $A_{260}/A_{280}$ ratio was checked using NanoVue (GE) and it usually ranged between 1.7 and 1.9. The actual dsDNA concentrations were measured using PicoGreen assay. Salt- and protein-free self-ligated high molecular weight (HMW) Fab smear was subjected to 1.5 kb Fab release using SfiI. 32 U of SfiI (Roche) was added per μg of Fab in buffer M (Roche), and incubated overnight at 50° C. Aliquots (1-2 μg) of SfiI released Fabs were saved for agarose gel analysis, and the remaining was gel purified using column based gel extraction.

The analytical gels (FIG. 25) show that more than 90% linear Fabs participated in HMW smear formation and a similar percentage showed 1.5 kb SfiI release. It was concluded therefore that the entire process was successful in generating Fab pools containing more than 90% SfiI ligatable Fabs. Table 39 provides an account of ligatable Fab making with respect to starting material at each step and percentage recovery. ~3.4 µg of kappa and ~4.65 µg of lambda Fab was finally prepared for ligation with SfiI digested pCOMB3XSS vector.

TABLE 39

| Step | Kappa Fab (in µg) | Lambda Fab (in µg) |
| --- | --- | --- |
| Starting material | ~100 | ~96 |
| Blunting | ~98 | ~94 |
| After blunting & clean up | ~37.15 | ~51.8 |
| After phosphorylation & clean up | ~28 | ~38.2 |
| Self-Ligation | ~28 | ~38.2 |
| Microcon Salting out | 13.5 | 16.9 |
| Sfi I digestion & gel extraction | 3.375 | 4.65 |
| Salting out by Microcon DNA Fast flow column | 5.166 (Vector + Fabs) | 6.5 (Vector + Fabs) |

140 ng of SfiI digested pCOMB3XSS vector was ligated with 140 ng of SfiI-digested Fab (1:2 molar ratio for vector:insert) in 20 µl reactions using 1 U/µg of T4 DNA ligase (Roche), and incubated overnight at 16° C. To ligate a total of ~3.4 µg of Kappa and ~4.65 µg of Lambda Fab, required number of ligations was set up as amply described in preceding sections. After overnight (16 h) incubation, the ligation mixtures were heat inactivated at 70° C. for 15 min and pooled together. Kappa and lambda Fabs were processed separately. The pools were subjected to salt removal and buffer exchange with water three times using Microcon spin-filters. The $A_{260}/A_{280}$ ratio was checked using NanoVue and ranged between 1.7 and 1.9. The actual dsDNA concentration was measured using PicoGreen assay. After the salt removal, the total recovery of ligated material was 5.2 and 6.5 µg (vector+Fab), respectively, for Kappa and Lambda ligations.

Based on the estimate (Table 37, FIG. 24B) that a maximum of 272 ng of purified ligated DNA (vector+insert) can be electroporated per 50 µl TG1 cells in 2 mm gap BioRad cuvettes with optimized electoporation parameters before decrease in efficiency, the library transformations were set up accordingly. To make kappa library (5166 ng, vector+ Fab), total 20 transformations were performed in 2 sets (10 transformations/set), which resulted in 2 sub-libraries for Kappa. This was equivalent to transforming ~258 ng DNA (129 ng of ligated vector) per 50 µl cells. Cultures were incubated at 37° C. and 250 rpm for 1 h. 10 ml culture generated after 10 transformations (Set 1) was diluted to 15 ml and spread on total 5 large LB agar plates (245×245 mm) containing 50 µg/ml carbenicillin and 2% glucose at the quantum of 3 ml/plate. The Kappa library was therefore plated on a total of 10 plates (Sets 1 and 2; kappa sub-libraries 001 and 002; see Table 40). 500 aliquots of each sub-library were kept aside for calculating the transformation efficiency of the sub-libraries.

Similarly, to make the Lambda library (6500 ng, vector+ Fab), total 30 transformations were performed in 3 sets (10 transformations/set), which resulted into 15 large plates and 3 sub-libraries for Lambda (Sets 3-5; lambda sub-libraries 001, 002, and 003; see Table 40). This was equivalent to transforming ~216 ng DNA (108 ng of ligated vector) per 500 cells. 50 µl aliquots of each sub-library were again kept aside for calculating the transformation efficiency of the sub-libraries.

To calculate the efficiency of transformation per µg, the 50 µl aliquots saved from each kappa and lambda sub-libraries were diluted 1:1000, 1:5000, 1:25000, 1:50000 and 1:100000 in Recovery Medium. 100 µl of each dilution was plated in triplicates on 90 mm LB agar plates containing 50 µg/ml carbenicillin and 2% glucose. After overnight incubation at 37° C., matted growth was observed on the large library plates while the efficiency plates showed well isolated colonies. Summarized results of respective transformation efficiencies and library sizes are presented in Table 40.

Bacterial lawn from each large plate was scraped using sterile scrapers in 5 ml of LB+1% glucose broth (4 ml for scraping+1 ml rinsing). Scraped cultures from each sub-library were pooled in single tube, equal volumes of storage medium (65% glycerol, 100 mM Tris pH 8.0, 25 mM $MgSO_4$) was then added, 50 µl of aliquots were saved to calculate cfu/ml of each sub-library, the bacterial suspension was aliquoted in size appropriate for future work, and stored at −80° C. as individual sub-libraries. The two sub-libraries of kappa were labeled as HsNκFab001 and HsNκFab002, where Hs stand for *Homo sapiens*, and N stands for Naïve. Similarly, 3 sub-libraries were created for lambda Fabs, and labeled HsNλFab001, HsNλFab002 and HsNλFab003.

TABLE 40

| S. No | Sample ID | Transformation efficiency (cfu/µg) | Total amount of vector transformed (µg) | Library size of each sub-type | Total library size of each type (Kappa/Lambda) in cfu | Total library size (cfu) |
| --- | --- | --- | --- | --- | --- | --- |
| SET-1 | HsNκFab001 | 9.00E+08 | 1.29 | 1.2E+09 | 2.0E+09 | 3.4E+09 |
| SET-2 | HsNκFab002 | 6.63E+08 | 1.29 | 8.6E+08 | | |
| SET-3 | HsNλFab001 | 4.14E+08 | 1.08 | 4.5E+08 | 1.4E+09 | |
| SET-4 | HsNλFab002 | 4.29E+08 | 1.08 | 4.6E+08 | | |
| SET-5 | HsNλFab003 | 4.22E+08 | 1.08 | 4.6E+08 | | |

To calculate cfu/ml of the individual sub-libraries, a log dilution method was used. 20 µl of the saved aliquot was mixed with 180 µl of LB medium to give $10^{-1}$ dilution. Log dilutions were prepared from this stock till $10^{-10}$ dilution in a final volume of 200 µl was reached. 100 µl each from the last four dilutions ($10^{-7}$, $10^{-8}$, $10^{-9}$ and $10^{-10}$) were plated on LB plates containing 100 µg/ml carbenicillin and 2% glucose. Plates were incubated overnight at 37° C. Colony counts were taken next morning, and the resultant cfu/ml ranged between $0.675$-$1.82 \times 10^{10}$ cfu/ml.

To estimate the quality of the library, a limited number of kappa and lambda clones made by the self-ligation strategy were analyzed. A total of 96 clones (48 each for kappa and lambda) were picked and plasmid DNA extracted at small scale. To confirm Fab identity, PCR was carried out with the plasmid DNA as templates and Fab end-specific primers (SEQ ID 32/SEQ ID 34). All the 48 clones each of kappa and lambda subtypes were positive for Fab specific PCR amplification (100% positive). Upon confirmation that all the 96 clones are Fab positive, the PCR products were subjected to BstNI fingerprinting for diversity analysis. None of the kappa and lambda clones showed any repeat pattern and each clone was different.

A sample set of clones from each library were subjected to dideoxy sequencing using the same set of 5 primers as described in Example 18. The Fab sequence of each clone was analyzed following an algorithm of contig building from sequence chromatograms, and visual verification of anomalous base calls. Contigs were then manually annotated for landmarks such as the SfiI sites at 5' and 3' ends, the $V_L$, $V_H$, $C_L$ and $C_H1$ domains, and for completeness of the individual light and heavy chains from Start to the Stop codons. The results of the manual analysis and annotation are summarized in Table 41. Based on the available data, ~80% of the clones from either kappa or lambda libraries prepared by the novel self-ligation method are full length translatable Fabs.

The sequences of $V_L$ and $V_H$ domains of all clones were also submitted to the IMGT database for detailed annotation on the germline family, framework and CDRs, as well as differences in amino acids compared to reference human sequences. Results for family coverage are shown in Table 42. Remaining annotations from the IMGT database are summarized in Tables 43-44 for a subset of sequenced clones. 83-93% of all analyzed clones had V-domains without any stop codons, and therefore, functional.

TABLE 41

| Categories | | Total | % |
|---|---|---|---|
| Kappa library | | | |
| Clones reviewed | | 34 | |
| No Contig | | 2 | 6 |
| 2-trace/Incomplete Contigs | | 32 | 0 |
| Readable clones | | 32 | 94 |
| | 5' SfiI | 32 | 100 |
| | 3' SfiI | 32 | 100 |
| No Good | | 4 | 13 |
| | LC off-frame | 3 | 9 |
| | HC off-frame | 2 | 6 |
| | Both LC & HC off-frame | 4 | 13 |

TABLE 41-continued

| Categories | | Total | % |
|---|---|---|---|
| Good | Both LC & HC in-frame | 28 | 88 |
| Lambda library | | | |
| Clones reviewed | | 40 | |
| No Contig | | 1 | 3 |
| 2-trace/Incomplete Contigs | | 2 | 5 |
| Readable clones | | 37 | 93 |
| | 5' SfiI | 37 | 100 |
| | 3' SfiI | 37 | 100 |
| No Good | | 10 | 27 |
| | LC off-frame | 4 | 11 |
| | HC off-frame | 6 | 16 |
| | Both LC & HC off-frame | 10 | 27 |
| Good | Both LC & HC in-frame | 27 | 73 |

TABLE 42

| Clone | Gene family | No. of clones analyzed | Total coverage in different gene family | Percentage (%) |
|---|---|---|---|---|
| VH (Kappa and Lambda both) | | | | |
| VH | VH1 | 62 | 10 | 16 |
| | VH2 | | 11 | 18 |
| | VH3 | | 13 | 21 |
| | VH4 | | 22 | 35 |
| | VH5 | | 6 | 10 |
| | VH6 | | 0 | 0 |
| $V_K$ | | | | |
| VK | VK1 | 29 | 13 | 45 |
| | VK2 | | 2 | 7 |
| | VK3 | | 9 | 31 |
| | VK4 | | 0 | 0 |
| | VK5 | | 0 | 0 |
| $V_\lambda$ | | | | |
| | VL1 | 33 | 9 | 27 |
| | VL2 | | 3 | 9 |
| | VL3 | | 3 | 9 |
| | VL4 | | 4 | 12 |
| | VL5 | | 0 | 0 |
| | VL6 | | 0 | 0 |
| | VL7 | | 0 | 0 |
| | VL8 | | 3 | 9 |
| | VL9 | | 0 | 0 |
| | VL10 | | 0 | 0 |

TABLE 43

(Varaible Kappa Light Chain (VK) full-length sequences disclosed as SEQ ID NOS 116-125 and Variable Lambda Light Chain (VL) full-length sequences disclosed as SEQ ID NOS 126-135, respectively, in order of appearance)
Variable Kappa Light Chain (VL)

| Clone | FR1 | CDR1 | FR2 | CDR2 | FR3 |
|---|---|---|---|---|---|
| K1 | ELVMTQSPSTL-SASVGD RVTITCRAS | QSISSW | LAWYQQKPGKAPKLLIY | AAS | SLQSGVPSRFSGSGSGTDFTLTISSLQAEDV AVYYC |
| K2 | ELTLTQSPSTL-SASVGD RVAITCRAS | QDIVTW | LAWYQHKPGQSPKLLIY | KAS | TLQIGVPSRFSGSRSGRDFSLFISGLQPDDV ATYYC |
| K3 | ELVMTQSPSSL-SASVGD RVTITCRAS | QGIRGS | LAWYQQKPGRAPKLLVY | ATS | RLETGVPSRFSGSGSGTDYTLTISSLQPEDF ATYYC |

TABLE 43-continued

| Clone | FR1 | CDR1 | FR2 | CDR2 | FR3 |
|---|---|---|---|---|---|
| K5 | ELTLTQSPGTLSL-SPGE RATLSCRAS | QSVSSSY | LAWYQRKPGQAPRLLIY | GAS | SRATGIPDRFSGSGSGTDFTLTISRLEPEDF AVYYC |
| K6 | ELTLTQSPGTLSL-SPGE RATLSCRAS | QSVSSSY | LAWYQQKPGQAPRLLIY | GAS | SRATGIPDRFSGSGSGTDFTLTISRLEDEDF AVYYC |
| K7 | ELQMTQSPSTL-SASVGD RVTITCRAS | QNINSW | LAWYQQKPGKAPNLLIY | KAS | ALESGVPSRFSGSGSGTDFTLTISDLQPEDF ATYYC |
| K8 | ELVMTQSPSSL-SASVGD RVTITCRAS | QSISSY | LNWYQQKPGKAPKLLIY | AAS | SLQSGVPSRFSGSGSGTDFTLTISSLQPEDF ATYYC |
| K9 | ELVMTQSPLSLPVTPGE PASISCRSS | SLLHSNGYNY | LDWYLQKPGQSPQLLIY | LGS | NRASGVPDRFSGSGSGTDFTLKISRVEAEDV GVYYC |
| K10 | ELVMTQSPLSLPVTPGE PASISCRSS | SLLHSNGYNY | LDWYLQKPGQSPQLLIY | LGS | NRASGVPDRFSGSGSGTDFTLKISRVEAEDV GVYYC |
| K17 | ELPLTQSPGTLSL-SPGE RATLSCRAS | QSVTNSQ | LAWYQQKPGQPPRLLIY | DAT | TRATGIPDRFSGSGSGADFTLTISRLEPEDF AVYYC |

Variable Kappa Light Chain (VL)

| Clone | CDR3 | FR4 | Germline | Family | Percentage Identity |
|---|---|---|---|---|---|
| K1 | QQYYSTPYT | FGQGTKLEIK | Homsap IGKV1-5*01 F | VK1 | 93.2 |
| K2 | QQYKAFWT | SGQGTKVDVN | Homsap IGKV1-5*03 F (see comment) | VK1 | 82.1 |
| K3 | QQSYSTFPT | FGGGTKVEIK | Homsap IGKV1-NL1*01 F | VK1 | 92.8 |
| K5 | QQYGSSQWT | FGQGTKVEIK | Homsap IGKV3-20*01 F | VK3 | 96.4 |
| K6 | QQYGSSPLT | FGQGTRLEIK | Homsap IGKV3-20*01 F | VK3 | 97.2 |
| K7 | QQFKSYPLT | FGGGTKVEIK | Homsap IGKV1-5*03 F | VK1 | 93.6 |
| K8 | QQSYSTPYS | FGQGTKLEIK | Homsap IGKV1-39*01 F, or Homsap IGKV1D-39*01 F | VK1 | 98.2 |
| K9 | MQALQTPRT | FGQGTKVEIK | Homsap IGKV2-28*01 F, or HomsapIGKV2D-28*01 F | VK2 | 99.0 |
| K10 | MQALQTPRT | FGQGTKVEIK | Homsap IGKV2-28*01 F, or Homsap IGKV2D-28*01 F | VK2 | 99.0 |
| K17 | QQHGHSIT | FGGGTKVEVK | Homsap IGKV3-20*01 F | VK3 | 92.2 |

Variable Light Chain (VK)

| Clone | FR1 | CDR1 | FR2 | CDR2 | FR3 |
|---|---|---|---|---|---|
| L1 | ELVVTQEPSFSVSPGG TVTLTCGLS | SGSVSTSYY | PSWYQQTPGQAPRTLIY | STN | TRSSGVPDRFSGSILGNKAALTITGAQADDE SDYYC |
| L2 | ELELTQPPSVSVAPGQ TARITCGGN | NIGSKS | VHWHQQKPGQAPVLVWY | DDS | DRPSGIPERFSGSNSGNTATLIISRVEAGDE ADYYC |
| L6 | ELVMTQPPSVSGAPGQ RVTISCTGS | SSNIGSNT | VHWYQQLPGTAPKLLIY | GNS | NRPSGVPDRFSGSKSGTSASLAITGLQAEDE ADYYC |
| L8 | ELMVTQEPSFSVSPGG TVTLTCGLS | SGSVSTSYY | PSWYQQTPGQAPRTLIY | STN | TRSSGVPDRFSGSILGNKAALTITGAQADDE SDYYC |
| L9 | ELVVTQEPSFSVSPGG TVTLTCGLS | SGSVSTSYY | PSWYQQTPGQAPRTLIY | STN | TRSSGVPDRFSGSILGNKAALTITGAQADDE SDYYC |
| L11 | ELVLTQSPSASASLGA SVKLTCTLS | SGHSSYA | IAWHQQQPEKGPRYLMK | LNSDGSH | SKGDGIPDRFSGSSSGAERYLTISSLQSEDE ADYYC |
| L12 | ELVMTQPPSVSGAPGQ RVTISCTGS | SSNIGAGYD | VHWYQQLPGTAPKVLIY | ATT | NRLSGVPDRFSGSKSGTSATLGITGLQTGDE ADYYC |
| L13 | ELALTQPPSASGSPGE SVTIFCTGT | SSDVGRYDY | VSWYQQYPGNAPKLIIY | EVT | NRPSGVPDRFSGSKSGNTASLTVSGLQAEDE ADYYC |
| L14 | ELVMTQPPSVSAAPGQ KVTISCSGS | SSNIGNNY | VSWYQQLPGTAPKLLIY | DNN | KRPSGIPDRFSGSKSGTSATLGITGLQTGDE ADYYC |
| L17 | ELVLTQSPSASASLGA SVKLTCTLS | SGHSSYA | IAWHQQQPEKGPRYLMK | LNSDGSH | SKGDGIPDRFSGSSSGAERYLTISSLQSEDE ADYYC |

Variable Kappa Light Chain (VK)

| Clone | CDR3 | FR4 | Germline | Family | Percentage Identity |
|---|---|---|---|---|---|
| L1 | VLYMGSGIWV | FGGGTKLTVL | Homsap IGLV8-61*01 F | VL8 | 98.6 |
| L2 | QVWDSSSDHPL | FGGGTKLTVL | Homsap IGLV3-21*02 F | VL3 | 96.4 |
| L6 | QSYDSSLSGSV | FGGGTKLTVL | Homsap IGLV1-40*01 F (see comment) | VL1 | 96.5 |
| L8 | VLYMGSGISV | FGGGTKLTVL | Homsap IGLV8-61*01 F | VL8 | 97.9 |
| L9 | VLYMGSGISV | FGGGTKLTVL | Homsap IGLV8-61*01 F | VL8 | 98.3 |

TABLE 43-continued

| | | | | |
|---|---|---|---|---|
| L11 | QTWTGTGIWV | FGGGTKLTVL | Homsap IGLV4-69*01 F | VL4 | 99.3 |
| L12 | GTWDSSLSAVV | FGGGTKLTVL | Homsap IGLV1-40*01 F, or Homsap IGLV1-50*01 ORF | VL1 | 89.6 |
| L13 | SSYAGSNNLV | FGGGTKLTVL | Homsap ILGV2-8*01 F | VL2 | 94.8 |
| L14 | GTWDSSLSAVV | FGGGTKLTVL | Homsap IGLV1-51*01 F | VL1 | 98.3 |
| L17 | QTWGTGIQV | FGGGTKLTIL | Homsap IGLV4-69*01 F | VL4 | 99.3 |

TABLE 44

(Table 44 discloses the full-length sequence of SEQ ID NOS 136-150, 328-329, and 151-155, respectively, in order of appearance)

| Clone | FR1 | CDR1 | FR2 | CDR2 |
|---|---|---|---|---|
| K1 | QITLKESGPTLVKPTQTLTLTCTFS | GFSLSTSGVG | VGWIRQPPGKALEWLAL | IYWDDDK |
| K2 | QVQLVQSGAEVKKPGASVKVSCKAS | GYTFTSYY | MHWVRQAPRQGLEWMGI | INPSGGST |
| K3 | QITLKESGGGLVQPGGSLRLSCAAS | GFTFSSYS | MNWVRQAPGKGLEWVSS | ISSSSSYI |
| K5 | QITLKESGPTLVKPTQTLTLTCTFS | GFSLSTSGVG | VGWIRQPPGKALEWLAL | IYWDDDK |
| K6 | EVQLVQSGAEVKKPGSSVKVSCKAS | GGTFSSYA | ISWVRQAPGQGLEWMGG | IIPIFGTA |
| K7 | QVQLVQSGAEVKKPGSSVKVSCKAS | GGTFSSYA | ISWVRQAPGQGLEWMGG | IIPIFGTA |
| K8 | QVQLQESGPGLVKPSETLSLTCTVS | GGSISSYY | WSWIRQPPGKGLEWIGY | IYYSGST |
| K9 | QVQLQESGPGLVKPSETLSLTCTVS | GGSINAHDFY | WAWVRQPPGKGLEWLGS | ISHTGST |
| K10 | QVQLQESGPGLVKPSETLSLTCTVS | GGSINAHDFY | WAWVRQPPGKGLEWLGS | ISHTGST |
| K17 | QVQLQESGPGLVKPSGTLSLTCAVS | GGSISSSNW | WSWVRQPPGKGLEWIGE | INHSGST |
| L1 | QVQLQQWGAGLLKPSETLSLTCSVS | GGSFGDYQ | WTWIRQPPGKGLEWIGK | ISGTGGA |
| L2 | QITLKESGPVLVKPTETLTLTCTVS | GFSLSNARMG | VSWIRQPPGKALEWLAH | IFSNDEK |
| L6 | EVQLLESGGGLVQPGGSLRLSCAAS | GFTFSSYW | MSWVRQAPGKGLEWVAN | IKQDGSEK |
| L8 | QVQLVQSGAEVKKPGESLKISCKGS | GYSFTSYW | IGWVRQMPGKGLEWMGI | IYPGDSDT |
| L9 | QITLKESGAEVKKPGSSVKVSCKAS | GGTFSSYA | ISWVRQAPGQGLEWMGG | IIPFFDTA |
| L11 | QVQLQESGPGLVKPSETLSLTCAVS | GGSISGYY | WSWIRQPPGKGLEWIGD | VYYSGST |
| L12 | QITLKESGPTLVKPTQTLTLTCTFS | GFSLSTSGVG | VGWIRQPPGKALEWLAL | IYWDDDK |
| L13 | QVQLQQWGAGLLKPSGTLSLTCAVS | GGSISSSNW | WSWVRQPPGKGLEWIGE | IYHSGST |
| L14 | EVQLVQSGGGLVQPGGSLRLSCAAS | GFTFSSYW | MHWVRQAPGKGLEWVSA | ISGSGGST |
| L17 | EVQLVQSGAEVKKPGESLKISCKGS | GYSFTSYW | IGWVRQATGQGLEWMGW | MNPNSGNT |

| Clone | FR3 | CDR3 | FR4 |
|---|---|---|---|
| K1 | RYSPSLKSRLTITKDTSKNQVVLTMTNMDPVDTATYYC | AHNRYSSGWYFDY | WGQGTLVTVSS |
| K2 | SYAQKFQGRVTMTRDTSTSTVYMELSSLRSEDTAVYYC | ARQGGTDYWYFDL | WGRGTLVTVSP |
| K3 | YYADSVKGRFTISRDNAKNSLYLQMNSLRAEDTAVYYC | ARVTGDPPYYFDY | WGQGTLVTVSP |
| K5 | RYSPSLKSRLTITKDTSKNQVVLTMTNMDPVDTATYYC | AHMGTLVDY | WGQGTLVTVSP |
| K6 | NYAQKFQGRVTITADESTSTAYMELSSLRSEDTAVYYC | ARDLGGEWLFFDY | WGQGTLVTVSP |
| K7 | NYAQKFQGRVTITADESTSTAYMELSSLRSEDTAVYYC | ARDRRITMVRGVITNWFDP | WGQGTLVTVSS |
| K8 | NYNPSLKSRVTISVDTSKNQFSLKLSSVTAADTAVYYC | ARDHHSGWFDP | WGQGTLVTVSS |
| K9 | YLNPSLRSRVTLSIDISNNQFSLKLSSVTAADTAIYYC | AGPPGYCTATTCYEWYFDF | WGRGTLVTVSP |
| K10 | YLNPSLRSRVTLSIDISNNQFSLKLSSVTAADTAIYYC | AGPPGYCTATTCYEWYFDF | WGRGTLVTVSP |
| K17 | NYNPSLKSRVTISVDTSKNQFSLKLSSVTAADTAVYYC | ARGLFWFDP | WGQGTLVTVSS |
| L1 | TYSPSLKTRVAISIDGSKNQFYLELSSLTAADTALYYC | ARGDYDGSSYEGGWYYFDH | WGQGTLVTVSS |

TABLE 44-continued (Table 44 discloses the full-length sequence of SEQ ID NOS 136-150, 328-329, and 151-155, respectively, in order of appearance)

| | | | |
|---|---|---|---|
| L2 | SYSTSLKSRLTISKDTSKSQVVLTMTNMDPVDTATYYC | ARIRAGQLDFDY | WGQGTLVTVSP |
| L6 | YYVDSVKGRFTISRDNAKNSLYLQMNSLRAEDTAVYYC | ARDRTGVFDY | WGQGTLVTVSS |
| L8 | RYSPSFQGQVTISADKSISTAYLQWSSLKASDTAMYYC | ARGGYGSGSNWFDP | WGQGTLVTVSS |
| L9 | NYAQKFQGRVTITADESTSTAYMELSSLRSEDTAVYYC | ARDKGL**YQLLWPRDTIF*LV | LLEGTLVTVSP |
| L11 | KDNPSLKSRVTMSVDPSKNEFFLKVNSVTAADTAVYYC | ARVNGGGVDY | WGQGTLVTVSP |
| L12 | RYSPSLKSRLTITKDTSKNQVVLTMTNMDPVDTATYYC | AHSRGYYGSGSYYNFDY | WGQGTLVTVSS |
| L13 | NYNPSLKSRVTISVDTSKNQFSLKLSSVTAADTAVYYC | ARSIVVRGVPFDY | WGQGMLVTVSP |
| L14 | YYADSVKGRFTISRDNSKNTLYLQMNSLRAEDTAVYYC | AKDKWGELPYYFDY | WGQGTLVTVSP |
| L17 | GYAQKFQGRVTITRNTSISTAYMELSSLRSEDTAVYYC | ARGRRYCSGGSCRNYYFDY | WGQGTLVTVSP |

| Clone | Germline | Family | Percentage Identity |
|---|---|---|---|
| K1 | Homsap IGHV2-5*02F | VH2 | 100.0 |
| K2 | Homsap IGHV1-46*01F, or Homsap IGHV1-46*03F | VH1 | 99.7 |
| K3 | Homsap IGHV3-21*01F, or Homsap IGHV3-21*02F | VH3 | 95.8 |
| K5 | Homsap IGHV2-5*02F | VH2 | 100.0 |
| K6 | Homsap IGHV1-69*01F, or Homsap IGHV1-69D*01F | VH1 | 99.7 |
| K7 | Homsap IGHV1-69*01F, or Homsap IGHV1-69D*01F | VH1 | 100.0 |
| K8 | Homsap IGHV4-59*01F | VH4 | 100.0 |
| K9 | Homsap IGHV4-39*01F, or Homsap IGHV4-39*02F or Homsap IGHV4-39*07F | VH4 | 88.0 |
| K10 | Homsap IGHV4-39*01F, or Homsap IGHV4-39*02F or Homsap IGHV4-39*07F | VH4 | 88.0 |
| K17 | Homsap IGHV4-4*02F | VH4 | 98.6 |
| L1 | Homsap IGHV4-34*01F, or Homsap IGHV4-34*12F | VH4 | 87.0 |
| L2 | Homsap IGHV2-26*01F | VH2 | 99.7 |
| L6 | Homsap IGHV3-7*03F | VH3 | 99.7 |
| L8 | Homsap IGHV5-51*01F | VH5 | 99.7 |
| L9 | Homsap IGHV1-69*12F | VH1 | 96.2 |
| L11 | Homsap IGHV4-59*03F | VH4 | 93.7 |
| L12 | Homsap IGHV2-5*02F | VH2 | 100.0 |
| L13 | Homsap IGHV4-4*02F | VH4 | 97.6 |
| L14 | Homsap IGHV3-23*04F | VH3 | 95.8 |
| L17 | Homsap IGHV1-8*02F | VH1 | 92.7 |

Example 23

Further Studies on Barriers to Successful Vector Ligation

In order to obtain a larger naïve antibody phage display library, the present invention also herein discloses alternate methods and protocols. SYBR Safe™, which is also a dsDNA-intercalating dye similar to ethidium bromide, has been reported to improve ligation efficiencies for synthetic scFv libraries (Martineau P, 2010. Synthetic antibody libraries. In: Antibody Engineering, Vol. 1). The rationale is that exposure of ethidium bromide-stained gels to UV light results in DNA damage, and thus in lower cloning efficiency. To test this idea as set in prior art, 20 µg of pCOMB3XSS vector was triple digested with SacI-SfiI-SacI as illustrated in Example 13. 10 µg of digested pCOMB3XSS vector product per gel was run on two different 1% low melting agarose gels casted in 1×TAE and run at 5V/cm for 90 min. Gel #1 was stained in 0.01 µg/ml ethidium bromide while Gel #2 was stained in a 1:10000 dilution of SYBR Safe™ in Milli-Q water. Both gels were stained for 20 min while shaking gently in darkened laboratory area. The vector backbone (~3.3 kb) and stuffer (~1.7 kb) from both gels were excised and purified using QiaQuik kit. DNA fragments were eluted in nuclease-free water and quantified by Picogreen assay. Respective vector and stuffer ligations and transformation into TG1 cells were performed as illustrated in Example 11 along with appropriate experimental controls. Table 45 shows that ligation/transformation efficiencies can be increased at least three-folds in TG1 cells by using the method according to Martineau (2010; Synthetic antibody libraries. In: Antibody Engineering; Vol. 1).

primer (SEQ ID 34) are identical to the forward primer (SEQ ID 32). It is further noted that during final overlap assembly, the $V_L$-$C_L$ and $V_H$-$C_H1$ templates already contain the annealing site of these two primers. Therefore, it is not inconceivable that the 5' end of either primer can anneal in the wrong orientation on the newly generated templates in the PCR reaction after the $2^{nd}$ cycle (i.e. after formation of the first double-stranded blunt template). Four different combinations of amplicons may occur in the initial few cycles of PCR as shown in Table 46.

TABLE 46

| 5' end/3' end | Amplified product (Right/Wrong) | 5' Sfi I | 3' Sfi I | Product (%) |
|---|---|---|---|---|
| SEQ ID 32/SEQ ID 34 | Right | Yes | Yes | 25 |
| SEQ ID 34/SEQ ID 32 | Wrong | No | No | 75 |
| SEQ ID 32/SEQ ID 32 | Wrong | Yes | No | |
| SEQ ID 34/SEQ ID 34 | Wrong | No | Yes | |

Figure 25:
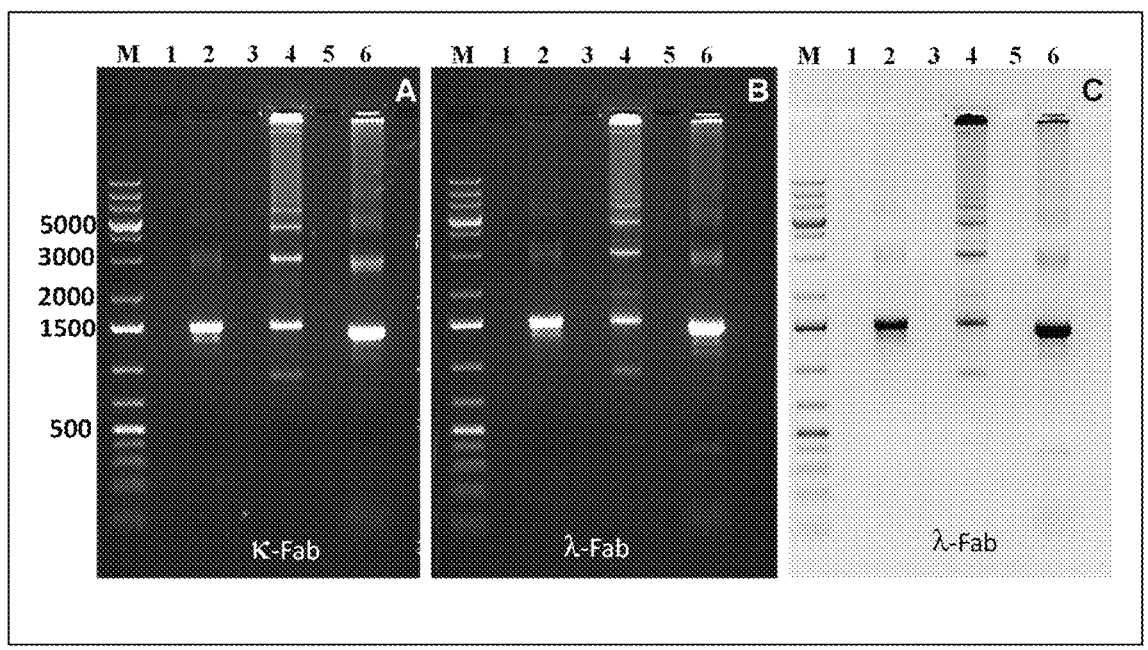
FIG. 25 depicts self-ligation of linear Fabs for final large Fab library making. Panels A and B show the epifluorescent image for kappa and lambda Fabs, respectively, while panel C is the photographic negative of the lambda Fab gel (panel B). Lanes 2 contain the 500 ng of Fab pool alone, while lanes 4 contain 1 µg of sample of Fab self-ligation mixtures after 16 h of incubation at 16° C. Lanes 6 contain SfiI digested salt purified self-ligated ligation mixture. Lanes 3 and 5 are empty. M is the 1 kb plus DNA marker from Fermentas. Numbers on the left show marker size in base pairs. Samples were run in a 1% agarose gel prepared in 1×TBE containing 0.1 µg/ml ethidium bromide and run at 5V/cm for 1.5 h.

Based on Table 46, a likely consequence will be the dominance of 75% of the incorrectly amplified products over 25% of the correctly amplified products due to the exponential nature of amplification in standard PCR reactions of 25-30 cycles, which may result in data as set out in Table 18 and FIGS. 17, 23 and 25.

The present invention discloses alternate forward amplifying primers for final Fab fusion that are non-homologous to the original reverse primer (SEQ ID 32) along with 5' overhangs of different length (SEQ ID 35-37). The concept

TABLE 45

| Sample ID | DNA (pg) | Total culture volume (µl) | Dilution of culture | Plating volume (µl) | Theritical plating volume (µl) | Numner of colonies on plate | Total colonies in culture | efficiency per µg | Average efficiency per µg | |
|---|---|---|---|---|---|---|---|---|---|---|
| SYBR safe_stuffer + Vector_SET-1 | 2100 | 1000 | 1000 | 100 | 0.1 | 1079 | 10790000 | 5.14E+09 | 4.41E+09 | |
| SYBR safe_stuffer + Vector_SET-3 | 2100 | 1000 | 1000 | 100 | 0.1 | 773 | 7730000 | 3.68E+09 | | |
| EtBr_stuffer + Vector_SET-2 | 2100 | 1000 | 1000 | 100 | 0.1 | 570 | 5700000 | 2.71E+09 | 1.57E+09 | |
| EtBr_stuffer + Vector_SET-3 | 2100 | 1000 | 1000 | 100 | 0.1 | 90 | 900000 | 4.29E+08 | | |
| SYBR safe_Vector control | 2100 | 1000 | 10 | 100 | 10 | 13 | 1300 | 6.19E+05 | 6.19E+05 | 0.1% vector background |
| EtBr_Vector control | 2100 | 1000 | 10 | 100 | 10 | 7 | 700 | 3.33E+05 | 3.33E+05 | 0.2% vector background |

FIGS. 17, 23, and 25 illustrate that a significant portion of self-circularized smear is not converting into ~1.5 kb ligatable Fab molecules after digestion with SfiI. This indicates that not all of the Fab molecules in a given PCR-amplified population have digestible/correct SfiI ends. Data presented in Table 18 also demonstrates this fact (incorrect SfiI ends in DNA sequence of 20% of TOPO cloned Fabs). The incorrect SfiI ends in DNA sequence stems from the inherent properties of the forward and reverse primers used for final Fab amplification being SEQ ID 32 and SEQ ID 34. FIG. 26 shows the sequences of these primers and their pairwise alignment against each other.

Figure 27:
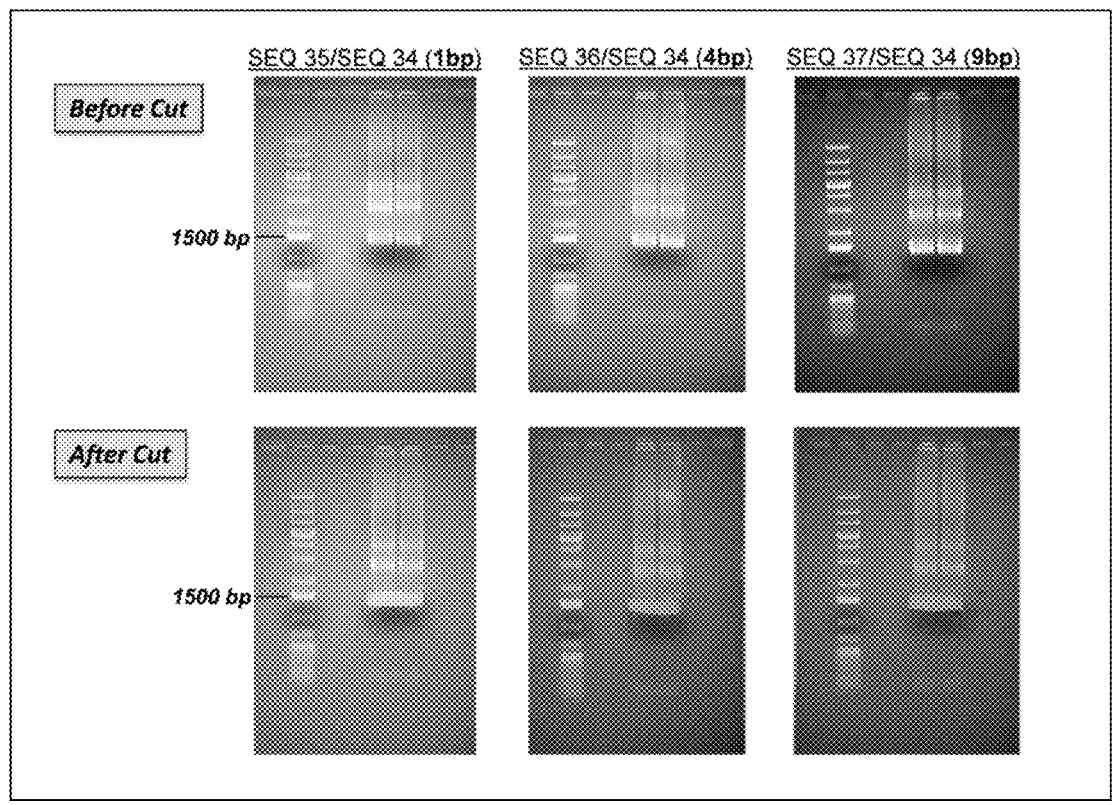
FIG. 27 depicts conventional SfiI digestion of PCR assembled kappa Fab pool. All PCR overlap products digested with SfiI were run on 1.2% gels cast in 1×TAE containing 1×SYBR Safe™, and run at 5V/cm for 90 min. Top panels show images of these gels after the run, while bottom panels show the same gels after cutting out the 1.5 kb band of the SfiI digested Fab pool. The primers used for final Fab assembly, along with the length of the overhangs 5' of the annealing site, are indicated on the top of each column.

Based on FIG. 26 it is noted that (a) the first 18 nucleotides at the 5' end of either primer are identical and (b) overall, 30 out of 39 nucleotides (76.9%) of the reverse for designing the latter aspect of these novel primers may be found in the table titled "Cleavage Close To 5' Ends" in any New England Biolabs annual catalog (New England Biolabs Product Catalog and Technical Reference, 2007). Alignment of these newly designed forward primers against SEQ ID 34 showed 20-36% identity only, as opposed to the 77% identity calculated with the original pair. The primer pairs as set out herein were tested to assemble a $V_\kappa$-$C_\kappa$ and a $V_H$-$C_H1$ pool into fused Fabs, and then digest the Fab pool with SfiI (FIG. 27).

The gel-extracted SfiI-digested Fab pools were ligated to triple digested pCOMB3XSS, and the ligation mixes transformed in high efficiency TG1 cells (Lucigen) using methods exemplified in Examples 21 and 22. The results are presented at Table 47.

TABLE 47

| Sample ID | DNA (pg) | Total culture vol (μl) | Dilution of culture | Plating vol (by considering dilution) | Theoretical Plating vol (μl) | No of colonies (per plate) | No of colonies (in total volume) | efficiency/μg | Avg Efficiency (cfu/μg) |
|---|---|---|---|---|---|---|---|---|---|
| SEQ ID 35/SEQ ID 34 (1 bp) Plating-1 | 2100 | 1000 | 200 | 100 | 0.5 | 2448 | 4896000 | 2.33E+09 | 1.11E+09 |
| SEQ ID 35/SEQ ID 34 (1 bp) Plating-2 | 2100 | 1000 | 200 | 100 | 0.5 | 830 | 1660000 | 7.90E+08 | |
| SEQ ID 35/SEQ ID 34 (1 bp) Plating-3 | 2100 | 1000 | 400 | 100 | 0.25 | 106 | 424000 | 2.02E+08 | |
| SEQ ID 36/SEQ ID 34 (4 bp) Plating-1 | 2100 | 1000 | 200 | 100 | 0.5 | 810 | 1620000 | 7.71E+08 | 1.42E+09 |
| SEQ ID 36/SEQ ID 34 (4 bp) Plating-2 | 2100 | 1000 | 200 | 100 | 0.5 | 1155 | 2310000 | 1.10E+09 | |
| SEQ ID 36/SEQ ID 34 (4 bp) Plating-3 | 2100 | 1000 | 400 | 100 | 0.25 | 1261 | 5044000 | 2.40E+09 | |
| SEQ ID 37/SEQ ID 34 (9 bp) Plating-1 | 2100 | 1000 | 200 | 100 | 0.5 | 750 | 1500000 | 7.14E+08 | 9.02E+08 |
| SEQ ID 37/SEQ ID 34 (9 bp) Plating-2 | 2100 | 1000 | 200 | 100 | 0.5 | 730 | 1460000 | 6.95E+08 | |
| SEQ ID 37/SEQ ID 34 (9 bp) Plating-3 | 2100 | 1000 | 400 | 100 | 0.25 | 680 | 2720000 | 1.30E+09 | |
| Stuffer control_Plating-1 | 2100 | 1000 | 1000 | 100 | 0.1 | 479 | 4790000 | 2.28E+09 | 1.72E+09 |
| Stuffer control_Plating-2 | 2100 | 1000 | 1000 | 100 | 0.1 | 245 | 2450000 | 1.17E+09 | |
| pUC control | 40 | 1000 | 100 | 100 | 1 | 430 | 430000 | 1.08E+10 | 1.08E+10 |

Examination of the transformation efficiency of test Fab pools (Avg Efficiency column in Table 47) demonstrates that the test Fab pool amplified by the SEQ ID 36/SEQ ID 34 pair shows the best transformation efficiency, which is very close to the transformation efficiency of stuffer control (underlined values in Table 47). Homology between amplifying primers and transformation efficiency appear to be negatively correlated—more the homology, lesser the efficiency of transformation. When homologies are identical (SEQ ID 35 and SEQ ID 36—both are 20% homologous to SEQ ID 34), the one with 4 bp 5' overhang (SEQ ID 36) performs better than the one with 1 bp overhang (SEQ ID 35). It is to be noted that the transformation efficiencies presented in Table 45 were obtained with diluted ligation mixtures as detailed in Example 12, which are 2-3 folds less efficient when compared with cleaned up ligation mix samples as illustrated in Example 21. The methods disclosed herein enable achieving the large naïve antibody phage display library as set out herein.

Example 24 pSSY1—A New Phage Vector that is a Distinct Improvement Over pCOMB3XSS

FIG. 13 illustrates that the digestion of the plasmid pCOMB3XSS with SfiI is incomplete, and Example 10 points out that the rationale for such a behavior may lie in the dcm methyltransferase sensitive pentanucleotide core of the 5' and 3' sites, which will leave these sites hemimethylated if a dcm+ host is used for plasmid propagation. Although this problem can be alleviated by use of commercial dam−/dcm− E. coli strains, Example 13 further illustrates the practical difficulties of using such a plasmid preparation for routine Fab ligations. Detailed examination of the pCOMB3XSS plasmid illuminates further design issues as listed below (positions of nucleotides are identical to the one available the Barbas lab site—see http://www.scripps.edu/barbas/content/pcomb_images/pcomb_images_files/pComb_Text_Files/pComb3XSS.txt):

1. Both the light chain and heavy chain stuffers are designed in such a way that they are translatable in E. coli;
2. In the case of the light chain stuffer, this is predicted to produce a 55 aa' protein including the OmpA periplasmic leader;
3. In the case of heavy chain stuffer, this is predicted to produce a 351 aa' protein that includes the E. coli thioredoxin gene (GenBank M10424.1; nt1584-1940) along with the pelB periplasmic leader at the N-terminal, and the CTD (C-terminal domain) of the bacteriophage fd gene III at the C-terminal;
4. The light chain stuffer includes part of Fab like clones (nt527-977—identical to VH fragment of GenBank AB608265 and nt930-1469—identical to GenBank lambda clone L22157.1);
5. The 6×His tag (SEQ ID NO: 156) is internal to the hemagglutinin (HA) tag, which may result in difficult detection and/or purification based on the popular Immobilized Metal Affinity Chromatography (IMAC) format.

Figure 28:
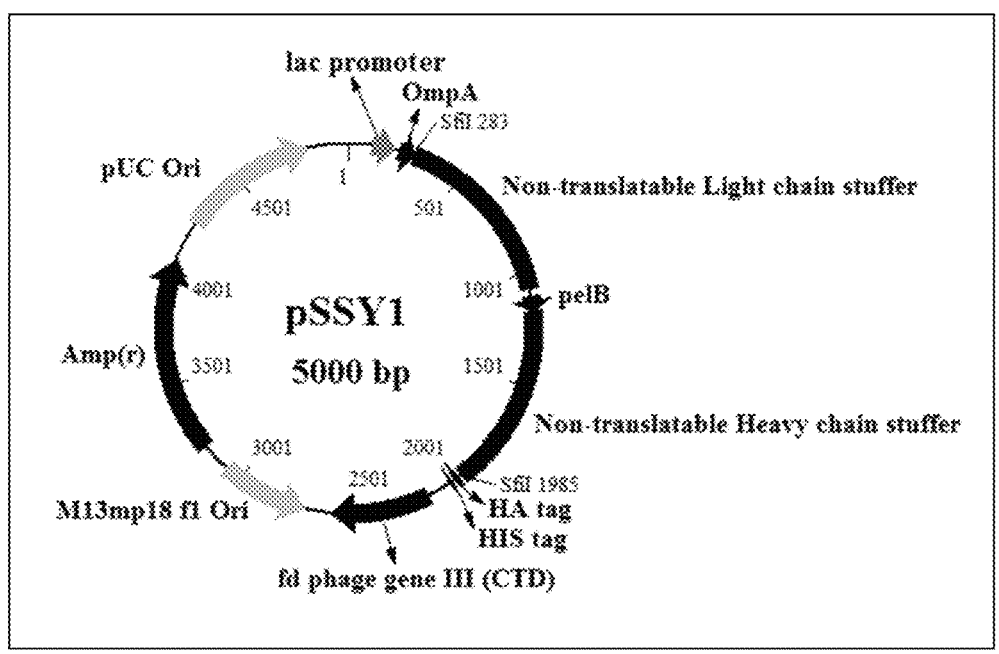
FIG. 28 depicts circular plasmid map of pSSY1 (SEQ ID 38).

In order to improve the shortcomings as set out herein above, the present invention discloses the design of a novel vector that (a) does not have such nucleotides in the pentanucleotide core of the 5' and 3' SfiI sites that can be cytosine methylated by dam or dcm methyltransferases, (b) that has stuffers of non-prokaryotic origin which cannot be translated using the start codons of OmpA or pelB leaders thus increasing plasmid stability during propagation, yet allow distinction between a Fab insert and the parental clone by appropriate restriction digestion followed by resolution on an agarose gel, and in which (c) the HA tag is internal to the 6×His tag (SEQ ID NO: 156) to avoid potential bottlenecks during application of standard IMAC protocols on candidate Fabs. Other desirable features, such as those that allow $V_L/V_H$ or light chain/heavy chain domain shuffling as restriction fragments with low probability of cleavage within V-domains (Persic L et al., 1991) will be apparent to the practitioner of the art of antibody cloning. SEQ ID 38 provides the complete sequence of this vector (pSSY1), while FIG. 28 shows a map of the same in a circular plasmid form.

The new vector pSSY1 is identical in copy number, plasmid/phage replication Ori's, antibiotic marker and in the use of the CTD of fd gIII as pCOMB3XSS, but enables better use both for phage display as well as protein expression. Table 48 shows that while it takes pCOMB3XSS two restriction digestions (SacI-SfiI) to achieve zero vector background, pSSY1 achieves the same with a single digestion of SfiI. This is clearly indicative of the beneficial effects of changing the pentanucleotide core of the two SfiI sites in this plasmid. Furthermore, this table also demonstrates that the SfiI-digested pSSY1 vector is as efficient in the stuffer re-ligation test as is the double digested pCOMB3XSS vector.

TABLE 48

| Sample ID | DNA transformed/50 μl of TG1 cells | No. of colonies | Plating dilution | Plating volume (μl) | Efficiency/μg DNA transformed |
|---|---|---|---|---|---|
| Vector Control_pCOMB3XSS_Direct SfiI | 100 pg | 6 | 1:1001 | 100 | $2.8 \times 10^7$ |
| Vector Control_pCOMB3XSS_SacI-SfiI | 100 pg | 0 | 1:1000 | 100 | — |
| Vector Control_pSSY1_Direct SfiI | 100 pg | 0 | 1:1000 | 100 | — |
| Stuffer_pCOMB3XSS_SacI-SfiI | 100 pg | 840 | 1:1000 | 100 | $4.2 \times 10^9$ |
| Stuffer_pSSY1_Direct SfiI | 100 pg | 790 | 1:1000 | 100 | $3.95 \times 10^9$ |
| pUC control | 10 pg | 926 | 1:1000 | 100 | $9.26 \times 10^{10}$ |

Example 25

Building an Ultra-Large Library on pSSY1 Backbone

RNA was isolated from a pool of 15 donors using characterized PBMC's from CTL (Cellular Technologies Ltd., Cleveland, Ohio, USA) and pooled with commercial RNAs of bone marrow, spleen and tonsil from one donor each (AMS Biotechnology, Abingdon, Oxford, UK).

The RNA preparations were mixed 40:20:20:20 (PBMC: bone marrow: spleen: tonsil), and cDNA was prepared from this pooled sample as detailed in Example 1. To test the quality of the prepared cDNA, new primer pairs specific for each of $V_H$, $V_\kappa$ and $V_\lambda$ domains was used on the pooled cDNA with 50 ng template per 50 μl reaction. The resultant amplicons were of correct size with minimal non-specific amplification (FIG. 29), suggesting that the quality of the cDNA is acceptable. For maxi-cDNA preparation from pooled total RNA of human PBMC, spleen, bone marrow and tonsil's, 130 reactions were assembled with 1 μg of total RNA per reaction. Yield was estimated by the RiboGreen Method. The total yield of cDNA was 26.7 μg.

PCR amplifications to make final kappa and lambda Fab fragments were carried out using methods as described previously (see Examples 3-9). The changes introduced were (a) to include a 3' SfiI site in the $C_H1$ template that would not be methylated by dcm methyltransferase (SEQ ID 39) as illustrated in Example 24, (b) to use $C_\kappa$ and $C_\lambda$ templates that have 3' sequences comparable to the intergenic sequence between light and heavy chain stuffers of pSSY1 (SEQ ID 40-41), (c) to include 5' SfiI sites in all V-domain forward primers that would not be methylated by dcm methyltransferase (SEQ ID 42-54; FIG. 28) and (d) to use a final overlap forward primer (SEQ ID 55) as exemplified in Example 23 and as appropriate to the pSSY1 vector.

Based on efficiencies obtained from new primers (Table 47), it was surmised that to generate 20 μg each of final ligatable kappa and lambda Fabs, 100 μg of each type of Fab would be required to start the process. First overlap (SOE) PCR's were performed using equimolar amounts of V and C genes. Total 100 SOE reactions for each light chain and 200 SOE reactions for heavy chain were set up. The final yields after QIAEXII gel extraction were 27 μg for $V_\lambda C_\lambda$, 38.5 μg for $V_\kappa C_\kappa$ and 93.4 μs for $V_H C_H1$ as measured by Picogreen assay. Second overlap (SOE) PCR's were similarly performed using equimolar amounts of $V_L C_L$ and $V_H C_H1$ amplicons. A total of 775 PCRs were performed each for kappa and lambda chains. The final yields after QIAEXII gel extraction were 96 μs for λ-Fab and 98.5 μs for κ-Fab, respectively, as measured by Picogreen assay.

Both kappa and lambda fabs were subjected to SfiI digestion separately. 32 U of SfiI was added per μg of Fab in buffer M (Roche), and incubated overnight at 50° C. Digested Fabs were gel purified using QIAEXII gel extraction kit and DNA was eluted in nuclease free water. Fabs were quantified by Picogreen assay, with final yields of ~17.2 μg of kappa and ~17.5 μg of lambda, respectively. The $A_{260}/A_{280}$ ratio was checked using NanoVue and ranged between 1.7 and 1.9. pSSY1 vector was prepared by overnight SfiI digestion as illustrated in Example 10.

140 ng of SfiI digested pSSY1 vector was ligated with 140 ng of SfiI-digested Fab (1:2 molar ratio for vector:insert) in 20 μl reactions using 1 U/μg of T4 DNA ligase, and incubated overnight at 16° C. To ligate a total of ~17.2 μg of Kappa and ~17.5 μg of Lambda Fab, required number of ligations was set up as amply described in preceding examples. After overnight (16 h) incubation, the ligation mixtures were nick-sealed at 37° C. for 1 h followed by heat inactivation at 70° C. for 15 min and pooled together. Kappa and lambda Fabs were processed separately. The pools were subjected to salt removal and buffer exchange with water three times using Microcon spin-filters. The $A_{260}/A_{280}$ ratio was checked using NanoVue and ranged between 1.7 and 1.9. The actual dsDNA concentration was measured using PicoGreen assay. After the salt removal, the total recoveries of ligated material were 28 and 18.15 μg (vector+Fab), respectively, for Kappa and Lambda ligations.

Based on Table 37 and FIG. 24B, it is surmised that a maximum of 272 ng of purified ligated DNA (vector+insert) can be electroporated per 50 μl TGI cells in 2 mm gap BioRad cuvettes with electoporation parameters as set out in Example 20. To make kappa library (26384 ng, vector+Fab), total 97 transformations were performed in 8 sets (12-13 transformations/set), which resulted in 8 sub-libraries for Kappa. ~12 ml cultures generated after 12-13 transformations per set were transferred to 125 ml corning flasks and incubated at 37° C. and 250 rpm for 1 h. Transformed cultures from each such set were spread on 7 large LB agar plates (245 mm×245 mm) containing 50 μg/ml carbenicillin and 2% glucose at the quantum of ~1.5 ml/plate. The Kappa library was therefore plated on a total of 62 plates (kappa sub-libraries 001-008; see Table 49). 50 μl aliquots of each sub-library were kept aside for calculating the transformation efficiency of the sub-libraries.

Similarly, to make the Lambda library (18033 ng, vector+Fab), total 66 transformations were performed in 6 sets (7-13 transformations/set), which resulted into 39 large plates and 6 sub-libraries for Lambda (lambda sub-libraries 001.1-006.1; see Table 49). 50 µl aliquots of each sub-library were again kept aside for calculating the transformation efficiency of the sub-libraries.

to calculate cfu/ml of each sub-library, the bacterial suspension was aliquoted in size appropriate for future work, and stored at −80° C. as individual sub-libraries. The 8 sub-libraries of kappa were labeled as HsN3kFab001-HsN3kFab008, where Hs stand for *Homo sapiens*, and N stands for Naïve. Similarly, 6 sub-libraries were created for lambda Fabs, and labeled HsN2LFab001.1-HsN2LFab006.1.

TABLE 49

| Sample ID | DNA (pg) | Total no of transformations in sub-set | Total DNA transformed in sub-set (in ng) | Total culture vol (µl) | Dilution of culture | Plating vol (by considering dilution) | Theoretical Plating vol (µl) |
|---|---|---|---|---|---|---|---|
| HsNkFab001 | 272000 | 12 | 3264 | 1000 | 100000 | 100 | 0.001 |
| HsNkFab002 | 272000 | 12 | 3264 | 1000 | 100000 | 100 | 0.001 |
| HsNkFab003 | 272000 | 12 | 3264 | 1000 | 500000 | 100 | 0.0002 |
| HsNkFab004 | 272000 | 12 | 3264 | 1000 | 500000 | 100 | 0.0002 |
| HsNkFab005 | 272000 | 12 | 3264 | 1000 | 500000 | 100 | 0.0002 |
| HsNkFab006 | 272000 | 12 | 3264 | 1000 | 500000 | 100 | 0.0002 |
| HsNkFab007 | 272000 | 12 | 3264 | 1000 | 500000 | 100 | 0.0002 |
| HsNkFab008 | 272000 | 13 | 3536 | 1000 | 500000 | 100 | 0.0002 |
| HsN2LFab001.1 | 272000 | 13 | 3536 | 1000 | 500000 | 100 | 0.0002 |
| HsN2LFab002.1 | 272000 | 13 | 3536 | 1000 | 500000 | 100 | 0.0002 |
| HsN2LFab003.1 | 272000 | 13 | 3536 | 1000 | 500000 | 100 | 0.0002 |
| HsN2LFab004.1 | 275000 | 10 | 2750 | 1000 | 800000 | 100 | 0.000125 |
| HsN2LFab005.1 | 275000 | 10 | 2750 | 1000 | 800000 | 100 | 0.000125 |
| HsN2LFab006.1 | 275000 | 7 | 1925 | 1000 | 800000 | 100 | 0.000125 |

| Sample ID | Number of colonies | Total colonies in 1000 µl culture | Efficiency/µg | Size of sub-set (cfu) | Total Size of Fab type (in cfu) | Total library size (in cfu) |
|---|---|---|---|---|---|---|
| HsNkFab001 | 522 | 522000000 | 1.92E+09 | 6.26E+09 | 1.26E+11 | 3.06E+11 |
| HsNkFab002 | 605 | 60500000 | 2.22E+09 | 7.26E+09 | | |
| HsNkFab003 | 195 | 97500000 | 3.58E+09 | 1.17E+10 | | |
| HsNkFab004 | 332 | 1660000000 | 6.10E+09 | 1.99E+10 | | |
| HsNkFab005 | 215 | 1075000000 | 3.95E+09 | 1.29E+10 | | |
| HsNkFab006 | 495 | 2475000000 | 9.10E+09 | 2.97E+10 | | |
| HsNkFab007 | 420 | 2100000000 | 7.72E+09 | 2.52E+10 | | |
| HsNkFab008 | 206 | 1030000000 | 3.79E+09 | 1.34E+10 | | |
| HsN2LFab001.1 | 363 | 1815000000 | 6.67E+09 | 2.36E+10 | 1.79E+11 | |
| HsN2LFab002.1 | 220 | 1100000000 | 4.04E+09 | 1.43E+10 | | |
| HsN2LFab003.1 | 291 | 1455000000 | 5.35E+09 | 1.89E+10 | | |
| HsN2LFab004.1 | 545 | 4360000000 | 1.59E+10 | 4.36E+10 | | |
| HsN2LFab005.1 | 680 | 5440000000 | 1.98E+10 | 5.44E+10 | | |
| HsN2LFab006.1 | 435 | 3480000000 | 1.27E+10 | 2.44E+10 | | |

Percentage vector background: 0.1%

To calculate the efficiency of transformation per µg, these 50 µl aliquots from each kappa and lambda sub-libraries were diluted 1:25000, 1:100000, 1:500000 and 1:800000 in Recovery Medium (Lucigen). 100 µl of each dilution was plated in triplicates on 90 mm LB agar plates containing 50 µg/ml carbenicillin and 2% glucose. After overnight incubation at 37° C., matted growth was observed on the large library plates while the efficiency plates showed well isolated colonies. Summarized results of respective transformation efficiencies and library sizes are presented in Table 49.

Bacterial lawn from each large plate was scraped using sterile scrapers in 5 ml of LB+1% glucose broth (3 ml for scraping+2 ml rinsing). Scraped cultures from each sub-library were pooled in single tube, Equal volumes of storage medium was then added and 50 µl of aliquot was saved aside To calculate cfu/ml of the individual sub-libraries, a log dilution method was used. 20 µl of the saved aliquot was mixed with 180 µl of LB medium to give $10^{-1}$ dilution. Log dilutions were prepared from this stock till $10^{-1}$ dilution in a final volume of 200 µl was reached. 100 µl each from the last four dilutions ($10^{-7}$, $10^{-8}$, $10^{-9}$ and $10^{-10}$ were plated on LB plates containing 100 µg/ml carbenicillin and 2% glucose. Plates were incubated overnight at 37° C. Colony counts were taken next morning, and the resultant cfu/ml ranged between 0.63-5.4×$10^{10}$ cfu/ml.

A total of 96 clones (48 each for kappa and lambda) were picked and plasmid DNA extracted at small scale. To confirm Fab identity, PCR was carried out with the plasmid DNA as templates and vector backbone-specific primers. For diversity analysis, the PCR products were subjected to BstNI fingerprinting after confirmation that most of the clones from either library are Fab positive (97% for kappa, 100% for lambda). BstNI fingerprinting shows that none of the kappa and lambda clones showed any repeat pattern and each clone is different. 96 clones from each library were subjected to dideoxy sequencing using the same two vector backbone specific and one $C_H1$ specific primers as described in Example 18. However, the two pelB adjacent region specific primers were replaced with $C_\kappa$-specific forward and reverse sequencing primers for the kappa clones, and with $C_\lambda$-specific forward and reverse sequencing primers for the lambda clones. The Fab sequence of each clone was analyzed following a routine algorithm of contig building from sequence chromatograms, and visual verification of anomalous base calls. Contigs were then manually annotated for landmarks such as the SfiI sites at 5' and 3' ends, the $V_L$, $V_H$, $C_L$ and $C_H$ domains, and for completeness of the individual light and heavy chains from Start to the Stop codons. The results of the manual analysis and annotation are summarized in Table 50.

TABLE 50

| Categories | | Total | % |
|---|---|---|---|
| Proportions K1-K96 | | | |
| Clones reviewed | | 96 | |
| No Contig | | 0 | 0 |
| 2-trace/Incomplete Contigs | | 8 | 8 |
| Readable clones | | 88 | 92 |
| | 5' SfiI | 88 | 100 |
| | 3' SfiI | 88 | 100 |
| No Good | | 28 | 32 |
| | LC off-frame | 3 | 3 |
| | HC off-frame | 23 | 26 |
| | Both LC & HC off-frame | 2 | 2 |
| Good | Both LC & HC in-frame | 60 | 68 |

TABLE 50-continued

| Categories | | Total | % |
|---|---|---|---|
| Proportions L1-L96 | | | |
| Clones reviewed | | 96 | |
| No Contig | | 1 | 1 |
| 2-trace/Incomplete/Reseq Contigs | | 2 | 2 |
| Readable clones | | 93 | 97 |
| | 5' SfiI | 93 | 100 |
| | 3' SfiI | 93 | 100 |
| No Good | | 20 | 22 |
| | LC off-frame | 4 | 4 |
| | HC off-frame | 13 | 14 |
| | Both LC & HC off-frame | 3 | 3 |
| Good | Both LC & HC in-frame | 73 | 78 |

Figure 30:
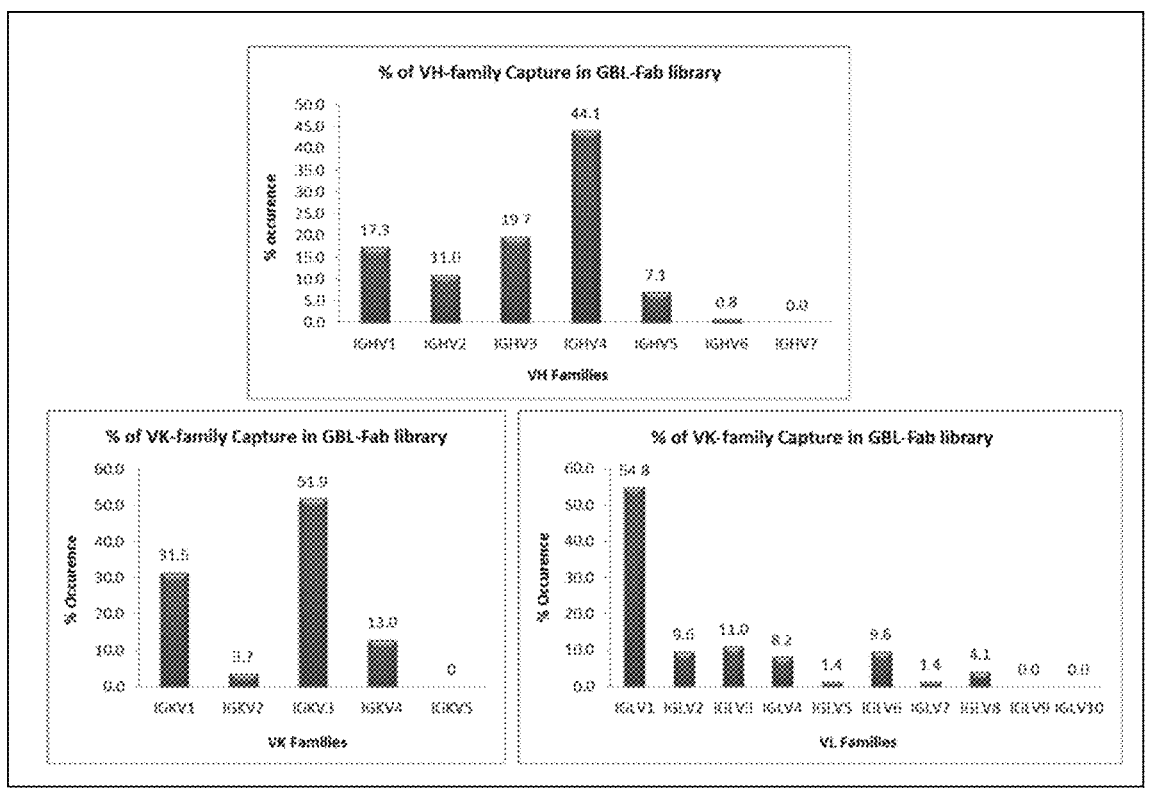
FIG. 30 depicts V-family coverage of the ultra-large library.

The sequences of $V_L$ and $V_H$ domains of all "good" clones (i.e. clones in which both LC and HC are in-frame) were also submitted to the IMGT database for detailed annotation on the germline family, framework and CDRs. Summarized results for family coverage are shown in FIG. 30, while Tables 51-53 contain remaining annotations from the IMGT database for a subset of clones.

Figure 29:
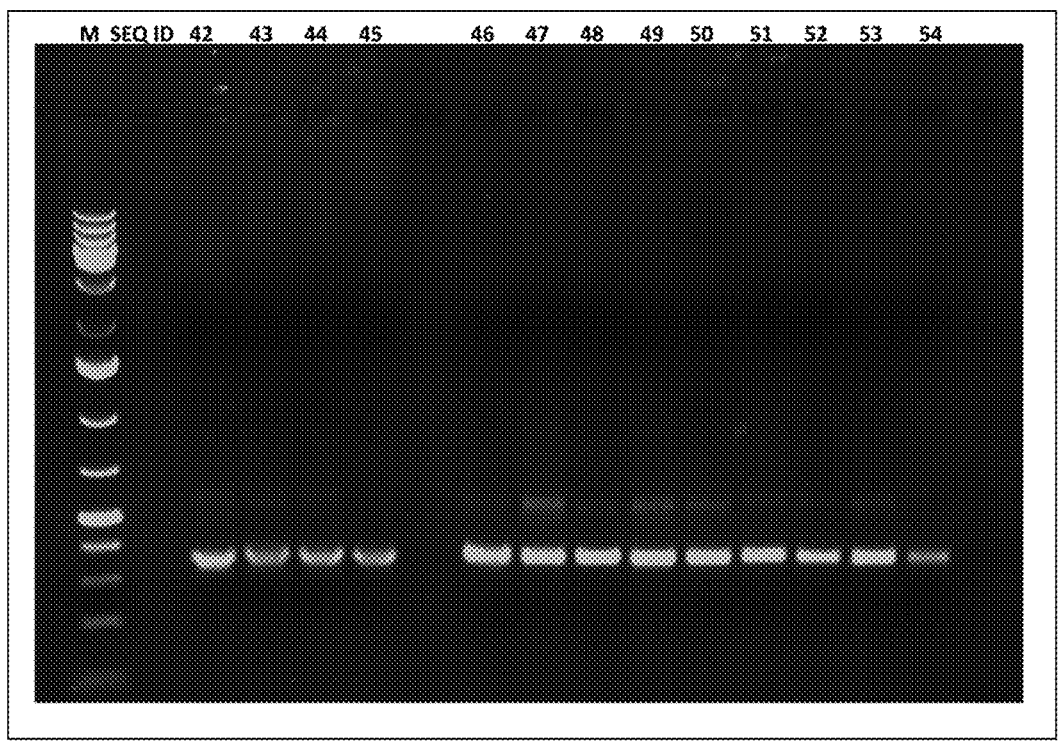
FIG. 29 depicts verification of the quality of prepared cDNA by testing variable gene amplifications. This figure shows test amplification by a $V_\kappa$-specific reverse primer (SEQ ID 13) paired with all $V_\kappa$ forward primers (SEQ ID 42-45) and test amplification by a $V_\lambda$ reverse primer (SEQ ID 23) paired with all $V_\lambda$ forward primers (SEQ ID 46-54). Numbers on the top of the gel shows SEQ IDs of respective forward primers. Products were analyzed in 1.2% agarose gels prepared in 1×TBE containing 0.1 µg/ml ethidium bromide and run at 5V/cm for 1.5 h. M is the 1 kb plus DNA marker from Fermentas.

This analysis showed that except for two families each for $V_H$ (VH6, VH7) and $V_\lambda$ (VL9, VL10), and one family of $V_\kappa$ (VK5), all other families were represented in these clones (FIG. 29). As these families are represented by fewer variants as compared to the other families, it is possible that a clone belonging to such families has been missed both because of their rarity and low sampling number in this sequence dataset. 44.1% of all $V_H$ domains belonged to the VH4 family and 19.7% belonged to VH3, while other families (VH1, VH2 and VH5) were in the range of 5-17%. Similarly, 4 families of $V_\kappa$ and 8 families of $V_\lambda$ were represented. In kappa family, 51.9% of clones belonged to the VK3 family and 31.5% to the VK1 family. Representation of other families was between 5 and 13%. In lambda family, the representation was 54.8% for VL1, 11% for VL3, and remaining families (VL2, VL4, VL6, VL7, VL8 and VL9) were in the 0-10% range.

TABLE 51

(Table 51 discloses the full-length sequence of SEQ ID NOS 157-176, respectively, in order of appearance)

| Clone | FR1-IMGT | CDR1-IMGT | FR2-IMGT | CDR2-IMGT | FR3-IMGT |
|---|---|---|---|---|---|
| K1 | ELVMTQSPDSLAVSLGERATINCKSS | QSVLYSSNNKNY | LAWYQQKPGQPPKLLIY | WAS | TRESGVPDRFSGSGSGTDFTLTISSLQAEDVAVYYC |
| K2 | ELVLTQSPGTLSVSPGERATLSCRAS | QNINNNY | LAWYQQKPGQGLRLLIS | GAS | SRATGIPHRFVGSGSWTDFTLTIIRLEPEDFAVYFC |
| K3 | ELVMTQSPLSLPVTPGEPASISCRSS | QSLLHLNGYNY | LDWYLQKPGQSPQLLIY | LSS | NRASGVPDRFSGSGSGTDFTLKISRVEADVGVYYC |
| K4 | ELQMTQSPATLSASVGDRVTITCRAS | QSVSRY | INWYQQKSGKAPKLLIY | RAS | TLQTGVPSRFSGSGSGTEFTLTISSLQPDDFATYYC |
| K5 | ELVMTQSPGTLSLSPGERATLSCRAS | QSVSSSY | LAWYQQKPGQAPRLLIY | GAS | TRATGIPDNFSGSGSGRDFTLTISRLEPEDFAVYYC |
| K6 | ELVLTQSPGTLSLSPGDRATLSCRAS | QSVSGNY | LAWYQQKPGQAPRLLIF | GTS | SRATDIPDRFSGSVSGTDFTLTIGSLEPEDFALYYC |
| K7 | ELVMTQSPSSVSASVGDRVTITCRAS | QGISSW | LAWYQQKPGKAPKLLIY | AAS | SLQSGVPSRFSGSGSGTDFTLTISSLQPEDFATYYC |
| K8 | ELVLTQSPGALSLSPGERATLSCRAS | QSVGSSY | LAWYQHKPGQAPRLLIY | DAD | NRATGIPDRFSGTGSGTDFTLTISRLEPEDFAVYYC |
| K9 | ELVMTQSPSSLSASVGDRVTIACRTS | QSITTY | LNWYQQIPGKAPKLLIY | AAS | SLQTGVPARFTGSGSGTDFTLTISSLQAEDVAVYYC |
| K10 | ELQMTQSPGSSSASVGDTVTITCRSS | QNIRKF | LNWYQQKPGKAPRLLIY | GAS | NLQSDVPSRFRGSGSGTQFSLTITDLRPEDFATYYC |
| K11 | ELTLTQSPDSLSLSPGERATLSCRAS | QSISRNS | LVWYQQKPGQAPSLLIY | DAS | TRAAGTPDRFSGSGSGTDFTLTISRLEPEDFAVYYC |
| K12 | ELVMTQSPSSLSASVGDRVTITCRAS | QTVSGS | LNWYQQKPGKAPKLLIY | AAS | SLQSGVPSRFSGSGSGTDFTLTISSLQPEDFATYYC |
| K13 | ELVMTQSPDSLAVSLGERATITCKSS | QSVFFSPNSKNY | LAWYQLKPGQAPKLLIS | WAS | AREFGVPDRFSGSGSGTDFTLTISSLQAEDVALYYC |

TABLE 51-continued

| | | | | | |
|---|---|---|---|---|---|
| K14 | ELVMTQSPVSLSVTPGQPASIS CKSS | QSLLHRDGKTY | FFWYLQKPGQPPQLLVY | EVS | KRFSGVPDRFRGSGSGTDFTLRISRV EAEDVGVYYC |
| K15 | ELTLTQSPATLSVSPGQRATLS CRAS | QSVSSSY | VAWYQQKPGQTPRLLIY | GAS | SRATGIPARFSGSGSGTEFTLTISRL EPEDFAVYYC |
| K16 | ELTLTQSPDTLSVSPGERVTLS CRAS | QSVSTN | LAWYQQRPAQPPRLLIY | GAS | SRATGIPDRFSGSGSGTDFTLTISRL EPEDFAVYYC |
| K17 | ELVMTQSPATLSVSPGERATLS CRAS | QSVSSD | LAWYQQRPGQAPRLFIY | GAS | SRATGIPDRFRGSGSGTDFTLTISRL EPEDFAVYYC |
| K18 | ELQMTQSPSSLSASVGDRVTIT CRAS | QSIINY | LTWYQFKPGKAPKLLIH | TTS | SLQNGVPSRFSGSGSGTDFTLTISSL QPEDAATYYC |
| K19 | ELTLTQSPATLSVSPGGRATLS CRTS | QSVNSK | LAWYQQKPGQAPRLLIY | DAS | TRATGIPDRFSGSGSGTDFTLTISRL EPEDFAVYYC |
| K20 | ELVLTQSPGTLSLSPGQRATLS CRAS | QSVSSTY | LAWYQQKPGQAPRLLIY | GAS | TRATGVPGRFSGSGSGTEFTLTISSL QSEDFAVYYC |

| Clone | CDR3-IMGT | FR4-IMGT | Germline | Amino acid difference from germline | Family | Percentage Identity |
|---|---|---|---|---|---|---|
| K1 | QQYYSTPPT | FGGGTKVEIK | IGKV4-1*01 F | 2 | VK4 | 98.99 |
| K2 | QQYGSSPNT | FGQGTKLEIK | IGKV3-20*01 F | 15 | VK3 | 92.20 |
| K3 | IQALQTYT | FGQGTKLEIR | IGKV2-28*01 F | 5 | VK2 | 97.62 |
| K4 | QQYKTYWT | FGQGTKVESK | IGKV1-5*03 F | 15 | VK1 | 89.61 |
| K5 | QQYGSSPFT | FGPGTKVDIK | IGKV3-28*01 F | 5 | VK3 | 97.16 |
| K6 | HQYGTAPHT | FGQGTKLEIK | IGKV3-28*01 F | 14 | VK3 | 92.20 |
| K7 | QQATNFPPT | FGGGTKVEIK | IGKV1-12*02 F | 5 | VK1 | 97.13 |
| K8 | QQYGSSPTY | FGPGTKLEIK | IGKV3-20*01 F | 7 | VK3 | 95.74 |
| K9 | QQYRDIPDT | FGQGTKLEIK | IGKV1-39*01 F | 18 | VK1 | 87.87 |
| K10 | QQSFKTPPYT | FGQGTKVEIR | IGKV1-39*01 F | 22 | VK1 | 94.59 |
| K11 | QQYGSSPLT | FGGGTKVEIK | IGKV3-28*01 F | 14 | VK3 | 89.01 |
| K12 | QQSYSTPRYT | FGQGTKLEIK | IGKV1-39*01 F | 7 | VK1 | 94.98 |
| K13 | QQYFNLPRT | FGQGTKLEIK | IGKV4-1*01 F | 16 | VK4 | 90.91 |
| K14 | MQTIQLPHT | FGQGTKLEIK | IGKV2D-29*01 F | 12 | VK2 | 94.22 |
| K15 | QQYGSSPYT | FGQGTKLEIK | IGKV3-20*01 F | 9 | VK3 | 92.91 |
| K16 | HNHYGSSPPWT | FGQGTKVEIK | IGKV3-20*01 F | 12 | VK3 | 92.11 |
| K17 | HQYGSSPMYT | FGQGTKLEIK | IGKV3-20*01 F | 9 | VK3 | 94.98 |
| K18 | EQTKIAPYT | FGQGTKLEIK | IGKV1-39*01 F | 16 | VK1 | 96.77 |
| K19 | QQYGGSPVYT | FGQGTKLEIK | IGKV1-39*01 F | 11 | VK1 | 88.17 |
| K20 | QQSQDRAS | FGQGTKVEIK | IGKV3-20*01 F | 9 | VK3 | 91.76 |

TABLE 52

(Table 52 discloses the full-length sequence of SEQ ID NOS 177-196, respectively, in order of appearance)

| Clone | CDR1-IMGT | FR2-IMGT | CDR2-IMGT | FR3-IMGT | CDR3-IMGT |
|---|---|---|---|---|---|
| L1 | SSNIRSNT | VNWYQQFPGTAPKLLIY | SNN | QRPSGVPDRFSGSKSGTSASLAISGLQSEDEADYYC | AAWDDSLNGPV |
| L2 | SSNIGSNT | VNWYQQLPGTAPKLLIY | SNN | QRPSGVPDRFSGSKSGTSASLAISGLQSEDEADYYC | AAWDDSLNGPV |
| L3 | VSNIGSNI | VSWYQQFPGKAPKLLIY | NDS | QRPSGVPDRFSGSKSGTSASLAISGLQSEDEAEYYC | ATWDDILRGRV |
| L4 | SSNIGRNS | VHWYQQFPGTAPKLLLY | TNN | QRPSGVPDRFSGSRSGTSASLAISGLRSEDESDYYC | AAWDDSLRGVV |
| L5 | SGSIASNY | VQWSQQRPGSSPTTVIY | EDN | QRPSGVPDRFSGSIDSSSNSASLTISGLKTESEADYYC | QSSDSSNWV |
| L6 | SSNIGSNP | VNWYQQLPGTAPRLLVY | SND | QRPSGVPARFSASRYASSVSLSIRGLRSEDEAVYHC | SSWDDSXDGRV |
| L7 | SSNIGSTFD | VNWYQQLPGTAPKVLIY | GNN | NRPSGVPDXFSGSKSGASASLAINGLQAEDEADYYC | QSFDSSLRGSV |
| L8 | RSNIGSSN | VYWYQQFPGTPAKLLIY | RNN | QRPSGVPDRFSGSRSGTSASLAISDLRSDDEADYYC | AAWDASLNGVA |
| L9 | GGSIASKY | VQWYQLRPGSAPTTVIY | ENN | QRPSGVPARFSGSLDTSSNSASLTISGLKTEDEADYYC | QSSTSTNDRI |
| L10 | SRDIGSDNY | VSWYQYRPGRAPKIIIY | EVH | KRPSGVPDRFSGSKSGNTASLTVSGLQAEDEADYYC | SSNGGGGLLV |
| L11 | SSNIGRNS | VNWYHQFPGTAPNLLIY | GSN | QRPSGVPDRFSGSKSGTSASLAISGLQSEDEADYYC | AAWDDSLRGRL |
| L12 | NSNIGSHT | GNWYQQLPGAAPRLLIY | MNN | KRPSGIPERFSGSKSGNTATLTIDRVEPGDEADFFC | QVWSDTYHWV |
| L13 | NSNIGSNT | VNWYQQLPGTPAKLLIY | SDD | QRPSGVPDRFSGSKSGTSASLAIGGLQSEDEADYYC | SAWDDSLDGPL |
| L14 | NLWDKY | VSWYQQRPGQPPVLLLY | RDN | MRPSGIPERFSGSNSDNTATLTISGTQAMDEADYYC | QVWGTDSYV |
| L15 | SSNIGSNY | VSWYQQLPGTAPKLLIY | DNN | KRPSGIPDRFSGSKSGTSATLAISGLQTGDEADYYC | ATWDDILRGRV |
| L16 | SGSIAGNY | VWQYQQRPGSSPTTVMY | EDN | QRPSGVPDRFSGSIDSSSNSASLTISGLRAEDEADYYC | QSYDSNNHVV |

TABLE 52-continued

| | | | | |
|---|---|---|---|---|
| L17 | SSNIGSNT | VNWYQQLPGTPAKLLIY | SNN | QRPSGVPDRFSGSKSGTSASLAISGLQSEDEADYYC | AAWDDSLNGPV |
| L18 | SDVNVDNYN | IYWYQQKPGSPPRYLLY | YYSDSDK | GQGSGVPSRFSGSKDASANTGILLISGLQSEDEADYYC | MIWPSNAWV |
| L19 | KLGDKY | ACWYXXKPGQSPVLIY | XDX | KXPSXIPERFSGSXSGNTATLTXSGTQXMDEXDYYC | XXXDSXTAVV |
| L20 | SSNIGSNT | VNWYQQLPGTAPKLLIY | NSN | QRPSGVPDRFSGSKSGTSASLAISGLQSEDEADYDC | AAWDDSLNGYV |

| Clone | FR4-IMGT | Germline | Amino acid difference from germline | Family | Percentage Identity |
|---|---|---|---|---|---|
| L1 | FGGGTKLTVL | IGLV1-44*01 F | 6 | VL1 | 96.14 |
| L2 | FGGGTKLTVL | IGLV1-44*01 F | 2 | VL1 | 97.89 |
| L3 | FGGGTKLSVL | IGLV1-44*01 F | 15 | VL1 | 92.63 |
| L4 | FGGGTHLTVL | IGLV1-47*02 F | 11 | VL1 | 94.04 |
| L5 | FGGGTKLTVL | ITLV6-57*01 F | 4 | VL6 | 97.25 |
| L6 | FDGGTRLTVL | IGLV1-44*01 F | 23 | VL1 | 88.42 |
| L7 | FGGGTRLTVL | IGLV1-40*01 F | 13 | VL1 | 93.06 |
| L8 | FGGGTKVTVL | IGLV1-47*01 F | 11 | VL1 | 92.63 |
| L9 | FGGGTKLTVL | IGLV6-57*01 F | 14 | VL6 | 90.72 |
| L10 | FGGGTKLTVL | IGLV2-8*01 F | 17 | VL2 | 92.71 |
| L11 | FGGGTKVTVL | IGLV1-44*01 F | 10 | VL1 | 93.68 |
| L12 | FGGGTKLTVL | IGLV1-44*01 F | 32 | VL1 | 82.11 |
| L13 | FGGGTRVTVL | IGLV1-44*01 F | 8 | VL1 | 95.79 |
| L14 | FGTGTKLSVL | IGLV3-1*01 F | 22 | VL3 | 85.30 |
| L15 | FGGGTKLSVL | IGLV1-51*01 F | 10 | VL1 | 94.39 |
| L16 | FGGGTKLTVL | IGLV6-57*01 F | 7 | VL6 | 96.22 |
| L17 | FGGGTKLTVL | IGLV1-44*01 F | 2 | VL1 | 98.25 |
| L18 | FGGGTKLTVL | IGLV5-37*01 F | 7 | VL5 | 97.06 |
| L19 | XGGGTKLTVL | IGLV3-1*01 F | 19 | VL3 | 91.04 |
| 2L9 | FGTGTKVTVL | IGLV1-44*01 F | 5 | VL1 | 97.54 |

TABLE 53

(Table 53 discloses the full-length sequence of SEQ ID NOS 197-236, respectively, in order of appearance)

| Clone | FR1-IMGT | CDR1-IMGT | FR2-IMGT | CDR2-IMGT | FR3-IMGT |
|---|---|---|---|---|---|
| K1 | QVQLVQSGAELKQPGESLKISCKGS | EYIFTNYW | IVWVRQMPGKGLEWMGV | IYPGDSHT | RYSPSFQGQVTISADKSITTAYLQWSSLEASDTAIYYC |
| K2 | QITLKESGPTLVKPTQTLTLTCTFS | GISLSTSGVG | VGWIRQPPGKALEWLAL | IYWDDDK | RYSPSLSRLTITKDTSKNQVVLTMTNMDPVDTATYYC |
| K3 | EVQLVESGGGLVRPGGSLTLSCAAS | GFTFPDAW | MSRVRQSPGTGLEWVGR | IQSKKDGGAA | VFAAPVKGRFSISRDDSKTTPFFQMNSMKPEESAVYFC |
| K4 | EVQLVESGGGLVQPGGSLRLSCAAS | RFTFSRYW | IHWVRLVPGKGLVWVSR | ISPDGNSI | SYADSVKGRFTISRDNAENTLYLQMNGLRAEDTAVYYC |
| K5 | QVQLQESGPGLVKPSETLSLTCTVS | GYSISSAYH | WGWIRQPPGKGLEWIGN | IYHSGST | SYNPSLKSRVTILIDTSKSQFSLKLSSVTAADTAVYYC |
| K6 | QITLKESGPTLVKPTQTLTLTCTFS | GFSFSARDVG | VGWIRQPPGKALEWLAL | IYWDDAK | YYSPSLKSRLTITKDTSKNQVVLTMTNMDPVDTATYYC |
| K7 | QVQLQESGSGLVKPSQTLSLTCAVS | GGSISSGGYS | WSWIRQPPGKGLEWIGY | IYYSGST | NYNPSLKSRVTISVDTSKNQFSLNLTSVTAADTAVYYC |
| K8 | QVQLVESGGGLVQPGRSLRLSCAAS | GFIFSSYA | MHWVRQAPGKGLEWVAL | ISYDGTNK | HYADSVKGRFTVSRDDSKNTLYLQMNSLRAEDSAVYYC |
| K9 | EVQLVESGGGLVQPGGSLRLSCAAS | GFTFSTYE | MNWVRQAPGKGLEWVSY | ISSSGSTI | YYADSVEGRFTISRDNARNSLFLQMNSLRAEDTATYYC |
| K10 | QVQLVESGAEVKKPGASVKVSCKAS | GYTFTSYY | MHWVRQAPGQGLEWMGI | INPSGGST | SYAQKFQGRVTMTRDTSTSTVYMELSSLRSEDTAVYYC |
| K11 | EVQLVESGGALAQPGGSLRLSCAAS | GFIFDDYG | MHWVRQVPRKGLEWVSG | ISGNSVDI | GYADSVDGRFTISRDNAKNSLYLMENSLRPEDTALYYC |
| K12 | QVQLVQSGGDLVQPGGSLRLSCAAS | GFTFSNHW | INWVRQAPGKGLEWVAN | INEDGTIK | YYVDSVKGRFTISRDYAKNSVYLQMNSLRAEDTAVYYC |
| K13 | QVQLVQSGAEVKKPGASVKVSCKAS | GYSFTGYY | IHWVRQAPGQGLEWMGW | MNPNSGNT | GYAQKFQGRVTMTRNTSISTAYMELSSLRSEDTAVYFC |
| K14 | EVQLVESGAEVKKPGASVKVSCKAS | GYTFTGYY | MHWVRQAPGQGLEWMGW | INPNSGGT | NYAQKFQGRVTMTRDTSISTAYMELSRLRSDDTAVYYC |
| K15 | QVQLQESGPGLVKPSETLSLICTVS | GGSISSYY | WSWIRQPPGKGLEWIGY | IYYTGSS | EYNPSLKSRVTISIDTPKNQFSVKLTSVTAADTAIYYC |
| K16 | EVQLVESGAEVKKPGESLKISCKGS | GYSFTSYW | IGWVRQMPGKGLEWMGI | IYPGDSDT | RYSPSFQGQGTISADKSISTAYLQWSSLKASDTAMYYC |
| K17 | QVQLVESGGGLVQPGGSLRLSCAAS | GFTFSSYE | MNWVRQAPGKGLEWVSY | ITGSGYTI | YYADSVKGRFTISRDNAKKLLYLQMDSLRAEDTAVYYC |
| K18 | EVQLVESGGGVLQPGGSLRLSCAAS | GFTFNSYI | MSWVRQAPGKGPEWVSS | IGASGLNT | FYADSVKGRFTISRDIPKNTLYLQMNGLRVEDTAIYYC |
| K19 | QVQLVESGGGLVHPGRSLRLSCATS | GFIFDDYA | MHWVRQAPGKGLEWVSG | ISWNGGRI | GYEDSVKGRFTISRDNAKNSLTLEMNSLRAEDTALYYC |
| K20 | QVQLQQWGAGLLKPSETLSLTCGVY | DGSFSGYS | WSWVRQSPGKGLEWIGE | ISHRGVT | DYNPFLKSRVTISLDVKSRQFSLQLTSLTAADTATYYC |

TABLE 53-continued

| | | | | |
|---|---|---|---|---|
| L1 | QVQLQQWGAGLLKPSETLSLTCAVY | GGSFSGYY | WNWIRQPPGKGLEWIGE | NNHSGST | NYNPSLKSRVTISVDTSKNQFSLRLRSVTAADTAVYYC |
| L2 | QVQLQESGPGLVKPSETLSLTCTVS | GDSMSSYY | WSWIRQPAGKGLEWIGR | FYSSASI | SYNPSLQSRVTMSVDTSKNQFSLKLTSVTAADTAVYYC |
| L3 | QVQLVQSGAEVKKPGASVKVSCKAF | GYSFTDYF | IHWVRQAPGQGLEWMGW | INPNSGAT | KYAQKFQGRVTMTRDTSISTAFMDLSSLTSDDTAVYFC |
| L4 | QITLKESGPTLVKPTQTLTITCTFS | GSSLSTSGEA | LGWIRQPPGKALEWLAL | IFWDGDK | RYRPSLKSRLSITKDTSKNQVVLKMTNMDPVDTATYHC |
| L5 | QITLKESGPTLVKPTQTLTLACTFS | AFSLSTSGVG | VGWFRQPPGKALEWLAL | IYWDDDK | RYSPSLKSRLTITKDTSKNQVVLTMTNMDPVDTATYYC |
| L6 | EVQLVQSGAEVKKPGSSVKVSCKAS | GDTFSNYA | INWVRQAPGQGLEWMGW | INAYNGHT | NYAWKLQGRVTMTTDTSTSTAYMELRSLRSDDTAVYYC |
| L7 | QVQLQQWGAGLLKPSETLSLTCAVY | GESFSGHY | WAWIRQPPGKGLEWIGE | IEYSGPT | NYNPSLKSRVSMSVYTSKKRFFLKLTSVTAADTAVYYC |
| L8 | QVQLQQWGSGLLKPSETLSLTCAVY | GGSFSGHY | WSWIRQPPGRGLEWIGE | INHGGST | SYNPSLKSRVSISVDTSEQFSLTLSSVTAADTAVYYC |
| L9 | QVQLQQWGAGLLKPSETLSLTCAVY | GGSFSGYY | WSWIRQPPGKGLEWIGE | INHSGST | NYNPSLKGRGTISLDTTKNQFSLRLSSMTAADTAVYYC |
| L10 | PXELXESGPGLVKPSETLSLTCVS | GGSLNSSTNF | WGWIRQPPGKGLEWIAT | IYWSGYT | QYNPSLKSRVTTSEDTSKNQFSLKMTSVTAADTAIYYC |
| L11 | QVQLQQWGAGLLKPSETLSLTCAVY | GGSFSGFY | WTWIRRHPGKGLEWIGE | INDRGST | SYNPSLKSRVTISIDTSKSLFSLKLTSVTAADTAVYYC |
| L12 | QVQLQQWGAGLLKPSETLSLTCAVY | GGSFSGYY | WSWIRQPPGKGLEWIGE | INHSGST | NYNPSLKSRVTISVDTSKNQFSLRLSSVTAADTAVYYC |
| L13 | QVQLVQSGAEVKKPGESLKISCKAS | GYIFTNYW | IGWVRQMPGKGLEWMGL | IHPGDSDT | RYSPFFQGQVTISADKSINTAYLQWSSLQGSDTAMYFC |
| L14 | QVQLVQSGAEVKKSEGSLKISCRGS | GYRFATYW | IGWVRQLPGKGLEWMGI | IYPGDTTS | RYSPSPQGQVTISADKSINTAYLQWSTLKASDTAMYYC |
| L15 | QVQLQQWGAGLLKPSETLSLTCAVS | GGSFSTYY | WSWIRQPPGKGLEWIGE | ISHIGYT | NYSPSLKGRVTISLATSKNEFSLRLNSVTAADTAMYYC |
| L16 | QVQLQESGPGLVKPSETLSLTCTVS | GGSISTYY | WSWIRQPAGKGLEWIGR | FYASGGT | HYNPSLKSRVTMSVDTSKNQFSLKLISVTAADTAVYYC |
| L17 | QVQLQESGPGLVKPSETLSLTCTVS | GDSMSSYY | WSWIRQPAGKGLEWIGR | FYSSASI | SYNPSLQSRVTMSVDTSKNQFSLKLTSVTAADTAVYYC |
| L18 | EVQLVQSGAEVKKPGSSVKVSCKAS | GDTFSNYA | INWVRQAPGQGLEWMGW | INAYNGHT | NYAQKLQGRVTMTTDTSTSTAYMELRSLRSDDTAVYYC |
| L19 | QVQLQQWGAGLLKPSETLSLTCAVY | GGSFSGYY | WSWIRQPPGKGLEWIGE | INHSGST | NYNPSLKSRVTISVDTSKNQFSLKLSSVTAADTAVYYC |
| L20 | QVQLVQSGAEVKKPGASVKVSCKAF | GYSFTDYF | IHWVRQAPGQGLEWMGW | INPNSGAT | KYAQKFQGRVTMTRDTSISTAFMDLSSLTSDDTAVYFC |

| Clone | CDR3-IMGT | FR4-IMGT | Germline | Amino acid difference from germline | Family | Percentage Identity |
|---|---|---|---|---|---|---|
| K1 | ATSPLTYGYYLDY | WGQGTLVTVSS | IGHV5-51*01 F | 12 | VH5 | 95.5 |
| K2 | AHRQRLGYSYTWAAEYFQH | WGQGLTVTVSP | IGHV2-5*02 F | 1 | VH2 | 99.7 |
| K3 | TSHLDYGDYEGWYFDL | WGHGTRVTVSP | IGHV3-15*01 F | 23 | VH3 | 86.4 |
| K4 | VIWPTPMITDLDV | WGQGTAVTVSP | IGHV3-74*01 F | 11 | VH3 | 93.1 |
| K5 | ATVAVAGTKWFGP | WGQGTLVTVSS | IGHV4-38-2*02 F | 7 | VH4 | 96.9 |
| K6 | GHKGVIAVRYFDY | WGQGTTVTVSP | IGHV2-5*02 F | 7 | VH2 | 94.2 |
| K7 | ARHYKGFDL | WGQGTLVTVSS | IGHV4-30-4*07 F | 4 | VH4 | 95.5 |
| K8 | VRALLTAAGPEDV | WGQGTTVTVSS | IGHV3-30*04 F | 9 | VH3 | 94.1 |
| K9 | AAKVGLDF | WGRGTLVTVSP | IGHV1-46*01 F | 7 | VH1 | 99.7 |
| K10 | ARDGDTGFHDPFDI | WGQGTLVTVSS | IGHV3-9*01 F | 1 | VH3 | 92.4 |
| K11 | VKAWTVVGATTDSFDF | WGQGTLVTVSP | IGHV3-7*01 F | 14 | VH3 | 94.1 |
| K12 | ARRSGGPFDY | WGQGTLVTVSP | IGHV1-8*02 F | 13 | VH1 | 96.9 |
| K13 | ARATVTPLYYYYMDV | WGKGTLVTVSS | IGHV1-2*02 F | 6 | VH1 | 99.3 |
| K14 | ARDEPRSEWYSSSYYFDY | WGQGTLVTVSP | IGHV4-59*01 F | 2 | VH4 | 94.7 |
| K15 | ARSRSPYYYPEAFDP | WGQGTLVTVSS | IGHV5-51*01 F | 9 | VH5 | 99.7 |
| K16 | ARLSRSGYPTCDY | WGQGTLVTVSP | IGHV3-48*03 F | 1 | VH3 | 96.9 |
| K17 | ALGYDY | WGQGTLVTVSS | IGHV3-23*04 F | 7 | VH3 | 92.7 |
| K18 | AKALVVGKNWFDP | WGQGTLVTVSS | IGHV3-9*01 F | 14 | VH3 | 95.5 |
| K19 | AKGPTAGYYNYMDV | WGKGTLVNVSS | IGHV4-34*01 F | 8 | VH4 | 88.8 |
| K20 | ARLEPGNFWFDP | WGQGTLVTVSS | IGHV4-34*01 F | 17 | VH4 | 94.4 |
| L1 | ARGFLGGMDV | WGQGTLVTVSS | IGHV4-34*01 F | 4 | VH4 | 97.5 |
| L2 | VSGWYRAFVSY | WGQGTLVTVSS | IGHV4-4*07 F | 9 | VH4 | 94.4 |
| L3 | ARFEGVVPTILHSGYDY | WGQGTLVTVSS | IGHV1-2*02 F | 12 | VH1 | 94.4 |
| L4 | AHRLFYQSITSYGNPFDI | WGQGMTVTVSS | IGHV2-5*02 F | 10 | VH2 | 94.8 |
| L5 | AHRPRPDYFGSGSYMAFDP | WGQGTLVTVSS | IGHV2-5*02 F | 3 | VH2 | 98.6 |
| L6 | ARDMVRGVILWFDP | WGQGTLVTVSS | IGHV1-18*04 F | 9 | VH1 | 94.8 |
| L7 | ARAPMVRGVPPDFDY | WGQGTLVTVSS | IGHV4-34*01 F | 13 | VH4 | 91.6 |
| L8 | ARGGDYYDDYIAD | WGQGTLVTVSS | IGHV4-34*01 F | 8 | VH4 | 95.4 |
| L9 | ARESTTYGYGRFDL | WGRGTLVTVSS | IGHV4-34*01 F | 6 | VH4 | 97.2 |
| L10 | ARLNFGVERLDY | WGQGTLVTVSP | IGHV4-39*01 F | 20 | VH4 | 89.3 |
| L11 | ARGGLDGDYASL | WGQGALVTVSS | IGHV4-34*01 F | 11 | VH4 | 94.4 |
| L12 | ASRRSYDEILTPYILVD | SGQGNLVTVSP | IGHV4-34*01 F | 1 | VH4 | 98.9 |
| L13 | ASGGKYYFDH | WGQGTLVTVSS | IGHV5-51*01 F | 11 | VH5 | 95.1 |
| L14 | ARLERVVSRNLYIGMDV | WGQGTTVTVSP | IGHV5-51*01 F | 12 | VH5 | 94.8 |

TABLE 53-continued

| | | | | | | |
|---|---|---|---|---|---|---|
| L15 | ARGLRVGGCSGGYCDPFSY | WGQGALVTVSS | IGHV4-34*01 F | 13 | VH4 | 91.9 |
| L16 | TRASGTGTTGFDY | WGQGTLVTVSS | IGHV4-4*07 F | 7 | VH4 | 96.8 |
| L17 | VSGWYRAFVSY | WGQGTLVTVSS | IGHV4-4*07 F | 9 | VH4 | 94.4 |
| L18 | ARDMVRGVILWFDP | WGQGTLVTVSS | IGHV1-18*01 F | 9 | VH1 | 94.8 |
| L19 | ARPRGYSGYDFDY | WGQGTLVTVSS | IGHV4-34*01 F | 0 | VH4 | 99.3 |
| L20 | ARFEGVVPTILHSGYDY | WGQGTLVTVSS | IGHV4-34*01 F | 2 | VH4 | 99.3 |

Example 26

Phage Conversions and Solid Phase Panning

For preparative large scale conversion of a total of $3.4 \times 10^9$ cfu of naïve human phagemid library obtained at Example 22 and represented at Table 40 from bacteria to phages, 10-fold excess of bacterial cells of each of the 5 sub-libraries were inoculated in the culture medium in defined volumes to get final $OD_{600}$~0.1. 10-fold excess cells as a primary inoculum of the library size were chosen to get a complete representation from each of the independent transformants of the stored library. Each of the 5 sub-libraries (Table 40) was inoculated independently into 400 ml of medium. Inoculated primary library cultures were grown till 0.5 $OD_{600}$, and used for infection using VCSM13. The infected cultures were finally diluted 10-fold for phage propagation in overnight culture (volume ~4000 ml) at reduced temperature to favor the solubility of the antibody fragment-pIII fusion polypeptides (Thie et al., 2008). The phages from overnight culture were obtained by two successive centrifugations. Efficient screening of phage display library requires high purity of the input phages. Double precipitation by polyethylene glycol (PEG 8000) was used to purify the phages. The yield of phages in terms of phage titer was determined as (a) transducing or colony forming units (cfu) by infecting E. coli TG1 cells with appropriate dilutions; and (b) using the following empirical formula (Bonnycastle L L C et al., 2001. General phage methods. In: *Phage Display: A Laboratory Manual*):

$$Phage/ml = OD_{260} \times Dilution\ factor \times 22.14 \times 10^{10}$$

The total phage yield from each of the 5 sub-libraries from one batch was determined to be in the range of $2-4 \times 10^{14}$ cfu. These library stock phages were stored at $1-2 \times 10^{13}$/ml at −80° C. The converted library was checked for presence of full length Fabs (~1.5 kb) by colony PCR of 12 randomly selected clones.

Figure 31:
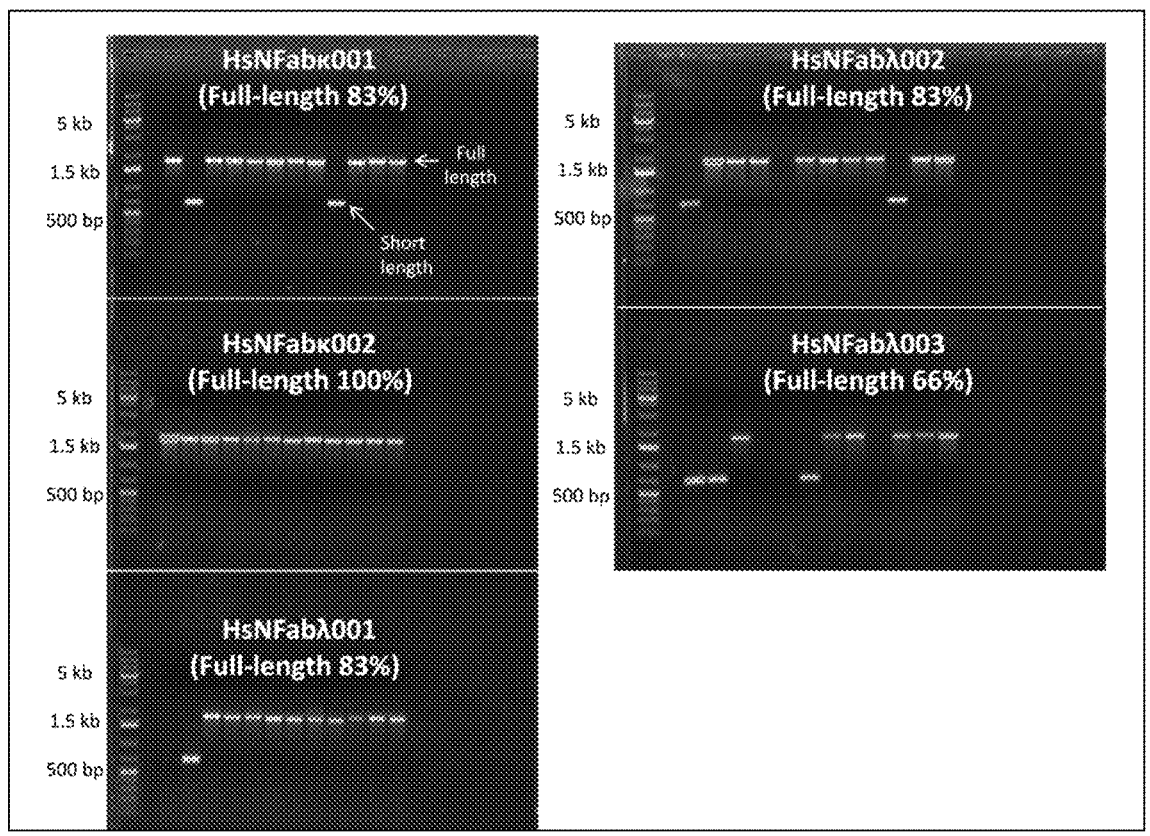
FIG. 31 depicts quality check of phage library by colony PCR from phage transductant clones. The Fab inserts were PCR-amplified from diluted culture of randomly selected clones using vector backbone primers. Products were analyzed on a 1% agarose gel prepared in 1×TBE containing 0.1 µg/mL ethidium bromide and run at 5V/cm for 1.5 h.

FIG. 31 demonstrates the results of conversion of the said library into phage format. From the results, it is evident that short length clones are present (up to ~20%) after conversion. To remove the majority of short length clones after amplification and during panning, it necessitated formulation of novel strategies as set out herein below to obtain high percentage of full length clones, preferably with lesser number of panning.

A method of removing short length clones from an ultra-large scFv library during solid phase panning has been described (de Bruin R et al., 1999). The method set out in de Bruin R et al., 1999, was examined herein. 2 sets of 12×8-well PolySorp strips (Nunc) were arranged on 96-well frames (2 PolySorp 96-well plates). Plate 1 was coated with 10 µg/mL of a bait antigen in carbonate-bicarbonate buffer, pH 9.6, for 1 h at 37° C. Plate 2 was used as a "No coat control" in which the coating buffer (carbonate-bicarbonate buffer, pH 9.6) alone was added. After the incubation, wells in plates 1 and 2 were blocked with 2% BSA in 1×TBS for 1 h at 37° C. $1 \times 10^{12}$ pfu/mL of mixed kappa and lambda phages were transferred to all wells of plates 1 and 2 and incubated for 2 h at 37° C. The unbound phages from plates 1 and 2 were removed by 15 washes with 1×TBST followed by 10 washes with 1×TBS. All washes were carried out in a microplate washer (BioRad Model PW-40). Following the washes, a step elution approach was used as described (de Bruin R et al., 1999). After a 10 min pre-incubation, four successive elutions were performed after 10 min of incubation each at 37° C. The titers of eluted phages from each step were calculated by transducing aliquots in E. coli (TG1 strain; Table 54).

TABLE 54

| S. No. | Test Sample (High pH Elution) | Host | Expected Outcome | Observed Titer (cfu/ml) |
|---|---|---|---|---|
| 1 | TG1 | | 0 | 0 |
| 2 | TG1 + Diluent + 37° C. + 30 min | | 0 | 0 |
| 3 | Input phage (pool of sub-lirary phages) | | 0 | 0 |
| 4 | Diluent | | 0 | 0 |
| 5 | No coat (20 min) | TG1 | 0 | 0 |
| 6 | 0 min | TG1 | | $1 \times 10^6$/ml |
| 7 | 10 min | TG1 | | $1.7 \times 10^5$/ml |
| 8 | 20 min | TG1 | | $2 \times 10^5$/ml |
| 9 | 30 min | TG1 | | $1.9 \times 10^5$/ml |
| 10 | 40 min | TG1 | | $1.2 \times 10^5$/ml |
| 11 | 60 min | TG1 | | $5 \times 10^5$/ml |

A sample of the transductants was screened by colony PCR for estimating the size of the inserts. This analysis showed insignificant decrease in the proportion of short length Fabs after different lengths of incubation with triethylamine. Furthermore, sequencing demonstrated that most of the full-length Fabs were not translatable due to the presence of in-frame STOP codons.

Example 27

Apparent Success of Panning Despite Presence of Short Length Clones

All eluates from individual time points of Table 54 were carried forward for panning in the next two rounds. Bait antigen concentration was reduced to 5 µg/ml in the $2^{nd}$ round and 2 µg/ml in the $3^{rd}$ round. Phage eluate titers were monitored at each round of panning, converted to phagemid format by TG1 transduction, and stored as glycerol stocks. These glycerol stocks were converted to phage format (amplified) by VCSM13 transduction before each round of panning. Bait-specific phage ELISA was carried out from these amplified eluate pools from the $2^{nd}$ and $3^{rd}$ rounds. For this purpose, 8-well PolySorp strips (Nunc) were arranged on 96-well frames and coated with bait antigen as described in Example 26. A parallel set of strips were also set up without antigen coating. 100 µl of respective phage pools with an average start titer of $2 \times 10^{12}$/mL and end titer of $2.6 \times 10^9$/mL were added into respective wells, and incubated for 2 h at 37° C. After washing 3 times using TBST, 100 µl of HRP conjugated anti-gVIII detection antibody was added at 1:5000 dilutions per well and incubated at 37° C. for 1 h.

Unbound detection antibody was removed by washing 3 times with TBST followed by 3 times with TBS. 100 µl of TMB substrate was then added per well and incubated for 20 min in dark. Reaction was stopped by addition of 2M $H_2SO_4$ and color generated was read at 450 nm. The $A_{450}$ values highlighted in Table 55 represent the titer of the respective $2^{nd}$ round phage pool (PO3) giving $A_{450}$ close to 0.5, which is ~10 times higher the value of No coat control read i.e. 0.06. This data suggests that phages after the $2^{nd}$ round of panning are enriched for antigen reactivity over the library clones (compare titers from library pools that have 10× values over background $A_{450}$ values against titers from panned pools).

TABLE 55

| Phage titer | P03 | | | | | |
|---|---|---|---|---|---|---|
| | 0' | 10' | 20' | 30' | 40' | 60' |
| Coating: No Coat Detection using HRP conjugated gene VIII antibody | | | | | | |
| $2.0 \times 10^{12}$/ml | 0.06 | 0.06 | 0.06 | 0.06 | 0.06 | 0.06 |
| $6.7 \times 10^{11}$/ml | 0.06 | 0.07 | 0.07 | 0.06 | 0.06 | 0.07 |
| $2.2 \times 10^{11}$/ml | 0.06 | 0.06 | 0.06 | 0.06 | 0.06 | 0.07 |
| $7.3 \times 10^{10}$/ml | 0.06 | 0.06 | 0.06 | 0.06 | 0.06 | 0.06 |
| $2.4 \times 10^{10}$/ml | 0.06 | 0.06 | 0.06 | 0.06 | 0.06 | 0.06 |
| $8.0 \times 10^{9}$/ml | 0.06 | 0.06 | 0.06 | 0.06 | 0.06 | 0.06 |
| $2.6 \times 10^{9}$/ml | 0.06 | 0.06 | 0.06 | 0.06 | 0.06 | 0.06 |
| −C, +P | 0.06 | 0.06 | 0.06 | 0.06 | 0.06 | 0.07 |
| Coating: Antigen @ 2 µg/ml Detection using HRP conjugated gene VIII antibody | | | | | | |
| $2.0 \times 10^{12}$/ml | 1.81 | 2.12 | 2.54 | 2.01 | 2.19 | 2.32 |
| $6.7 \times 10^{11}$/ml | 1.13 | 1.67 | 1.98 | 2.04 | 2.26 | 2.31 |
| $2.2 \times 10^{11}$/ml | 0.62 | 0.82 | 1.10 | 1.05 | 1.62 | 0.99 |
| $7.3 \times 10^{10}$/ml | 0.30 | 0.48 | 0.52 | 0.57 | 0.93 | 0.66 |
| $2.4 \times 10^{10}$/ml | 0.12 | 0.22 | 0.19 | 0.17 | 0.29 | 0.23 |
| $8.0 \times 10^{9}$/ml | 0.09 | 0.11 | 0.11 | 0.11 | 0.13 | 0.13 |
| $2.6 \times 10^{9}$/ml | 0.07 | 0.08 | 0.07 | 0.07 | 0.07 | 0.09 |
| +C, −P | 0.06 | 0.06 | 0.06 | 0.06 | 0.06 | 0.06 |

| Phage titer | P03 | | | | | |
|---|---|---|---|---|---|---|
| | K001 | K002 | L001 | L002 | L003 | VCSM13 |
| Coating: No Coat Detection using HRP conjugated gene VIII antibody | | | | | | |
| $4.0 \times 10^{12}$/ml | 0.06 | 0.06 | 0.06 | 0.06 | 0.06 | 0.06 |
| $1.3 \times 10^{12}$/ml | 0.06 | 0.06 | 0.07 | 0.07 | 0.06 | 0.06 |
| $4.3 \times 10^{11}$/ml | 0.06 | 0.07 | 0.07 | 0.07 | 0.07 | 0.07 |
| $1.4 \times 10^{11}$/ml | 0.07 | 0.06 | 0.06 | 0.06 | 0.07 | 0.06 |
| $4.6 \times 10^{10}$/ml | 0.06 | 0.06 | 0.06 | 0.07 | 0.07 | 0.06 |
| $1.6 \times 10^{10}$/ml | 0.06 | 0.06 | 0.06 | 0.06 | 0.06 | 0.06 |
| $5.3 \times 10^{9}$/ml | 0.06 | 0.06 | 0.06 | 0.06 | 0.06 | 0.07 |
| −C, +P | 0.07 | 0.06 | 0.07 | 0.07 | 0.07 | 0.07 |
| Coating: Antigen @ 2 µg/ml Detection using HRP conjugated gene VIII antibody | | | | | | |
| $4.0 \times 10^{12}$/ml | 2.68 | 2.07 | 1.77 | 1.95 | 0.36 | 1.13 |
| $1.3 \times 10^{12}$/ml | 2.04 | 2.24 | 2.02 | 1.84 | 0.22 | 1.15 |
| $4.3 \times 10^{11}$/ml | 1.16 | 1.20 | 1.26 | 1.28 | 0.11 | 0.50 |
| $1.4 \times 10^{11}$/ml | 0.51 | 0.61 | 0.77 | 0.77 | 0.11 | 0.24 |
| $4.6 \times 10^{10}$/ml | 0.19 | 0.21 | 0.31 | 0.27 | 0.07 | 0.10 |
| $1.6 \times 10^{10}$/ml | 0.10 | 0.11 | 0.16 | 0.13 | 0.06 | 0.08 |
| $5.3 \times 10^{9}$/ml | 0.07 | 0.08 | 0.09 | 0.10 | 0.06 | 0.07 |
| +C, −P | 0.06 | 0.06 | 0.06 | 0.06 | 0.07 | 0.06 |

Figure 32:
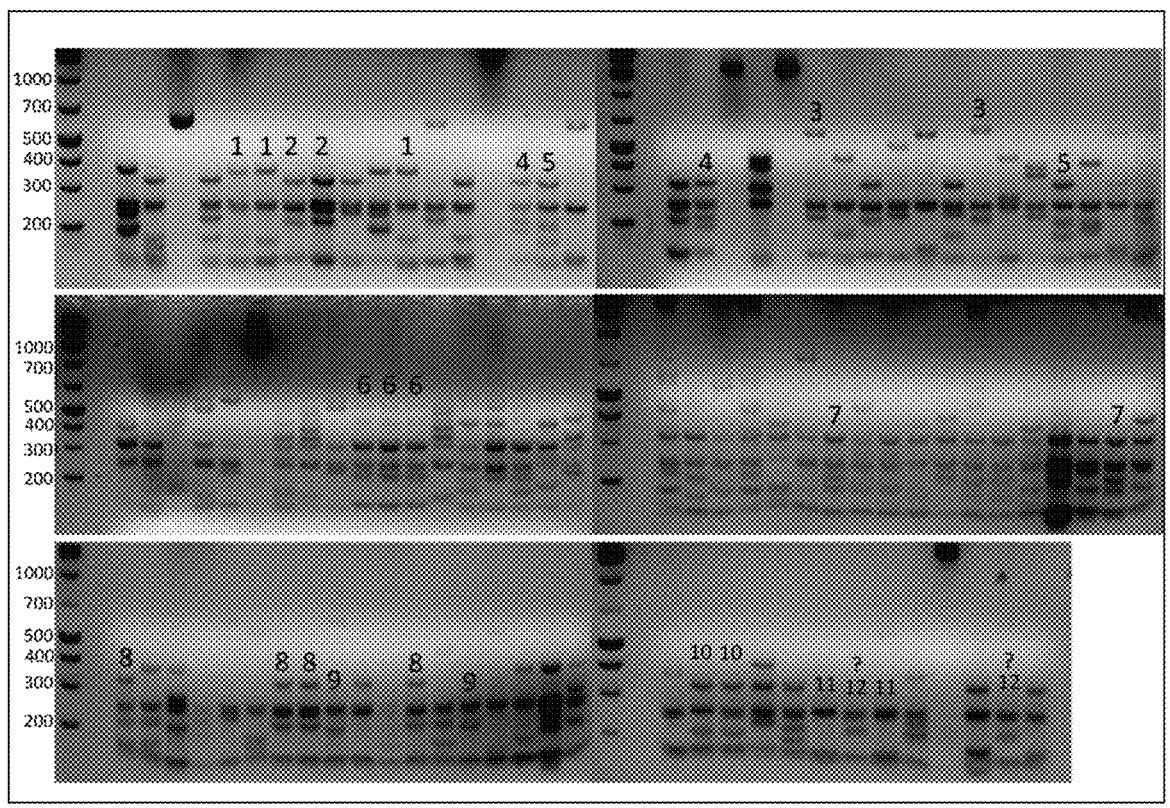
FIG. 32 depicts BstNI fingerprinting of P04 clones (from $3^{rd}$ round panned pools against target antigen). The digests were run on 3% agarose gel to analyze the restriction pattern. Agarose gel in invert mode is shown for better contrast between banding patterns. Products were run in 1×TBE buffer containing 0.1 µg/mL ethidium bromide in 3% agarose gel prepared in same buffer for 2.5 h at 6V/cm. Numbers on top of lanes indicate respective repeat pattern clones. Number at the left shows respective DNA marker positions in bp.

The anti-antigen ELISA for freshly prepared P03 (Round 2 panned) and P04 (Round 3 panned) phage pools conducted simultaneously. However, when compared to the previous round, there was no enrichment of ELISA reactivity in P04 phages, suggesting that the panning process has reached a saturation point. This conclusion was also supported by BstNI fingerprinting of full length clones from P04 (102 clones). For this purpose, an aliquot of the PCR products from the colony PCR exercise was used as sample for each clone. This analysis clearly shows a number of clones with repeat fingerprints indicating successful panning and discovery of apparently genuine binders against the target antigen (FIG. 32).

To isolate monoclonal binders from rounds 2 & 3 of panning, 576 individual clones (phagemids) from round 2 and 288 from round 3 were picked up and analyzed by colony PCR. 20 of these full-length clones were converted to phage format by VCSM13 transduction, and the phage preparations tested for their ELISA reactivity against the bait antigen as previous. Table 56 shows that all of these were ELISA reactive.

TABLE 56

| Phage titer per ml | Phage: CO4_Full-Length_Monoclonal_Hits (PEG ppt). | | | | | | | | | | |
|---|---|---|---|---|---|---|---|---|---|---|---|
| | 23 | 24 | 25 | 26 | 27 | 28 | 29 | 30 | 31 | 32 | 33 |
| $1.0 \times 10^{12}$ | 1.28 | 1.72 | 1.19 | 1.78 | 1.46 | 1.71 | 1.83 | 1.63 | 1.48 | 1.55 | 1.65 |
| $3.3 \times 10^{11}$ | 0.76 | 1.10 | 0.87 | 0.92 | 0.73 | 0.98 | 0.45 | 1.06 | 0.48 | 0.76 | 0.55 |
| $1.0 \times 10^{11}$ | 0.11 | 0.27 | 0.23 | 0.23 | 0.16 | 0.26 | 0.15 | 0.43 | 0.14 | 0.20 | 0.16 |
| $3.3 \times 10^{10}$ | 0.05 | 0.11 | 0.10 | 0.09 | 0.08 | 0.10 | 0.08 | 0.14 | 0.08 | 0.08 | 0.09 |
| $1.0 \times 10^{10}$ | 0.05 | 0.06 | 0.10 | 0.06 | 0.05 | 0.06 | 0.06 | 0.06 | 0.05 | 0.07 | 0.05 |
| $3.3 \times 10^{9}$ | 0.05 | 0.05 | 0.05 | 0.05 | 0.05 | 0.05 | 0.05 | 0.06 | 0.05 | 0.06 | 0.05 |
| $1.0 \times 10^{9}$ | 0.05 | 0.04 | 0.04 | 0.05 | 0.05 | 0.05 | 0.05 | 0.04 | 0.05 | 0.04 | 0.05 |
| +C −P | 0.04 | 0.04 | 0.04 | 0.04 | 0.04 | 0.04 | 0.04 | 0.04 | 0.04 | 0.04 | 0.04 |

| Phage titer per ml | Phage: CO4_Full-Length_Monoclonal_Hits (PEG ppt). | | | | | | | | |
|---|---|---|---|---|---|---|---|---|---|
| | 34 | 35 | 36 | 37 | 38 | 39 | 40 | 41 | 42 |
| $1.0 \times 10^{12}$ | 1.15 | 1.39 | 1.70 | 1.65 | 1.73 | 1.47 | 1.63 | 1.69 | 1.41 |
| $3.3 \times 10^{11}$ | 1.58 | 0.54 | 0.49 | 0.70 | 0.89 | 0.65 | 0.64 | 0.40 | 0.31 |
| $1.0 \times 10^{11}$ | 0.42 | 0.16 | 0.18 | 0.21 | 0.20 | 0.23 | 0.22 | 0.16 | 0.13 |
| $3.3 \times 10^{10}$ | 0.12 | 0.07 | 0.07 | 0.08 | 0.08 | 0.08 | 0.08 | 0.07 | 0.07 |

TABLE 56-continued

| | | | | | | | | | |
|---|---|---|---|---|---|---|---|---|---|
| $1.0 \times 10^{10}$ | 0.06 | 0.05 | 0.05 | 0.05 | 0.06 | 0.05 | 0.06 | 0.05 | 0.05 |
| $3.3 \times 10^{9}$ | 0.06 | 0.05 | 0.05 | 0.05 | 0.05 | 0.05 | 0.05 | 0.05 | 0.05 |
| $1.0 \times 10^{9}$ | 0.05 | 0.04 | 0.05 | 0.04 | 0.04 | 0.04 | 0.04 | 0.04 | 0.04 |
| +C −P | 0.04 | 0.04 | 0.04 | 0.04 | 0.04 | 0.04 | 0.04 | 0.04 | 0.04 |

However, when the antigen ELISA positive clones were sequenced with five primers as detailed in Example 18, all of them were off-frame, which necessitates screening of a large number of clones to arrive at in-frame binder clones.

Example 28

Fabs can be Detected by Westerns in Periplasmic Extracts

Figure 33:
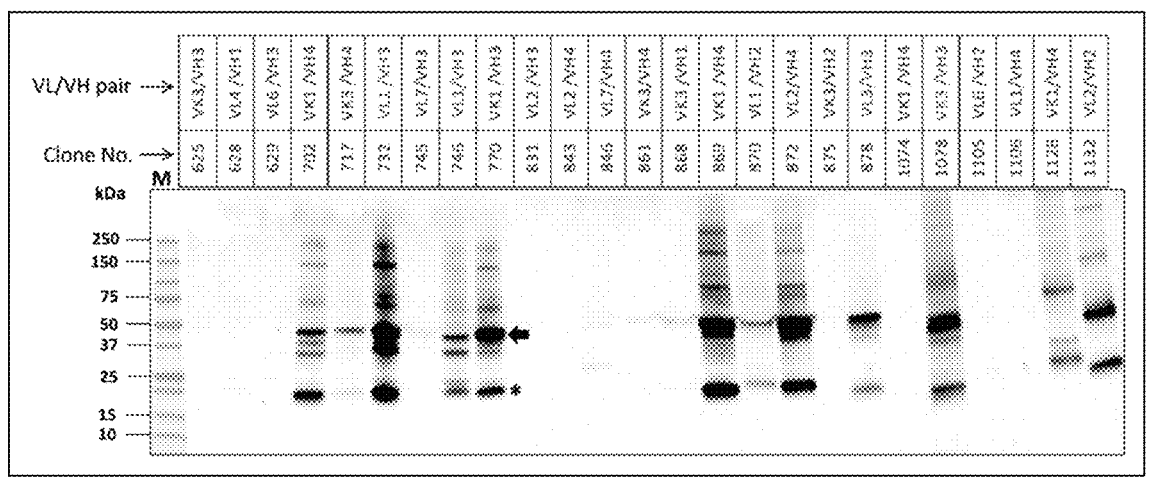
FIG. 33 depicts periplasmic Western of Fabs. Western blots of periplasmic extracts were obtained from a panning campaign such as described in Examples 26 and 27 and probed with a HRP-conjugated rabbit polyclonal IgG (Jackson ImmunoResearch #309-036-003). Arrow indicates the presumed ~50 kDa Fab heterodimer, while the * indicates the presumed 23 or 27 kDa monomer (light or heavy chain). Box on top indicates the clone number along with the $V_L/V_H$ families to which these clones belong. Numbers along the left edge of each image represent molecular weight of the markers in kDa (Pre-stained All-Blue SDS-PAGE marker; BioRad).

The present invention also discloses an alternate solution to arrive at in-frame binder clones without sequencing at this stage. Accordingly, the present invention screens monoclonal antigen binders not as phage fusions, but as soluble Fabs expressed in non-suppressor strains. This strategy takes advantage of the amber STOP codon placed between the tags and the CTD of gIII in either pCOMB3XSS or pSSY1 vectors, which is read as a Gln or Phe residue in supE or supF strains but as a translational stop codon in non-suppressor strains (Hoogenboom H R et al., 1991). FIG. 33 suggests that an anti-human light & heavy chain-specific serum can recognize ~50 kDa bands in periplasmic extracts of monoclonals obtained from a panning campaign after immunoblotting.

The presence of ~50 kDa bands in the periplasm of monoclonal hits demonstrates targeted expression of Fabs as per their design (leader sequences of both light and heavy chains are designed to be periplasmically targeted). Furthermore, the procedure enables a higher throughput compared to individual clone transductions and reformatting to phages before ELISA. The concept set out in this example enabled the design of a novel screening procedure, which is further illustrated in the subsequent examples.

Example 29

Hit Selection as a Series of Gates

Based on the evidence from Examples 26, 27 and 28 regarding short and off-frame clones, a series of gates was conceived to weed out short clones and off-frame clones. The present invention discloses a method of utilising colony PCR and non-amber suppressor strains for expressing full length clones and for weeding out off-frame clones by the detection of ~50 kDa immunoreactive bands on Western blots of periplasmic extracts from non-suppressor cells as illustrated in FIG. 33. Affinity ranking followed by bioassay validation were also conceived, as well as a stop condition.

Example 30

Application of the Logical Gates to a Biotinylated Antigen for a Panning Campaign and Resultant Outcome The concept as set out in Example 29 is tested herein by means of solution panning (Chames P and Baty D. 2010. Phage display and selection on biotinylated antigens. In: *Antibody Engineering; Vol.* 1) using a model biotinylated antigen. For preparative large scale conversion of a total of $3.06 \times 10^{11}$ cfu of naïve human phagemid library (Example 25, Table 49) from bacteria to phages, 2-10-folds excess of bacterial cells of each 14 sub-libraries were targeted for inoculation in the culture medium in sufficient volumes (~800 ml) to get final $OD_{600}$~0.1. Reaching 10-folds excess while maintaining 0.1 OD600 within reasonable culture volumes is often difficult for ultra-large libraries and a 3.3-folds excess has been used previously (Schwimmer et al., 2013). Table 57 shows that a 3× representation of the library was sampled.

TABLE 57

Calculation for inoculum volume to maintain 3x size of the library

| Library subset ID | Size of Subset (cfu) | 3x Size of subset | OD 600 @ 500 dilution | Subset cfu/ml | Vol (ml) require for 3x size of sub-library |
|---|---|---|---|---|---|
| HsN3kFab001 | 6.26E+09 | 1.88E+10 | 0.153 | 7.65E+10 | 0.246 |
| HsN3kFab002 | 7.26E+09 | 2.18E+10 | 0.147 | 7.35E+10 | 0.296 |
| HsN3kFab003 | 1.17E+10 | 3.51E+10 | 0.118 | 5.90E+10 | 0.595 |
| HsN3kFab004 | 1.99E+10 | 5.98E+10 | 0.114 | 5.70E+10 | 1.048 |
| HsN3kFab005 | 1.29E+10 | 3.87E+10 | 0.121 | 6.05E+10 | 0.640 |
| HsN3kFab006 | 2.97E+10 | 8.91E+10 | 0.128 | 6.40E+10 | 1.392 |
| HsN3kFab007 | 2.52E+10 | 7.56E+10 | 0.128 | 6.40E+10 | 1.181 |
| HsN3kFab008 | 1.34E+10 | 4.02E+10 | 0.134 | 6.70E+10 | 0.600 |
| HsN2LFab001.1 | 2.36E+10 | 7.08E+10 | 0.186 | 9.30E+10 | 0.761 |
| HsN2LFab002.1 | 1.43E+10 | 4.29E+10 | 0.177 | 8.85E+10 | 0.485 |
| HsN2LFab003.1 | 1.89E+10 | 5.67E+10 | 0.169 | 8.45E+10 | 0.671 |
| HsN2LFab004.1 | 4.36E+10 | 1.31E+11 | 0.241 | 1.21E+11 | 1.085 |
| HsN2LFab005.1 | 5.40E+10 | 1.62E+11 | 0.24 | 1.20E+11 | 1.350 |
| HsN2LFab006.1 | 2.44E+10 | 7.32E+10 | 0.208 | 1.04E+11 | 0.704 |

Inoculated primary library cultures were grown till 0.5 $OD_{600}$, and used for infection using VCSM13. The infected cultures were finally diluted 10-fold for phage propagation in overnight cultures (500 ml; 1×2 L flask per sub-library) at reduced temperature and harvested as illustrated in Example 26. Phage yields from each of the 14 sub-libraries from one conversion round ranged between $0.2\text{-}2 \times 10^{15}$ pfu.

Figure 34:
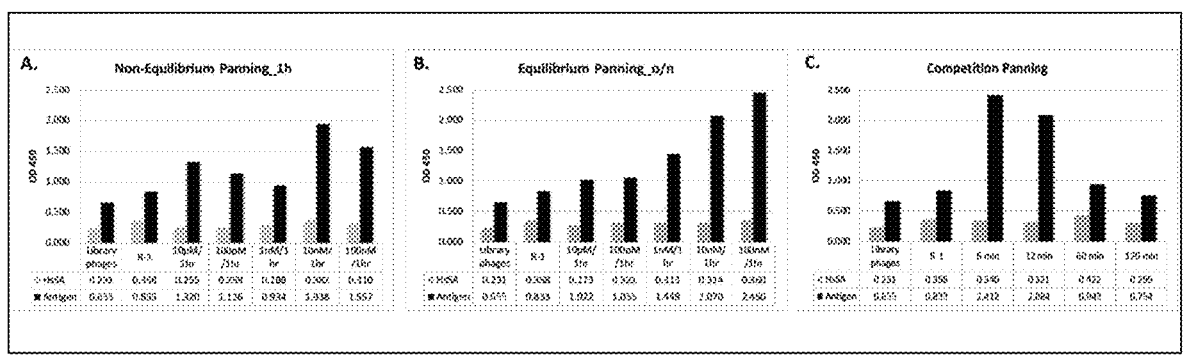
FIG. 34 depicts phage pool ELISA. Panel A shows simultaneous comparison amongst phage pools derived from the naïve library, round 1 and round 2 solution panning eluates. Phages were incubated with 500 nM biotinylated antigen in round 1 for 1 h at RT, followed by various concentrations of the same antigen in round 2 under the same incubation conditions. Black bars indicate reactivity against the target antigen immobilized on Polysorp wells while grey bars indicate reactivity of the same pool against human serum albumin (HsSA) immobilized in parallel wells. Higher reactivity in antigen-specific wells suggests enrichment of antigen-specific binders by the $2^{nd}$ round, although bait dose dependent enrichment is not seen. Panel B shows the same simultaneous comparison amongst phage pools derived from the naïve library, round 1 and round 2 solution panning eluates as in panel A, with the exception that phages were allowed to incubate with the antigen for 16 h at RT in round 2. Bait dose dependence is apparent under longer incubation conditions from round 2. Panel C shows the same simultaneous comparison amongst phage pools derived from the naïve library, round 1 and round 2 solution panning eluates as in panels A and B, with the exception that phages were incubated with 10 nM biotinylated antigen for 1 h at RT before addition of 100 nM non-biotinylated antigen for various lengths of time in round 2. The persistence of enrichment over 2 h suggests presence of high affinity (slow dissociation) binders in such pools.

Above library stock phages were used freshly for panning the model biotinylated antigen in solution phase (Chames P and Baty D. 2010. Phage display and selection on biotinylated antigens. In: *Antibody Engineering; Vol.* 1). In brief, 500 nM of biotinylated antigen was incubated with $3 \times 10^{13}$ pfu of pre-blocked library phages (representing 100× of the library) for 1 h while 200 μl of M280 streptavidin coated beads were washed and similarly pre-blocked with 2% milk in phosphate buffered saline (1×PBS). The pre-blocked phages were allowed to incubate with the beads for different lengths of time to mimic antigen-antibody equilibration in the presence or absence of 100-folds molar excess of the unbiotinylated antigen, and then washed repeatedly in Tween-20 containing PBS before eluting in 200 μl of 50 mM DTT. Eluted phages were diluted in water and brought immediately to pH 7.4 by addition of adequate amounts of 10×PBS. The eluted phages were titered by transduction in TG1 cells, and amplified in the same host before the next round of panning. Phage pool ELISA was carried out from such amplified phages as described in Example 27 to determine enrichment of binder pools at each round. FIG. 34 shows that both bait dose dependence and enrichment over rounds of panning are observed by following either the equilibrium or competition model (Hawkins R E et al., 1992).

Figure 35:
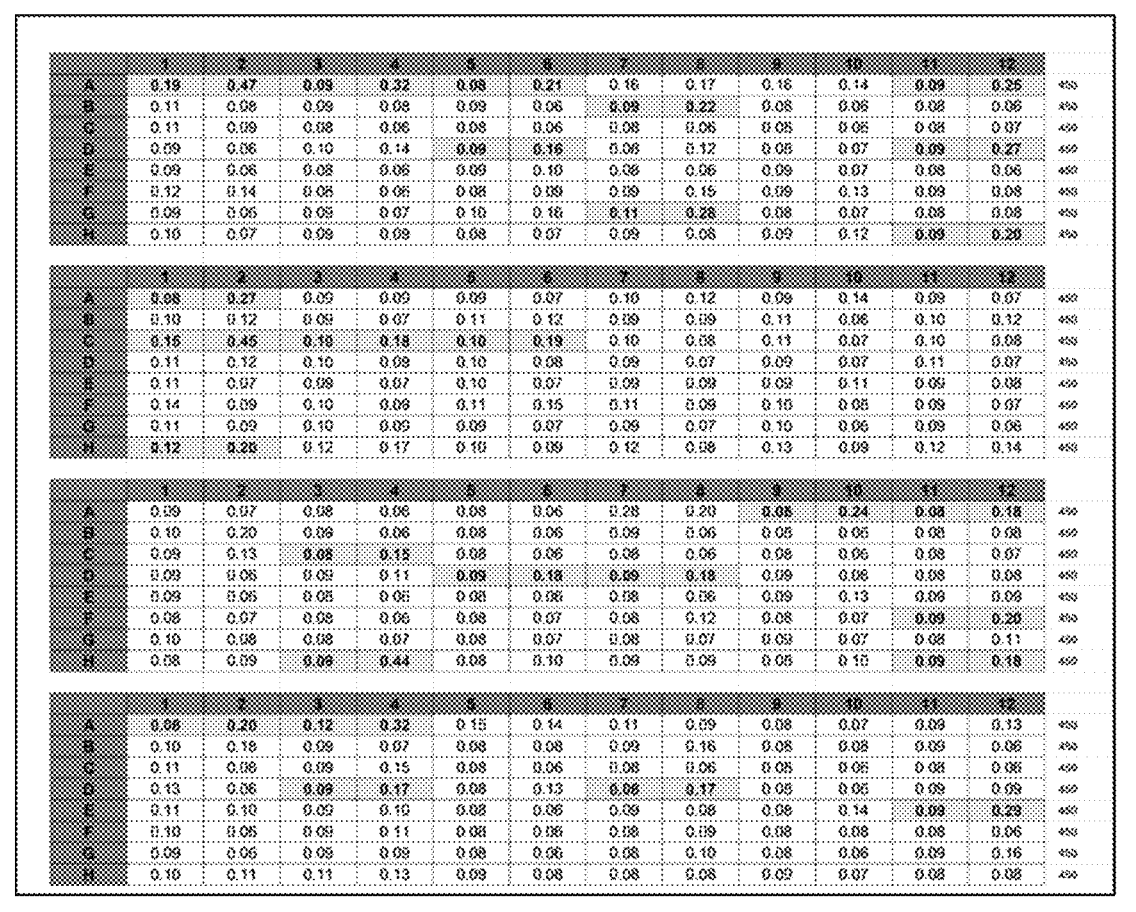

To isolate monoclonal binders from rounds 2 & 3 of panning, 1536 individual phagemid-encoding recombinants were picked up and analyzed by colony PCR. 1162 full-length clones were grown in 10 ml cultures and induced with 1 mM IPTG overnight to express Fabs. Whole cell lysates were prepared with PopCulture™ reagent (Novagen, Merck), and tested in indirect ELISA where the model antigen was coated on Polysorp plates and the antigen-bound Fabs detected with a HRP-conjugated polyclonal Fab. FIG. 35 shows an example of detection of such binders.

Figure 36:
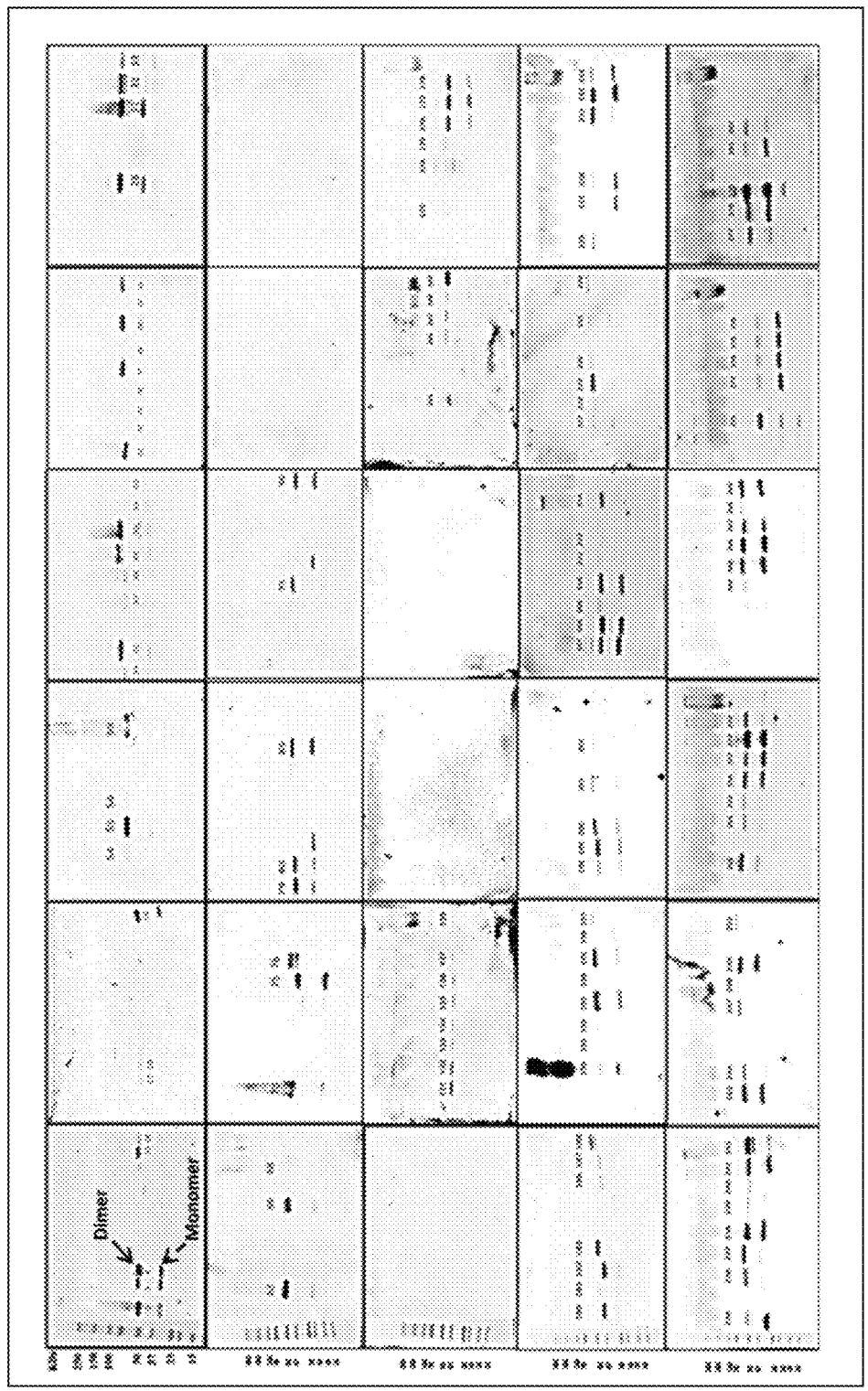
FIG. 36 depicts the periplasmic gate. The image is a composite of 30 Western blots of periplasmic extracts from a solution panning campaign. The blots were probed with a HRP-conjugated rabbit polyclonal IgG (Jackson ImmunoResearch 309-036-003). Arrows indicate the presumed ~50 kDa Fab heterodimer and the presumed 23 or 27 kDa monomer (light or heavy chain). Labels on top of each lane indicate the clone number. Numbers along the left edge of each image represent molecular weight of the markers in kDa (Pre-stained All-Blue SDS-PAGE marker; BioRad).

282 ELISA positive monoclonals were again expressed in 10 ml culture volumes as previous, and periplasmic extracts prepared as described (Humphreys D P and Bowering L, 2009. Production of antibody Fab' fragments in *E. coli*. In: *Therapeutic Monoclonal Antibodies: From Bench to Clinic*). These extracts were resolved on SDS polyacrylamide gels, blotted onto nitrocellulose membranes, and probed with anti-human Fab specific polyclonal serum to identify those clones where the expressed Fab is clearly detectable in the periplasm. FIG. 36 shows a partial view of such a "periplasmic gate," while Table 58 provides a summary of the gating procedure (Example 29) applied to this panning campaign.

On sequencing a subset of these periplasmic hits, all sequenced clones showed STOP codon within 100 bp of ATG of heavy chain suggesting that the assumptions underlying the gating procedure are insufficient for eliminating off-frame clones.

Example 31

The Concept of Chain Switch

Figure 37:
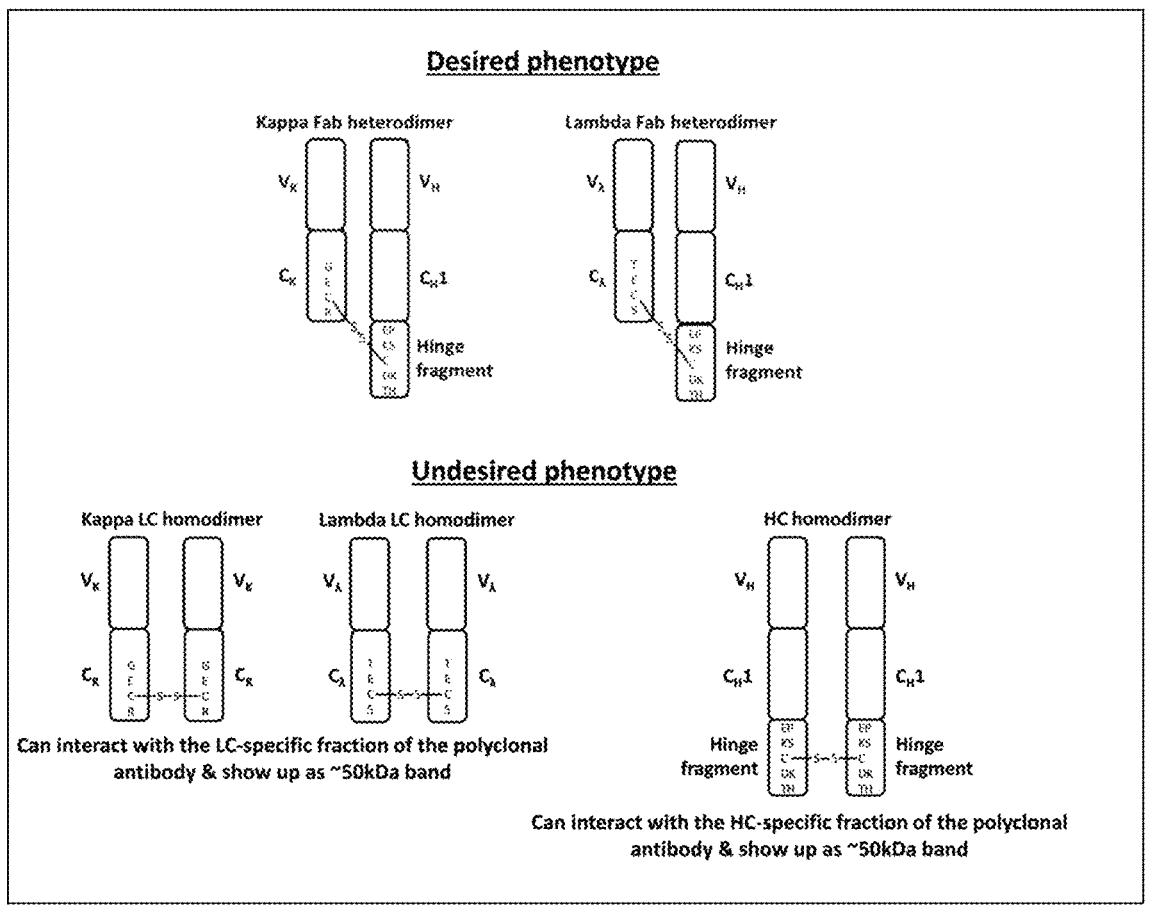
FIG. 37 depicts the confounding nature of a polyclonal detection antibody for Fab hit identification.

Example 30 indicates that the Western signals obtained from the subset of triple gated clones during periplasmic screening originate from the use of polyclonal antibodies on non-reduced gels, where a ~50 kDa band can derive both from LC-HC heterodimers (~23 kDa LC+~27 kDa HC; desired phenotype), LC-LC or HC-HC homodimers (~23 kDa LC+~23 kDa LC or ~27 kDa HC+~27 kDa HC; undesired phenotype; FIG. 37). The present invention utilizes antibodies that would be able to detect the HC or LC unambiguously as part of the ~50 kDa dimer. Westerns were optimized for two different light chain-specific (kappa and lambda) and two different heavy chain C-terminal tag-specific (polyhistidine and hemagglutinin) antibodies. The

TABLE 58

| Panning Round | Panning condition | Number of clones analyzed from antigen reactive phage pools | Number of full length clothes | Number of antigen reactive monoclonal hits | Number of hits that express in pertiplasm |
|---|---|---|---|---|---|
| R1 | $3 \times 10^{13}$ phages_vs_500 nM antigen | | | | |
| R2 | $10^{11}$ phages_vs_10pM antigen_1 hr | 192 | 187 (97.4%) | 46 (24%) | 14 (7.3%) |
| | $10^{11}$ phages_vs_100 pM antigen_1 hr | | | | |
| | $10^{11}$ phages_vs_1 nM antigen_1 hr | | | | |
| | $10^{11}$ phages_vs_10 nM antigen_1 hr | 192 | 183 (95.3%) | 37 (19.3%) | 22 (11.5%) |
| | $10^{11}$ phages_vs_100 nM antigen_1 hr | | | | |
| | $10^{11}$ phages_vs_10 pM antigen_o/n | 192 | 168 (87.5%) | 31 (16.1%) | 22 (11.5%) |
| | $10^{11}$ phages_vs_100 pM antigen_o/n | | | | |
| | $10^{11}$ phages_vs_1 nM antigen_o/n | | | | |
| | $10^{11}$ phages_vs_10 nM antigen_o/n | | | | |
| | $10^{11}$ phages_vs_100 nM antigen_o/n | 192 | 117 (60.9%) | 67 (34.9%) | 39 (20.3%) |
| | $10^{11}$ phages_vs_10 nM antigen_Competition elution_6 min | 192 | 74 (38.5%) | 23 (12%) | 2 (1.0%) |
| | $10^{11}$ phages_vs_10 nM antigen_Competition elution_120 min | | | | |
| | $10^{11}$ phages_vs_10 nM antigen_Competition elution_60 min | | | | |
| | $10^{11}$ phages_vs_10 nM antigen_Competition elution_120 min | 192 | 168 (87.5%) | 32 (16.7%) | 12 (6.3%) |
| R3 | $10^{11}$ phages_vs_1 pM @ 10 pM antigen_1 hr | | | | |
| | $10^{11}$ phages_vs_1 nM @ 10 nM antigen_1 hr | | | | |
| | $10^{11}$ phages_vs_1 pM @ 10 pM antigen_o/n | | | | |
| | $10^{11}$ phages_vs_10 nM @ 100 nM antigen_o/n | | | | |
| | $10^{11}$ phages_vs_1 nM @ 10 nM antigen_Competition elution_6 min | 192 | 126 (65.6%) | 32 (16.7%) | 8 (4.2%) |
| | $10^{11}$ phages_vs_1 nM@OnMantigen_Competition elution_120 min | 192 | 139 (72.4%) | 14 (7.3%) | 10 (5.2%) |
| Total | | 1536 | 1162 (75.7%) | 282 (8.4%) | 129 (8.4%) | hemagglutinin-specific mAb was chosen for repeat application to the antigen ELISA reactive hits isolated shown in Table 58.

Figure 38:
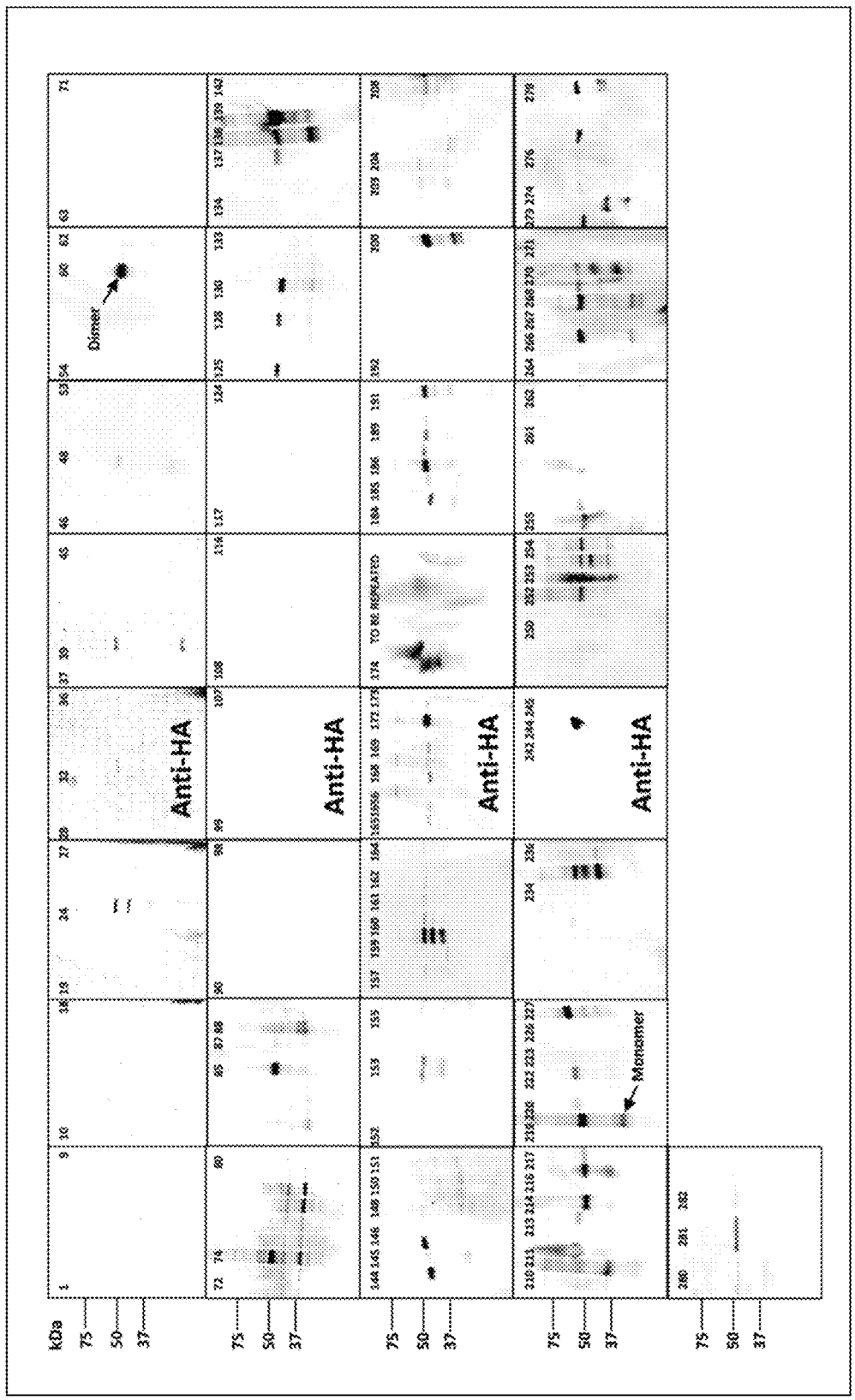
FIG. 38 depicts the revised periplasmic gate. The image is a composite of 33 Western blots of periplasmic extracts from a solution panning campaign as in Example 30. The blots were probed with a HRP-conjugated mouse monoclonal anti-HA IgG (clone 3F10; Roche). Arrows indicate the presumed ~50 kDa Fab heterodimer and the presumed 23 or 27 kDa monomer (light or heavy chain). Labels on top of each lane indicate the clone number. Numbers along the left edge of each image represent molecular weight of the markers in kDa (Pre-stained All-Blue SDS-PAGE marker; BioRad).
Figure 39:
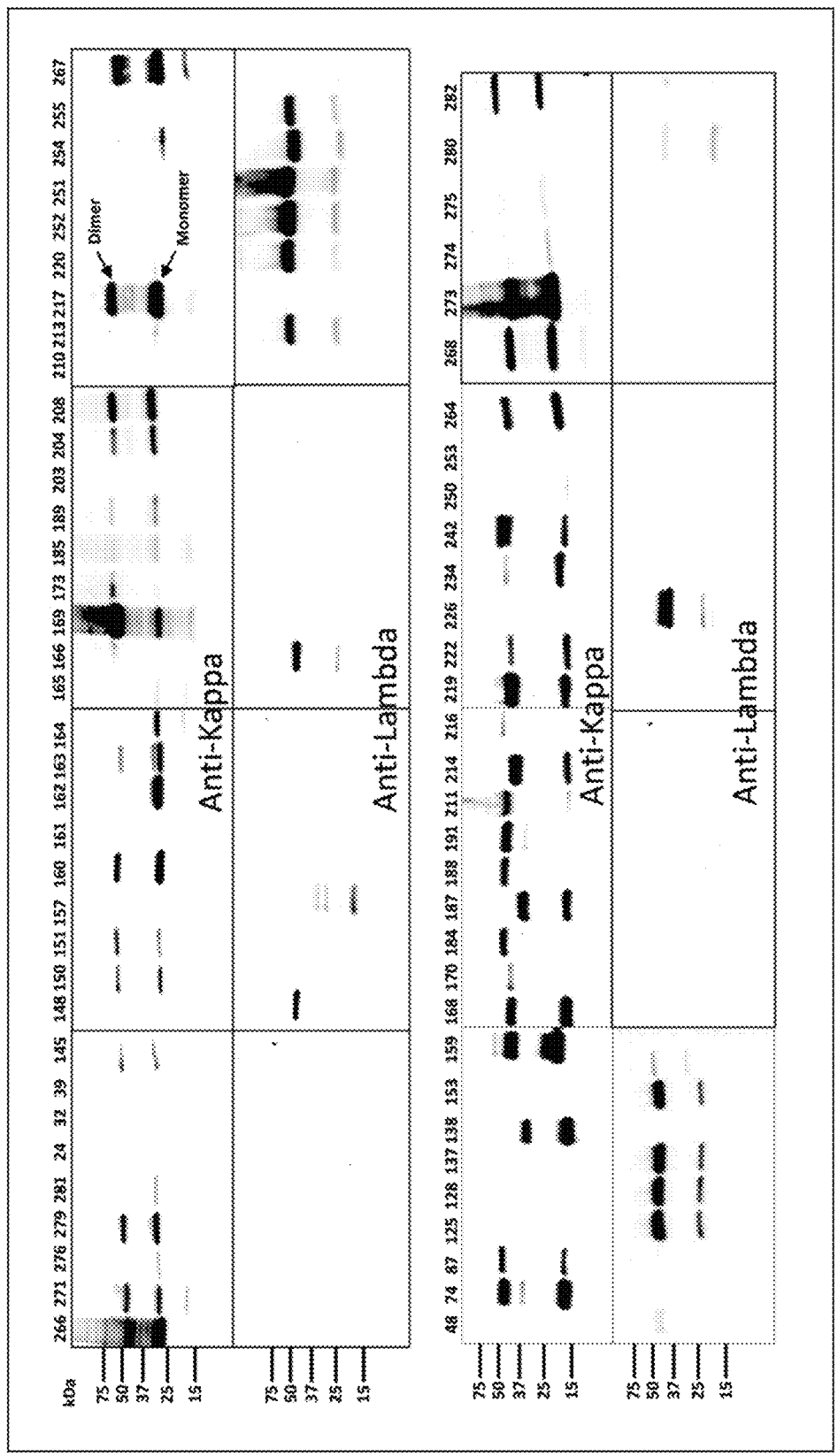
FIG. 39 depicts periplasmic subtyping by Western. The image is a composite of 16 Western blots of periplasmic extracts from a solution panning campaign as in Example 30. The blots were probed with a HRP-conjugated anti-kappa or anti-lambda monoclonal (Sigma). Arrows indicate the presumed ~50 kDa Fab heterodimer and the presumed 23 or 27 kDa monomer (light or heavy chain). Labels on top of each lane indicate the clone number. Numbers along the left edge of each image represent molecular weight of the markers in kDa (Pre-stained All-Blue SDS-PAGE marker; BioRad).

FIG. 38 shows application of this antibody to replace the polyclonal serum used in FIG. 36, while FIG. 39 shows application of kappa and lambda-specific antibodies to sub-type the periplasmic hits with anti-kappa or anti-lambda antibodies. Comparison between the two figures suggest that while the subtyping works perfectly in most cases, it is not foolproof either, as hits observed in the anti-heavy chain screening occasionally fail to show up in the anti-light chain screen (compare signals of clones 24, 32, 157, 161, 203 and 253 between FIGS. 38 and 39). Moreover, subtyping also shows presence of light chain signal in the monomeric band only (clones 162, 254, 274, 275, 276 and 281 in FIG. 39). On sequencing a subset of these heavy chain-light chain double positive periplasmic hits, most but not all sequenced clones again showed STOP codon within 100 bp of ATG of heavy chain.

Figure 40:
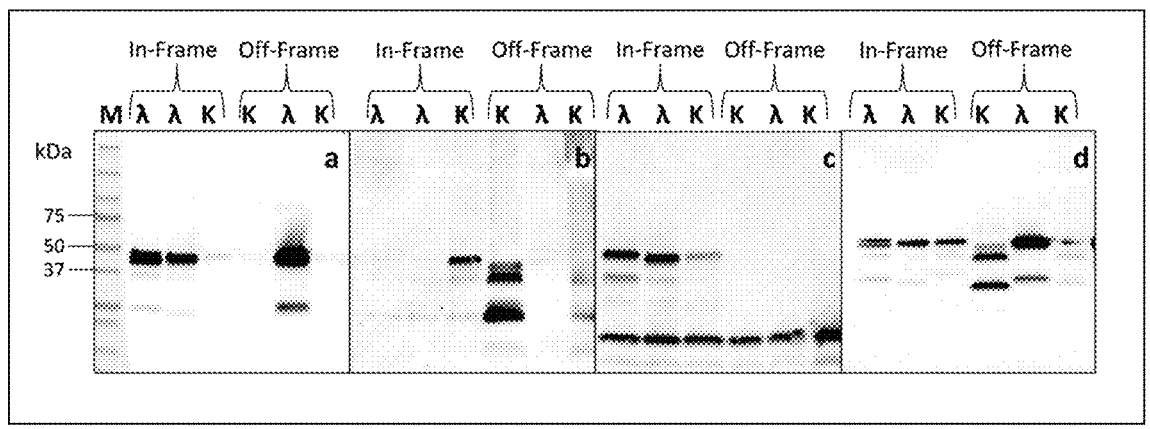
FIG. 40 depicts the in-frame versus off-frame clone experiment. Western analysis of periplasmic extracts from 3 deliberately tandem in-frame clones versus 3 deliberately off-frame (in the HC) clones in non-reduced conditions probed with anti-lambda (panel a), anti-kappa (panel b), anti-$C_H 1$ (panel c) and HRP-conjugated anti-Hu (H+L) F(ab')2 fragment antibodies (panel d).

To examine whether an antibody can distinguish between in-frame and off-frame clones, the periplasmic extracts were tested from 3 deliberately tandem in-frame clones versus 3 deliberately off-frame (in the HC) clones in non-reduced Westerns probed with anti-lambda, anti-kappa, anti-$C_H1$ and anti-Hu (H+L) F(ab')$_2$ antibodies. These clones were not reactive against any particular antigen, but chosen either from the parental library or discarded from a screening process, with the only feature that their periplasmic extracts would show ~50 kDa dimers in non-reduced SDS gels when probed with a HRP-conjugated anti-Hu (H+L) F(ab')$_2$ fragment (FIG. 40, panel d). This analysis showed that while the kappa or lambda chain-specific antibodies were unable to distinguish between in-frame or off-frame clones, the anti-$C_H1$ antibody was clearly able to do so (FIG. 40, panel c).

Figure 41:
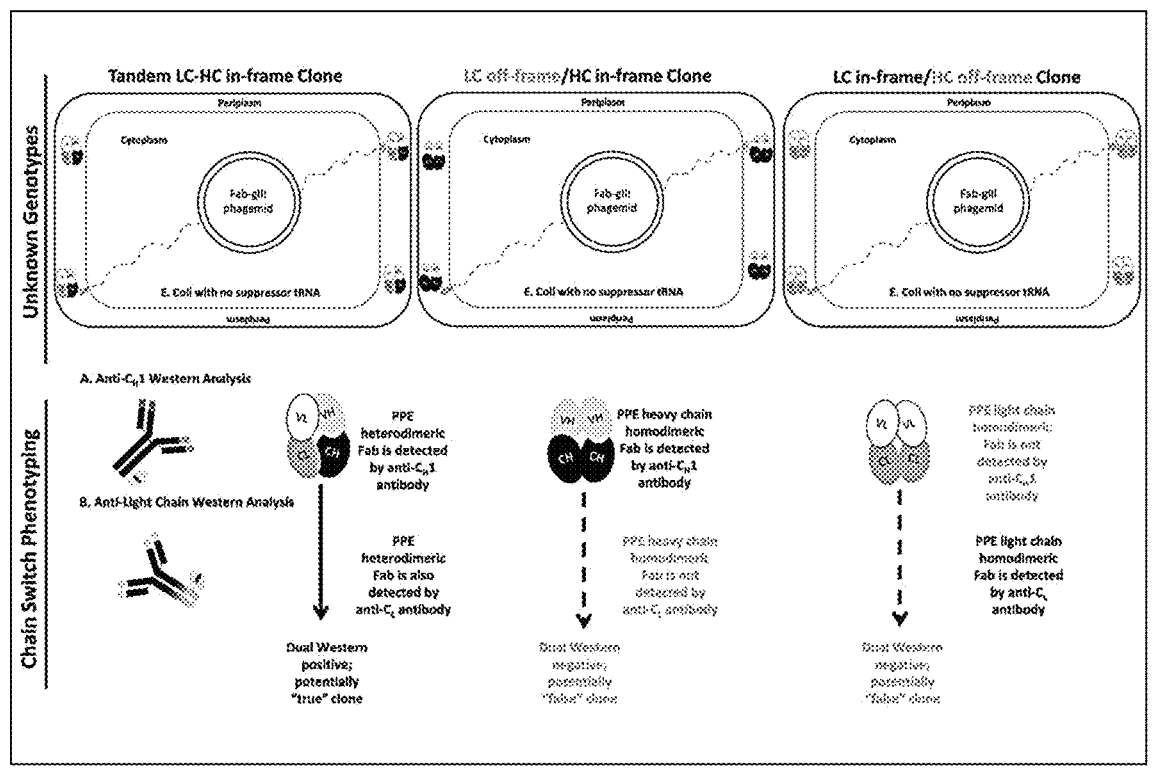
FIG. 41 depicts the chain-switch phenotyping concept to weed out false Fab protein hits away from true hits.

Based on this data, it is surmised that the apparent ability of the anti-$C_H1$ antibody to distinguish "true" LC-HC heterodimers (FIG. 40, panel c) simultaneous with the inability of the anti-LC antibodies to do so (FIG. 40, panels a & b) limits the detection of heterodimeric Fab clones by using any one sub-type specific antibody alone. Hence, the present invention discloses a novel method of successive switching of detection antibodies specific for the LC or HC to deduce the genotype of the clone by such chain-switching (FIG. 41).

The method of successive switching of detection antibodies enabled formulation of different gating order, in which a phage transduced "monoclonal" *E. coli* colony picked up from a selective media plate is first passed through the PCR filter to identify clones with 1.5 kb inserts, and the insert-positive clones are then induced to produce Fabs that are extracted from the periplasm. Western blots of these extracts probed with the anti-$C_H1$ antibody allows distinction of clones that produce either LC-HC heterodimers or HC-HC homodimers (both at ~50 kDa) at a detectable level (1-3 pg/band) in the periplasm. In the next step, these periplasmic extracts containing the hetero- or homodimers are allowed to bind the target antigen immobilized on polystyrene wells and detected with LC-specific detection antibody. This chain switch therefore detects only the antigen-bound LC-HC heterodimers that have actually translocated into the periplasm (clones with desirable attribute), and the antigen-bound HC-HC homodimers (undesirable clones) are not detected at all, and thus, filtered out. The combined approach therefore unambiguously assigns antigen-specific ELISA reactivity of the clones to heterodimeric Fabs that have detectably translocated to the periplasm and reflects "true" genotype of the clone from which the Fabs have been extracted.

Example 32

The Theory of Chain-Switch Applied to Develop a Quantitative ELISA

Figure 42:
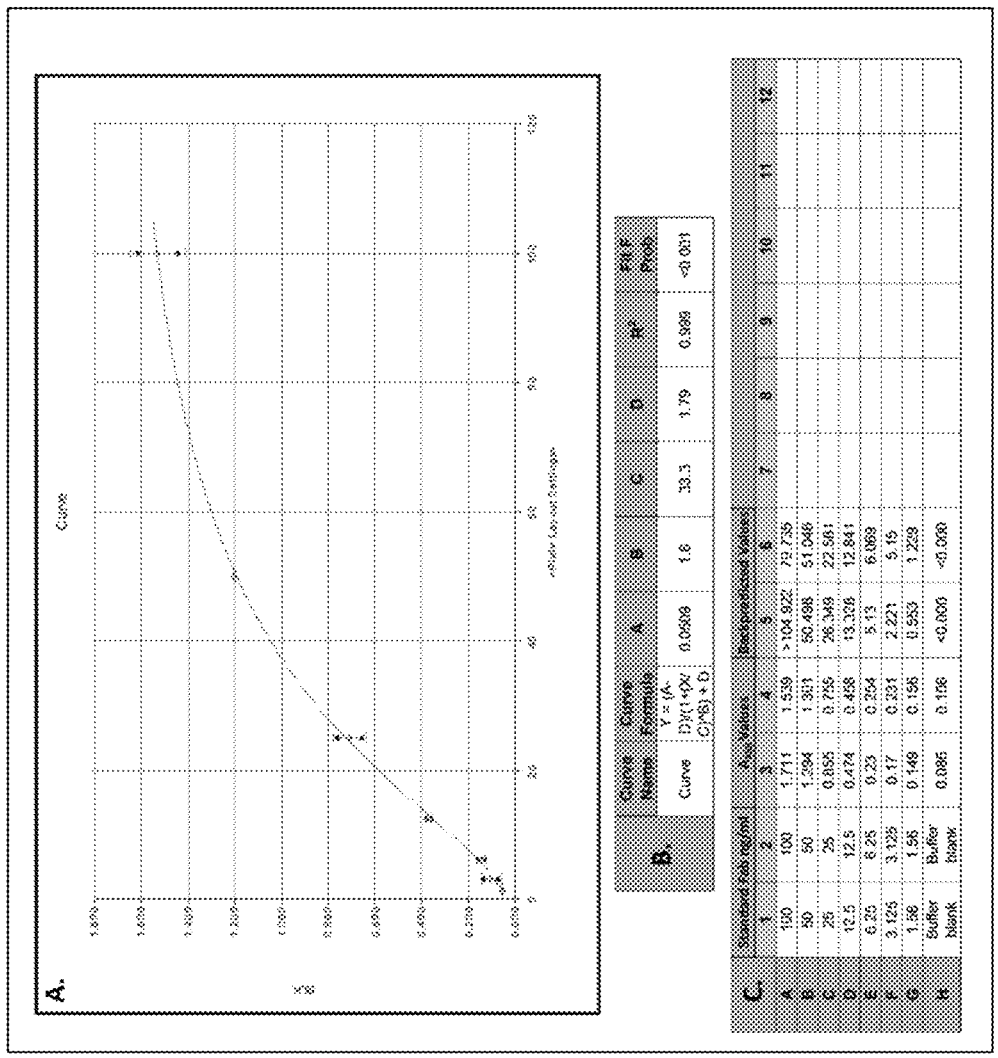
FIG. 42 depicts example of a fitted curve and back prediction from the Fab chain-switch quantitation ELISA. Panel A shows the 4-parameter fitted curve for mass of input standards on the X-axis versus output A450 values on the Y-axis while Panel B shows the estimates of the fit parameters as well as the goodness of the fit as indicated by the probability score from an F-test. Panel C shows the input Fab concentrations, the raw $A_{450}$ values and the back-predicted concentrations from the fitted curve.

Development of the concept of chain-switch ELISA illustrated at Example 31 enables development of a Fab quantification ELISA. In this system, periplasmic Fabs are captured through their heavy chain using a $C_H1$ specific antibody, and detected with a light chain-specific (anti-kappa or anti-lambda) antibody. Human Fab standards used are commercially available. Optimized binding and wash conditions allow a good dynamic range and assay linearity. FIG. 42 shows example of a fitted curve from human Fab standards.

Example 33

Quantitative ELISA Applied to Detect Off-Frame Clones

Figure 43:
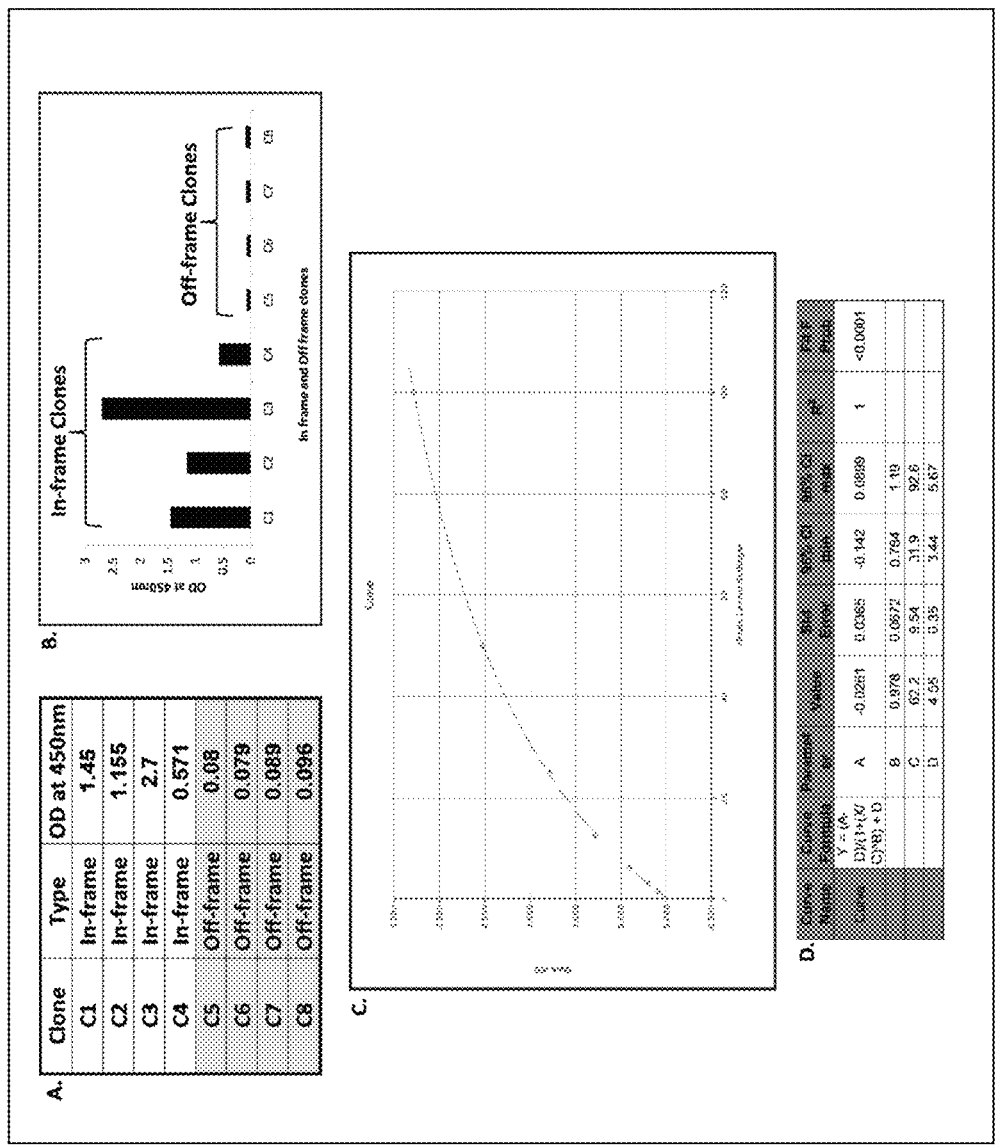
FIG. 43 depicts discrimination of in-frame clones and off-frame clones by qELISA. Panel A shows $A_{450}$ values, while Panel B shows the same data as a bar graph for easy visualization of the output. Panel C shows the fitted standard curve for this experiment, while Panel D shows the 4-PL fit parameters and the goodness-of-fit.

The chain switch ELISA as illustrated in Example 32 produces measurable signals from off-frame clones. The present invention also discloses a modified ELISA such that it detects Fabs from in-frame clones only. The present invention discloses detection of in-frame and off-frame clones according to the concept as illustrated in FIG. 40. Furthermore, the present invention discloses immobilization of the capture Fab on streptavidin surface to orient the $V_L$-$V_H$ paratopes at 90° to the plate surface for maximal interaction with the $C_H1$ epitope in the Fabs extracted from the periplasm. The results are presented at FIG. 43.

Example 34

Kinetic Ranking of Fabs by Surface Plasmon Resonance

Figure 44:
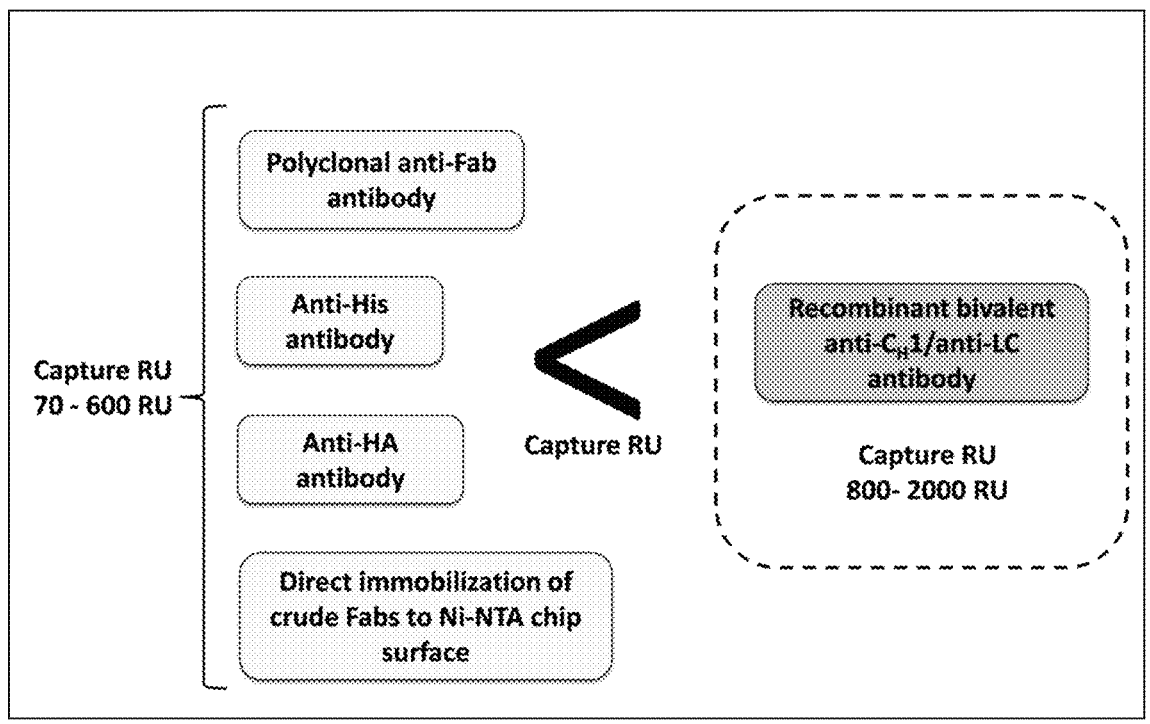
FIG. 44 depicts summary of maximum response units possible from various SPR Fab capture surfaces. Experiments were performed using ProteOn XPR36 instrument (BioRad) on GLC, GLM or NLC chips using recombinant standard human Fab or PPE-Fab. Running buffer was 20 mM PBS, pH 7.4 and 0.05% Tween-20 or 10 mM HEPES with 0.05% Tween-20. Capture antibodies viz. polyclonal anti-Fab, anti-His, anti-HA or 1:1 mixture of bivalent anti-$C_H 1$/anti-λ or anti-$C_H 1$/anti-κ were immobilized vertically on respective chip. 1:2 to 1:10 dilution of test Fabs and 5 µg/ml of standard Fabs were captured on respective horizontal channels for 180s-300s at 25 µl/min flow rate. If required, two consecutive captures were performed to increase the capture level and, surfaces were stabilized by $H_3PO_4$ injection for 18s at 100 µl/min. The sensorgrams were referenced appropriately and the Fab capture levels were noted. The bivalent anti-Fab antibodies resulted into maximum Fab capture level (800-2000 RU) compared to rest of the antibodies (70-600 RU).

The present invention investigates several SPR chip surfaces and discloses a bivalent antibody with dual heads for anti-$C_H1$/anti-$C_\kappa$ or anti-$C_H1$/anti-$C_\lambda$ capture (CaptureSelect™; Human Fab-kappa or Fab-lambda Kinetics Biotin Conjugates; Life Technologies/ThermoFisher). FIG. 44 shows that in pilot experiments, it could capture commercially available standard mixture of human Fabs or random in-frame Fabs from periplasmic extracts, significantly more than any other capture antibody. Furthermore, the surface could be used repeatedly without significant leaching of the capture Fab.

Figure 45:
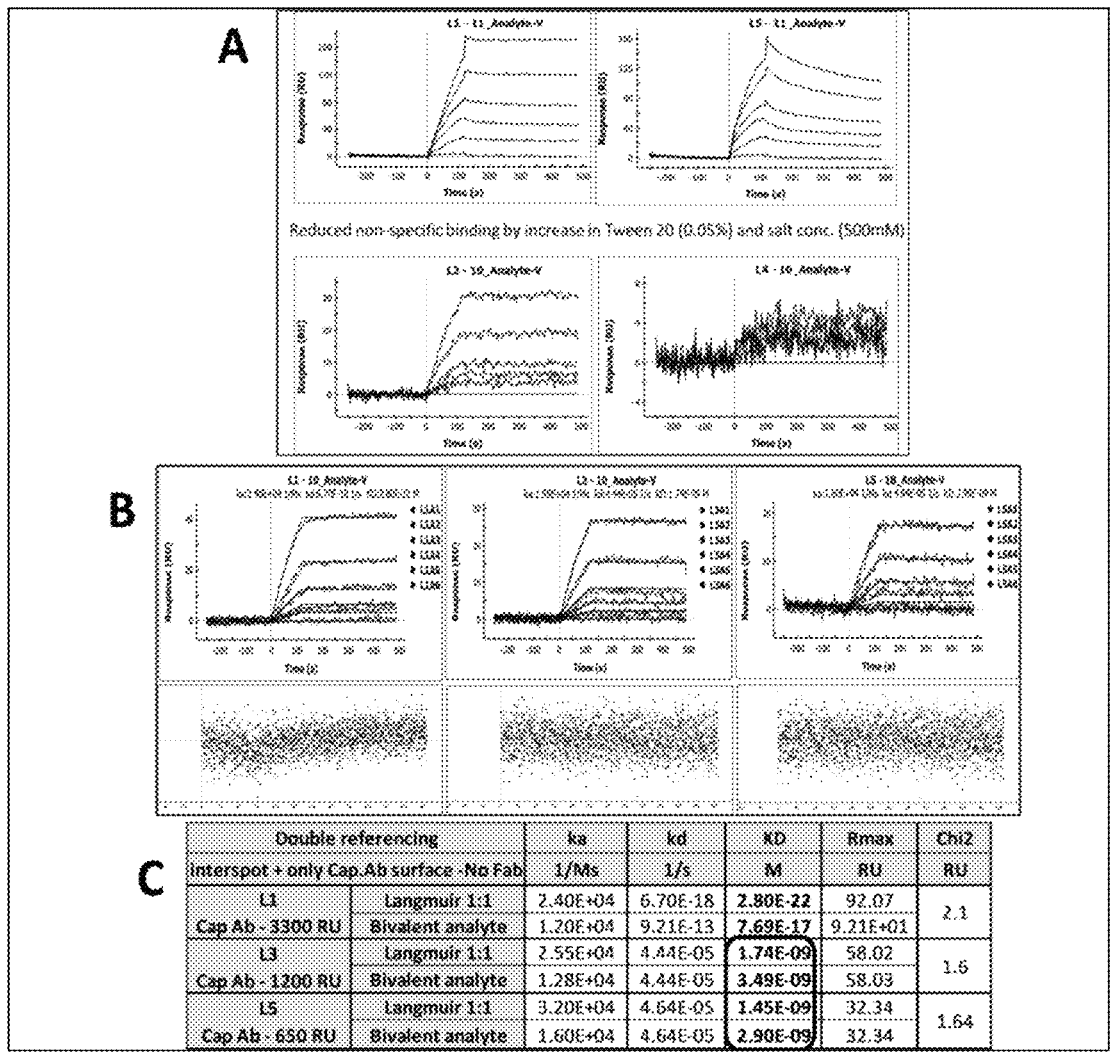
FIG. 45 depicts SPR based kinetic analysis of $VEGF_{165}$ interaction with purified Fab' fragment of Bevacizumab. Fab capture method was validated using the purified Fab' fragment of Bevacizumab as the ligand and $VEGF_{165}$ as the analyte. Running buffer was PBS, pH 7.4 containing either physiological salt/0.005% Tween-20 OR 0.5M NaCl/0.05% Tween-20. Panel A shows the SPR profile for troubleshooting of non-specific binding (NSB) of analyte ($VEGF_{165}$) to the capture surface. Increasing the Tween-20 and salt concentrations in running and sample buffers drastically reduced the NSB. Panel B shows the binding curves at different capture levels of the Fab' fragment along with their respective residuals plots. Panel C shows derived kinetic values ($k_a$, $k_d$ and $K_D$) and other relevant parameters at each capture level.

The present invention discloses the use of a known antibody-ligand pair to optimize the capture surface. For this purpose, in-house purified preparation of full length Bevacizumab (IgG) was digested with papain. The resulting Fab' fragments were purified away from the Fc fragments using a combination of affinity and size exclusion chromatography. After a short 2-stage optimization, this Fab' fragment could be shown to bind to $VEGF_{165}$ with kinetic parameters expected for a high affinity Fab (FIG. 45).

Figure 46:
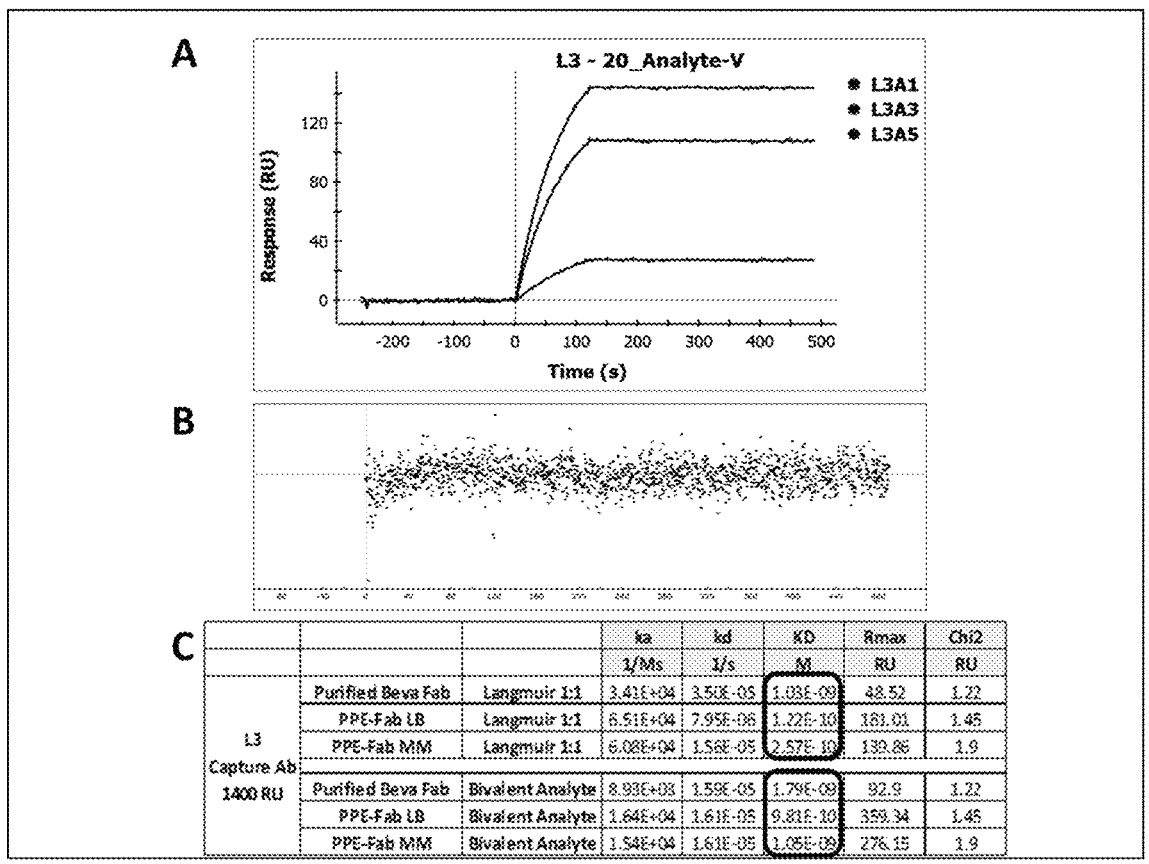
FIG. 46 depicts SPR based kinetic analysis of $VEGF_{165}$ interaction with expressed BevacizuFab present in crude periplasmic extracts. Fab capture method was validated using BevacizuFab as the ligand in periplasmically expressed Fab format and $VEGF_{165}$ as the analyte. Optimized conditions as described in FIG. 45 were used. Panel A shows the binding curves of BevacizuFab whereas Panel B shows its respective residual plot. Panel C shows corresponding kinetic values ($k_a$, $k_d$ and $K_D$) and other relevant parameters at each capture level (compare with panel C of FIG. 45). PPE-Fab LB and PPE-Fab MM refer to periplasmic extracts of BevacizuFab grown in different culture media.

The present invention also examines whether similar kinetic parameters would be observed if the Fab portion of the Bevacizumab IgG is presented to the surface and the ligand as a crude periplasmic extract. FIG. 46 demonstrates that crude periplasmic extracts of domain swapped "BevacizuFab" have highly similar kinetic parameters that are observed with purified Fab' fragment of Bevaciuzmab.

Example 35

Hit Selection as a Series of Revised Gates

Figure 47:
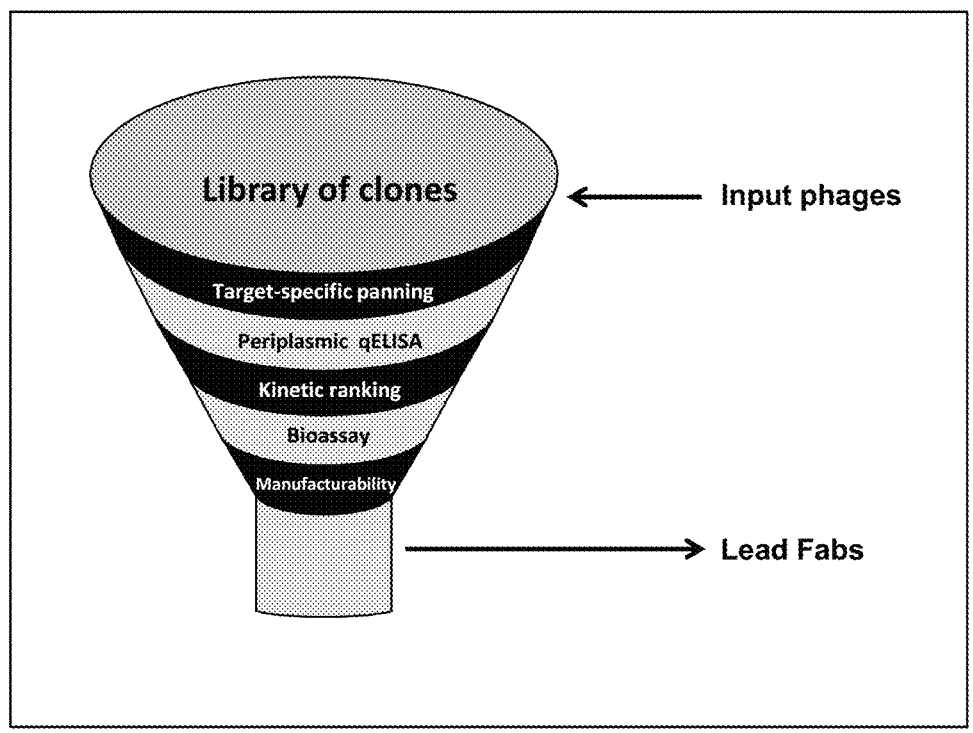
FIG. 47 depicts the funnel of antibody discovery from a Fab library.

Based on Examples 33-34, the present invention discloses a new series of gates that bypasses the problems of short and off-frame clones inherent in phage biology, that replaces phage-Fab fusions with Fab proteins for phenotypic assessment such as antigen-binding ability and kinetic stability while maintaining high fidelity for the underlying genotypic information during such phenotyping, that is amenable to high throughputs including automated high throughputs, and that allows rapid meaningful comparison among hits without tremendous input of labor and error-prone manipulations (FIG. 47).

Example 36

Applying the Staged Assessment Process to Find Anti-TNFα Binders

Human soluble TNFα (sTNFα; Uniprot P01375) is a 17.5 kDa protein in monomeric form and therefore, 1 µg/ml of a solution of sTNFα is equivalent to 57.1 nM. This mass-mole conversion was considered to decide input bait concentration during each round of panning. Commercially available biotinylated version of human TNFα (b-TNFα) from Acro-Biosystems (Cat #TNA-H821R, Lot #BL271R-65HS1-BQ) was used for panning. 200 µg of lyophilized powder in PBS, pH 7.4 was dissolved in 2 ml of sterile water to get final concentration of 0.1 mg/ml which was equivalent to 570 nM. Biotinylation chemistry used was NHS-LC-biotin and manufacturer claimed 1-3 biotin tags per mol of TNFα. Presence of trypsin cleavage site between gIII protein and heavy chain of Fab produced in pSSY1 will allow the elution of phages bound to such a biotinylated antigen.

Figure 48:
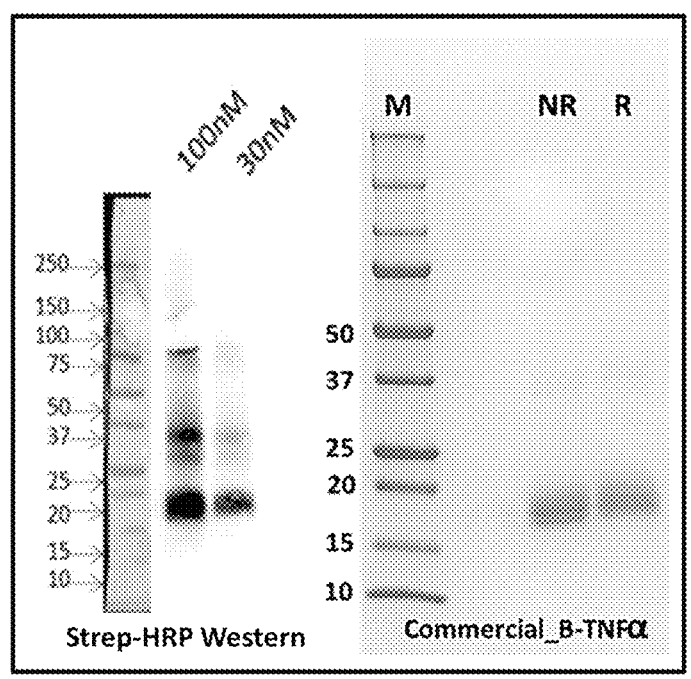
FIG. 48 depicts b-TNFα purity and quality check. Samples were heated at 90° C. for 5 min and 5 µg each of reduced and non-reduced proteins were electrophoresed in a 4-15% polyacrylamide gel at 150V for 40 min. The image on right shows the gel stained in Coomassie Brilliant Blue R-250 for 2 h and de-stained using water:methanol:acetic acid (50:40:10) for 2 h. M is Precision plus All Blue SDS-PAGE marker from Biorad-NR is for non-reduced, R is for reduced. For Western blotting, 100 nM (50 ng) and 30 nM (~16 ng) reduced protein samples were prepared and electrophoresed as previous and transferred to nitrocellulose membrane at 100V for 1.5 h. Blot was blocked for 1 h in 3% BSA in TBST (0.05% Tween-20) and probed with streptavidin-HRP (Dako #P0397) at 1:40000 dilution in 3% BSA for 1 h. Blot was developed using Clarity Western ECL substrate (Biorad #170-5060). Image of the resultant Western blot (left) was recorded using the ChemiDoc XRS system (Biorad).

Quality of b-TNFα was checked by Coomassie staining as well as Western blotting of SDS-PAA gels and found to be acceptable (FIG. 48). The number of biotin tags were verified using Quanti*Tag™ Biotin Kit (Vector Labs, Cat #BDK 2000). The number of biotin tags was ~4.7 mol/mol sTNFα.

200 µl beads (M280, Life Technologies/ThermoFisher) are used per round for panning. The bead saturating concentration for b-TNFα was examined. This process involves determining the optimal concentration of b-TNFα required to saturate the bead surfaces of 200 µl beads such that input antigen should be optimal for available bead binding surface area. It was determined by incubating a fixed volume of beads (40 µl), previously blocked for 1 h in 2% M-PBS, with varying concentration of b-TNFα (60, 80, 100, 120 nM) for a fixed amount of time (1 h). The flow through (FT) was saved for further analysis and beads were washed 8 times with 1×DPBS with 0.05% Tween-20 and 2 times using 1×DPBS without any Tween-20. 30 µl of load, FT and beads were loaded in 10% SDS-polyacrylamide gel and subjected to Western blotting.

It was observed that 100 nM b-TNFα showed more protein in the flow through compared to 60 and 80 nM, which indicates saturating concentration of b-TNFα is 80 nM for 400 beads. Therefore, it was determined that 400 nM b-TNFα should be used as a saturating concentration for 200 µl of M280 bead volume.

Antibody phages were generated by converting the $3.06 \times 10^{11}$ cfu library (Table 49) as described in Example 30. For the first round of panning, 100-fold excess library phages ($3 \times 10^{13}$ pfu) were transferred to a 5 ml protein Lobind tube (Eppendorf) and blocked for 1 h in 2 ml of 2% MPBS at 15 rpm on tube rotator. In parallel, 200 µl of streptavidin beads (M280 Dynabeads) were washed 3 times with 2 ml of 1×PBS, pH 7.4 and then kept for blocking in 2% MPBS as described for phages. Pre-blocked phages were then mixed and incubated with 400 nM of b-TNFα for 1 h on a Hula mixer at 15 rpm. After blocking of beads was completed, blocking solution was discarded by separating the beads to the side wall of the tube using magnet (DynaMag-5; Life Technologies/ThermoFisher). Antigen-phage antibody complexes were captured on streptavidin beads by mixing both and incubating for 1 h at room temperature and 15 rpm-4 µl of 100% Tween-20 was added to 2 ml mixture to get a final Tween concentration of 0.2%. Bead-Ag-Ab complex was drawn to the side wall of the tube using magnet and the unbound phages were discarded. The bead complex was subjected to washing 8 times using 2M-PBST (2% skimmed milk with 2% Tween-20) followed by 2 times with 1×PBS. Before the last wash, the bead complex was transferred to a fresh tube, and the beads were drawn to wall of the tube by the magnet. The antigen bound phages were eluted using 200 µl of 10 µg/ml of Trypsin for 30 min with intermittent finger-tapping. Eluate containing antigen specific phages was removed from the mixture using magnet and transferred to a fresh tube. The volume of the eluate was made up to 2 ml using 1×PBS and 40 µl was aliquoted separately for eluate titer estimation.

The eluate was subjected to phage amplification for the next panning round. For amplification, it was mixed with 1000-fold excess (2-10 ml) of log phase ($0.5 OD_{600}$) TG1 cells inoculated 2 h prior to elution step. Phages were allowed to infect the cells for 30 min without shaking at 37° C. and then incubated further for 1 h at 250 rpm without antibiotic. After 1 h, cells (10 ml) were diluted 1:10 in 90 ml of 2×YT medium with 100 µg/ml carbenicillin and grown further 1-2 h at 37° C. and 250 rpm. VCSM13 helper phage infection was done at 1:20 ratio and at 37° C. without shaking for 30 min. Helper phage infected cells were further grown at 250 rpm at same temperature for 30 min. Finally, 50 µg/ml kanamycin was added to the 100 ml culture and incubated overnight (16 h) at 30° C. and 250 rpm. Next day, amplified phages were PEG precipitated as described in Example 26.

Titer estimation of eluate was performed simultaneously in TG1 and Top10F' cells—purpose of latter was to get soluble Fabs for screening (Kontermann R E, 2010. Immunotube selections. In: *Antibody Engineering; Vol. 1*) whereas amplified phages were tittered only in TG1 at dilution $10^{-9}$ to $10^{-11}$. For titration, 20 µl of round 1 phage eluate was mixed with 180 µl of LB medium in wells of a sterile 96-well plate resulting in $10^{-1}$ dilution of phages. Similarly, log scale dilution of phages was performed up to $10^{-4}$ dilution. For titer estimation of amplified phages, dilution was performed up to $10^{-11}$. 100 µl of last three phage dilutions were mixed with 100 µl of log phase ($0.5 OD_{600}$) culture of TG1 or Top10F' cells in a fresh 96-well plate and incubated at 37° C. for 30 min. 100 µl of phage infected culture of all 3 dilutions were plated on LB plates containing 100 µg/ml carbenicillin and incubated overnight at 37° C. Next day, count of colonies was recorded and titer of the eluate was estimated.

Panning rounds 2, 3 and 4 were performed by keeping input phages constant ($10^{12}$ pfu) between rounds but one log decrease in b-TNFα concentration over each successive step. Table 59 shows eluate titer data for all 4 rounds. Titer data for amplified phages ranged between 1.4 and $6.0 \times 10^{13}$ pfu.

TABLE 59

| Target Antigen | b-TNF α input concentration | Panning Round | Number of colonies | | | | Titer (cfu/ml) | Elution vol | Total yield (cfu) |
|---|---|---|---|---|---|---|---|---|---|
| | | | $10^{-1}$ | $10^{-2}$ | $10^{-3}$ | $10^{-4}$ | | | |
| b-TNF | 400 nM | R-1 | NC | NC | NC | 110 | 2.20E+07 | 1.2 | 2.64E+07 |
| | 40 nM | R-2 | NC | NC | 50 | — | 1.0E+06 | 1.2 | 1.2E+06 |
| | 4 nM | R-3 | 51 | 4 | — | — | 1.0E+04 | 1.2 | 1.2E+04 |
| | 400 pM | R-4 | 1 | — | — | — | 2.0E+02 | 1.2 | 2.4E+02 |

Titer data discloses that eluate titer decreased proportionally with decrease in bait concentrations over the panning rounds. Yields of amplified phages from all 3 rounds were fairly similar. Round 4 phages were not amplified since process was stopped after fourth round and hence titer values for the same were not available.

Clones were screened in monoclonal soluble Fab formats and harvested as bacterial crude periplasmic extracts (PPE). Source of the clones was Top10F' titer plates generated during each round of panning. All the processes were performed in high throughput manner in 96-well format. To prepare the master plates of anti-TNFα monoclonal Fab clones, single well isolated colonies were picked up from Top10F' titer plates using sterile toothpicks and inoculated into 150 µl of LB medium containing 2% glucose and 100 µg/ml carbenicillin in sterile 96-well plate. Total 960 clones (10 plates×96) were inoculated from round 3 and round 4 plates. Plates were sealed with Breathe-Seal®, labelled appropriately with antigen name, panning round, date etc. and incubated overnight (16 h) at 37° C. and 250 rpm.

For expression of soluble Fabs, 50 µl from overnight culture of each clone was transferred using multichannel pipettes to 450 µl of CircleGrow medium (MP Biomedicals) containing 0.1% glucose and 100 µg/ml carbenicillin in sterile 96-deep well plates. Plates were sealed with Breathe-Seal® and incubated at 37° C. and 250 rpm until $OD_{600}$ reached 0.5-0.7. To the remainder 100 µl of overnight cultures, 33 µl of 45% LB-glycerol was added, mixed, and the plates stored in −80° C. as a glycerol stocks (Master Plates).

Induction was performed by adding IPTG to a final concentration of 1 mM in the deepwell plates after the cultures had reached log phase of growth. Plates were re-sealed with Breathe-Seal® after IPTG addition, and induced overnight (16 h) at 30° C. and 250 rpm. Overnight induced cultures were pelleted at 4000 rpm at 4° C. in 96-well swingout plate buckets for 30 min. Supernatants were discarded by inverting plates carefully and gently tapping on paper towel.

For extraction of periplasmic Fabs, 100 µl of periplasmic extraction buffer (100 mM Tris, pH 7.5, 10 mM EDTA, protease inhibitor cocktail) was added to each pellet using multichannel pipette and mixed gently for homogenous re-suspension. Plates were sealed and incubated at 30° C. and 150 rpm for 16 h. After overnight extractions, plates were centrifuged at 4000 rpm in swing out 96-well plate buckets for 30 min at 4° C. The supernatant is the periplasmic extract (PPE) containing soluble monoclonal Fab. PPEs were transferred to sterile 96-well plates labelled appropriately, and stored at 4° C. until analysis.

To select only full-length in-frame leads, clones were subjected to chain switch quantitative ELISA using kappa and lambda detection antibody as described in Example 33. Since kappa and lambda libraries were mixed before panning, parallel sets of each PPE extract were tested using kappa and lambda specific antibody. To perform the qELISA, required number of plates were coated with 100 µg/ml of biotinylated BSA (Sigma Cat #A8549) in 1×PBS containing 0.5% gelatin and incubated overnight at 4° C. Next day, they were washed three times with 1×PBS pH 7.4 containing 0.05% Tween-20 using automated 96-well plate washer. Streptavidin (ThermoFisher, Cat #21135) was captured over biotinylated BSA by adding 100 µl per well and incubated at 30° C. and 150 rpm for 1 h. Excess streptavidin was removed by washing three times as previous. 100 µl of biotinylated anti-$C_H1$ capture antibody (ThermoFisher, Cat #7103202500) was coated over the streptavidin surface and incubated at 30° C. for 1 h. Wells were blocked for 1 h using 200 µl of 1-2% BSA-PBS containing 100 µM of biotin. During blocking, standards were prepared using commercially available standard human Fab (MP Biomedicals, Cat #855909) at range of 100 ng/ml to 1.56 ng/ml in respective blocking solutions of kappa and lambda. Blocker was removed by washing three times as previous and crude periplasmic Fabs were captured over anti-$C_H1$ antibody by adding 100 µl of PPEs and Fab standards, and incubating the plates for 1 h at 30° C. Unbound Fabs were removed by washing three times as previous. Captured Fabs were detected using HRP conjugated anti-kappa at 1:2000 dilution (Sigma; Cat #SAB3701414) and anti-lambda at 1:10000 dilution (Sigma; Cat #A5175) with the antibodies prepared in respective blocking solutions. 100 µl of respective antibody was added per well and incubated at 37° C. for 1 h. Plates were washed three times before developing color by addition of 100 µl of TMB substrate and incubation at 37° C. for 20-30 min. Reaction was stopped by addition of 100 µl of 2M sulfuric acid and plates were read at 450 nM. Readings were recorded and standard graph was plotted using non-linear regression curves.

Figure 49:
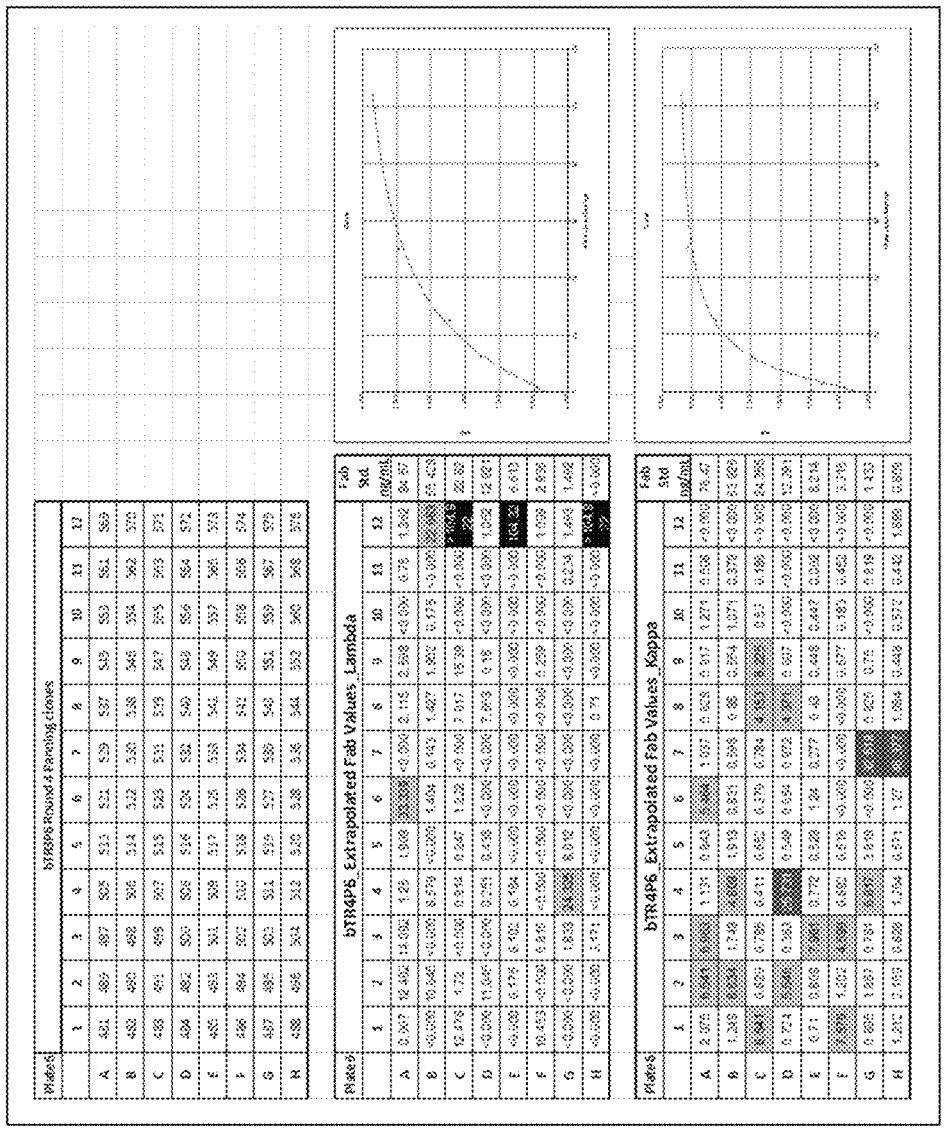
FIG. 49 depicts representative data for anti-TNFα soluble Fab screening using chain switch qELISA. Upper panel shows layout of plate 6 of the TNFα campaign with clone numbers 481 to 576. Middle panel shows standard curve and $A_{450}$ values using lambda detection antibody whereas bottom panel shows standard curve and A450 values using kappa detection antibody. Black color indicates high expressing clones, dark grey color indicates moderate expressing clones while light grey color indicates low expressing clones.

FIG. 49 shows the representative data of plate 6 for anti-TNFα soluble Fab screening using chain switch qELISA. qELISA positive clones were categorized into high (black shaded cells), moderate (dark grey shaded cells) and low (light grey shaded cells) expressers. Cutoff values for each category was determined empirically by taking set of in-frame and off-frame clones during method development (Example 33).

Out of 960 clones screened by qELISA, 108 clones were lambda positive while 373 clones were kappa positive. While selecting clones for kinetic ranking, higher priority is given to the high expressers followed by moderate and low expressers, respectively.

Chain switch qELISA will ensure elimination of off-frame Fabs and will select only full length in-frame clones but will not be able to declare whether they will bind against a target antigen. Target specific binding can be established by antigen-specific ELISA. The process described herein omits this ELISA step and directly screens clones using a SPR-based method. Kinetic ranking is certainly advantageous over ELISA, as it will provide valuable kinetic parameters ($k_{on}$, $k_{off}$) along with final affinity ($K_D$) value as well as allow to select only those clones with good off rates over others thus ensuring therapeutic or diagnostic application.

Based on this consideration, 100 clones were picked and their PPEs were generated at 50 ml scale by adjusting volumes and vessels to the 96-well system as described. PPEs were transferred to sterile 15 ml tubes and stored at 4° C. Before performing SPR studies, it was essential to remove extraction buffer that contains 100 mM Tris. Such a high buffer salt concentration might result into significant bulk effects during SPR studies with PBS as running and sample buffer. All PPEs were therefore buffer exchanged using 10 ml capacity tangential flow systems (Millipore; 10 kDa cut off) into 1×PBS in the presence of protease inhibitor cocktail (Roche). The volumes of dialysates were further reduced by $\frac{1}{4}^{th}$ resulting in total 100× compression of the original culture volume of a given total $OD_{600}$. Buffer exchanged PPEs were transferred to sterile 1.5 or 2.0 ml tubes and stored at −20° C. until use.

Figure 50:
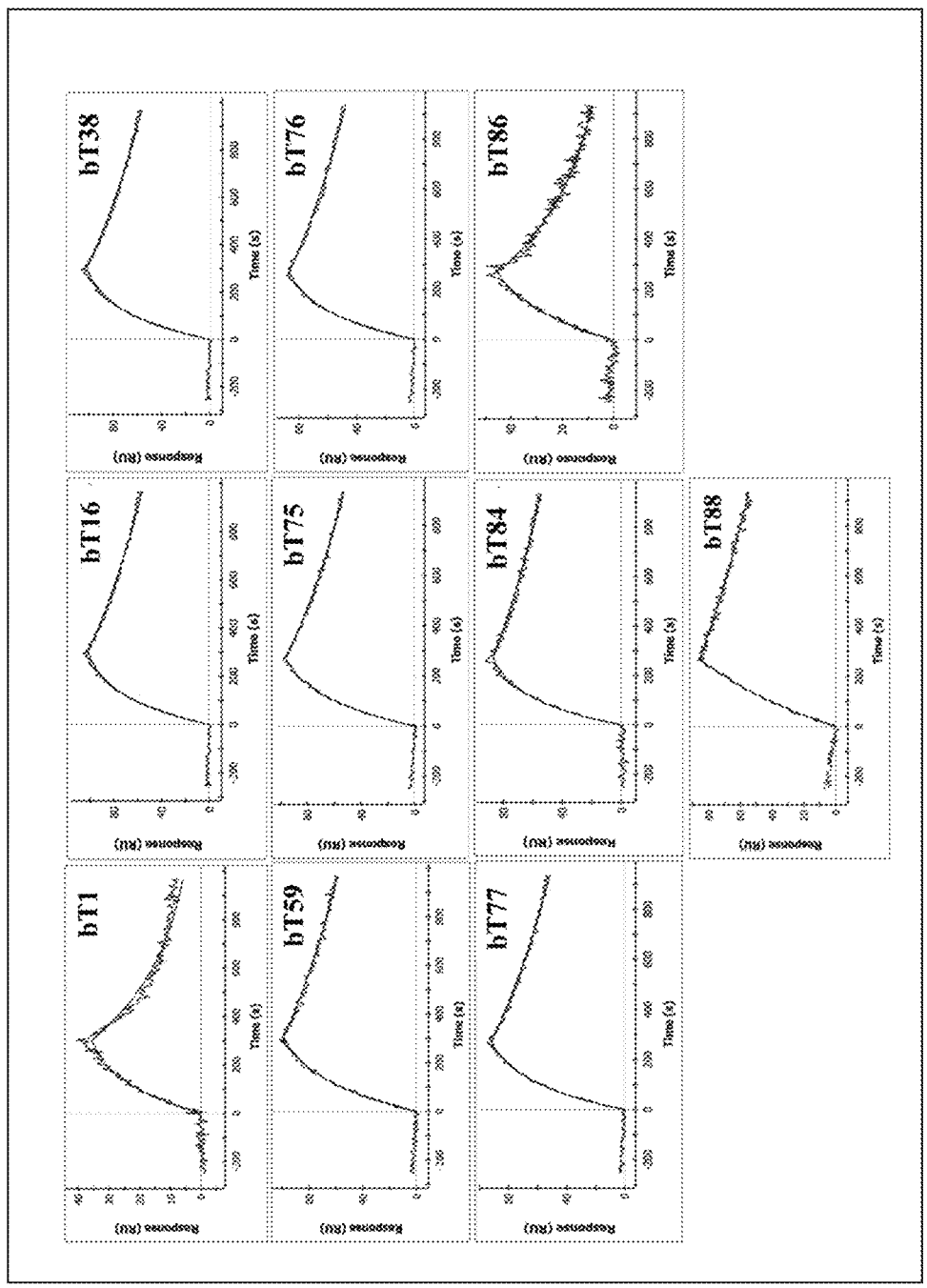
FIG. 50 depicts kinetic screening profiles of SPR positive clones of anti-TNFα at 500 nM analyte concentration. Experiments were performed using ProteOn XPR36 instrument (BioRad) on neutravidin-coated (NLC) chips. Running buffer was 20 mM PBS, pH 7.4 with 0.5M salt and 0.05% Tween-20. Capture antibody was 1:1 mixture of biotinylated bivalent anti-$C_H$1/anti-λ and anti-$C_H$1/anti-κ antibodies. Three different concentrations (10, 3 and 1 μg/ml) of this mixture were immobilized vertically in duplicate; one as a test surface while other as reference surface for respective capture concentration on the NLC chip. 1:10 dilutions of test Fabs were captured on respective horizontal channels for 300s at 25 μl/min flow rate. Two to three consecutive captures were performed to saturate the capture surface. One horizontal channel was dedicated as reference channel where non-specific (non-TNFα binder) commercial human Fab was used to saturate the surface such that the reference surface exactly mimics the test surface. Before the analyte injection, the baseline was stabilized using three consecutive injections of running buffer at 100 μl/min for 60s. The system was paused for 5 min after the $1^{st}$ buffer injection followed by the remaining two—this helps to stabilize the signal rapidly. 500 nM of analyte (sTNFα) was injected horizontally at 25 μl/min for 120s (2 min) followed by dissociation for 300s (5 min). Surfaces were regenerated using glycine pH 2.0 for 60s followed by second injection for 30s. The sensorgrams were referenced appropriately and analyzed using Langmuir 1:1 fitting models. Resultant affinity constant values ($k_a$, $k_d$, $K_D$), and other relevant parameters like Rmax and $\chi^2$ were noted.

First round affinity ranking of 100 qELISA positive clones was done using a single concentration (500 nM) of sTNFα (bacterially produced in-house product). SPR positives from first round screening were then analyzed carefully with analyte dose titration to get reliable kinetic values. All studies were done using crude PPEs extracted at 50 ml scale as described in the preceding paragraph. FIG. 50 shows kinetic screening profiles and tentative kinetic parameters respectively for SPR positive clones of TNFα using single analyte concentration (500 nM).

10 clones out of 100 (10%) qELISA positive hits were SPR positive. Before performing careful analysis using dose titration, all the SPR positive clones were sequenced with five primers as described in Example 25 and all were found to be full length tandem light chain-heavy chain in-frame clones (Table 60). This data indicates that gating system as illustrated in this Example is 100% foolproof as claimed (claim 28). Further, these 10 anti-TNFα hits were categorized as per their epitope specificity by a process called epitope binning (Abdiche et al., 2009). In this manner, all available SPR hits can be tested against each other and can be categorized into epitope specific bins. Only one representative clone from each bin is taken forward for further studies. 10 anti-TNFα clones were injected in R×C manner in sets of 5 as shown in FIG. 51.

Figure 51:
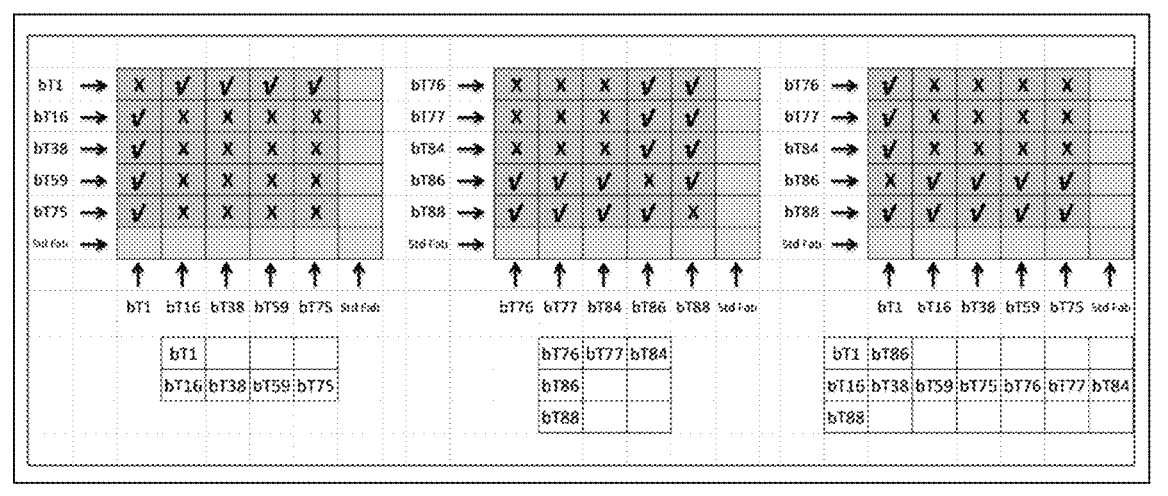

As evident from FIG. 51, the 10 anti-TNFα clones can be categorized into three epitope specific bins. The first bin contains two clones viz. bT1 and bT86, the second bin contains seven clones viz. bT16, bT38, bT59, bT75, bT76, bT77 and bT84, while the third bin contains a single clone viz. bT88. Table 60 summarizes the data bins of anti-TNFα Fabs. One representative clone of each bin was taken forward for further studies. Next step was to carefully analyze these three clones by analyte dose titration to get reliable kinetic parameters ($k_a$ and $k_d$) and affinity values ($K_D$).

TABLE 60

| S. NO | Clone ID | Family | SPR Binder | SPR Bin | DNA sequencing LC | DNA sequencing HC |
|---|---|---|---|---|---|---|
| 1 | bT1† | Lambda | + | 1 | + | + |
| 2 | bT16* | Kappa | + | 2 | + | + |
| 3 | bT38** | Kappa | + | 2 | + | + |
| 4 | bT59** | Kappa | + | 2 | + | + |
| 5 | bT75** | Kappa | + | 2 | + | + |
| 6 | bT76** | Kappa | + | 2 | + | + |
| 7 | bT77** | Kappa | + | 2 | + | + |
| 8 | bT84** | Kappa | + | 2 | + | + |
| 9 | bT86† | Lambda | + | 1 | + | + |
| 10 | bT88* | Kappa | + | 3 | + | + |

Figure 52:
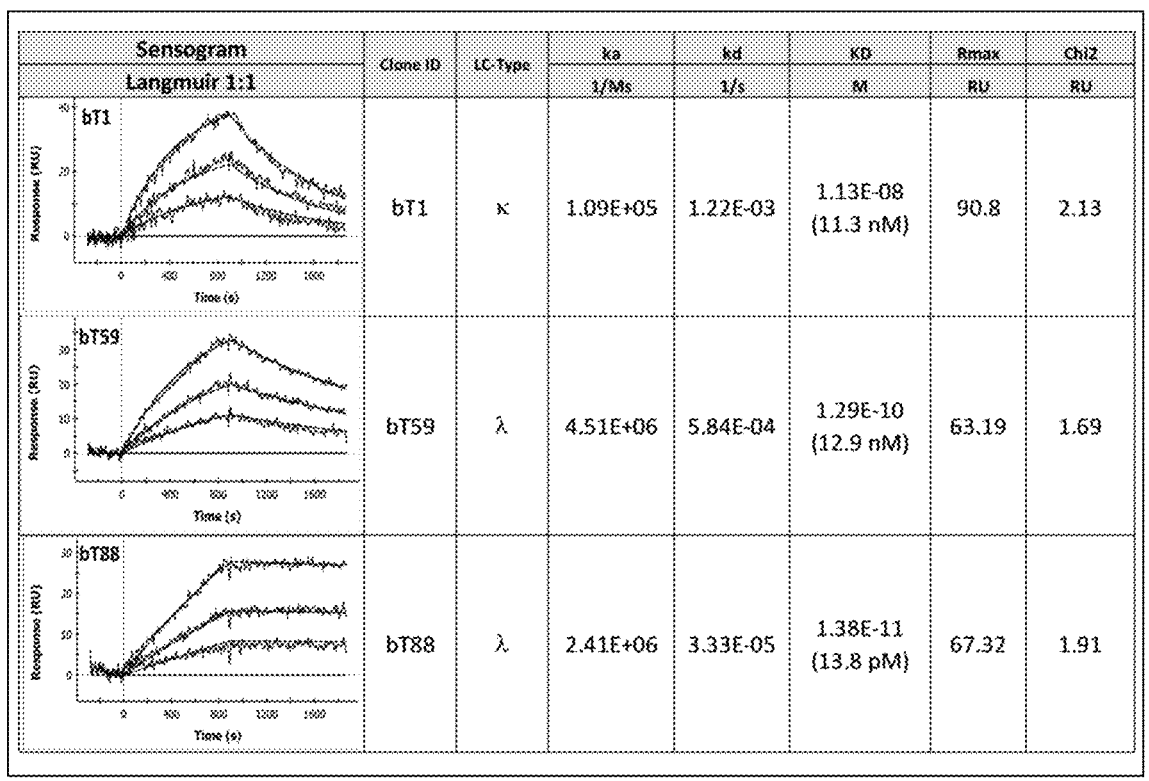
FIG. 52 depicts summarized view of SPR profiles and parameters of anti-TNFα monoclonal Fabs bT1, bT59 and bT88. Biotinylated bivalent anti-$C_H$1/anti-κ and anti-$C_H$1/anti-λ capture antibody was immobilized at three different concentrations (10, 3 and 1 μg/ml) vertically in duplicate; one as a test surface while other as the reference surface for respective capture concentration on NLC chip. 1:10 dilutions of test Fabs were captured on three vertical channels (L1, L3 and L5) for 300s at 25 μl/min flow rate. Two to three consecutive captures were performed to saturate the capture surface. Reference surfaces (L2, L4 and L6) were saturated using non-specific (non-TNFα binder) commercial human Fab to exactly mimic the test surfaces. Before the analyte injection, baseline was stabilized using three consecutive injections of running buffer at 100 μl/min for 60s. The system was paused for 10 min after first buffer injection followed by the remaining two—this helps to stabilize the signal rapidly. Five concentrations (reciprocal dilution) of sTNFα ranging between 10 nM-0.625 nM for bT1 and 1000 pM to 62.5 pM for bT59 and bT88 were injected horizontally at 25 μl/min for 900s (15 min) followed by dissociation for 900s (15 min). Surfaces were regenerated using glycine pH 2.0 for 60s followed by second injection for 30s. For data analysis, last three concentrations were considered i.e. 2.5 nM-0.625 nM for bT1 whereas for bT59 and bT88, the range used was 250 pM to 62.5 pM. The sensorgrams were referenced appropriately and analyzed using Langmuir 1:1 fitting models. Resultant affinity constant values ($k_a$, $k_d$, $K_D$), and other relevant parameters like $R_{max}$ and $\chi^2$ were noted as required.

†Identical lambda sequences;
*Unique kappa sequences;
**Identical kappa sequence FIG. 52 shows summarized view of SPR profiles and parameters of all three clones. It is evident from the FIG. 52 that, all relevant SPR parameters ($R_{max}$, $\chi 2$) falls within the range. The affinity value ($K_D$) of bT1 was 11.3 nM, bT59 was 12.9 nM and for bT88 it was 13.8 pM.

Example 37

Applying the Staged Assessment Process to Find Anti-PfRh5 Binders

*P. falciparum* reticulocyte-binding protein homolog 5 (PfRh5; UniProt Q8IFM5) is a 59.8 kDa protein and therefore, 1 µg/ml of a solution of PfRh5 is equivalent to 16.7 nM. This mass-mole conversion was considered to decide input bait concentration during each round of panning. In-house preparation of PfRh5 was used for this study.

Figure 53:
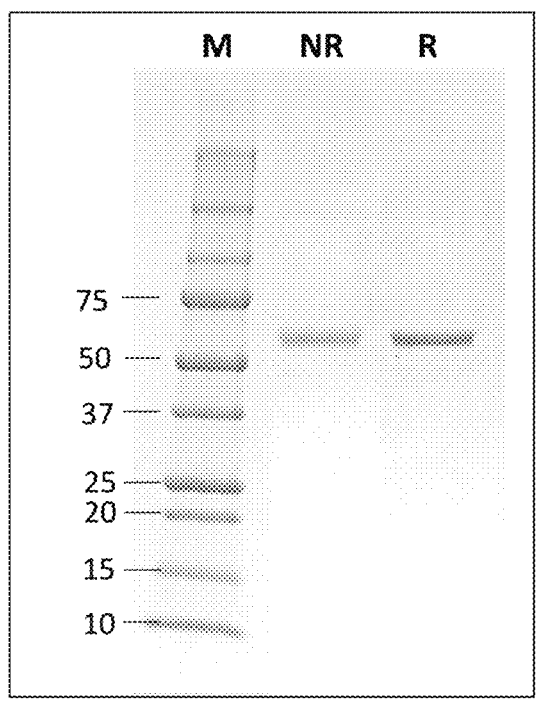
FIG. 53 depicts PfRh5 purity and quality check. Samples were heated at 90° C. for 5 min and 2 μg each of reduced and non-reduced proteins were electrophoresed in a 4-15% polyacrylamide gel at 150V for 40 min; gel was stained in Coomassie Brilliant Blue R-250 for 2 h and de-stained using water:methanol:acetic acid (50:40:10) for 2 h. M is Precision plus All Blue SDS-PAGE marker from Biorad-NR=non-reduced, R=reduced.

The quality of the protein was checked by Coomassie staining of SDS-PAA gels and found to be acceptable (FIG. 53). Sulfo-NHS-biotin (Pierce) was used for biotinylating purified antigen as described in Example 30. The Quanti*Tag™ Biotin Kit (Vector Labs, Cat #BDK 2000) was used to estimate the biotin tags, and it was determined to be 2.22 (~2) mol/mol of PfRh5.

Antibody phages were generated by converting the 3.06× $10^{11}$ cfu library (Table 49) as described in Example 30. For solution panning of b-PfRh5, M280 Dynabeads were used. Four rounds of panning, elution and titer estimations were performed as described in Example 36 with two changes— (a) 500 nM of b-PfRh5 was used as the start bait concentration with one log reduction at each round up to 500 pM for fourth round and (b) elution was performed using 50 mM DTT in carbonate buffer pH 8.5 for 30 min. Table 61 shows eluate titer data for all 4 rounds. Titers of amplified phages ranged between 0.15-1.9× $10^{13}$ pfu. Round 4 phages were not amplified since the panning process was stopped after the fourth round.

TABLE 61

| Antigen ID | Panning round | Ag coating concentration | No of colonies @ $10^{-3}$ | No of colonies @ $10^{-4}$ | Titer (cfu/ml) | Volume of eluate | Final phage yield (cfu) |
|---|---|---|---|---|---|---|---|
| b-Rh5 | R1 | 500 nM | 60 | 15 | 3.0E+06 | 2 | 6.0E+06 |
|  | R2 | 50 nM | 26 | 2 | 2.1E+05 | 2 | 4.3E+05 |
|  | R3 | 5 nM | 72 | — | 1.4E+06 | 2 | 2.9E+06 |
|  | R4 | 0.5 nM | 51 | — | 1.0E+06 | 2 | 2.0E+06 |

Figure 54:
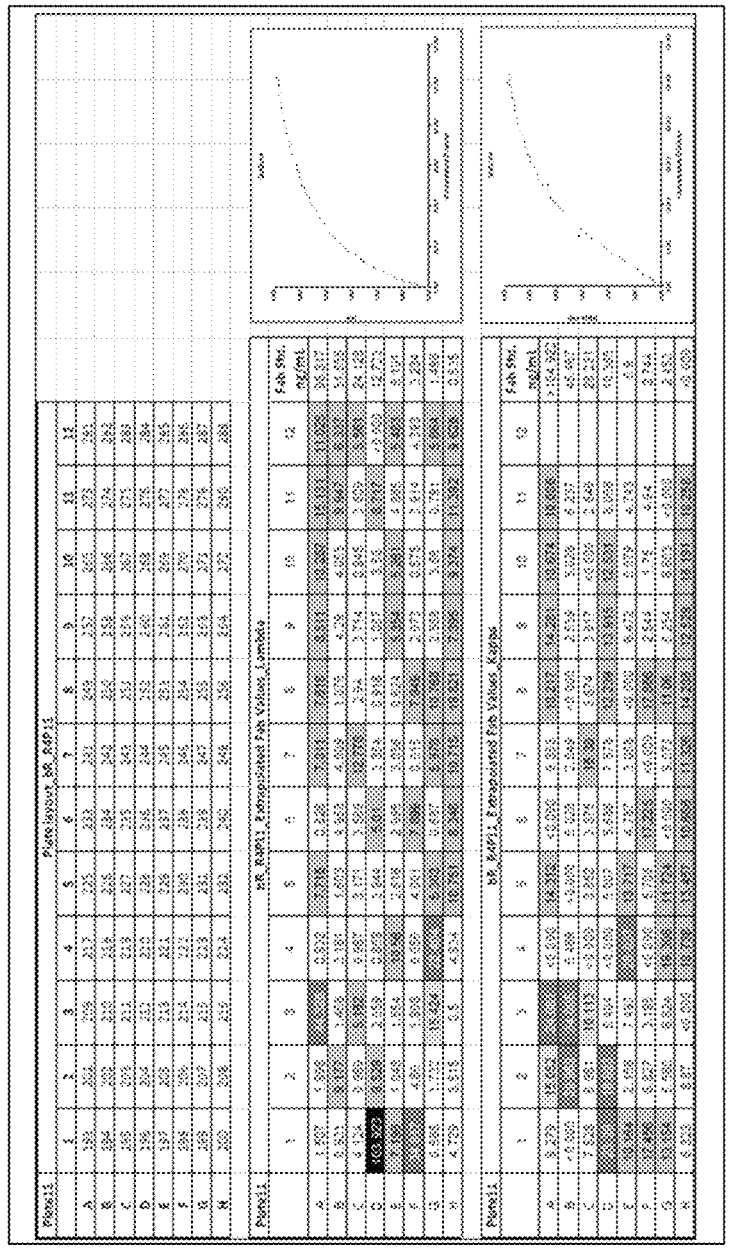
FIG. 54 depicts representative data for anti-PfRh5 soluble Fab screening using chain switch qELISA. Upper panel shows layout of plate 11 of the Rh5 campaign with clone numbers 193 to 288. Middle panel shows standard curve and A450 values using lambda detection antibody whereas bottom panel shows standard curve and $A_{450}$ values using kappa detection antibody. Black color indicates high expressing clones, dark grey color indicates moderate expressing clones while light grey color indicates low expressing clones.
Figure 55:
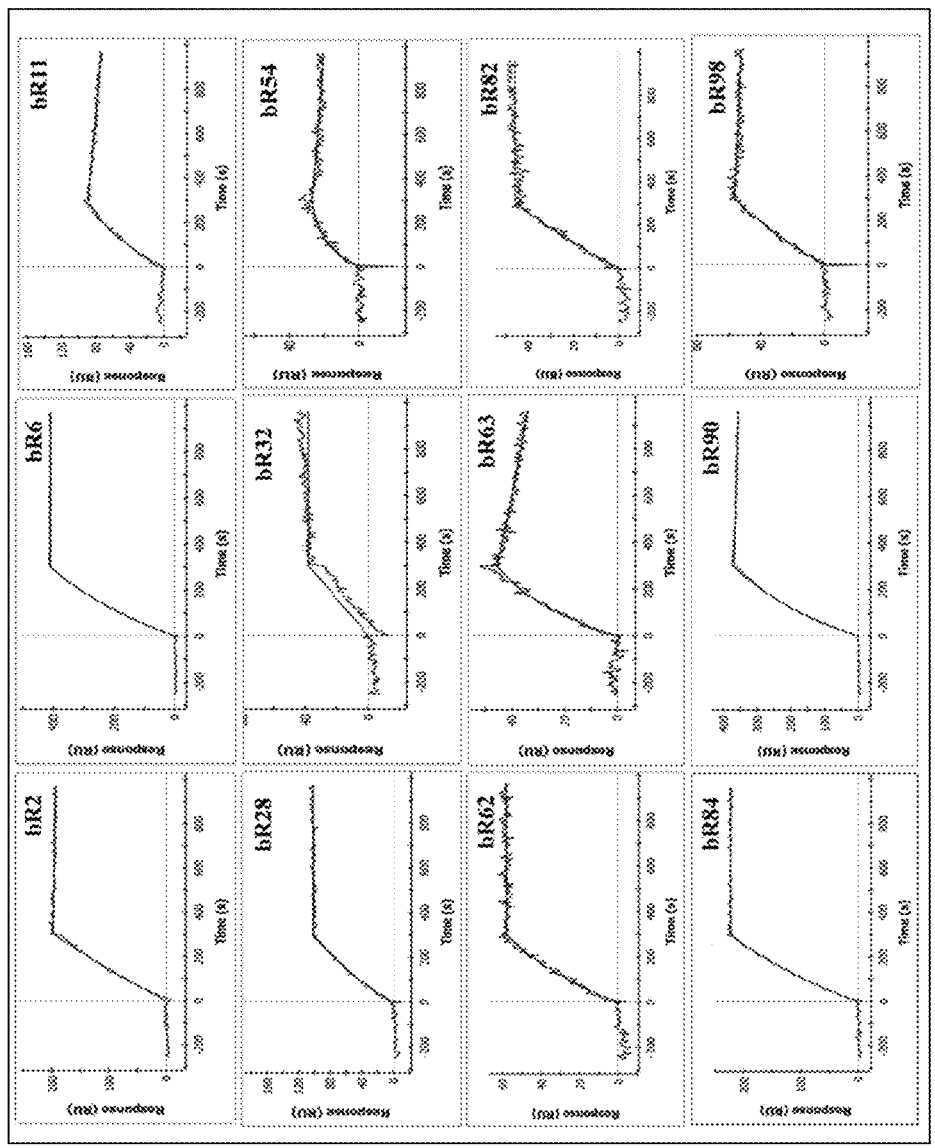
FIG. 55 depicts kinetic screening profiles of SPR positive clones of anti-PfRh5 at 500 nM analyte concentration. Biotinylated bivalent anti-$C_H$1/anti-λ capture antibody was immobilized at 3 μg/ml on L1 to L3 channels and similarly anti-$CH_1$/anti-κ was immobilized on L4 to L6 channels of a NLC chip in the vertical direction. 1:5 dilutions of a set of five test Fabs at a time were captured in horizontal direction for 300s at 25 μl/min flow rate. Two consecutive captures were performed to saturate the capture surface. Reference surfaces (sixth horizontal channel) was saturated using non-specific (non-PfRh5 binder) commercial human Fab to exactly mimic the test surfaces. Before the analyte injection, baseline was stabilized using three consecutive injections of running buffer at 100 μl/min for 60s. The system was paused for κ min after first buffer injection followed by the remaining two—this helps to stabilize the signal rapidly. Single concentration of 500 nM of PfRh5 was injected horizontally on all six horizontal channels at 25 µl/min for 120s (2 min) followed by dissociation for 300s (5 min). Surfaces were regenerated using glycine pH 2.0 for 60s followed by second injection for 30s. The sensorgrams were referenced appropriately and analyzed using Langmuir 1:1 fitting models.

192 clones each from the 3$^{rd}$ and 4$^{th}$ round of panning were taken forward for further screening. A total of 384 clones were thus expressed in 96-well plates and screened for full length clones using chain switch ELISA as exemplified in Example 36. FIG. 54 shows the representative data of plate 11 for anti-Rh5 soluble Fab screening using chain switch qELISA. Positive clones were categorized into high (black shaded cells), moderate (dark grey shaded cells) and low (light grey shaded cells) expressers.

qELISA showed that 86 clones were lambda positive while 65 clones were kappa positive. While selecting clones for kinetic ranking, clone prioritization was carried out as described in Example 36. 100 clones (50 each from kappa and lambda qELISA positives) were picked for kinetic screening. 50 ml scale expression, periplasmic extraction and buffer exchange was performed as described in Example 36. First round affinity ranking of 100 qELISA positive clones was done using a single concentration (500 nM) of PfRh5. 12 clones out of 100 (12%) qELISA positive hits were SPR positive (FIG. 55).

Before performing careful analysis using dose titration, all the SPR positive clones were sequenced with five primers as described in Example 25. 2 clones could not be sequenced accurately enough to build contigs. Of the 10 clones that could be read, all were found to be full length tandem light chain-heavy chain in-frame clones (Table 62). This data indicates that gating system as illustrated in this Example is also 100% foolproof as claimed (claim 28).

TABLE 62

| S. NO | Clone ID | Family | Panning round | SPR Binding | Bin as per sequencing | DNA sequencing LC | DNA sequencing HC |
|---|---|---|---|---|---|---|---|
| 1 | bR2 | Lambda | R3 | + | 4 | + | + |
| 2 | bR6 | Lambda | R4 | + | 5 | + | + |
| 3 | bR11 | Lambda | R4 | + | 6 | + | + |
| 4 | bR28 | Lambda | R4 | + | 3 | + | + |
| 5 | bR32 | Lambda | R4 | + | 3 | + | + |
| 6 | bR54 | Kappa | R3 | + | 2 | + | + |
| 7 | bR62 | Kappa | R4 | + | 1 | + | + |
| 8 | bR63 | Kappa | R4 | + | 1 | + | + |
| 9 | bR82 | Lambda | R4 | + | ? | No contig | No contig |
| 10 | bR84 | Lambda | R4 | + | ? | No contig | No contig |
| 11 | bR90 | Lambda | R4 | + | 7 | + | + |
| 12 | bR98 | Kappa | R4 | + | 1 | + | + |

Figure 56:
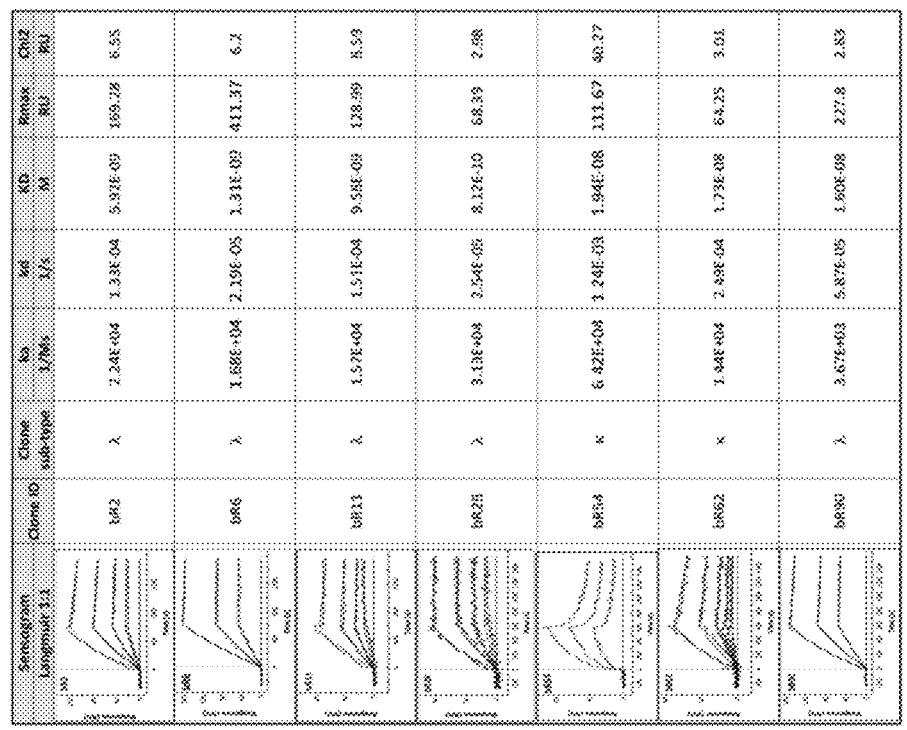
FIG. 56 depicts summarized view of SPR profiles and parameters of anti-PfRh5 monoclonal Fabs. Biotinylated bivalent anti-$C_H$1/anti-λ capture antibody was immobilized at 3 µg/ml on L1 to L3 and similarly anti-$C_H$1/anti-κ was immobilized on L4 to L6 channels of a NLC chip in the vertical direction. 1:5 dilutions of test Fab were captured on four vertical channels; L1 and L2 for lambda clones while channels L3 and L4 for kappa clones for 300s at 25 µl/min flow rate. Two consecutive captures were performed to saturate the capture surface. The reference surfaces (L3 and L6) were saturated using non-specific (non-Rh5 binder) commercial human Fab to exactly mimic the test surfaces. Before the analyte injection, baseline was stabilized using three consecutive injections of running buffer at 100 µl/min for 60s. The system was paused for 10 min after first buffer injection followed by the remaining two—this helps to stabilize the signal rapidly. Five concentrations (reciprocal dilution) of PfRh5 ranging between 500 nM-31.25 nM were injected in the horizontal direction for 600s (10 min). Dissociation of bound Fabs to target antigens was carried out for 900s (15 min) with running buffer. Surfaces were regenerated using glycine pH 2.0 for 60s followed by second injection for 30s. For data analysis, the sensorgrams were referenced appropriately and analyzed using Langmuir 1:1 fitting models. Resultant affinity constant values ($k_a$, $k_d$, $K_D$) were noted as required.

One representative clone from each sequence bin was taken forward to generate reliable kinetic parameters ($k_a$ and $k_d$) and affinity values ($K_D$) by analyte dose titration as set in FIG. 56. The highest affinity value ($K_D$) was observed for bR28 (0.81 nM).

Example 38

Applying the Staged Assessment Process to Find Anti-PfCSP Binders

*Plasmodium falciparum* CSP (PfCSP; Uniprot Q7K740_PLAF7) is a 42.5 kDa protein and therefore, 1 µg/ml of a solution of PfCSP is equivalent to 23.5 nM. This mass-mole conversion was considered to decide input bait concentration during each round of panning. Purified PfCSP was available in-house.

Figure 57:
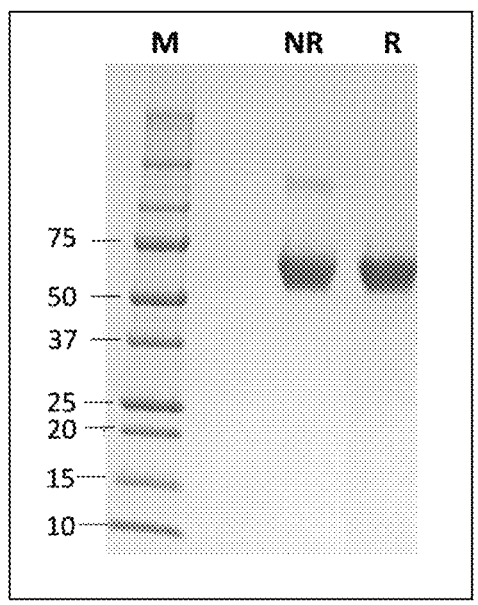
FIG. 57 depicts PfCSP purity and quality check. Samples were heated at 90° C. for 5 min and 5 µg each of reduced and non-reduced proteins were electrophoresed in a 4-15% polyacrylamide gelat 150V for 40 min; gel was stained in Coomassie Brilliant Blue R-250 for 2 h and de-stained using water:methanol:acetic acid (50:40:10) for 2 h. M is Precision plus All Blue SDS-PAGE marker from Biorad-NR is for non-reduced, R is for reduced.

The quality of the protein was checked by Coomassie staining of SDS-PAA gels and found to be acceptable (FIG. 57). PfCSP is known to run at a higher than calculated molecular weight on such gels (Plassmeyer M L et al., 2009). The quality of the protein was acceptable for panning. To biotinylate the protein, sulfo-NHS-SS-biotin chemistry was used as illustrated in Example 30, which allows the elution of phages bound to antigen by DTT. The Quanti*Tag™ Biotin Kit (Vector Labs, Cat #BDK 2000) was used to estimate the number of biotin tags and it was determined to be 3.65 (~4) mol/mol of PfCSP.

Antibody phages were generated by converting the 3.06× $10^{11}$ cfu library (Table 49) as described in Example 30. For solution panning of b-PfCSP, M280 Dynabeads were used. Four rounds of panning, elution and titer estimations were performed as described in Example 36 with two changes—(a) 500 nM of PfCSP was used as the start bait concentration with one log reduction at each round up to 500 pM for fourth round and (b) elution was performed using 50 mM DTT in carbonate buffer pH 8.5 for 30 min. Table 63 shows eluate titer data for all 4 rounds. Titers for amplified phages ranged between 1.1-9.2×$10^{12}$ pfu.

TABLE 63

| Target Antigen | b-PfCSP input concentration | Panning Round | Number of colonies $10^{-1}$ | $10^{-2}$ | $10^{-3}$ | $10^{-4}$ | Titer (cfu/ml) | Elution-vol (ml) | Total yield (cfu) |
|---|---|---|---|---|---|---|---|---|---|
| b-PfCSP | 500 nM | R-1 | NC | NC | 10 | 2 | 4.0E+05 | 2 | 8.0E+05 |
|  | 50 nM | R-2 | NC | 51 | 50 | — | 1.0E+05 | 2 | 2.0E+05 |
|  | 5 nM | R-3 | NC | 4 | 28 | — | 5.6E+05 | 2 | 1.1E+06 |
|  | 500 pM | R-4 | NC | NC | 602 | — | 1.2E+07 | 2 | 2.4E+07 |

Table 63 reveals that eluate titer increased proportionally with decrease in bait concentration over the panning rounds, which is considered a typical sign of successful panning (McCafferty J. 1996. Phage display: Factors affecting panning efficiency. In: *Phage Display of Peptides and Proteins: A Laboratory Manual*; Kontermann R E, 2010. Immunotube selections. In: *Antibody Engineering; Vol.* 1). Yields of amplified phages from all three rounds were fairly similar. Round 4 phages were not amplified as the process was stopped after the fourth round.

Figure 58:
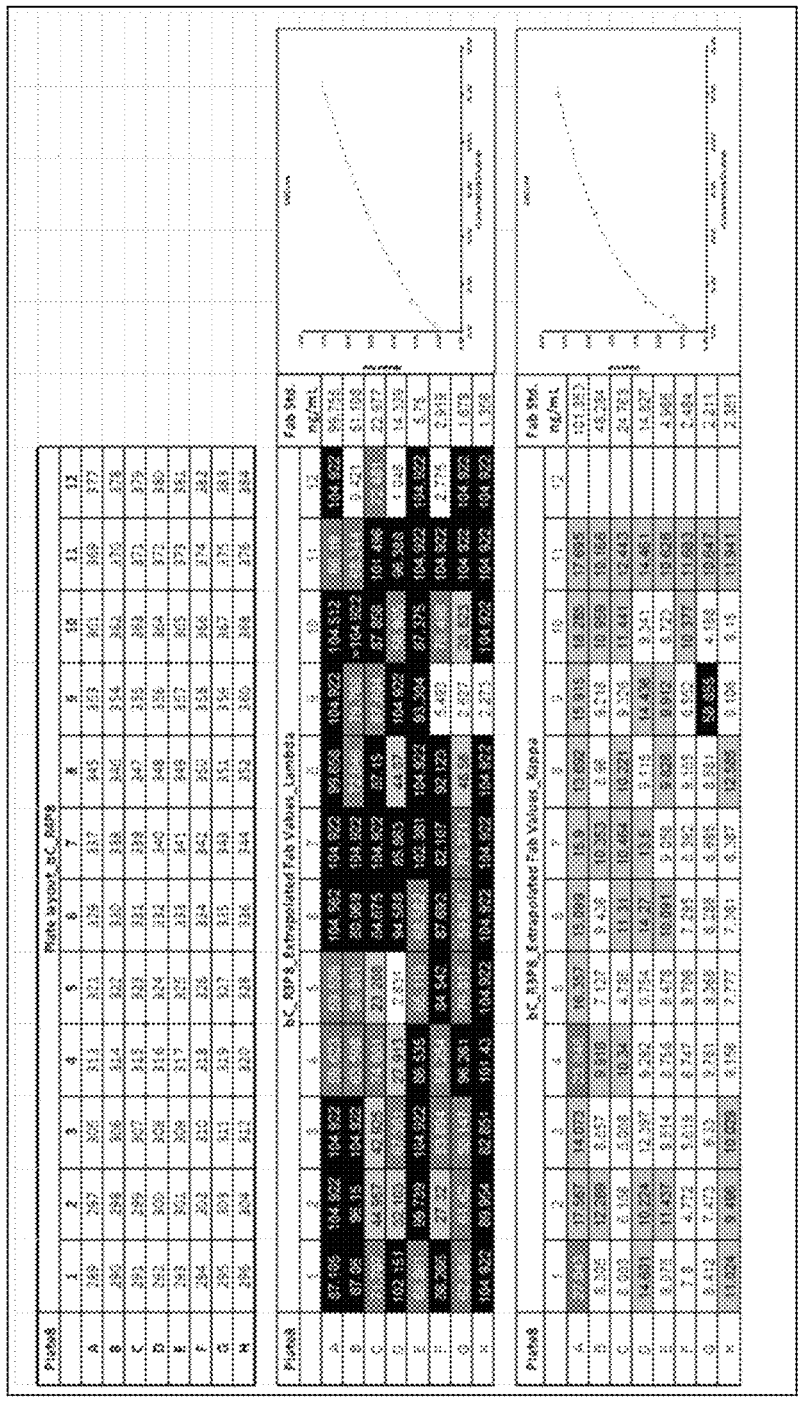
FIG. 58 depicts representative data for anti-PfCSP soluble Fab screening using chain switch qELISA. Upper panel shows layout of plate 8 of the PfCSP campaign with clone numbers 289 to 384. Middle panel shows standard curve and $A_{450}$ values using lambda detection antibody whereas bottom panel shows standard curve and $A_{450}$ values using kappa detection antibody. Black color indicates high expressing clones; dark grey color indicates moderate expressing clones while light grey color indicates low expressing clones.

Clones were screened in monoclonal soluble Fab formats and harvested as bacterial crude periplasmic extracts as described in Example 36. FIG. 58 shows the representative data of plate 8 for anti-PfCSP soluble Fab screening using chain switch qELISA. Positive clones were categorized as described in Example 36.

Figure 59:
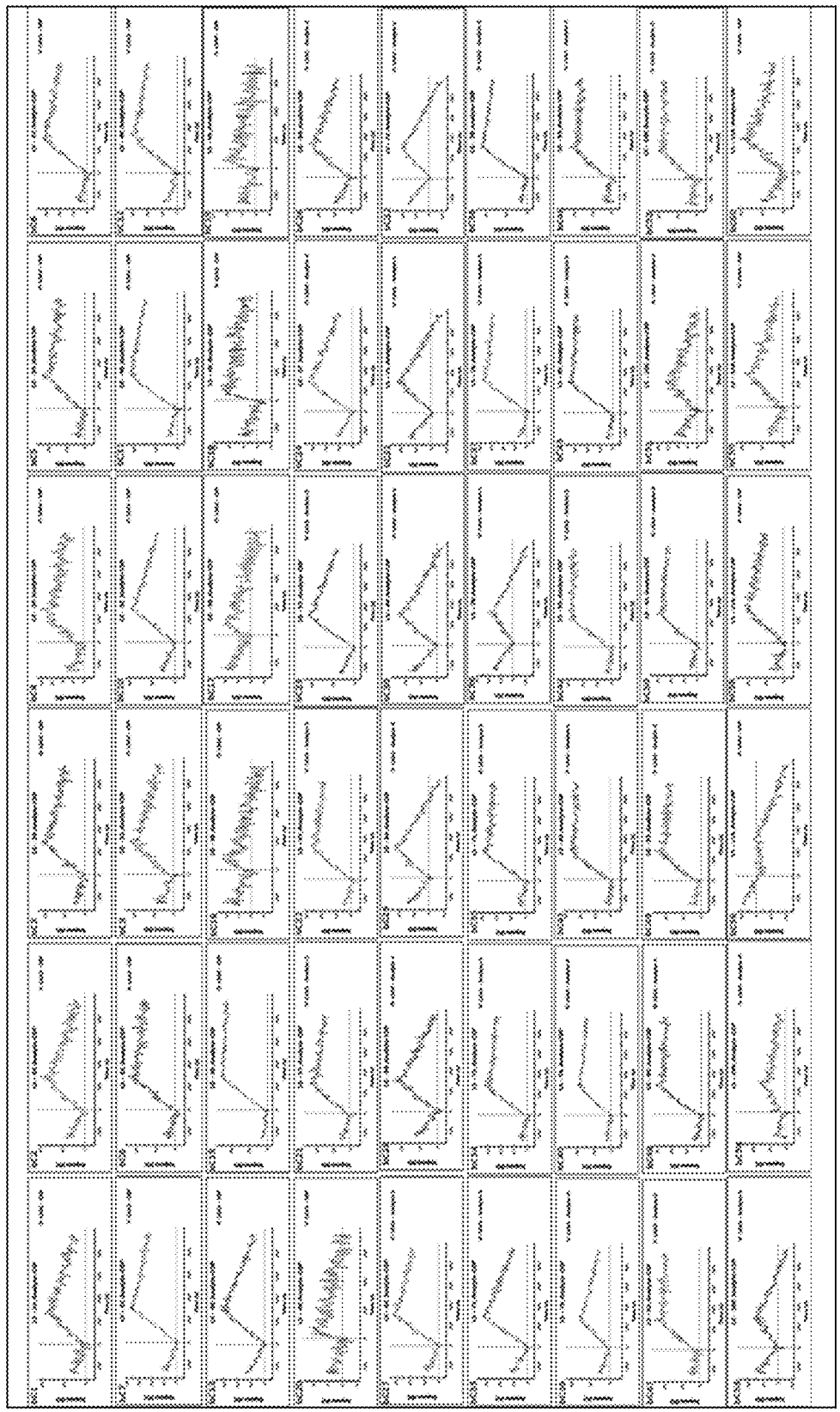
FIGS. 59A and 59B depicts kinetic screening profiles of SPR positive clones of anti-PfCSP at 500 nM analyte concentration (depicted as two parts FIG. 59A and FIG. 59B). 1:1 mixture of biotinylated bivalent anti-$C_H$1/anti-κ and anti-$C_H$1/anti-µ capture antibodies were immobilized at three different concentrations (10, 3 and 1 µg/ml) vertically in duplicate. 1:5 dilutions of a set of five test Fabs at a time were captured in horizontal direction for 300s at 25 µl/min flow rate. Two consecutive captures were performed to saturate the capture surface. Reference surface (sixth horizontal channel) was saturated using non-specific (non-PfCSP binder) commercial human Fab to exactly mimic the test surfaces. Before the analyte injection, baseline was stabilized using three consecutive injections of running buffer at 100 µl/min for 60s. The system was paused for 5 min after first buffer injection followed by the remaining two—this helps to stabilize the signal rapidly. Single concentration of 500 nM was injected horizontally on all six horizontal channels at 25 µl/min for 120s (2 min) followed by dissociation for 300s (5 min). Surfaces were regenerated using glycine pH 2.0 for 60s followed by second injection for 30s. The sensorgrams were referenced appropriately and analyzed using Langmuir 1:1 fitting models.
Figure 59:
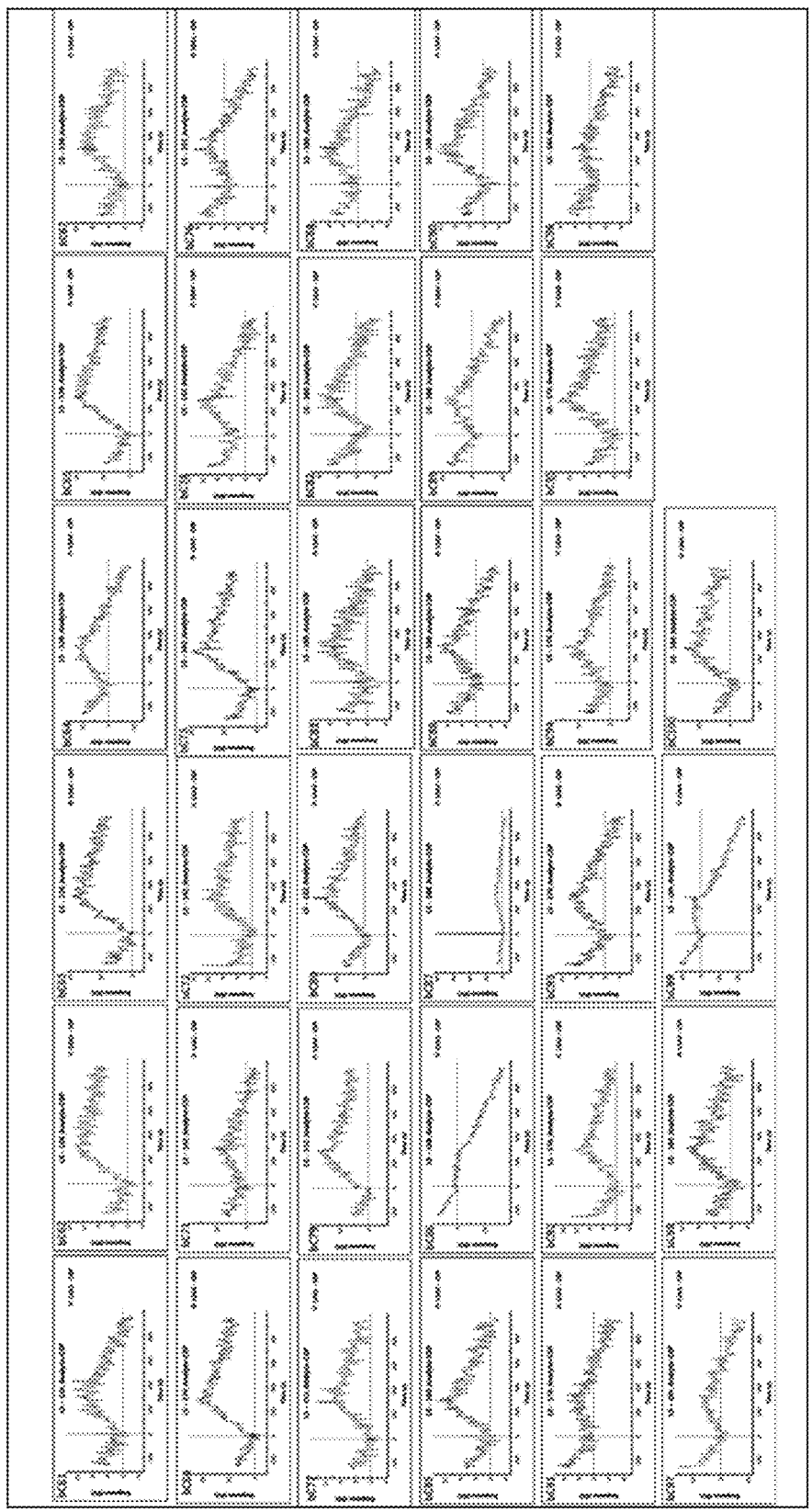

Out of 384 clones screened by qELISA, 201 clones were lambda positive while 105 clones were kappa positive. While selecting clones for kinetic ranking, clone prioritization was carried out as described in Example 36. 100 clones (50 each from kappa and lambda qELISA positives) were picked for kinetic screening. 50 ml scale expression, periplasmic extraction and buffer exchange was performed as described in Example 36. First round affinity ranking of 100 qELISA positive clones was done using a single concentration (500 nM) of PfCSP. As set out in FIG. 59, 87 out of 100 clones were SPR positive from this low-resolution screening.

Before performing careful analysis using dose titration, all the SPR positive clones were sequenced with two primers to determine the variable light and heavy chains. 80 clones were sequence readable, of which 75 clones had identical sequences and the remainder five (bC52, bC54, bC61, bC71 and bC72) had unique sequences. The complete sequences of bC3 (one representative of the major cluster of 75 clones), bC52, bC54, bC61, bC71 and bC72 were obtained by dideoxy sequencing with five primers as described in Example 25 for determining the tandem LC-HC structure of the encoded Fabs. 5 clones were full length in-frame (bC3, bC52, bC61, bC71 and bC72) while one clone (bC54) had stop codon in the variable heavy chain. This data indicates that gating system as illustrated in Example 35 is ~83% foolproof in the case of PfCSP (Table 64).

TABLE 64

| Clone staus | No of clones | In percentage (%) |
|---|---|---|
| Total Number of clones | 100 | |
| First shot SPR positive clones | 87 | 87 |
| Un readable (by sequencing) | 7 | 8.0 |
| Readable clones (by sequencing) | 80 | 92.0 |
| Clones with identical sequence | 75 | 93.8 |
| Clones with unique sequence | 5 | 6.3 |
| Total no of diverse clones (unique) | 6 | 73 |
| Off-frame clones | 1 | 16.7 |
| In-frame clones | 5 | 83.3 |

These five clones were further categorized into five bins as per uniqueness in their sequences and data shown in Table 65.

TABLE 65

| S. NO | Clone ID | Family | Panning round | SPR | Bin as per sequencing | DNA sequencing LC | DNA sequencing HC |
|---|---|---|---|---|---|---|---|
| 1 | bC3* | Lambda | R3 | + | 1 | + | + |
| 2 | bC52 | Lambda | R3 | + | 2 | + | + |
| 3 | bC61 | Lambda | R3 | + | 3 | + | + |
| 4 | bC71 | Lambda | R3 | + | 4 | + | + |
| 5 | bC72 | Lambda | R3 | + | 5 | + | + |

Note:
bC3* is one of the representative of the major cluster containing 75 clones.

The full length in-frame clones were taken forward to generate reliable kinetic parameters ($k_a$ and $k_d$) and affinity values ($K_D$) by analyte dose titration. FIG. 60 shows summarized view of SPR profiles and parameters of all five clones.

The examples of antibody discovery process for human sTNFα and antigens from *Plasmodium falciparum* origin signifies that the ultra-large naïve antibody phage display library combined with antibody discovery funnel approach described herein can generate therapeutic grade antibodies directly from library without the need of affinity maturation as evidenced by sub-nanomolar and picomolar range $K_D$ values of hits. The process is also rapid as it consumes about 4-5 weeks between initiating 4 successive rounds of panning to establishing kinetic parameters of antigen-specific Fabs as water-dissolved proteins. As the latter property is the most important assumption before CQAs for antibody manufacturing can even apply, the process as exemplified herein is therefore conducive to direct manufacturability assessment of the discovered antibodies from phage display libraries without involvement of intermediate steps such as phenotyping as phage-Fv fusions and the requirement to convert from phage format to plasmid format by re-cloning for expression analysis as set in prior art.

REFERENCES CITED

1. Abdiche Y N, Malashock D S, Pinkerton A, Pons J. (2009) Exploring blocking assays using Octet, ProteOn, and Biacore biosensors. *Anal Biochem* 386: 172-180.
2. Alt N, Zhang T Y, Motchnik P, Taticek R, Quarmby V, Schlothauer T, Beck H, Emrich T, Harris R J. (2016) Determination of critical quality attributes for monoclonal antibodies: using quality by design principles. *Biologicals* 44:291-305.
3. Andris-Widhopf J, Steinberger P, Fuller R, Rader C, and Barbas C F, III. (2001). Generation of antibody libraries: PCR amplification and assembly of light- and heavy-chain coding sequences. Chapter 9 in: *Phage Display: A Laboratory Manual*; (eds. Carlos F. Barbas III, Dennis R. Burton, Jamie K. Scott and Gregg J. Silverman); Cold Spring Harbor Laboratory Press, Cold Spring Harbor, N.Y.; pp 9.1 to 9.113.
4. Authors unknown (2007-2008) Cleavage close to the end of DNA fragments (linearized vectors); Appendix item 10 in *New England Biolabs Product Catalog and Technical Reference*; New England Biolabs, Ipswich, Mass., USA.
5. Authors Unknown. (2015) Protocol: Use of Glycerol Stocks and Preparation of Transfection-Quality Plasmid DNA; Broad Institute, Boston, Mass.
6. Azzazy H M, Highsmith W E. (2002) Phage display technology: clinical applications and recent innovations. *Clin. Biochem* 35:425-445.

7. Barbas C F III, Kang A S, Lerner R A, Benkovic S J. (1991) Assembly of combinatorial antibody libraries on phage surfaces: The gene III site. *P Natl Acad Sci USA* 88:7978-7982.
8. Barnes W M. (1994) PCR amplification of up to 35-kb DNA with high fidelity and high yield from lambda bacteriophage templates. *P Natl Acad Sci USA* 91:2216-2220.
9. Better M, Chang C P, Robinson R R, Horwitz A H. (1988) *Escherichia coli* secretion of an active chimeric antibody fragment. *Science* 240:1041-1043.
10. Boder E T, Wittrup K D. (1997) Yeast surface display for screening combinatorial polypeptide libraries. *Nat Biotechnol* 15:553-557.
11. Bonnycastle L L C, Menendez A, Scott J K (2001) General phage methods; Chapter 15 in *Phage Display: A Laboratory Manual*; Cold Spring Harbor Laboratory Press, Cold Spring Harbor, N.Y.; pp 15.1-15.30.
12. Bradbury A. (2010) Cloning hybridoma cDNA by RACE. Chapter 2 in: *Antibody Engineering; Volume 1*; (eds. R. Kontermann and S. Dübel); Springer-Verlag, Berlin-Heidelberg; pp 15-20.
13. Brüggemann M, Taussig M J. (1997) Production of human antibody repertoires in transgenic mice. *Curr Opin Biotechnol* 8:455-458.
14. Buckler D R, Park A, Viswanathan M, Hoet R M, Ladner R C. (2008) Screening isolates from antibody phage-display libraries. *Drug Discov Today* 13:318-24. doi: 10.1016/j.drudis.2007.10.012.
15. Burton D R. (1995) Phage display. *Immunotechnology* 1:87-94.
16. Burton D R. (2001). Overview: Amplification of antibody genes. Chapter 7 in: *Phage Display: A Laboratory Manual*; (eds. Carlos F. Barbas III, Dennis R. Burton, Jamie K. Scott and Gregg J. Silverman); Cold Spring Harbor Laboratory Press, Cold Spring Harbor, N.Y.; pp 7.1-7.4.
17. Canziani G A, Klakamp S, Myszka D G. (2004) Kinetic screening of antibodies from crude hybridoma samples using Biacore. *Anal Biochem* 325:301-307.
18. Carter P, Presta L, Gorman C M, Ridgway J B, Henner D, Wong W L, Rowland A M, Kotts C, Carver M E, Shepard H M. (1992) Humanization of an anti-p185$^{HER2}$ antibody for human cancer therapy. *P Natl Acad Sci USA* 89:4285-4289.
19. Casadevall A, Janda A. (2012) Immunoglobulin isotype influences affinity and specificity. *P Natl Acad Sci USA* 109:12272-12273. doi: 10.1073/pnas.1209750109.
20. Chames P, Van Regenmortel M, Weiss E, Baty D. (2009) Therapeutic antibodies: successes, limitations and hopes for the future. *Br J Pharmacol* 157:220-33. doi: 10.1111/j.1476-5381.2009.00190.x.
21. Chames, P and Baty, D. (2010) Phage display and selections on biotinylated antigens; Chapter 11 in: *Antibody Engineering, Volume 1* (eds. Roland E Kontermann and Stefan Dübel); Springer-Verlag, Berlin Heidelberg; pp 151-164.
22. Chen C, Snedecor B, Nishihara J C, Joly J C, McFarland N, Andersen D C, Battersby J E, Champion K M. (2004) High-level accumulation of a recombinant antibody fragment in the periplasm of *Escherichia coli* requires a triple-mutant (degP prc spr) host strain. *Biotechnol Bioeng* 85:463-474.
23. Chester K A, Hawkins R E. (1995) Clinical issues in antibody design. *Trends Biotechnol* 13:294-300. DOI: 10.1016/S0167-7799(00)88968-4.
24. Cho N, Hwang B, Yoon J K, Park S, Lee J, Seo H N, Lee J, Huh S, Chung J, Bang D. (2015) De novo assembly and next-generation sequencing to analyse full-length gene variants from codon-barcoded libraries. *Nat Commun* 6:8351. doi: 10.1038/ncomms9351.
25. Chowdhury P S. (2002) Targeting random mutations to hotspots in antibody variable domains for affinity improvement. Chapter 24 in: *Methods in Molecular Biology, vol. 178: Antibody Phage Display: Methods and Protocols* (eds. Philippa M. O'Brien and Robert Aitken); Humana Press Inc., Totowa, N.J.; pp 269-285.
26. de Boer M, Chang S Y, Eichinger G, Wong H C. (1994) Design and analysis of PCR primers for the amplification and cloning of human immunoglobulin Fab fragments. *Hum Antibodies Hybridomas* 5:57-64.
27. de Bruin R, Spelt K, Mol J, Koes R, Quattrocchio F. (1999) Selection of high-affinity phage antibodies from phage display libraries. *Nat Biotechnol* 17:397-399.
28. de Haard H J, van Neer N, Reurs A, Hufton S E, Roovers R C, Henderikx P, de Bruïne A P, Arends J W, Hoogenboom H R. (1999) A large non-immunized human Fab fragment phage library that permits rapid isolation and kinetic analysis of high affinity antibodies. *J Biol Chem* 274:18218-18230.
29. de Haard, H J W (2002) Construction of large naïve Fab libraries; Chapter 5 in *Methods in Molecular Biology, vol. 178: Antibody Phage Display: Methods and Protocols* (eds. Philippa M. O'Brien and Robert Aitken); Humana Press, Totowa, N.J.; pp 87-100.
30. Dechiara T M, Poueymirou W T, Auerbach W, Frendewey D, Yancopoulos G D, Valenzuela D M. (2009) VelociMouse: fully ES cell-derived FO-generation mice obtained from the injection of ES cells into eight-cell-stage embryos. *Methods Mol Biol* 530:311-324. doi: 10.1007/978-1-59745-471-1_16.
31. Diamante L, Gatti-Lafranconi P, Schaerli Y, Hollfelder F. (2013) In vitro affinity screening of protein and peptide binders by megavalent bead surface display. *Protein Eng Des Sel* 26:713-724.
32. Dobson C L, Minter R R, Hart-Shorrock C P. (2012) Naïve antibody libraries from natural repertoires. Chapter 17 in: *Phage Display in Biotechnology and Drug Discovery* (eds. Sachdev S Sidhu and Clarence Ronald Geyer), 2$^{nd}$ Ed. CRC Press, Boca Raton, Fla.; pp 455-493.
33. Drake A W, Papalia G A. (2012) Biophysical considerations for development of antibody-based therapeutics. Chapter 5 in: *Development of antibody-based therapeutics* (eds. Mohmmad A. Tabrizi, Gadi G. Bornstein and Scott L. Klakamp); Springer Science+Business Media, New York, N.Y.; pp 95-139.
34. Eisenhardt S U, Peter K (2010) Phage display and subtractive selection on cells. Chapter 12 in: *Antibody Engineering; Volume 1*; (eds. Roland E Kontermann and Stefan Dübel); Springer-Verlag, Berlin-Heidelberg; pp 165-181.
35. Ewert S, Honegger A, Plückthun A. (2004) Stability improvement of antibodies for extracellular and intracellular applications: CDR grafting to stable frameworks and structure-based framework engineering. *Methods* 34:184-199. DOI: 10.1016/j.ymeth.2004.04.007.
36. Foote J, Eisen H N. (1995) Kinetic and affinity limits on antibodies produced during immune responses. *P Natl Acad Sci USA* 92:1254-1256.
37. Frenzel A, Schirrmann T, Hust M. (2016) Phage display-derived human antibodies in clinical development and therapy. *mAbs* 8:1177-1194. DOI: 10.1080/19420862.2016.1212149.

38. Gelfand D H, White T J. (1990) Thermostable DNA polymerases. Chapter 16 in: *PCR protocols: A guide to methods and applications*. (eds. Michael J. Innis, David H. Gelfand, John J. Sninsky, and Thomas J. White); Academic Press, Inc.; San Diego, Calif.; pp 129-141.
39. Geyer C R, McCafferty J, Dübel S, Bradbury A R M, Sidhu S S. (2012) Recombinant antibodies and in vitro selection technologies. Chapter 2 in: *Antibody Methods and Protocols* (eds. Gabriele Proetzel and Hilmer Ebersbach); *Method Mol Biol* 901:11-32. DOI 10.1007/978-1-61779-931-0_2.
40. Glanville J, D'Angelo S, Khan T A, Reddy S T, Naranjo L, Ferrara F, Bradbury A R. (2015) Deep sequencing in library selection projects: what insight does it bring? *Curr Opin Struct Biol* 33:146-160. doi: 10.1016/j.sbi.2015.09.001.
41. Glennie M J, Johnson P W M. (2000) Clinical trials of antibody therapy. *Immunol Today* 21:403-410.
42. Green L L. (1999) Antibody engineering via genetic engineering of the mouse: XenoMouse strains are a vehicle for the facile generation of therapeutic human monoclonal antibodies. *J Immunol Methods* 231:11-23.
43. Green M R, Sambrook J. (2012a) Concentrating and desalting nucleic acids with microconcentrators. Protocol 6 of Chapter 1 in: *Molecular Cloning: A Laboratory Manual; Vol.* 1 (eds. Michael R Green and Joseph Sambrook); 4$^{th}$ Ed. Cold Spring Harbor Laboratory Press; Cold Spring Harbor, N.Y.; pp 28-29.
44. Green M R, Sambrook J. (2012b) PCR amplification of GC-Rich Templates. Protocol 4 of Chapter 7 in: *Molecular Cloning: A Laboratory Manual*; Vol. 1 (eds. Michael R Green and Joseph Sambrook); 4$^{th}$ Ed. Cold Spring Harbor Laboratory Press; Cold Spring Harbor, N.Y.; pp 484-489.
45. Green M R, Sambrook J (2012c) Cloning in plasmid vectors: Blunt end cloning; Protocol 6 of Chapter 3 in *Molecular Cloning: A Laboratory Manual; 4$^{th}$ Ed.; Vol.* 1 (eds. Michael R Green and Joseph Sambrook); Cold Spring Harbor Laboratory Press; Cold Spring Harbor, N.Y.; pp 186-188.
46. Griffiths A D, Williams S C, Hartley O, Tomlinson I M, Waterhouse P, Crosby W L, Kontermann R E, Jones P T, Low N M, Allison T J, Prospero T D, Hoogenboom H R, Nissim A, Cox J P L, Harrison J L, Zaccolo M, Gherardi E, Winter G. (1994) Isolation of high affinity human antibodies directly from large synthetic repertoires. *EMBO J* 13:3245-3260.
47. Hai S-H, McMurry J A, Knopf P M, Martin W, de Groot A S (2009) Immunogenicity screening using in silico methods: Correlation between T-Cell epitope Content and clinical immunogenicity of monoclonal antibodies. Chapter 22 in: *Therapeutic Monoclonal Antibodies: From Bench to Clinic* (ed. Zhiqiang An); John Wiley & Sons, Inc., Hoboken, N.J.; pp 417-437.
48. Hanes J, Plückthun A. (1997) In vitro selection and evolution of functional proteins by using ribosome display. *P Natl Acad Sci USA* 94:4937-4942.
49. Harlow E, Lane D. (1988) Immunoassays. Chapter 14 in *Antibodies: A Laboratory Manual* (eds. Ed Harlow and David Lane); Cold Spring Harbor Laboratory Press; Cold Spring Harbor, N.Y.; pp 553-612.
50. Hawkins R E, Russell S J, Winter G. (1992) Selection of phage antibodies by binding affinity: Mimicking affinity maturation. *J Mol Biol* 226:889-896.
51. Hay F C, Westwood O M R. (2002) Preparation of human B-cell hybridoma. Section 2.8.2. of Chapter 1: Isolation and structure of immunoglobulins in: Practical Immunology; 4$^{th}$ Ed. (eds. Frank C. Hay and Olwyn M. R. Westwood); Blackwell Science Ltd; Oxford, UK; pp 58-59.
52. Heckman K L, Pease L R. (2007) Gene splicing and mutagenesis by PCR-driven overlap extension. *Nat Protocols* 2:924-932.
53. Higuchi R, Krummell B, Saiki R K. (1988). A general method of in vitro preparation and specific mutagenesis of DNA fragments: study of protein and DNA interactions. *Nucl Acids Res* 16:7351-7367.
54. Hoet R M, Cohen E H, Kent R B, Rookey K, Schoonbroodt S, Hogan S, Rem L, Frans N, Daukandt M, Pieters H, van Hegelsom R, Neer N C, Nastri H G, Rondon I J, Leeds J A, Hufton S E, Huang L, Kashin I, Devlin M, Kuang G, Steukers M, Viswanathan M, Nixon A E, Sexton D J, Hoogenboom H R, Ladner R C. (2005) Generation of high-affinity human antibodies by combining donor-derived and synthetic complementarity-determining-region diversity. *Nat Biotechnol* 23:344-448. DOI: 10.1038/nbt1067.
55. Holliger P, Prospero T, Winter G. (1993) "Diabodies": Small bivalent and bispecific antibody fragments. *P Natl Acad Sci* 90:6444-6448.
56. Honegger A. (2008) Engineering antibodies for stability and efficient folding. *Handb Exp Pharmacol Vol.* 181; pp 47-68. DOI: 10.1007/978-3-540-73259-43.
57. Hoogenboom H R, Griffiths A D, Johnson K S, Chiswell D J, Hudson P, Winter G. (1991) Multi-subunit proteins on the surface of filamentous phage: methodologies for displaying antibody (Fab) heavy and light chains. *Nucl Acids Res* 19:4133-4137.
58. Horlick R A, Macomber J L, Bowers P M, Neben T Y, Tomlinson G L, Krapf I P, Dalton J L, Verdino P, King D J. (2013) Simultaneous surface display and secretion of proteins from mammalian cells facilitate efficient in vitro selection and maturation of antibodies. *J Biol Chem* 288:19861-19869.
59. Horton R M, Hunt H D, Ho S N, Pullen J K, Pease L R. (1989) Engineering hybrid genes without the use of restriction enzymes: gene splicing by overlap extension. *Gene* 77:61-68.
60. Humphreys D P. (2003) Production of antibodies and antibody fragments in *Escherichia coli* and a comparison of their functions, uses and modification. *Curr Opin Drug Disc* 6:188-196.
61. Humphreys D P, Bowering L. (2009) Production of antibody Fab' fragments in *E. coli*. Chapter 27 in: *Therapeutic Monoclonal Antibodies: From Bench to Clinic* (ed. Zhiqiang An); John Wiley & Sons, Inc., Hoboken, N.J.; pp 589-622.
62. Hust M, Thie H, Schirrmann, Dübel S. (2009) Antibody phage display; Chapter 8 in: *Therapeutic Monoclonal Antibodies: From Bench to Clinic* (ed. Zhiqiang An); John Wiley & Sons, Inc., Hoboken, N.J.; pp 191-211.
63. Hust M, Mersmann M. (2010) Phage display and selection in microtitre plates. Chapter 10 in: *Antibody Engineering; Volume* 1; (eds. Roland E Kontermann and Stefan Dübel); Springer-Verlag, Berlin-Heidelberg; pp 139-149.
64. Jones R H, Mollitoris B A (1984) A statistical method for determining the breakpoint of two lines; *Anal Biochem* 141:287-290.
65. Jones P T, Dear P H, Foote J, Neuberger M, Winter G. (1986) Replacing the complementarity-determining regions in a human antibody with those from a mouse. *Nature* 321:522-525.

66. Kepert J F, Cromwell M, Engler N, Finkler C, Gellermann G, Gennaro L, Harris R, Iverson R, Kelley B, Krummen L, McKnight N, Motchnik P, Schnaible V, Taticek R. (2016) Establishing a control system using QbD principles. *Biologicals* 44: 319-331.
67. Kirsch M, Zaman M, Meier D, Dübel S, Hust M. (2005) Parameters affecting the display of antibodies on phage. *J Immunol Methods* 301:173-185.
68. Knappik A, Ge L, Honegger A, Pack P, Fischer M, Wellnhofer G, Hoess A, Wölle J, Plückthun A, Virnekäs B. (2000) Fully synthetic human combinatorial antibody libraries (HuCAL) based on modular consensus frameworks and CDRs randomized with trinucleotides. *J Mol Biol* 296:57-86. DOI: 10.1006/jmbi.1999.3444.
69. Köhler G, Milstein C. (1975) Continuous cultures of fused cells secreting antibody of predefined specificity. *Nature* 256:495-497.
70. Kontermann R E. (2010) Immunotube selections. Chapter 9 in: *Antibody Engineering; Volume 1*; (eds. Roland E Kontermann and Stefan Dübel); Springer-Verlag, Berlin-Heidelberg; pp 127-137.
71. Kortt A A, Lah M, Oddie G W, Gruen $C_L$, Burns J E, Pearce L A, Atwell J L, McCoy A J, Howlett G J, Metzger D W, Webster R G, Hudson P J. (1997) Single-chain Fv fragments of anti-neuraminidase antibody NC10 containing five- and ten-residue linkers form dimers and with zero-residue linker a trimer. *Protein Eng* 10:423-433.
72. Küchenhoff H (1996) An exact algorithm for estimating breakpoints in segmented generalized linear models; *Sonderforschungsbereich* 386: Paper 27; 1-12.
73. Labrijn A F, Aalberse R C, Schuurman J. (2008) When binding is enough: nonactivating antibody formats. *Curr Opin Immunol* 20:479-485. doi: 10.1016/j.coi.2008.05.010.
74. Lawson A D G, Chaplin L C, Lang V, Sehdev M, Spitali M, Popplewell A, Weir N, King D J. (1997) Two-site assays for measuring recombinant antibody quality. *BIA J* 1:23.
75. Lefranc M-P. (2001) IMGT, the international ImMunoGeneTics database. *Nucl Acids Res* 29:207-209.
76. Leonard P, Säfsten P, Hearty S, McDonell B, Finlay W, O'Kennedy R. (2007) High throughput ranking of recombinant avian scFv antibody fragments from crude lysates using Biacore A100. *J Immunol Methods* 323:172-179.
77. Liu A Y, Robinson R R, Murray E D Jr, Ledbetter J A, Hellström I, Hellström K E. (1987) Production of a mouse-human chimeric monoclonal antibody to CD20 with potent Fc-dependent biologic activity. *J Immunol* 139:3521-3526.
78. Lonberg N. (2008) Fully human antibodies from transgenic mouse and phage display platforms. *Curr Opin Immunol* 20:450-459. doi: 10.1016/j.coi.2008.06.004.
79. Løset G Å, Løbersli I, Kavlie A, Stacy J E, Borgen T, Kausmally L, Hvattum E, Simonsen B, Hovda M B, Brekke O H. (2005) Construction, evaluation and refinement of a large human antibody phage library based on the IgD and IgM variable gene repertoire. *J Immunol Methods* 299:47-62. DOI: 10.1016/j.jim.2005.01.014.
80. Lou J, Marzari R, Verzillo V, Ferrero F, Pak D, Sheng M, Yang C, Sblattero D, Bradbury A. (2001) Antibodies in haystacks: how selection strategy influences the outcome of selection from molecular diversity libraries. *J Immunol Methods* 253:233-242.
81. Lowe D, Vaughan T J (2009) Human antibody repertoire libraries; Chapter 7 in: *Therapeutic Monoclonal Antibodies: From Bench to Clinic* (ed. Zhiqiang An); John Wiley & Sons, Inc., Hoboken, N.J.; pp 169-188.
82. Marks J D, Tristem M, Karpas A, Winter G. (1991) Oligonucleotide primers for polymerase chain reaction amplification of human immunoglobulin variable genes and design of family-specific oligonucleotide probes. *Eur J Immunol* 21:985-991.
83. Martineau P. (2010) Synthetic antibody libraries. Chapter 6 in: *Antibody Engineering; Volume 1*; (eds. Roland E Kontermann and Stefan Dübel); Springer-Verlag, Berlin-Heidelberg; pp 85-97.
84. McCafferty J. (1996) Phage display: Factors affecting panning efficiency. Chapter 15 in: *Phage Display of Peptides and Proteins: A Laboratory Manual;* (eds. Brian K. Kay, Jill Winter, John McCafferty); Academic Press Inc., San Diego, Calif.; pp 261-276.
85. Meijer P J, Andersen P S, Haahr Hansen M, Steinaa L, Jensen A, Lantto J, Oleksiewicz M B, Tengbjerg K, Poulsen T R, Coljee V W, Bregenholt S, Haurum J S, Nielsen L S. (2006) Isolation of human antibody repertoires with preservation of the natural heavy and light chain pairing. *J Mol Biol* 358:764-772. DOI: 10.1016/j.jmb.2006.02.040.
86. Ostermeier M, Benkovic S J. (2000) A two-phagemid system for the creation of non-phage displayed antibody libraries approaching one trillion members. *J Immunol Methods* 237:175-186.
87. Pavoni E, Monteriù G, Cianfriglia M, Minenkova O. (2007) New display vector reduces biological bias for expression of antibodies in *E. coli*. *Gene* 391:120-129. DOI: 10.1016/j.gene.2006.12.009.
88. Persic L, Roberts A, Wilton J, Cattaneo A, Bradbury A, Hoogenboom H R. (1997) An integrated vector system for the eukaryotic expression of antibodies or their fragments after selection from phage display libraries. *Gene* 187:9-18.
89. Petropoulos K. (2012) Phage display. Chapter 3 in: *Antibody Methods and Protocols* (eds. Gabriele Proetzel and Hilmer Ebersbach); *Methods Mol Biol* 901:33-51. doi: 10.1007/978-1-61779-931-0_3.
90. Plassmeyer M L, Reiter K, Shimp R L Jr, Kotova S, Smith P D, Hurt D E, House B, Zou X, Zhang Y, Hickman M, Uchime O, Herrera R, Nguyen V, Glen J, Lebowitz J, Jin A J, Miller L H, MacDonald N J, Wu Y, Narum D L. (2009) Structure of the *Plasmodium falciparum* circumsporozoite protein, a leading malaria vaccine candidate. *J Biol Chem* 284:26951-26963. doi: 10.1074/jbc.M109.013706.
91. Prassler J, Thiel S, Pracht C, Polzer A, Peters S, Bauer M, Nörenberg S, Stark Y, Kölln J, Popp A, Urlinger S, Enzelberger M. (2011) HuCAL PLATINUM, a synthetic Fab library optimized for sequence diversity and superior performance in mammalian expression systems. *J Mol Biol* 413:261-278. doi: 10.1016/j.jmb.2011.08.012.
92. Quintero-Hernández V, Juárez-González V R, Ortiz-León M, Sánchez R, Possani L D, Becerril B. (2007) The change of the scFv into the Fab format improves the stability and in vivo toxin neutralization capacity of recombinant antibodies. *Mol Immunol* 44:1307-1315.
93. Rader C. (2012a) Selection of human Fab libraries by phage display. Chapter 5 in: *Antibody Methods and Protocols* (eds. Gabriele Proetzel and Hilmer Ebersbach); *Methods Mol Biol.* 901:81-99. doi: 10.1007/978-1-61779-931-0_5.
94. Rader C. (2012b) Generation of human Fab libraries for phage display. Chapter 4 in: *Antibody Methods and Protocols* (eds. Gabriele Proetzel and Hilmer Ebersbach); *Methods Mol Biol.* 901:53-79. doi: 10.1007/978-1-61779-931-0_5.

95. Ravn U, Didelot G, Venet S, Ng K T, Gueneau F, Rousseau F, Calloud S, Kosco-Vilbois M, Fischer N. (2013) Deep sequencing of phage display libraries to support antibody discovery. *Methods* 60:99-110. doi: 10.1016/j.ymeth.2013.03.001.

96. Roberts R W, Szostak J W. (1997) RNA-peptide fusions for the in vitro selection of peptides and proteins. *P Natl Acad Sci USA* 94:12297-12302.

97. Rothe C, Urlinger S, Löhning C, Prassler J, Stark Y, Jäger U, Hubner B, Bardroff M, Pradel I, Boss M, Bittlingmaier R, Bataa T, Frisch C, Brocks B, Honegger A, Urban M. (2008) The human combinatorial antibody library HuCAL GOLD combines diversification of all six CDRs according to the natural immune system with a novel display method for efficient selection of high-affinity antibodies. *J Mol Biol* 376:1182-1200. doi: 10.1016/j.jmb.2007.12.018.

98. Röthlisberger D, Honegger A, Plückthun A. (2005) Domain interactions in the Fab fragment: a comparative evaluation of the single-chain Fv and Fab format engineered with variable domains of different stability. *J Mol Biol* 347:773-789. DOI: 10.1016/j.jmb.2005.01.053.

99. Sambrook J, Russell D W. (2001a) Preparation of cDNA libraries and gene identification. Chapter 11 in: *Molecular Cloning: A Laboratory Manual; Vol.* 2 (eds. Joseph Sambrook and David W. Russell); 3$^{rd}$ Ed. Cold Spring Harbor Laboratory Press; Cold Spring Harbor, N.Y.; pp 11.1-11.133.

100. Sambrook J, Russell D W. (2001b) The Hanahan method for preparation and transformation of competent *E. coli*: High efficiency transformation. Protocol 23 of Chapter 1 in: *Molecular Cloning: A Laboratory Manual; Vol.* 1 (eds. Joseph Sambrook and David W. Russell); 3$^{rd}$ Ed. Cold Spring Harbor Laboratory Press; Cold Spring Harbor, N.Y.; pp 1.105-1.111.

101. Sambrook J and Russell D W (2001c) Recovery of DNA from agarose gels: electroelution in dialysis bags; Protocol 4 of Chapter 5 in *Molecular Cloning: A Laboratory Manual; Vol.* 1 (eds. Joseph Sambrook and David W. Russell); 3$^{rd}$ Ed; Cold Spring Harbor Laboratory Press, Cold Spring Harbor, N.Y.; pp 5.23-5.25.

102. Sarkar G, Sommer S S. (1990). The "megaprimer" method of site-directed mutagenesis. Biotechniques 8:404-407.

103. Sblattero D, Bradbury A. (1998) A definitive set of oligonucleotide primers for amplifying human V regions. *Immunotechnology* 3:271-278.

104. Schräml M, Biehl M. (2012) Kinetic screening in the antibody development process. Chapter 11 in: *Antibody Methods and Protocols* (eds. Gabriele Proetzel and Hilmer Ebersbach); *Method Mol Biol* 901:171-181. DOI 10.1007/978-1-61779-931-0_11.

105. Schräml. M, von Proff L. (2012) Temperature-dependent antibody kinetics as a tool in antibody lead selection. Chapter 12 in: *Antibody Methods and Protocols* (eds. Gabriele Proetzel and Hilmer Ebersbach); *Method Mol Biol* 901:183-194. DOI 10.1007/978-1-61779-931-012.

106. Schwimmer L J, Huang B, Giang H, Cotter R L, Chemla-Vogel D S, Dy F V, Tam E M, Zhang F, Toy P, Bohmann D J, Watson S R, Beaber J W, Reddy N, Kuan H F, Bedinger D H, Rondon I J. (2013) Discovery of diverse and functional antibodies from large human repertoire antibody libraries. *J Immunol Methods* 391:60-71. doi: 10.1016/j jim. 2013.02.010.

107. Scott J K, CF Barbas III. (2001). Phage-display vectors. Chapter 2 in: *Phage Display: A Laboratory Manual;* (eds. Carlos F. Barbas III, Dennis R. Burton, Jamie K. Scott and Gregg J. Silverman); Cold Spring Harbor Laboratory Press, Cold Spring Harbor, N.Y.; pp 2.1 to 2.19.

108. Skerra A, Plückthun A. (1991) Secretion and in vivo folding of the Fab fragment of the antibody McPC603 in *Escherichia coli*: influence of disulphides and cis-prolines. *Protein Eng* 4:971-979.

109. Smith G P. (1985) Filamentous fusion phage: Novel expression vectors that display cloned antigens on the virion surface. *Science* 228:1315-1317.

110. Steukers M, Schaus J-M, van Gool R, Hoyoux A, Richalet P, Sexton D J, Nixon A E, Vanhove M. (2006) Rapid kinetic-based screening of Fab fragments. *J Immunol Methods* 310:126-135.

111. Sumida T, Doi N, Yanagawa H. (2009) Bicistronic DNA display for in vitro selection of Fab fragments. *Nucl Acids Res* 37(22):e147. doi:10.1093/nar/gkp776.

112. Tabrizi M A. (2012) Considerations in establishing affinity design goals for development of antibody-based therapeutics. Chapter 6 in: *Development of antibody-based therapeutics* (eds. Mohmmad A. Tabrizi, Gadi G. Bornstein and Scott L. Klakamp); Springer, New York, N.Y.; pp 141-151.

113. Thiagarajan G, Semple A, James J K, Cheung J K, Shameem M. (2016) A comparison of biophysical characterization techniques in predicting monoclonal antibody stability. *mAbs* 8:1088-1097. doi: 10.1080/19420862.2016.1189048.

114. Thie H, Schirrmann T, Paschke M, Dübel S, Hust M. (2008) SRP and Sec pathway leader peptides for antibody phage display and antibody fragment production in *E. coli*. *N Biotechnol.* 25:49-54. doi: 10.1016/j.nbt.2008.01.001.

115. Tiller T, Meffre E, Yurasov S, Tsuiji M, Nussenzweig M C, Wardemann H. (2008) Efficient generation of monoclonal antibodies from single human B cells by single cell RT-PCR and expression vector cloning. *J Immunol Methods* 329:112-124. DOI: 10.1016/j.jim.2007.09.017.

116. Tiller T, Schuster I, Deppe D, Siegers K, Strohner R, Herrmann T, Berenguer M, Poujol D, Stehle J, Stark Y, Heßling M, Daubert D, Felderer K, Kaden S, Kölln J, Enzelberger M, Urlinger S. (2013) A fully synthetic human Fab antibody library based on fixed VH/VL framework pairings with favorable biophysical properties. *mAbs* 5:445-470. doi: 10.4161/mabs.24218.

117. Tindall K R, Kunkel T A. (1988) Fidelity of DNA synthesis by the *Thermus aquaticus* DNA polymerase. *Biochemistry* 27:6008-6013.

118. Tomimatsu K, Matsumoto S E, Tanaka H, Yamashita M, Nakanishi H, Teruya K, Kazuno S, Kinjo T, Hamasaki T, Kusumoto K, Kabayama S, Katakura Y, Shirahata S. (2013) A rapid screening and production method using a novel mammalian cell display to isolate human monoclonal antibodies. *Biochem Biophys Res Commun* 441:59-64. doi: 10.1016/j.bbrc.2013.10.007.

119. van Blarcom T J, Harvey B R. (2009) Bacterial display of antibodies. Chapter 11 in: *Therapeutic Monoclonal Antibodies: From Bench to Clinic* (ed. Zhiqiang An); John Wiley & Sons, Inc., Hoboken, N.J.; pp 255-281.

120. Vaughan T J, Williams A J, Pritchard K, Osbourn J K, Pope A R, Earnshaw J C, McCafferty J, Hodits R A, Wilton J, Johnson K S. (1996) Human antibodies with sub-nanomolar affinities isolated from a large non-immunized phage display library. *Nat Biotechnol* 14:309-314.

121. von Behring E A, Kitasato S. (1890) Ueber das Zustandekommen der Diphtherie-Immunität und der Tetanus-Immunität bei Thieren. *Deutsch Med. Wochenschr* 49:1113-1114.

122. Warrens A N, Jones M D, Lechler R I. (1997) Splicing by overlap extension by PCR using asymmetric amplification: an improved technique for the generation of hybrid proteins of immunological interest. *Gene* 186:29-35.
123. Waterhouse P, Griffiths A D, Johnson K S, Winter G. (1993) Combinatorial infection and in vivo recombination: a strategy for making large phage antibody repertoires. *Nucl Acids Res* 21:2265-2266.
124. Weaver-Feldhaus J M, Lou J, Coleman J R, Siegel R W, Marks J D, Feldhaus M J. (2004) Yeast mating for combinatorial Fab library generation and surface display. *FEBS Lett* 564:24-34.
125. Webster R. (2001). Filamentous phage biology. Chapter 1 in: *Phage Display: A Laboratory Manual*; (eds. Carlos F. Barbas III, Dennis R. Burton, Jamie K. Scott and Gregg J. Silverman); Cold Spring Harbor Laboratory Press, Cold Spring Harbor, N.Y.; pp 1.1-1.37.
126. Weidner K M, Denzin L K, Voss E W, Jr. (1992) Molecular stabilization effects of interactions between anti-metatype antibodies and liganded antibody. *J Biol Chem* 267:10281-10288.
127. Winter G, Griffiths A D, Hawkins R E, Hoogenboom H R. (1994) Making antibodies by phage display technology. *Annu Rev Immunol* 12:433-455.

We claim:

1. A process for producing a naïve antibody phage display library (APDL) having a size ranging from between $3.06 \times 10^{11}$ to $9.13 \times 10^{11}$ cfu, the process comprising:
   i) immune repertoire capture to obtain a Fab comprising the steps of;
      a. RNA isolation and cDNA synthesis;
      b. amplification of $V_L$ lambda, $V_L$ kappa, and $V_H$ domains using primers comprising SEQ ID Nos. 1-23 and 42-54;
      c. amplification of C domains using SEQ ID Nos. 24-26 and using primers comprising SEQ ID Nos. 27-31;
      d. overlap PCR of light chains by fusion of Vκ and Cκ domains and $V_\lambda$ and $C_\lambda$ domains obtained from steps (b) and (c), respectively, using primers comprising SEQ ID Nos. 30, 35-37 and 55;
      e. overlap PCR of heavy chains obtained from fusion of $V_H$ and $CH_1$ domains obtained from steps (b) and (c) using primers comprising SEQ ID Nos. 28 and 33;
      f. overlap PCR of light chains and heavy chains obtained from steps (d) and (e) respectively to obtain Fabs using primers comprising SEQ ID Nos. 34-37 and 55; and
      g. purifying the amplicons at each step; and
   ii) displaying the captured immune repertoire of step (i) in a vector comprising a nucleotide sequence set forth in SEQ ID No. 38; wherein the APDL comprises a $1.26 \times 10^{11}$ to $2.55 \times 10^{11}$ cfu kappa library and a $1.79 \times 10^{11}$ to $3.59 \times 10^{11}$ cfu lambda library.

2. The process of claim 1, wherein the amplification of variable lambda domains is conducted in a two-step PCR using primers comprising SEQ ID Nos. 14-23 and 46-54, and comprises the steps of:
   i) obtaining a mixture of cDNA template, polymerase enzyme, primers, buffer and dNTP mix in an aqueous solution;
   ii) subjecting the mixture of step (i) to a temperature range of 90° C. to 96° C. to denature the templates; and
   iii) simultaneous annealing and extension of the denatured templates from (ii) at a temperature of 65° C. to 72° C. to obtain a first set of variable lambda domains with a diverse $V_\lambda$ repertoire capture.

3. The process of claim 2, wherein the amplification of variable kappa domains is conducted in a three-step PCR using primers comprising SEQ ID Nos. 9-13 and 42-45, and comprises the steps of:
   i) obtaining a mixture of cDNA template, polymerase enzyme, primers, buffer and dNTP mix in an aqueous solution;
   ii) subjecting the mixture of step (i) to a temperature range of 90° C. to 96° C. to denature the templates;
   iii) annealing the primers to the denatured templates from step (ii) at a temperature range of 55° C. to 70° C.; and
   iv) extension of the primers on annealed templates from step (iii) at temperature of 65° C. to 72° C. to obtain a first set of variable kappa domains with a diverse $V_\kappa$ repertoire capture.

4. The process of claim 3, wherein the amplification of variable heavy domains is conducted in a three-step PCR using primers comprising SEQ ID Nos. 1-8, and comprises the steps of:
   i) obtaining a mixture of cDNA template, polymerase enzyme, primers, buffer and dNTP mix in an aqueous solution;
   ii) subjecting the mixture of step (i) to a temperature range of 90° C. to 96° C. to denature the templates;

iii) annealing the primers to the denatured templates from step (ii) at a temperature range of 55° C. to 70° C.; and iv) extension of the primers on annealed templates from step (iii) at a temperature of 65° C. to 72° C. to obtain a first set of variable heavy domains with a diverse $V_H$ repertoire capture.

5. The process of claim 4, wherein the amplification of $C_H1$ domains is conducted as a three-step PCR using primers comprising SEQ ID Nos. 27-28 and templates comprising SEQ ID Nos. 24 and 39, and comprises the steps of:

i) obtaining a mixture of synthetic $C_H1$-domain template, polymerase enzyme, primers, buffer and dNTP mix in an aqueous solution;

ii) subjecting the mixture of step (i) to a temperature range of 90° C. to 96° C. to denature the templates;

iii) annealing the primers to the denatured templates from step (ii) at a temperature range of 55° C. to 70° C.; and iv) extension of the primers on annealed templates from step (iii) at a temperature of 65° C. to 72° C. to obtain a first set of constant heavy domains.

6. The process of claim 5, wherein the amplification of Cκ and $C_\lambda$ domains are conducted in a two-step PCR using primers comprising SEQ ID Nos. 29-31 and templates comprising SEQ ID Nos. 25-26 and 40-41, and comprises the steps of:

i) obtaining a mixture of synthetic $C_\kappa$ and $C_\lambda$ domains, polymerase enzyme, primers, buffer and dNTP mix in an aqueous solution;

ii) subjecting the mixture of step (i) to a temperature range of 90° C. to 96° C. to denature the templates; and iii) simultaneous annealing and extension of the denatured templates from step (ii) at a temperature of 65° C. to 72° C. to obtain a first set of constant kappa and lambda domains.

7. The process of claim 6, wherein the fusion of Vκ and Cκ domains and Vλ and Cλ domains are conducted in a two-step PCR using primers comprising SEQ ID Nos. 30, 32, 35-37 and 55, and comprises the steps of:

i) obtaining a mixture of the first set of variable lambda domains, the first set of variable kappa domains, and the first set of constant kappa and lambda domains, polymerase enzyme, primers, buffer and dNTP mix in an aqueous solution;

ii) subjecting the mixture of step (i) to a temperature range of 90° C. to 96° C. to denature the templates; and iii) simultaneous annealing and extension of the denatured templates from step (ii) at a temperature of 65° C. to 72° C. to obtain lambda and kappa light chain repertoires.

8. The process of claim 7, wherein the fusion of $V_H$ and CH1 domains is conducted in a three-step PCR using primers comprising SEQ ID Nos. 28 and 33, and comprises the steps of:

i) obtaining a mixture of the first set of variable heavy domains and the first set of constant heavy domains, respectively, polymerase enzyme, primers, buffer and dNTP mix in an aqueous solution;

ii) subjecting the mixture of step (i) to a temperature range of 90° C. to 96° C. to denature the templates;

iii) annealing the primers to the denatured templates from step (ii) at a temperature range of 55° C. to 70° C.; and iv) extension of the primers on annealed templates from step (iii) at a temperature of 68° C. to 72° C. to obtain heavy chain repertoires.

9. The process of claim 8, wherein the fusion PCR of light and heavy chains are conducted in a two-step PCR using primers comprising SEQ ID Nos. 34, 35-37 and 55, and comprises the steps of:

i) obtaining a mixture of lambda and kappa light chain repertoires and heavy chain repertoires, polymerase enzyme, primers, buffer and dNTP mix in an aqueous solution;

ii) subjecting the mixture of step (i) to a temperature range of 90° C. to 96° C. to denature the templates; and iii) simultaneous annealing and extension of the denatured templates from step (ii) at a temperature of 65° C. to 72° C. to obtain lambda and kappa Fab repertoires.

10. The process of claim 8, wherein the fusion PCR of light and heavy chains are conducted in a three-step PCR using primers comprising SEQ ID Nos. 34, 35-37 and 55, and comprises the steps of:

i) obtaining a mixture of lambda and kappa light chain repertoires and heavy chain repertoires, polymerase enzyme, primers, buffer and dNTP mix in an aqueous solution;

ii) subjecting the mixture of step (i) to a temperature range of 90° C. to 96° C. to denature the templates;

iii) annealing the primers to the denatured templates from step (ii) at a temperature of 55° C. to 70° C.; and iv) extension of the primers on annealed templates from step (iii) at a temperature of 65° C. to 72° C. to obtain lambda and kappa Fab repertoires.

11. The process of claim 1, wherein displaying the captured immune repertoire in a vector comprises the steps of:

i) ligating the Fabs to a linearized phagemid vector; and ii) transforming the ligated mixture into a suitable host.

12. The process of claim 11, wherein the ligation of Fab repertoires obtained using SEQ ID Nos. 34-37 in a phagemid vector is conducted by:

i) restriction digestion of the linear Fab population with 32 U/μg SfiI at 50° C. for 16 h to release linear Fabs with sticky ends followed by agarose gel purification; and ii) sticky end ligation of linear Fabs obtained at step (i) in a phagemid vector at a temperature of 16° C. for 16 h followed by 37° C. for 1 h and heat-inactivation at 70° C. for 15 min.

13. The process of claim 11, wherein the ligation of Fab repertoires obtained using SEQ ID Nos. 34 and 55 in a phagemid vector is conducted by:

i) restriction digestion of the linear Fab population with 32 U/μg SfiI at 50° C. for 16 h to release linear Fabs with sticky ends followed by agarose gel purification; and ii) sticky end ligation of linear Fabs obtained at step (i) in a phagemid vector at a temperature of 16° C. for 16 h followed by 37° C. for 1 h and heat-inactivation at 70° C. for 15 min.

14. The process of claim 11, wherein transformation is carried out at a DNA to cell volume ratio of 25 ng to 400 ng or 10 ng to 350 ng or 200 ng to 300 ng per 50 μl of ultracompetent cells at a voltage in the range of 1500V to 3500V or 2500V to 3200V, capacitance in the range of 10 μF to 30 μF or 20 μF to 28 μF and resistance of 100Ω to 400Ω or 250Ω to 350Ω in a cuvette of 0.1 cm or 0.2 cm or 0.4 cm inter-electrode distance.

15. The method of claim 11, wherein the host is an amber suppressor t-RNA encoding host selected from the group consisting of TG1, XL-1 Blue and ER2537.

16. The process of claim 1, wherein the APDL is obtained from 15 μg to 160 μg of ligated DNA or 20 μg to 100 μg of ligated DNA or 40 µg to 50 µg of ligated DNA according to claim 12, wherein the kappa subtype is obtained from 10 µg to 70 µg of ligated DNA or 20 µg to 50 µg of ligated DNA or 25 µg to 30 µg of ligated DNA in a single step of transformation with an efficiency of $1.92 \times 10^9$ to $1.98 \times 10^{10}$ cfu/µg, wherein the lambda subtype is obtained from 5 µg to 60 µg of ligated DNA or 8 µg to 50 µg of ligated DNA or 10 µg to 20 µg of ligated DNA in a single step of transformation with an efficiency of $1.92 \times 10^9$ to $9.1 \times 10^9$ cfu/µg.

17. A method of obtaining manufacturable antibodies as soluble Fabs from the APDL of claim 1, comprising the steps of:
   i) target specific panning to obtain enriched binder population;
   ii) periplasmic quantitative ELISA (qELISA);
   iii) kinetic ranking;
   iv) bioassay; and
   v) manufacturability assessment;
   wherein the method results in a phenotype to expected genotype correlation of >90% in the antibodies so obtained at step (iii).

18. A method of claim 17, wherein the periplasmic qELISA comprises the steps of:
   i) obtaining soluble Fabs from single bacterial colonies of enriched binder population from eluate titer plates by picking single clones from titer plates of non-amber suppressor hosts followed by liquid culture in 96-well deepwell plates for overnight growth at 37° C. and 250 rpm and diluting the overnight cultures 10-folds for allowing growth to log phase; inducing the log phase cultures with 1 mM IPTG and allowing overnight growth at 30° C. and 250 rpm followed by centrifuging the cultures in 96-well plates to pellet down the induced cells and periplasmic extraction of the pelleted cells by using high concentrations of EDTA in a buffered solution while slowly shaking the buffer-suspended cells in the same 96-well plate overnight at 30° C. and finally by centrifugation of the buffer-suspended cells to isolate the diffused periplasmic fraction away from the spheroplast and cell debris;
   ii) coating the surface of 96-well charged polystyrene plates with a capture antibody against heavy chain; or coating the surface with avidin or streptavidin or neutravidin, the surface is coated with streptavidin at a concentration ranging between 20 µg/ml and 100 µg/ml;
   iii) capturing the soluble Fab from step (i) on the coated surface of step (ii), wherein the capture antibody is selected from the group comprising goat anti-Human IgG(H+L) F(ab')2 fragment or Biotin Anti-IgG-CH1 Conjugate, the biotinylated anti-CH1 antibody at a concentration of 1000 ng/ml to 100 ng/ml;
   iv) detecting light chains by utilization of light chain specific antibody to identify full length, tandem in-frame, heterodimeric, soluble Fabs, wherein the light chain specific antibody is selected from the group comprising goat anti-human lambda LC specific peroxidase conjugate, goat anti-human kappa LC specific peroxidase conjugate, goat anti-human F(ab')2-HRP, mouse anti-human kappa light chain peroxidase conjugate, mouse anti-human kappa light chain monoclonal and rabbit anti-human kappa chain monoclonal at a dilution ranging between 1 to 10000 for anti-lambda and 1 to 2000 for anti-kappa.

19. The method of claim 17, wherein the kinetic ranking comprises the steps of:
   i) obtaining soluble Fabs from quantitative ELISA positive clones identified according to the method of claim 1 in 50 ml individual cultures;
   ii) dialyzing the obtained Fabs from step (i) against 1×PBS;
   iii) use of running buffer of physiological strength and pH for kinetic analysis—the buffer could be phosphate, HEPES, or phosphate containing NaCl or KCl concentration of 0.25 to 0.75M and Polyoxyethylene (20) sorbitan monolaureate concentration of 0.005 to 0.05%;
   iv) selecting the SPR (surface plasmon resonance) chip immobilization surface from the group comprising charged dextran, charged alginate, nickel nitrilotetraacetic acid coated on charged dextran or alginate surface, or streptavidin or neutravidin coated on charged dextran or alginate surface;
   v) selecting the immobilization chemistry from the group comprising amine coupling using EDAC (1-Ethyl-3-(3-dimethylaminopropyl) carbodiimide) and sulfo-NHS (Nhydroxysuccinimide), Ni2+ charging using 10 mM nickel sulfate, or streptavidin-biotin recognition chemistry for the SPR surface at step (i);
   vi) immobilizing the anti-Fab capture antibody on the chip surface from step (v), wherein the capture antibody is selected from the group comprising anti-Fab IgG, anti-tag antibody such as anti-His or anti-HA, biotinylated anti-$C_H1$, biotinylated bivalent anti-$C_H1$/anti$C_\lambda$, biotinylated anti-$C_H1$/anti-$C_\kappa$, a 50:50 mixture of both biotinylated bivalent anti-$C_H1$/anti$C_\lambda$ and biotinylated anti-$C_H1$/anti-$C_\kappa$;
   vii) capturing the crude periplasmic Fabs obtained from step (ii) on the capture antibody-coated surface of the chip from step (vi);
   viii) signal stabilization by 1 to 3 rounds of running buffer injection over the chip surface with intermediate pause of 2 min to 15 min;
   ix) testing the analyte response on captured Fabs of step (vii) at an optimal concentration of analyte to distinguish between target antigen binders and non-binders;
   x) removing the Fab-analyte complex of step (ix) using regenerating reagent selected from the group comprising 2M MgCl2, 0.85% H3PO4, 50 mM NaOH or 10 mM glycine, pH 2.0 for the surface to be re-used for the next round of screening.

* * * * *